US009950057B2

(12) United States Patent
Kawaoka et al.

(10) Patent No.: US 9,950,057 B2
(45) Date of Patent: Apr. 24, 2018

(54) HIGH TITER RECOMBINANT INFLUENZA VIRUSES WITH ENHANCED REPLICATION IN MDCK OR VERO CELLS OR EGGS

(71) Applicant: Wisconsin Alumni Research Foundation (WARF), Madison, WI (US)

(72) Inventors: Yoshihiro Kawaoka, Middleton, WI (US); Gabriele Neumann, Madison, WI (US); Jihui Ping, Madison, WI (US)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 0 days.

(21) Appl. No.: 14/332,121

(22) Filed: Jul. 15, 2014

(65) Prior Publication Data

US 2015/0017205 A1    Jan. 15, 2015

Related U.S. Application Data

(60) Provisional application No. 61/846,460, filed on Jul. 15, 2013.

(51) Int. Cl.
*A61K 39/145* (2006.01)
*C12N 7/00* (2006.01)

(52) U.S. Cl.
CPC ............... *A61K 39/145* (2013.01); *C12N 7/00* (2013.01); *C12N 2760/16121* (2013.01); *C12N 2760/16134* (2013.01)

(58) Field of Classification Search
CPC ............ C12N 7/00; C12N 2760/16134; A61K 39/145; A61K 39/12; C07K 14/005
See application file for complete search history.

(56) References Cited

U.S. PATENT DOCUMENTS

| | | | |
|---|---|---|---|
| 4,071,618 | A | 1/1978 | Konobe et al. |
| 4,659,569 | A | 4/1987 | Mitsuhashi et al. |
| 5,166,057 | A | 11/1992 | Palese et al. |
| 5,716,821 | A | 2/1998 | Wertz et al. |
| 5,789,229 | A | 8/1998 | Wertz et al. |
| 5,820,871 | A | 10/1998 | Palese et al. |
| 5,840,520 | A | 11/1998 | Clarke et al. |
| 5,854,037 | A | 12/1998 | Palese et al. |
| 5,948,410 | A | 9/1999 | Van Scharrenburg et al. |
| 5,994,526 | A | 11/1999 | Meulewaeter et al. |
| 6,033,886 | A | 3/2000 | Conzelmann |
| 6,037,348 | A | 3/2000 | Colacino et al. |
| 6,146,642 | A | 11/2000 | Garcia-Sastre et al. |
| 6,169,175 | B1 | 1/2001 | Frace et al. |
| 6,194,546 | B1 | 2/2001 | Newton et al. |
| 6,455,298 | B1 | 9/2002 | Groner et al. |
| 6,544,785 | B1 | 4/2003 | Palese et al. |
| 6,656,720 | B2 | 12/2003 | Groner et al. |
| 6,825,036 | B2 | 11/2004 | Makizumi et al. |
| 6,872,395 | B2 | 3/2005 | Kawaoka |
| 6,951,752 | B2 | 10/2005 | Reiter et al. |
| 6,951,754 | B2 | 10/2005 | Hoffmann |
| 6,974,695 | B2 | 12/2005 | Vogels et al. |
| 7,037,707 | B2 | 5/2006 | Webster et al. |
| 7,176,021 | B2 | 2/2007 | Kawaoka |
| 7,226,774 | B2 | 6/2007 | Kawaoka |
| 7,312,064 | B2 | 12/2007 | Hoffmann |
| 7,507,411 | B2 | 3/2009 | Zhou et al. |
| 7,566,458 | B2 | 7/2009 | Yang et al. |
| 7,585,657 | B2 | 9/2009 | Kawaoka |
| 7,588,769 | B2 | 9/2009 | Kawaoka |
| 7,670,837 | B2 | 3/2010 | Schwartz |
| 7,833,788 | B2 | 11/2010 | Pau et al. |
| 7,883,844 | B2 | 2/2011 | Nouchi et al. |
| 7,955,833 | B2 | 6/2011 | Reiter et al. |
| 7,959,930 | B2 | 6/2011 | De Wit et al. |
| 7,972,843 | B2 | 7/2011 | Hoffmann |
| 7,993,924 | B2 | 8/2011 | Billeter et al. |
| 8,012,736 | B2 | 9/2011 | Hoffman et al. |
| 8,048,430 | B2 | 11/2011 | Yang et al. |
| 8,057,806 | B2 | 11/2011 | Kawaoka et al. |
| 8,093,033 | B2 | 1/2012 | Kemble et al. |
| 8,114,415 | B2 | 2/2012 | Hoffmann et al. |
| 8,119,337 | B2 | 2/2012 | Gregersen |
| 8,119,388 | B2 | 2/2012 | Schwartz et al. |
| 8,309,099 | B2 | 11/2012 | Hoffmann |
| 8,354,114 | B2 | 1/2013 | Lu et al. |
| 8,357,376 | B2 | 1/2013 | Liu et al. |

(Continued)

FOREIGN PATENT DOCUMENTS

| | | |
|---|---|---|
| AU | 2012204138 B2 | 5/2014 |
| AU | 2014202470 | 11/2016 |

(Continued)

OTHER PUBLICATIONS

"U.S. Appl. No. 12/912,411, Advisory Action mailed Feb. 5, 2014", 3 pgs.
"U.S. Appl. No. 12/912,411, Examiner Interview Summary mailed Feb. 11, 2014", 2 pgs.
"U.S. Appl. No. 12/912,411, Final Office Action mailed Jan. 14, 2015", 10 pgs.
"U.S. Appl. No. 12/912,411, Final Office Action mailed Oct. 25, 2013", 11 pgs.
"U.S. Appl. No. 12/912,411, Non Final Office Action mailed Jun. 7, 2013", 9 pgs.
"U.S. Appl. No. 12/912,411, Non Final Office Action mailed Sep. 24, 2014", 12 pgs.

(Continued)

*Primary Examiner* — Barry A Chestnut
(74) *Attorney, Agent, or Firm* — Schwegman Lundberg & Woessner, P.A.

(57) ABSTRACT

The invention provides a composition useful to prepare high titer influenza viruses, e.g., in the absence of helper virus, which includes internal genes from an influenza virus vaccine strain or isolate, e.g., one that is safe in humans, for instance, one that does not result in significant disease, that confer enhanced growth in cells in culture, such as MDCK cells, or in eggs.

17 Claims, 45 Drawing Sheets

(56) References Cited

U.S. PATENT DOCUMENTS

| | | |
|---|---|---|
| 8,409,843 B2 | 4/2013 | Kemble et al. |
| 8,460,914 B2 | 6/2013 | Gregersen |
| 8,475,806 B2 | 7/2013 | Kawaoka |
| 8,524,497 B2 | 9/2013 | Reiter et al. |
| 8,546,123 B2 | 10/2013 | Lewis |
| 8,574,591 B2 | 11/2013 | Hoffmann et al. |
| 8,574,593 B2 | 11/2013 | Yang et al. |
| 8,580,277 B2 | 11/2013 | Yang et al. |
| 8,591,914 B2 | 11/2013 | Yang et al. |
| 9,109,013 B2 | 8/2015 | Kawaoka et al. |
| 9,254,318 B2 | 2/2016 | Kawaoka et al. |
| 9,474,798 B2 | 10/2016 | Watanabe et al. |
| 2002/0164770 A1 | 11/2002 | Hoffmann |
| 2002/0197705 A1 | 12/2002 | Kawaoka |
| 2003/0035814 A1 | 2/2003 | Kawaoka et al. |
| 2003/0044962 A1 | 3/2003 | Makizumi et al. |
| 2003/0073223 A1 | 4/2003 | Groner et al. |
| 2003/0119183 A1 | 6/2003 | Groner |
| 2003/0194694 A1 | 10/2003 | Kawaoka |
| 2004/0002061 A1 | 1/2004 | Kawaoka |
| 2004/0063141 A1 | 4/2004 | Lok |
| 2004/0077086 A1 | 4/2004 | Reiter et al. |
| 2004/0219170 A1 | 11/2004 | Kawaoka |
| 2005/0003349 A1 | 1/2005 | Kawaoka |
| 2005/0037487 A1 | 2/2005 | Kawaoka et al. |
| 2005/0118140 A1 | 6/2005 | Vorlop et al. |
| 2005/0158342 A1 | 7/2005 | Kemble et al. |
| 2005/0186563 A1 | 8/2005 | Hoffmann |
| 2005/0202553 A1 | 9/2005 | Groner et al. |
| 2005/0232950 A1 | 10/2005 | Kawaoka |
| 2005/0266026 A1 | 12/2005 | Hoffmann et al. |
| 2006/0057116 A1 | 3/2006 | Kawaoka et al. |
| 2006/0166321 A1 | 7/2006 | Kawaoka et al. |
| 2006/0188977 A1 | 8/2006 | Schwartz et al. |
| 2006/0246092 A1 | 11/2006 | Neirynck et al. |
| 2007/0231348 A1 | 10/2007 | Kawaoka et al. |
| 2008/0233560 A1 | 9/2008 | Hoffmann |
| 2008/0254067 A1 | 10/2008 | Trepanier et al. |
| 2008/0274141 A1 | 11/2008 | Groner et al. |
| 2008/0311148 A1 | 12/2008 | Hoffmann |
| 2008/0311149 A1 | 12/2008 | Hoffmann |
| 2009/0074812 A1 | 3/2009 | Watanabe et al. |
| 2009/0081252 A1 | 3/2009 | Gregersen |
| 2009/0181446 A1 | 7/2009 | Nouchi et al. |
| 2010/0112000 A1 | 5/2010 | Schwartz |
| 2010/0183671 A1 | 7/2010 | Gregersen et al. |
| 2010/0247572 A1 | 9/2010 | Kawaoka |
| 2011/0027314 A1 | 2/2011 | Broeker |
| 2011/0045022 A1 | 2/2011 | Tsai |
| 2011/0110978 A1 | 5/2011 | Kawaoka et al. |
| 2011/0236417 A1 | 9/2011 | Watanabe et al. |
| 2012/0020997 A1 | 1/2012 | Hoffman et al. |
| 2012/0034600 A1 | 2/2012 | Gregersen |
| 2012/0115206 A1 | 5/2012 | Schwartz et al. |
| 2012/0156241 A1 | 6/2012 | De Wit et al. |
| 2012/0207785 A1 | 8/2012 | Fabry et al. |
| 2013/0095135 A1 | 4/2013 | Collignon et al. |
| 2013/0183741 A1 | 7/2013 | Park et al. |
| 2013/0316434 A1 | 11/2013 | Reiter et al. |
| 2014/0227310 A1 | 8/2014 | Li et al. |
| 2015/0368621 A1 | 12/2015 | Kawaoka et al. |
| 2016/0208223 A1 | 7/2016 | Kawaoka et al. |
| 2017/0067029 A1 | 3/2017 | Kawaoka et al. |
| 2017/0096645 A1 | 4/2017 | Watanabe et al. |

FOREIGN PATENT DOCUMENTS

| | | |
|---|---|---|
| CN | 1826407 B | 9/2013 |
| EP | 0702085 A1 | 3/1996 |
| EP | 1201760 A1 | 5/2002 |
| EP | 2010557 B1 | 2/2014 |
| EP | 1631663 B1 | 8/2016 |
| IL | 171831 A | 5/2015 |
| JP | 2004500842 A | 1/2004 |
| JP | 2005523698 A | 8/2005 |
| JP | 2005245302 A | 9/2005 |
| JP | 2005535288 A | 11/2005 |
| JP | 2009-532352 A | 9/2009 |
| JP | 4927290 B2 | 2/2012 |
| JP | 4927290 | 5/2012 |
| JP | 2014039551 A | 3/2014 |
| JP | 2014131516 A | 7/2014 |
| JP | 2016524915 A | 8/2016 |
| JP | 2016169225 A | 9/2016 |
| MX | 285206 | 3/2011 |
| NO | WO-2011/056591 A1 | 5/2011 |
| WO | WO-9610631 A1 | 4/1996 |
| WO | WO-9610632 A1 | 4/1996 |
| WO | WO-9640955 A1 | 12/1996 |
| WO | WO-9737000 A1 | 10/1997 |
| WO | WO-9802530 A1 | 1/1998 |
| WO | WO-9853078 A1 | 11/1998 |
| WO | WO-9928445 A1 | 6/1999 |
| WO | WO-0053786 A1 | 9/2000 |
| WO | WO-0060050 A2 | 10/2000 |
| WO | WO-0060050 A3 | 1/2001 |
| WO | WO-0179273 A2 | 10/2001 |
| WO | WO-0183794 A2 | 11/2001 |
| WO | WO-03068923 A2 | 8/2003 |
| WO | WO-03076462 A1 | 9/2003 |
| WO | WO-03091401 A2 | 11/2003 |
| WO | WO-2004094466 A2 | 11/2004 |
| WO | WO-2004094466 A3 | 11/2004 |
| WO | WO-2004/112831 A2 | 12/2004 |
| WO | WO-2004112831 A2 | 12/2004 |
| WO | WO-2004112831 A3 | 12/2004 |
| WO | WO-2005062820 A2 | 7/2005 |
| WO | WO-2007/126810 A2 | 11/2007 |
| WO | WO-2007126810 A3 | 11/2007 |
| WO | WO-2008/157583 A1 | 12/2008 |
| WO | WO-2008156778 A2 | 12/2008 |
| WO | WO-2008156778 A9 | 2/2009 |
| WO | WO-2008156778 C2 | 2/2009 |
| WO | WO-2012177924 A2 | 12/2012 |
| WO | WO-2013034069 A1 | 3/2013 |
| WO | WO-2014/195920 A2 | 12/2014 |
| WO | WO-2015/009743 A1 | 1/2015 |
| WO | WO-2015196150 A2 | 12/2015 |
| WO | WO-2015196150 A3 | 12/2015 |
| WO | WO-2017007839 A1 | 1/2017 |
| WO | WO-2017143236 A1 | 8/2017 |

OTHER PUBLICATIONS

"U.S. Appl. No. 12/912,411, Response filed Jan. 27, 2014 to Final Office Action mailed Oct. 25, 2013", 11 pgs.

"U.S. Appl. No. 12/912,411, Response filed Feb. 25, 2014 to Final Office Action mailed Oct. 25, 2013", 11 pgs.

"U.S. Appl. No. 12/912,411, Response filed Feb. 18, 2013 to Restriction Requirement mailed Oct. 17, 2012", 9 pgs.

"U.S. Appl. No. 12/912,411, Response filed Oct. 7, 2013 to Non Final Office Action mailed Jun. 7, 2013", 10 pgs.

"U.S. Appl. No. 12/912,411, Response filed Dec. 31, 2014 to Non Final Office Action mailed Sep. 24, 2014", 12 pgs.

"U.S. Appl. No. 12/912,411, Restriction Requirement mailed Oct. 17, 2012", 9 pgs.

"European Application Serial No. 10777154.5, Examination Notification Art. 94(3) mailed Oct. 6, 2014", 7 pgs.

"European Application Serial No. 10777154.5, Office Action mailed Jul. 4, 2012", 2 pgs.

"European Application Serial No. 10777154.5, Response filed Jan. 14, 2013 to Office Action mailed Jul. 4, 2012", 12 pgs.

"Hemagglutinin [Influenza A virus (A/swine/France/WVL13/1995(H1N1))]", GenBank Accession# AC025026, (May 22, 2009), 1 pg.

"International Application Serial No. PCT/US2010/054128, Preliminary Report on Patentability mailed May 10, 2012", 10 pgs.

"International Application U.S. Appl. No. PCT/US2010/054128, Search Report mailed Feb. 23, 2011", 6 pgs.

"International Application Serial No. PCT/US2010/054128, Written Opinion mailed Feb. 23, 2011", 8 pgs.

(56) References Cited

OTHER PUBLICATIONS

"International Application Serial No. PCT/US2014/046731, International Search Report mailed Nov. 25, 2014", 9 pgs.
"International Application Serial PCT/US2014/046731, Written Opinion mailed Nov. 25, 2014", 10 pgs.
"Japanese Application Serial No. 2012-536963, Office Action mailed Jan. 6, 2015", (w/ English Translation), 14 pgs.
"Japanese Application Serial No. 2012-536963, Voluntary Amendment filed Jun. 27, 2012", (w/ English Translation of Amended Claims), 17 pgs.
"Neuraminidase, partial [Influenza A virus (A/swine/France/WVL13/1995(H1N1))]", GenBank Accession# AC025028, (May 22, 2009), 2 pgs.
Brown, E. G., et al., "Genetic analysis of mouse-adapted influenza A virus identifies roles for the NA, PB1, and PB2 genes in virulence", *Virus Research*, 61(1), (May 1999), 63-76.
Dunham, Eleca J., et al., "Different Evolutionary Trajectories of European Avian-Like and Classical Swine H1N1 Influenza A Viruses", *Journal of Virology*, 83(11). (Jun. 2009), 5485-5494.
Forbes, Nicole E. et al., "Multifunctional Adaptive NS1 Mutations Are Selected upon Human Influenza Virus Evolution in the Mouse", *Plos One*, vol. 7, No. 2, (Feb. 21, 2012).
Jang, S.-W., et al., "Deoxygedunin, a Natural Product with Potent Neurotrophic Activity in Mice", PLoS ONE 5(7): e11528, (2010), 1-15.
Kistner, et al., "Cell culture (Vero) derived whole virus (H5N1) vaccine based on wild-type virus strain induces cross-protective immune responses", *Vaccine*, 25(32), (2007), 6028-6036.
Kovacova, A., et al., "Sequence similarities and evolutionary relationships of influenza virus A hemagglutinins". *Virus Genes*, 24(1), (2002), 57-63.
Lee, M. S, et al., "Genetic and pathogenic characterization of H6NI avian influenza viruses isolated in Taiwan between 1972 and 2005", *Avian Diseases* , 50(4), (Dec. 2006), 561-571.
Li, K. 8, et al, "Genesis of a highly pathogenic and potentially pandemic H5NI influenza virus in eastern Asia", *Nature*, 430(6996), (Jul. 8, 2004), 209-213.
Lin, Y P, et al., "Adaptation of egg-grown and transfectant influenza viruses for growth in mammalian cells: selection of hemagglutinin mutants with elevated pH of membrane fusion", *Virology*, 233(2), (1997), 402-410.
Murakami, Shin, et al., "Growth Determinants for H5N1 Influenza Vaccine Seed Viruses in MDCK Cells", *Journal of Virology*, vol. 82, No. 21, (Nov. 2008), 10502-10509.
Neumann, G., et al., "An Improved Reverse Genetics System for Influenza A Virus Generation and Its Implications for Vaccine Production", *Proc. Natl. Acad. Sci. USA*, 102(46), (2005), 16825-16829.
Neumann, G., et al., "Emergence and pandemic potential of swine-origin HIN1 influenza virus", *Nature (London)*, 459(7249), (Jun. 2009), 931-939.
Neumann, G., et al., "Reverse Genetics of Influenza Viruses—Applications in Research and Vaccine Design", *Monographs in Virology*, 27, (2008), 118-133.
Reed, M. L., et al., "Amino Acid Residues in the Fusion Peptide Pocket Regulate the pH of Activation of the H5N1 Influenza Virus Hemagglutinin Protein", *J. Virol.*, vol. 83(8), (2009), 3568-3580.
Romanova, et al., "Live cold-adapted influenza A vaccine produced in Vero cell line", *Virus Research*, 103, (2004), 187-193.
Xu, X., et al., "Reassortment and evolution of current human influenza A and B viruses", *Virus Research*, 103, (2004), 55-60.
Yi, Pu Lin, et al., "Adaptation of Egg-Grown and Transfectant Influenza Viruses for Growth in Mammalian Cells: Selection of Hemagglutinin Mutants with Elevated pH of Membrane Fusion", *Virology*, 233(2), 1997, 402-410.
"Chinese Application Serial No. 200780020095.1, Response filed Jan. 6, 2017 to Office Action mailed Nov. 2, 2016", 22 pgs.
"U.S. Appl. No. 15/292,595, Preliminary Amendment filed Dec. 27, 2016", 5 pgs.

"International Application Serial No. PCT/US2015/036803, International Preliminary Report on Patentability mailed Dec. 29, 2016", 10 pgs.
U.S. Appl. No. 09/834,095, filed Apr. 12, 2001, Viruses Comprising Mutant Ion Channel Protein.
U.S. Appl. No. 11/043,768, filed Jan. 26, 2005, Viruses Comprising Mutant Ion Channel Protein.
U.S. Appl. No. 10/827,995, filed Apr. 20, 2004, Viruses Encoding Mutant Membrane Protein.
U.S. Appl. No. 12/467,492, filed May 18, 2009, Viruses Encoding Mutant Membrane Protein.
U.S. Appl. No. 10/855,875, filed May 27, 2004, High Titer Recombinant Influenza Viruses for Vaccines and Gene Therapy.
U.S. Appl. No. 11/729,557, filed Mar. 29, 2007, High Titer Recombinant Influenza Viruses for Vaccines.
U.S. Appl. No. 15/000,851, filed Jan. 19, 2016, High Titer Recombinant Influenza Viruses for Vaccines.
U.S. Appl. No. 12/214,414, filed Jun. 18, 2008, Influenza M2 Protein Mutant Viruses as Live Influenza Attenuated Vaccines.
U.S. Appl. No. 15/292,595, filed Oct. 13, 2016, Influenza M2 Protein Mutant Viruses as Live Influenza Attenuated Vaccines.
U.S. Appl. No. 13/070,110, filed Mar. 23, 2011, Vaccines Comprising Mutant Attenuated Influenza Viruses.
U.S. Appl. No. 14/745,236, filed Jun. 19, 2015, Mutations that Confer Genetic Stability to Additional Genes in Influenza Viruses.
U.S. Appl. No. 15/203,581, filed Jul. 6, 2016, Influenza Virus Replication for Vaccine Development.
"European Application Serial No. 14745060.5, Office Action mailed Feb. 23, 2016", 2 pgs.
"International Application Serial No. PCT/US2014/046731, International Preliminary Report on Patentability mailed Jan. 28, 2016", 12 pgs.
Neumann. G., et al., "Generation of Influenza A virus entirely from cloned cDNAs", Proceedings of the National Academy of Science, 96, (Aug. 1999), 9345-9350.
Result 17, NCBI Blast nucleotide search of SEQ ID No. 2, database "nr".
Result 1, NCBI Blast nucleotide search of SEQ ID No. 3, database "nr"; Result 4, NCBI Blast nucleotide search of SEQ ID No. 4, database "nr".
Result 2, NCBI Blast nucleotide search of SEQ ID No. 5, database "nr"; Result 4, NCBI Blast nucleotide search of SEQ ID No. 6, database "nr".
Results 1, NCBI Blast nucleotide search of SEQ ID No. 7, database "nr"; Result 1, NCBI Blast nucleotide search of SEQ ID No. 8, database "nr".
Result 7, NCBI Blast nucleotide search of SEQ ID: 1, database "nr".
"", FLUMISTTM Package Insert Template, [Online]. Retrieved from the Internet: http://www.fda.gov/downloads/BiologicsBioodVaccines!Vaccines/ApprovedProducts/UCM294307.pdf, (Mar. 1, 2012).
"1.A.32 The Type B Influenza Virus NB Channel (NB-C) Family", Transport Protein Database, (University of California, San Diego, The Sailer Laboratory Bioinformatics Group) [online}. http://www.web.archive.org/web/200301311055254/http://tcdb.ucsd.edu/tcdb/tcfamilybrowse.php?tcname=1.A.32, (Archived Jan. 31, 2003), 1 pg.
"Application No. 2006-533439; Office Action Response Filed Jul. 9, 2010", 25.
"U.S. Appl. No. 09/834,095, Advisory Action mailed Jan. 8, 2004", 3 pgs.
"U.S. Appl. No. 09/834,095, Final Office Action mailed Aug. 26, 2003", 12 pgs.
"U.S. Appl. No. 09/834,095, Non-Final Office Action mailed Nov. 4, 2002", 12 pgs.
"U.S. Appl. No. 09/834,095, Notice of Allowance mailed Sep. 27, 2004", 13 pgs.
"U.S. Appl. No. 09/834,095, Office Action mailed Apr. 20, 2004", 11 pgs.
"U.S. Appl. No. 09/834,095, Response filed Feb. 4, 2003 to Office Action mailed Nov. 4, 2002", 14 pgs.
"U.S. Appl. No. 09/834,095, Response filed Jun. 12, 2003 to Restriction Requirement mailed Apr. 22, 2003", 2 pgs.

(56) References Cited

OTHER PUBLICATIONS

"U.S. Appl. No. 09/834,095, Response filed Jun. 18, 2004 to Office Action mailed Apr. 20, 2004", 11 pgs.
"U.S. Appl. No. 09/834,095, Response filed Aug. 1, 2002 to Restriction Requirement mailed Jul. 1, 2002", 3 pgs.
"U.S. Appl. No. 09/834,095, Response filed Nov. 26, 2003 to Final Office Action mailed Aug. 26, 2003", 10 pgs.
"U.S. Appl. No. 09/834,095, Restriction Requirement mailed Apr. 22, 2003", 5 pgs.
"U.S. Appl. No. 09/834,095, Restriction Requirement mailed Jul. 1, 2002", 9 pgs.
"U.S. Appl. No. 09/834,095, Supplemental Amendment filed Aug. 4, 2004", 7 pgs.
"U.S. Appl. No. 10/827,995, Final Office Action mailed Nov. 15, 2006", 10 pgs.
"U.S. Appl. No. 10/827,995, Non-Final Office Action mailed Jun. 2, 2006", 15 pgs.
"U.S. Appl. No. 10/827,995, Non-Final Office Action mailed Oct. 25, 2007", 7 pgs.
"U.S. Appl. No. 10/827,995, Notice of Allowance mailed Feb. 17, 2009", 9 pgs.
"U.S. Appl. No. 10/827,995, Notice of Allowance mailed Jul. 2, 2008", 9 pgs.
"U.S. Appl. No. 10/827,995, Notice of Allowance mailed Oct. 17, 2008", 7 pgs.
"U.S. Appl. No. 10/827,995, Notice of Non-Compliant Amendment Jul. 25, 2007", 4 pgs.
"U.S. Appl. No. 10/827,995, Proposed Examiners Amendment mailed Jun. 5, 2008", 6 pgs.
"U.S. Appl. No. 10/827,995, Response filed Mar. 3, 2008 to Office Action mailed Oct. 25, 2007", 10 pgs.
"U.S. Appl. No. 10/827,995, Response filed May 14, 2007 Final Office Action mailed Nov. 15, 2006", 16 pgs.
"U.S. Appl. No. 10/827,995, Response filed Aug. 13, 2007 to Notice of Non-Compliant Amendment Jul. 25, 2007", 16 pgs.
"U.S. Appl. No. 10/827,995, Response filed Aug. 17, 2006 Non-Final Office Action mailed Jun. 2, 2006", 15 pgs.
"U.S. Appl. No. 10/855,875 , Response filed May 17, 2012 to Non Final Office Action mailed Mar. 15, 2012", 15 pgs.
"U.S. Appl. No. 10/855,875, Final Office Action mailed Mar. 11, 2008", FOAR, 20 Pgs.
"U.S. Appl. No. 10/855,875, Final Office Action mailed Dec. 10, 2010", 15 pgs.
"U.S. Appl. No. 10/855,875, Final Office Action mailed Aug. 2, 2006", 34 pgs.
"U.S. Appl. No. 10/855,875, Non Final Office Action mailed Mar. 15, 2012", 15 pgs.
"U.S. Appl. No. 10/855,875, Non-Final Office Action mailed Feb. 19, 2010", 7 pgs.
"U.S. Appl. No. 10/855,875, Non-Final Office Action mailed Aug. 7, 2009", 32 pgs.
"U.S. Appl. No. 10/855,875, Non-Final Office Action mailed Nov. 6, 2008", 12 pgs.
"U.S. Appl. No. 10/855,875, Non-Final Office Action mailed Nov. 30, 2005", 13 pgs.
"U.S. Appl. No. 10/855,875, Non-Final Office Action mailed May 3, 2007", 13 pgs.
"U.S. Appl. No. 10/855,875, Notice of Allowance mailed Mar. 4, 2013", 8 pgs.
"U.S. Appl. No. 10/855,875, Preliminary Amendment filed Feb. 2, 2007", 14 pgs.
"U.S. Appl. No. 10/855,875, Response filed Mar. 18, 2011 to Final Office Action mailed Dec. 10, 2010", 15 pgs.
"U.S. Appl. No. 10/855,875, Response filed Aug. 17, 2010 to Non Final Office Action mailed Feb. 19, 2010", 20 pgs.
"U.S. Appl. No. 10/855,875, Response filed Jan. 29, 2007 Final Office Action mailed Aug. 2, 2007", 14 pgs.
"U.S. Appl. No. 10/855,875, Response filed Dec. 7, 2009 to Non Final Office Action mailed Aug. 7, 2009", 15 pgs.

"U.S. Appl. No. 10/855,875, Response Filed Dec. 7, 2009 to Non-Final Office Action mailed Aug. 7, 2009", 15 pgs.
"U.S. Appl. No. 10/855,875, Response filed Mar. 31, 2009 to Non Final Office Action mailed Nov. 6, 2008", 14 pgs.
"U.S. Appl. No. 10/855,875, Response filed May 1, 2006 Non-Final Office Action mailed Nov. 30, 2005", 13 pgs.
"U.S. Appl. No. 10/855,875, Response filed Aug. 18, 2008 to final Office Action mailed Mar. 11, 2008", 15 pgs.
"U.S. Appl. No. 10/855,875, Response filed Sep. 20, 2005 to Restriction Requirement mailed Jul. 26, 2005", 4 pgs.
"U.S. Appl. No. 10/855,875, Restriction Requirement mailed Dec. 23, 2011", 9 pgs.
"U.S. Appl. No. 10/855,875, Restriction Requirement mailed Jul. 26, 2005", 9 pgs.
"U.S. Appl. No. 10/855,875, Response filed Nov. 2, 2007 to Office Action mailed May 3, 2007", 16 pgs.
"U.S. Appl. No. 11/043,768 Non-Final Office Action mailed Sep. 27, 2010", 8 pgs.
"U.S. Appl. No. 11/043,768, Final Office Action mailed Jun. 27, 2008", 8 pgs.
"U.S. Appl. No. 11/043,768, Non-Final Office Action mailed Feb. 23, 2010", 6 pgs.
"U.S. Appl. No. 11/043,768, Non-Final Office Action mailed Feb. 23, 2009", 7 pgs.
"U.S. Appl. No. 11/043,768, Non-Final Office Action mailed Nov. 28, 2007", 9 pgs.
"U.S. Appl. No. 11/043,768, Notice of Allowance mailed Jun. 29, 2011", 12 pgs.
"U.S. Appl. No. 11/043,768, Response filed May 2, 2011 to Final Office Action mailed Feb. 3, 2011", 11 pgs.
"U.S. Appl. No. 11/043,768, Response filed Jun. 15, 2010 to Non Final Office Action mailed Feb. 23, 2010", 9 pgs.
"U.S. Appl. No. 11/043,768, Response filed Jun. 23, 2009 to Non Final Office Action mailed Feb. 23, 2009", 9 pgs.
"U.S. Appl. No. 11/043,768, Response filed Jun. 23, 2009 to Non-Final Office Action mailed Feb. 23, 2009", 9 pgs.
"U.S. Appl. No. 11/043,768, Response filed Sep. 13, 2007 to Restriction Requirement mailed Mar. 13, 2007", 10 pgs.
"U.S. Appl. No. 11/043,768, Response filed Oct. 26, 2010 to Non Final Office Action mailed Sep. 27, 2010", 11 pgs.
"U.S. Appl. No. 11/043,768, Response filed Dec. 12, 2008 to Final Office Action mailed Jun. 27, 2008", 9 pgs.
"U.S. Appl. No. 11/043,768, Response filed Mar. 10, 2008 to Office Action mailed Nov. 28, 2007", 12 pgs.
"U.S. Appl. No. 11/043,768, Restriction Requirement mailed Mar. 13, 2007", 9 pgs.
"U.S. Appl. No. 11/043,786, Final Office Action mailed Feb. 3, 2011", 10 pgs.
"U.S. Appl. No. 11/729,557, Advisory Action mailed May 9, 2011", 3 pgs.
"U.S. Appl. No. 11/729,557, Advisory Action mailed Dec. 24, 2014", 3 pgs.
"U.S. Appl. No. 11/729,557, Final Office Action mailed Feb. 2, 2011", 14 pgs.
"U.S. Appl. No. 11/729,557, Final Office Action mailed Aug. 20, 2009", 13 Pgs.
"U.S. Appl. No. 11/729,557, Final Office Action mailed Sep. 12, 2014", 14 pgs.
"U.S. Appl. No. 11/729,557, Non Final Office Action mailed Feb. 18, 2015", 13 pgs.
"U.S. Appl. No. 11/729,557, Non Final Office Action mailed Feb. 26, 2014", 16 pgs.
"U.S. Appl. No. 11/729,557, Non-Final Office Action mailed Jan. 30, 2009", 20 pgs.
"U.S. Appl. No. 11/729,557, Non-Final Office Action mailed Feb. 22, 2010", 16 pgs.
"U.S. Appl. No. 11/729,557, Non-Final Office Action mailed Aug. 23, 2010", 15 pgs.
"U.S. Appl. No. 11/729,557, Notice of Allowance mailed Sep. 30, 2015", 11 pgs.
"U.S. Appl. No. 11/729,557, Respons filed Jun. 22, 2010 to Non Final Office Action mailed Feb. 22, 2010", 33 pgs.

(56) References Cited

OTHER PUBLICATIONS

"U.S. Appl. No. 11/729,557, Response filed Apr. 27, 2011 to Final Office Action mailed Feb. 2, 2011", 14 pgs.
"U.S. Appl. No. 11/729,557, Response filed Apr. 30, 2009 to Non Final Office Action mailed Jan. 30, 2009", 18 pgs.
"U.S. Appl. No. 11/729,557, Response filed May 22, 2014 to Non Final Office Action mailed Feb. 26, 2014", 13 pgs.
"U.S. Appl. No. 11/729,557, Response filed May 28, 2008 to Restriction Requirement mailed Nov. 28, 2007", 13 pgs.
"U.S. Appl. No. 11/729,557, Response filed Jun. 22, 2010 to Non Final Office Action mailed Feb. 22, 2010", 16 pgs.
"U.S. Appl. No. 11/729,557, Response filed Jun. 22, 2015 to non Final Office Action mailed Feb. 18, 2015", 13 pgs.
"U.S. Appl. No. 11/729,557, Response filed Oct. 28, 2010 to Non Final Office Action mailed Aug. 23, 2010", 13 pgs.
"U.S. Appl. No. 11/729,557, Response filed Dec. 1, 2009 to Final Office Action mailed Aug. 26, 2009", 16 pgs.
"U.S. Appl. No. 11/729,557, Response filed Dec. 11, 2014 to Final Office Action mailed Sep. 12, 2014", 15 pgs.
"U.S. Appl. No. 11/729,557, Restriction Requirement mailed Nov. 28, 2007", 9 pgs.
"U.S. Appl. No. 12/214,414, Advisory Action mailed Feb. 2, 2016", 5 pgs.
"U.S. Appl. No. 12/214,414, Advisory Action mailed Apr. 15, 2015", 6 pgs.
"U.S. Appl. No. 12/214,414, Advisory Action mailed Oct. 21, 2011", 5 pgs.
"U.S. Appl. No. 12/214,414, Examiner Interview Summary mailed Dec. 11, 2015", 3 pgs.
"U.S. Appl. No. 12/214,414, Final Office Action mailed Jan. 20, 2015", 28 pgs.
"U.S. Appl. No. 12/214,414, Final Office Action mailed Aug. 2, 2011", 7 pgs.
"U.S. Appl. No. 12/214,414, Final Office Action mailed Nov. 18, 2015", 17 pgs.
"U.S. Appl. No. 12/214,414, Non Final Office Action mailed Jun. 12, 2014", 28 pgs.
"U.S. Appl. No. 12/214,414, Non Final Office Action mailed Dec. 10, 2010", 6 pgs.
"U.S. Appl. No. 12/214,414, Non-Final Office Action mailed Mar. 2, 2010", 9 pgs.
"U.S. Appl. No. 12/214,414, Notice of Allowance mailed Jun. 7, 2016", 18 pgs.
"U.S. Appl. No. 12/214,414, Response filed Jan. 19, 2016 to Final Office Action mailed Nov. 18, 2015", 14 pgs.
"U.S. Appl. No. 12/214,414, Response filed Feb. 18, 2016 to Final Office Action mailed Nov. 18, 2015", 14 pgs.
"U.S. Appl. No. 12/214,414, Response filed Mar. 26, 2015 to Final Office Action mailed Jan. 20, 2015", 13 pgs.
"U.S. Appl. No. 12/214,414, Response filed May 3, 2011 to Non Final Office Action mailed Dec. 10, 2010", 12 pgs.
"U.S. Appl. No. 12/214,414, Response filed Jul. 20, 2015 to Advisory Action mailed Apr. 15, 2015", 14 pgs.
"U.S. Appl. No. 12/214,414, Response filed Aug. 31, 2010 to Non Final Office Action mailed Mar. 2, 2010", 11 pgs.
"U.S. Appl. No. 12/214,414, Response filed Oct. 3, 2011 to Non Final Office Action mailed Aug. 2, 2011", 9 pgs.
"U.S. Appl. No. 12/214,414, Response filed Dec. 21, 2011 to Advisory Action mailed Oct. 21, 2011", 10 pgs.
"U.S. Appl. No. 12/467,492, Restriction Requirement mailed Nov. 22, 2010", 6 pgs.
"U.S. Appl. No. 12/912,411, Notice of Allowability mailed May 20, 2015", 7 pgs.
"U.S. Appl. No. 12/912,411, Notice of Allowance mailed Apr. 8, 2015", 11 pgs.
"U.S. Appl. No. 12/912,411, Response filed Mar. 16, 2015 to Final Office Action mailed Jan. 14, 2015", 9 pgs.
"U.S. Appl. No. 13/070,110, Final Office Action mailed Apr. 3, 2015", 18 pgs.
"U.S. Appl. No. 13/070,110, Final Office Action mailed Jun. 12, 2013", 7 pgs.
"U.S. Appl. No. 13/070,110, Final Office Action mailed Sep. 14, 2016", 12 pgs.
"U.S. Appl. No. 13/070,110, Non Final Office Action mailed Oct. 2, 2014", 24 pgs.
"U.S. Appl. No. 13/070,110, Non Final Office Action mailed Dec. 11, 2015", 19 pgs.
"U.S. Appl. No. 13/070,110, Non Final Office Action mailed Dec. 21, 2012", 7 pgs.
"U.S. Appl. No. 13/070,110, Preliminary Amendment filed Jun. 6, 2011", 4 pgs.
"U.S. Appl. No. 13/070,110, Response filed Mar. 22, 2013 to Non Final Office Action mailed Dec. 21, 2012", 8 pgs.
"U.S. Appl. No. 13/070,110, Response filed May 27, 2016 to Non Final Office Action mailed Dec. 11, 2015", 13 pgs.
"U.S. Appl. No. 13/070,110, Response filed Sep. 3, 2014 to Restriction Requirement mailed Jul. 8, 2014", 7 pgs.
"U.S. Appl. No. 13/070,110, Response filed Oct. 2, 2015 to Final Office Action mailed Apr. 3, 2015", 11 pgs.
"U.S. Appl. No. 13/070,110, Response filed Nov. 12, 2013 to Final Office Action mailed Jun. 12, 2013", 9 pgs.
"U.S. Appl. No. 13/070,110, Response filed Dec. 30, 2014 to Non Final Office Action mailed Oct. 2, 2014", 13 pgs.
"U.S. Appl. No. 13/070,110, Restriction Requirement mailed Jul. 8, 2014", 7 pgs.
"U.S. Appl. No. 14/745,236, Response filed Dec. 23, 2016 to Restriction Requirement mailed Sep. 23, 2016", 8 pgs.
"U.S. Appl. No. 14/745,236, Restriction Requirement mailed Sep. 23, 2016", 8 pgs.
"U.S. Appl. No. 15/000,851, Preliminary Amendment filed Feb. 3, 2016", 3 pgs.
"U.S. Appl. No. 15/000,851, Response filed Oct. 12, 2016 to Restriction Requirement mailed May 12, 2016", 11 pgs.
"U.S. Appl. No. 15/000,851, Restriction Requirement mailed May 12, 2016", 6 pgs.
"U.S. Appl. No. 15/000,851, Supplemental Amendment filed Apr. 4, 2016", 10 pgs.
"Application Serial No. 200480021259.9 Office Action Sep. 11, 2009", 7 pgs.
"Application Serial No. 200480021259.9 Office Action Response Filed Aug. 20, 2010", 26 pgs.
"Application Serial No. 2006-533439 Office Action mailed Mar. 9, 2010", 20 pgs.
"U.S. Appl. No. 12/214,414, Response filed Oct. 14, 2014 to Non Final Office Action mailed Jun. 12, 2014", 16 pgs.
"Australian Application Serial No. 2001255336, Examiner's First Report mailed Feb. 16, 2005", 2 pgs.
"Australian Application Serial No. 2001255336, Response filed Aug. 23, 2005 to Examiner's First Report dated Feb. 16, 2005", 10 pgs.
"Australian Application Serial No. 2004249133, First Examiner's Report mailed May 5, 2008", ERTR, 8.
"Australian Application Serial No. 2004249133, Response filed Mar. 30, 2009 to First Examiner's Report mailed May 5, 2008", 30 pgs.
"Australian Application Serial No. 2007245192, Office Action mailed Aug. 25, 2011", 2 pgs.
"Australian Application Serial No. 2007245192, Response filed Feb. 28, 2012 to Office Action mailed Aug. 25, 2011", 22 pgs.
"Australian Application Serial No. 2012204138, First Examiner Report mailed Jul. 16, 2013", 4 pgs.
"Australian Application Serial No. 2012204138, Response filed Dec. 24, 2013 to First Examiner Report mailed Jul. 16, 2013", 21 pgs.
"Australian Application Serial No. 2014202470, First Examiner Report mailed Jul. 20, 2015", 2 pgs.
"Australian Application Serial No. 2014202470, Respojnse filed Jul. 4, 2016 to Subsequent Examiners Report mailed Feb. 1, 2016", 3 pgs.
"Australian Application Serial No. 2014202470, Response filed Jul. 20, 2016 to Subsequent Examiners Report mailed Jul. 19, 2016", 15 pgs.

(56) References Cited

OTHER PUBLICATIONS

"Australian Application Serial No. 2014202470, Response filed Dec. 1, 2015 to First Examiner Report mailed Jul. 20, 2015", 22 pgs.
"Australian Application Serial No. 2014202470, Subsequent Examiners Report mailed Feb. 1, 2016", 2 pgs.
"Australian Application Serial No. 2014202470, Subsequent Examiners Report mailed Jul. 19, 2016", 3 pgs.
"Brazilian Application Serial No. PI0410702-0, Office Action mailed Mar. 13, 2012", W/ English Translation, 4 pgs.
"Brazilian Application Serial No. PI0410702-0, Response filed May 7, 2012 to Office Action mailed Mar. 13, 2012", W/ English Claims, 11 pgs.
"Canadian Application Serial No. 2,406,180, Office Action mailed Sep. 9, 2008", 5 pgs.
"Canadian Application Serial No. 2,406,180, Office Action mailed Nov. 10, 2011", 3 pgs.
"Canadian Application Serial No. 2,406,180, Office action mailed Nov. 23, 2009", 3 pgs.
"Canadian Application Serial No. 2,406,180, Office Action mailed Dec. 10, 2010", 2 Pgs.
"Canadian Application Serial No. 2,406,180, Response filed Jan. 26, 2009 to Official Action mailed Sep. 9, 2008", 22 pgs.
"Canadian Application Serial No. 2,406,180, Response filed May 21, 2010 to Office action mailed Nov. 23, 2009", 13 pgs.
"Canadian Application Serial No. 2,406,180, Response filed Jun. 14, 2011 to Office Action mailed Dec. 10, 2010", 10 pgs.
"Canadian Application Serial No. 2,522,081, Amendment After Allowance filed Aug. 10, 2012", 3 pgs.
"Canadian Application Serial No. 2,522,081, Office Action filed Nov. 18, 2011", 11 pgs.
"Canadian Application Serial No. 2,522,081, Office Action mailed Jun. 6, 2011", 2 pgs.
"Canadian Application Serial No. 2,522,081, Office Action mailed Aug. 30, 2010", 2 pgs.
"Canadian Application Serial No. 2,522,081, Office Action mailed Oct. 8, 2009", 6 pgs.
"Canadian Application Serial No. 2,522,081, Response filed Feb. 28, 2011 to Office Action mailed Aug. 30, 2010", 10 pgs.
"Canadian Application Serial No. 2,522,081, Response filed Apr. 8, 2010 to Office Action dated Oct. 8, 2009", 30 pgs.
"Canadian Application Serial No. 2,522,081, Response filed Nov. 18, 2011 to Office Action mailed Jun. 6, 2011", 11 pgs.
"Canadian Application Serial No. 2,525,953, Office Action mailed Jan. 21, 2016", 6 pgs.
"Canadian Application Serial No. 2,525,953, Office Action mailed Jul. 31, 2012", 4 pgs.
"Canadian Application Serial No. 2,525,953, Office Action mailed Aug. 1, 2016", 6 pgs.
"Canadian Application Serial No. 2,525,953, Office Action mailed Aug. 16, 2013", 3 pgs.
"Canadian Application Serial No. 2,525,953, Office Action mailed Nov. 6, 2014", 3 pgs.
"Canadian Application Serial No. 2,525,953, Office Action Response filed Dec. 22, 2011", 17 pgs.
"Canadian Application Serial No. 2,525,953, Response filed Feb. 14, 2014 to Office Action mailed Aug. 16, 2013", 16 pgs.
"Canadian Application Serial No. 2,525,953, Response filed Jul. 11, 2016 to Office Action mailed Jan. 21, 2016", 21 pgs.
"Canadian Application Serial No. 2,647,985 , Office Action mailed May 15, 2013", 3 pgs.
"Canadian Application Serial No. 2,647,985 , Response filed Sep. 30, 2013 to Office Action mailed May 15, 2013".
"Canadian Application Serial No. 205962, Office Action received Jun. 22, 2011", 4 pgs.
"Canadian Application Serial No. 2406180, Response filed May 7, 2012 to Office Action mailed Nov. 10, 2011", 11 pgs.
"Canadian Application Serial No. 2525953, Office Action mailed Jun. 22, 2011", 4 pgs.
"Chinese Application Serial No. 200480017037, First Office Action dated May 25, 2007", (w/ English Translation), 10 pgs.
"Chinese Application Serial No. 200480017037, Response filed Oct. 30, 2007 to First Office Action dated May 25, 2007", (w/ English Translation of Claims), 26 pgs.
"Chinese Application Serial No. 200480017037.X, Response filed May 14, 2010 to Third Office Action mailed Mar. 1, 2010", (w/ English Translation of Claims), 16 pgs.
"Chinese Application Serial No. 200480017037.X, Response filed Aug. 4, 2009 to Second Office Action mailed Mar. 20, 2009", (w/ English Translation of Amended Claims), 15 pgs.
"Chinese Application Serial No. 200480017037.X, Second Office Action mailed Mar. 20, 2009", (English Translation), 7 pgs.
"Chinese Application Serial No. 200480017037.X, Third Office Action mailed Mar. 1, 2010", (w/ English Translation), 9 pgs.
"Chinese Application Serial No. 200480021259.9, First Offiice Action issued on Aug. 24, 2007", (w/ English Translation), 9 pgs.
"Chinese Application Serial No. 200480021259.9, Notice of Reexamination mailed Jul. 3, 2012", (w/ English Translation), 10 pgs.
"Chinese Application Serial No. 200480021259.9, Office Action mailed Jan. 11, 2011", (w/ English Translation), 15 pgs.
"Chinese Application Serial No. 200480021259.9, Office Action mailed May 6, 2010", (w/ English Translation), 12 pgs.
"Chinese Application Serial No. 200480021259.9, Office Action mailed Jul. 3, 2012", (w/ English Translation), 10 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Offiice Action issued on Aug. 24, 2007", (w/ English Translation of Claims), 13 pgs.
"Chinese Application Serial No. 200480021259.9, Response filed Oct. 16, 2012 to Office Action mailed Jul. 3, 2012", (w/ English Translation of Claims), 13 pgs.
"Chinese Application Serial No. 200780020095.1, Decision on Rejection mailed Jul. 22, 2013", (w/ English Translation), 11 pgs.
"Chinese Application Serial No. 200780020095.1, First Office Action mailed Jun. 24, 2011", (w/ English Translation), 13 pgs.
"Chinese Application Serial No. 200780020095.1, Office Action mailed Jan. 29, 2013", (w/ English Translation), 10 pgs.
"Chinese Application Serial No. 200780020095.1, Office Action mailed Mar. 5, 2015", (w/ English Translation), 12 pgs.
"Chinese Application Serial No. 200780020095.1, Office Action mailed Apr. 26, 2016", (w/ English Summary), 4 pgs.
"Chinese Application Serial No. 200780020095.1, Office Action mailed May 3, 2012", With English Translation, 10 pgs.
"Chinese Application Serial No. 200780020095.1, Office Action mailed Nov. 2, 2016", (w/ English Translation), 11 pgs.
"Chinese Application Serial No. 200780020095.1, Response filed Jun. 9, 2013 to Office Action mailed Jan. 29, 2013", (w/ English Translation of Claims), 10 pgs.
"Chinese Application Serial No. 200780020095.1, Response filed Jun. 23, 2015 to Office Action mailed Mar. 5, 2015", (w/ English Translation of Claims), 16 pgs.
"Chinese Application Serial No. 200780020095.1, Response filed Jun. 30, 2016 to Office Action mailed Apr. 26, 2016", W/ English Translation of Claims, 22 pgs.
"Chinese Application Serial No. 200780020095.1, Response filed Sep. 17, 2012 to Office Action mailed May 3, 2012", (w/ English Translation of Claims), 17 pgs.
"Chinese Application Serial No. 200780020095.1, Response filed Nov. 5, 2013 to to Decision on Rejection mailed Jul. 22, 2013", (w/ English Translation of Claims), 12 pgs.
"Chinese Application Serial No. 200780020095.1, Response filed Nov. 8, 2011 to Office Action mailed Jun. 24, 2011", (w/ English Translation of Amended Claims), 20 pgs.
"Chinese Application Serial No. 200480021259.9, Office Action mailed May 8, 2009", W/ English Translation, 3 pgs.
"Eurasian Application No. 200501890, Notice of Allowance mailed Jun. 23, 2009", 2 pgs.
"Eurasian Application Serial No. 200501890, Office Action mailed Mar. 23, 2007", W/ English Translation, 2 pgs.
"Eurasian Application Serial No. 200501890, Office Action mailed Dec. 17, 2007", W/ English Translation, 6 pgs.

(56) References Cited

OTHER PUBLICATIONS

"Eurasian Application Serial No. 200501890, Office Action mailed Sep. 4, 2008", W/ English Translation, 1 pg.
"Eurasian Application Serial No. 200501890, Response filed Mar. 26, 2008 to Office Action mailed Dec. 17, 2007", W/ English Claims, 15 pgs.
"Eurasian Application Serial No. 200501890, Response filed Jun. 14, 2007 to Office Action mailed Mar. 23, 2007", W/ English Claims, 11 pgs.
"Eurasian Application Serial No. 200501890, Response filed Dec. 17, 2008 to Office Action", W/ English Claims, 13 pgs.
"Eurasian Application Serial No. 200501890, Response filed Dec. 17, 2008 to Office Action mailed Sep. 4, 2008", W/ English Claims, 2 pgs.
"European Application 04750333.9, Communication dated Oct. 12, 2006", 6 pgs.
"European Application 04750333.9, Communication dated Dec. 8, 2006", 4 pgs.
"European Application 04750333.9, Communication dated Apr. 11, 2008", 6 pgs.
"European Application 04750333.9, Response filed Oct. 4, 2007 to Communication dated Dec. 8, 2006", 42 pgs.
"European Application 04750333.9, Response filed Nov. 21, 2006 to Communication Oct. 12, 2006", 4 pgs.
"European Application Serial No. 01928486.8 Office Action mailed Oct. 1, 2009", 2 pgs.
"European Application Serial No. 01928486.8, Communication dated Aug. 10, 2007", 3 pgs.
"European Application Serial No. 01928486.8, Communication dated Sep. 20, 2005", 4 pgs.
"European Application Serial No. 01928486.8, Office Action mailed Feb. 19, 2009", 3 pgs.
"European Application Serial No. 01928486.8, Response filed Aug. 28, 2009 to Communication mailed Feb. 19, 2009", 5 pgs.
"European Application Serial No. 01928486.8, Response filed Jan. 21, 2008 to Communication dated Aug. 10, 2007", 11 pgs.
"European Application Serial No. 01928486.8, Response filed Jan. 30, 2006 to Communication dated Sep. 20, 2005", 9 pgs.
"European Application Serial No. 01928486.8, Response filed Dec. 9, 2009 to Office Action mailed Oct. 1, 2009", 11 pgs.
"European Application Serial No. 04750333.9, Office Action mailed Jan. 22, 2009", 5 pgs.
"European Application Serial No. 04750333.9, Response filed Oct. 21, 2008 to Communication mailed Apr. 11, 2008", 15 pgs.
"European Application Serial No. 04750333.9, Response filed Nov. 17, 2009 to Communication mailed Jan. 22, 2009", 17 pgs.
"European Application Serial No. 04750333.9, Summons to Attend Oral Proceedings mailed Aug. 3, 2011", 13 pgs.
"European Application Serial No. 04776133.3, Communication mailed Mar. 30, 2006", 3 pgs.
"European Application Serial No. 04776133.3, EP Office Action mailed Jan. 5, 2010", 4.
"European Application Serial No. 04776133.3, Examination Notification Art. 94(3) mailed Jul. 28, 2015", 4 pgs.
"European Application Serial No. 04776133.3, Examination Notification Art. 94(3) mailed Nov. 25, 2013", 5 pgs.
"European Application Serial No. 04776133.3, Response filed Jan. 25, 2007 to Communication mailed Mar. 30, 2006", 20 pgs.
"European Application Serial No. 04776133.3, Response filed Apr. 30, 2014 to Examination Notification Art. 94(3) mailed Nov. 25, 2013", 12 pgs.
"European Application Serial No. 04776133.3, Response filed Sep. 18, 2015 to Examination Notification Art. 94(3) mailed Jul. 28, 2015", 47 pgs.
"European Application Serial No. 04776133.3, Response to Office Action filed Jul. 15, 2010", Response to Office Action, 9 pgs.
"European Application Serial No. 07754132.4, Office Action mailed Apr. 28, 2009", 4 pgs.
"European Application Serial No. 07754132.4, Office Action mailed Sep. 5, 2011", 5 pgs.
"European Application Serial No. 07754132.4, Office Action mailed Nov. 2, 2012", 4 pgs.
"European Application Serial No. 07754132.4, Response filed Feb. 5, 2010 to Office Action mailed Apr. 28, 2009", 15 pgs.
"European Application Serial No. 07754132.4, Response filed Mar. 15, 2012 to Office Action mailed Sep. 5, 2011", 21 pgs.
"European Application Serial No. 07754132.4, Response filed May 10, 2013 to Office Action mailed Nov. 2, 2012", 14 pgs.
"European Application Serial No. 07754132.4, Response filed Jun. 26, 2013", 8 pgs.
"Evaluation of Medicines for human Use", EMEA/CPMP/BWP/2289/01, London, The European Agency for the Evaluation of Medicinal Products, Committee for Proprietary Medicinal Products (CPMP), (Feb. 20, 2003), 14.
"Fluzone® Influenza Virus Vaccine", Sanofi Aventis Pasteur, Swiftwater, (Jul. 2005), 12 pgs.
"Indian Application Serial No. 02082/KOLNP/2005, Examination Report mailed Mar. 17, 2008", 1 pg.
"Indian Application Serial No. 02082/KOLNP/2005, Examination Report mailed Dec. 28, 2007", 1 pg.
"Indian Application Serial No. 02082/KOLNP/2005, First Examination Report mailed Jan. 25, 2007", 9 pgs.
"Indian Application Serial No. 02082/KOLNP/2005, Response filed Jan. 22, 2008 to Examination Report mailed Dec. 28, 2007", 13 pgs.
"Indian Application Serial No. 02082/KOLNP/2005, Response filed Jun. 10, 2008 to Examination Report mailed Mar. 17, 2008", 3 pgs.
"Indian Application Serial No. 02082/KOLNP/2005, Response filed Nov. 19, 2007 to First Examination Report mailed Jan. 25, 2007", 26 pgs.
"Indian Application Serial No. 1026/KOLNP/2009, First Examiner Report mailed Mar. 13, 2014", 2 pgs.
"Indian Application Serial No. 2272/KOLNP/2005, First Examination Report mailed Mar. 17, 2008", 10 pgs.
"Indian Application Serial No. 2272/KOLNP/2005, Response filed Mar. 16, 2009 to Subsequent Examination Report mailed Mar. 6, 2009", 12 pgs.
"Indian Application Serial No. 2272/KOLNP/2005, Response filed Oct. 11, 2008 to First Examination Report mailed Mar. 17, 2008", 27 pgs.
"Indian Application Serial No. 2272/KOLNP/2005, Subsequent Examination Report mailed Mar. 6, 2009", 1 pg.
"Influenza B/lee/40, neuraminidase & nb (seg 6) rna", Database EM_VI E.B.I. Hinxton U.K., (Jun. 13, 1985).
"International Application No. PCT/US2004/016680, International Search Report", (Feb. 2, 2005), 7 pgs.
"International Application Serial No. PCT/US01/11963, Amendment filed Sep. 9, 2002 to Written Opinion dated Aug. 7, 2002", 12 pgs.
"International Application Serial No. PCT/US01/11963, International Preliminary Examination Report mailed Oct. 15, 2002", 13 pgs.
"International Application Serial No. PCT/US01/11963, International Search Report mailed May 7, 2002", 5 pgs.
"International Application Serial No. PCT/US01/11963, Response filed Sep. 9, 2002 to Written Opinion mailed Aug. 7, 2002", 12 pgs.
"International Application Serial No. PCT/US01/11963, Written Opinion mailed Jun. 14, 2002", 2 pgs.
"International Application Serial No. PCT/US01/11963, Written Opinion mailed Aug. 7, 2002", 6 pgs.
"International Application Serial No. PCT/US2004/012050, International Search Report mailed Feb. 2, 2005", 8 pgs.
"International Application Serial No. PCT/US2004/012050, Written Opinion mailed Feb. 2, 2005", 12 pgs.
"International Application Serial No. PCT/US2004/016680, International Preliminary Report on Patentability mailed Dec. 15, 2005", 11 pgs.
"International Application Serial No. PCT/US2007/007562, International Preliminary Report on Patentability mailed Oct. 9, 2008", 5 pgs.
"International Application Serial No. PCT/US2007/007562, International Search Report mailed Jan. 14, 2008", 8 pgs.
"International Application Serial No. PCT/US2007/007562, Written Opinion mailed Jan. 14, 2008", 9 pgs.

(56) References Cited

OTHER PUBLICATIONS

"International Application Serial No. PCT/US2008/007582, International Preliminary Report on Patentability mailed Jan. 7, 2010", 9 pgs.
"International Application Serial No. PCT/US2008/007582, International Search Report and Written Opinion mailed Feb. 18, 2009", 16 pgs.
"International Application Serial No. PCT/US2015/036803, International Search Report mailed Dec. 11, 2015", 8 pgs.
"International Application Serial No. PCT/US2015/036803, Invitation to Pay Add'l Fees and Partial Search Rpt mailed Oct. 2, 2015", 8 pgs.
"International Application Serial No. PCT/US2015/036803, Written Opinion mailed Dec. 11, 2015", 8 pgs.
"International Application Serial No. PCT/US2016/041172, International Search Report mailed Oct. 27, 2016", 6 pgs.
"International Application Serial No. PCT/US2016/041172, Written Opinion mailed Oct. 27, 2016", 8 pgs.
"Israel Application Serial No. 171831, Notification of Defects mailed Nov. 10, 2008", (English Translation), 10 pgs.
"Israel Application Serial No. 171372, Office Action mailed Feb. 21, 2010", (Translation), 2 pgs.
"Israel Application Serial No. 171372, Office Action mailed Nov. 6, 2008", (Translation), 12 pgs.
"Israel Application Serial No. 171831, Office Action mailed Feb. 21, 2010", 2 pgs.
"Israel Application Serial No. 171831, Response filed Jan. 20, 2011 to Office Action mailed Feb. 21, 2010", 3 pgs.
"Israel Application Serial No. 171831, Response filed Jun. 24, 2009 to Notification of Defects mailed Nov. 10, 2008", (w/ English Translation of Claims), 10 pgs.
"Israel Application Serial No. 238584, Office Action mailed Apr. 14, 2016", 3 pgs.
"Israel Application Serial No. 238584, Response filed Aug. 3, 2016 to Office Action mailed Apr. 14, 2016", (English Translation of Claims), 19 pgs.
"Israel Application Serial No. 171372,Office Action mailed Feb. 20, 2011", (Translation), 2 pgs.
"Israeli Application Serial No. 171372, Response filed Nov. 18, 2010 to Office Action mailed Feb. 21, 2010", (Translation), 19 pgs.
"Israeli Application Serial No. 171831, Office Action mailed Apr. 18, 2012", (English Translation), 2 pgs.
"Israeli Application Serial No. 171831, Response filed Nov. 6, 2012 to Office Action mailed Apr. 18, 2012", (w/ English Translation of Amended Claims), 54 pgs.
"Japanese Application No. 2001-576868, Office Action mailed May 31, 2011", (w/ English Translation), 5 pgs.
"Japanese Application No. 2001-576868, Response filed Apr. 26, 2011 to Office Action mailed Nov. 2, 2010", (w/ Translation of Amended Claims), 14 pgs.
"Japanese Application Serial No. 2001-576868, Office Action mailed Nov. 2, 2010", w/ English Translation), 10 pgs.
"Japanese Application Serial No. 2001-576868, Response filed Dec. 1, 2011 to Office Action mailed May 3, 2011", (w/ English Translation of Amended Claims), 37 pgs.
"Japanese Application Serial No. 2006-513125, Office Action mailed Mar. 9, 2010", (English Translation), 11 pgs.
"Japanese Application Serial No. 2006-513125, Response filed Aug. 30, 2010 to Office Action mailed Apr. 9, 2010", (w/ English Translation of Amended Claims), 60 pgs.
"Japanese Application Serial No. 2006-533439, Decision of Final Rejection mailed Aug. 14, 2012", (w/ English Translation), 5 pgs.
"Japanese Application Serial No. 2006-533439, Office Action mailed Mar. 27, 2012", w/ English Translation, 8 pgs.
"Japanese Application Serial No. 2006-533439, Response filed May 21, 2012 to Office Action mailed Mar. 27, 2012", (w/ English Translation of Amended Claims), 19 pgs.
"Japanese Application Serial No. 2006-533439, Response filed Aug. 3, 2011 to Office Action mailed Feb. 15, 2011", (w/ English Translation of Amended Claims), 18 pgs.
"Japanese Application Serial No. 2006-533439,Office Action mailed Feb. 15, 2011", (w/ English Translation), 13 pgs.
"Japanese Application Serial No. 2009-502945, Examiners Decision of Final Refusal mailed Nov. 12, 2013", (w/ English Translation), 8 pgs.
"Japanese Application Serial No. 2009-502945, Office Action mailed Oct. 23, 2012", (w/ English Translation), 16 pgs.
"Japanese Application Serial No. 2009-502945, Response filed Apr. 10, 2013 to Office Action mailed Oct. 23, 2012", (w/ English Translation of Claims), 18 pgs.
"Japanese Application Serial No. 2011-111048, Office Action mailed Jun. 25, 2013", (w/ English Translation), 7 pgs.
"Japanese Application Serial No. 2011-111048, Office Action mailed Sep. 18, 2012", (w/ English Translation), 10 pga.
"Japanese Application Serial No. 2011-111048, Response filed Sep. 25, 2012 to Office Action mailed Jun. 25, 2013", (w/ English Translation of Amended Claims), 18 pgs.
"Japanese Application Serial No. 2011-111048. Response filed Mar. 15, 2013", (w/ Translation of Amended Claims), 14 pgs.
"Japanese Application Serial No. 2012-273898, Office Action mailed Jun. 10, 2014", (w/ English Translation), 7 pgs.
"Japanese Application Serial No. 2012-273898, Response filed Sep. 4, 2014 to Office Action mailed Jun. 10, 2014", W/ English Claims, 9 pgs.
"Japanese Application Serial No. 2013-198377, Office Action mailed Jan. 6, 2015", (w/ English Translation), 9 pgs.
"Japanese Application Serial No. 2014-049025 Response filed Sep. 4, 2015 to Office Action mailed Jun. 16, 2015", (w/ Amended Claims), 12 pgs.
"Japanese Application Serial No. 2014-049025, Examiners Decision of Final Refusal mailed Feb. 2, 2016", W/ English Translation, 5 pgs.
"Japanese Application Serial No. 2014-049025, Office Action mailed Jun. 16, 2015", (w/ English Translation), 6 pgs.
"Japanese Application Serial No. 2006-513125, Final Office Action mailed Jan. 18, 2011", (English Translation), 4 pgs.
"Korean Application Serial No. 10-2005-7020077, Response filed Apr. 28, 2008 to Examination Report mailed Dec. 28, 2007", (w/ English Translation of Revised Claims), 41 pgs.
"Korean Application Serial No. 10-2005-7020077, Examination Report mailed Dec. 28, 2007", (w/ English Translation), 8 pgs.
"Korean Application Serial No. 10-2005-7020077, Notice of Preliminary Rejection mailed Jun. 28, 2007", (w/ EnglishTranslation), 9 pgs.
"Korean Application Serial. No. 10-2005-7020077, Response filed Aug. 28, 2007 to Notice of Preliminary Rejection mailed Jun. 28, 2007", (w/ EnglishTranslation), 40 pgs.
"Korean Application Serial No. 10-2005-7022564, Notice of Preliminary Rejection dated Jul. 25, 2007", W/ English Translation, 5 pgs.
"Korean Application Serial No. 10-2005-7022564, Office Action mailed Aug. 6, 2008", W/ English Translation, 4 pgs.
"Korean Application Serial No. 10-2005-7022564, Response and Amendment filed Dec. 29, 2008 to Office Action mailed Aug. 6, 2008", W/ English Translation, 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action mailed Aug. 6, 2008", (w/ English Translation of Claims), 16 pgs.
"Maxican Application Serial No. MX/a/2012/009249, Office Action mailed May 19, 2015", W/ English Translation, 1 pg.
"Mexican Application No. PA/a/2005/012712 Office Action—mailed Jul. 21, 2009", W/ English Translation, 9 pgs.
"Mexican Application Serial No. MX/a/2009/006341—Office Action", 2 pgs.
"Mexican Application Serial No. MX/a/2009/006341, Response filed Jun. 4, 2012", 12 pgs.
"Mexican Application Serial No. MX/a/2012/009249 Response filed Sep. 10, 2015 to Office Action mailed May 19, 2015", (w/ English Translation of Claims), 21 pgs.

(56) References Cited

OTHER PUBLICATIONS

"Mexican Application Serial No. MX/a/2012/009249, Office Action mailed Feb. 5, 2016", W/ English Claims, 2 pgs.
"Mexican Application Serial No. MX/a/2012/009249, Response filed Mar. 29, 2016 to Office Action mailed Feb. 5, 2016", (English Translation of Claims), 19 pgs.
"Mexican Application Serial No. PA/a/2005/011250, Office Action mailed Aug. 23, 2010", W/ English Translation, 4 pgs.
"Mexican Application Serial No. PA/a/2005/011250, Response Filed Dec. 20, 2010 to Office Action mailed Aug. 23, 2010", W/ English Claims, 14 pgs.
"Mexican Application Serial No. PA/a/2005/012712 ,Office Action Mailed Aug. 11, 2009", (English Translation), 5 pgs.
"Mexican Application Serial No. PA/a/2005/012712, Office Action mailed Jun. 9, 2010", W/ English Translation, 11 pgs.
"Mexican Application Serial No. PA/a/2005/012712, Office Action mailed Nov. 30, 2009", (w/ English Translation), 14 pgs.
"Mexican Application Serial No. PA/a/2005/012712, Office Action mailed May 12, 2010", (w/ English Translation), 19 pgs.
"Mexican Application Serial No. PA/a/2005/012712, Response filed Sep. 27, 2010", (w/ English Translation of Claims), 19 pgs.
"Mexico Application Serial No. PA/a/2005/012712, Official Action mailed Mar. 5, 2009", W/ English Translation, 2 pgs.
"New Zealand Application Serial No. 542935, Examination Report dated Feb. 25, 2008", 2 pgs.
"New Zealand Application Serial No. 542935, Examination Report mailed Jun. 14, 2006", 2 pgs.
"New Zealand Application Serial No. 542935, Response filed Jun. 30, 2008 to Examination Report dated Feb. 25, 2008", 32 pgs.
"New Zealand Application Serial No. 542935, Response filed Aug. 7, 2007 to Examination Report dated Jun. 14, 2006", 18 pgs.
"New Zealand Application Serial No. 542935, Voluntary Amendments filed Sep. 12, 2007", 10 pgs.
"New Zealand Application Serial No. 543446, Examination Report mailed Feb. 29, 2008", 2 pgs.
"New Zealand Application Serial No. 543446, Examination Report mailed May 2, 2008", ERTR-1, 2.
"New Zealand Application Serial No. 543446, Response mailed Mar. 20, 2008 to Examination Report mailed Feb. 29, 2008", 2 pgs.
"RecName: Full=Polymerase acidic protein {ECO:0000256|RuleBase;RU361280, ECO:0000256|SAAS:SAAS00262764}", XP002744257, retrieved from EBI accession No. UNIPROT:A3R6C9 Database accession No. A3R6C9 the whole document, (Apr. 3, 2007), 1 pgs.
"RecName: Full=Polymerase acidic protein {ECO:0000256|RuleBase;RU361280, ECO:0000256|SAAS:SAAS00262764}", XP002744258, retrieved from EBI accession No. UNIPROT:U3S198 Database accession No. U3S198 the whole document, (Dec. 11, 2013), 1 pg.
"Russian Federation Application No. 2005136233, Office Action mailed Dec. 25, 2007", 2 pgs.
"Russian Federation Application No. 2005136233, Response filed May 29, 2008 to Office Action mailed Dec. 25, 2007", (w/ Partial English Translation), 7 pgs.
"Russian Federation Application Serial No. 2005136233, First Office Action mailed Feb. 27, 2007", (w/ English Translation), 5 pgs.
"Russian Federation Application Serial No. 2005136233, Response filed Jun. 14, 2007 to First Office Action mailed Feb. 27, 2007", (English Translation of Claims), 6 pgs.
"Russian Federation Application Serial No. 2005136233, Response filed Nov. 20, 2007 to Office Action", (w/ English Translation of Amended Claims), 18 pgs.
"Singapore Application Serial No. 200506858-0, Examination Report mailed Feb. 9, 2007", 4 pgs.
"Singapore Application Serial No. 200506858-0, Response filed Dec. 22, 2006 to Written Opinion mailed Jul. 26, 2006", 18 pgs.
"Singapore Application Serial No. 200506858-0, Written Opinion mailed Jul. 26, 2006", 8 pgs.
"Singapore Application Serial No. 200507468-7, Examination Report mailed Mar. 19, 2008", 5 pgs.
"Singapore Application Serial No. 200507468-7, Invitation to Respond to Written Opinion mailed Jun. 12, 2007", 6 pgs.
"Singapore Application Serial No. 200507468-7, Response filed Nov. 7, 2007 to Invitation to Respond to Written Opinion mailed Jun. 12, 2007", 9 pgs.
"The Influenza Virus: Structure and Replication", Rapid Reference to Influenza. Elsevier Ltd, [Online]. Retrieved from the Internet: http://www. rapidreferenceinfluenza.com/chapter/B978-0-7234-3433-7.50009-8/aim/influenza-virus-structure, (2006).
"The Integral Membrane Proteins of Influenza A, B, and C Viruses", The Influenza Sequence Database, http://www.flu.lanl.gov/review/fluc.review2.html, (Observed Feb. 26, 2003), 1 pg.
"Ukraine Application Serial No. 200512619, Office Action mailed Feb. 27, 2009", W/ English Translation, 21 pgs.
"Ukraine Application Serial No. 200512619, Response filed Apr. 8, 2009 to Office Action mailed Feb. 27, 2009", W/ English Claims, 9 pgs.
"Ukrainese Application Serial No. 200512619, Office Action mailed Jun. 17, 2009", W/ No Translation, 3 pgs.
"Ukrainese Application Serial No. 200512619, Response filed Jan. 21, 2010 to Office Action mailed Jun. 17, 2009", W/ English Claims, 14 pgs.
Air, Gillian M., et al., "Antigenic, Sequence, and Crystal Variation in Influenza B Neuraminidase", Virology vol. 177,, (1990), 578-587.
Air, Gillian M., et al., "Antigenic, Sequence, and Crystal Variation in Influenza B Neuraminidase", Virology, 177(2), (1990), 578-587.
Author Unknown, "New Approaches to Influenza Vaccine", Medscape—Infections in Medicine, http://www.medscape.com/viewarticle/417404_3, (Observed Feb. 26, 1003), 4 pgs.
Avetisyan, G, et al., "Cell-mediated immune responses to influenza vaccination in healthy volunteers and allogeneic stem cell transplant recipients", Bone Marrow Transplant, (2005), 411-415.
Avilov, Sergiy V., et al., "Influenza A virus progeny vRNP trafficking in live infected cells studied with the virus-encoded fluorescently tagged PB2 protein", Vaccine, 30, (2012), 7411-7417.
Avilov, Sergiy V., et al., "Replication-Competent Influenza A Virus That Encodes a Split-Green Fluorescent Protein-Tagged PB2 Polymerase Subunit Allows", Journal of Virology, 86, (2012), 1433-1448.
Baez, M., et al., "Complete nucleotide sequence of the influenza A/PR/8/34 virus NS gene and comparison with the NS genes of the A/Udorn/72 and A/FPV/Rostock/34 strains", Nucleic Acids Research, 23(8), (1980), 5845-5858.
Bancroft, C. T, et al., "Evidence for segment-nonspecific packaging of the influenza a virus genome", J Virol., 76(14), (Jul. 2002), 7133-9.
Banerjee, A. K., et al., "Gene Expression of Vesicular Stomatitis Virus Genome RNA.", Virology, 188(2), (1992), 417-428.
Baron, M. D., et al., "Rescue of Rinderpest Virus From Cloned cDNA", Journal of Virology, 71(2), (1997), 1265-1271.
Basler, C. F, et al., "Mutation of Neuraminidase Cysteine Residues Yields Temprature-Sensitive Influenza Viruses", Journal of Virology, 73(10), (Jun. 30, 1999), 8095-8103.
Beare, A. S., "Trials in Man With Live Recombinants Made From A/PR/8/34 (H0 N1) and Wild H3 N2 Influenza Viruses", The Lancet, 2(7938), (1975), 729-732.
Betakova, T., et al., "The NB protein is an integral component of the membrane of influenza B virus.", J Gen Virol., 77 ( Pt 11), (Nov. 1996), 2689-94.
Bourmakina, S. V, et al., "Reverse genetics studies on the Filamentous morphology of influenza A Virus", Journal of General Virology (2003) 84,, (2003), 517-527.
Bowie, J. U., et al., "Deciphering the Message in Protein Sequences: Tolerance to Amino Acid Substitutions", Science, 247(4948), (1990), 1306-1310.
Boyer, J. C., et al., "Infectious transcripts and cDNA clones of RNA viruses", Virology, 198(2), (Feb. 1994), 415-426.
Brassard, D.L., et al., "Influenza B virus NB glycoprotein is a component of the virion", Virol., 220(2), No Document, (1996), 350-360.

(56) References Cited

OTHER PUBLICATIONS

Bridgen, A., "Rescue of a Segmented Negative-Strand RNA Virus Entirely From Cloned Complementary DNAs", Proc. Natl. Acad. Sci. USA, 93, (1996), 15400-15404.

Brooke, C B, "Biological activities of 'noninfectious' influenza A virus particles", Future Virol 9(1), (Jan. 2014), 41-51.

Buchholz, U. J., et al., "Generation of Bovine Respiratory Syncytial Virus (BRSV) From cDNA: BRSV NS2 is Not Essentiial for Virus Replication in Tissue Culture, and the Human RSV Leader Region Acts as a Functional BRSV Genome Promoter", Journal of Virology, 73(1), (1999), 251-259.

Bukreyev, A., et al., "Recovery of infectious respiratory syncytial virus expressing an additional, foreign gene", Journal of Virology, 70(10), (Oct. 1996), 6634-6641.

Castrucci, Maria R., et al., "Reverse genetics system for generation of an influenza A virus mutant containing a deletion of the carboxyl-terminal residue of M2 protein.", J Virol., 69(5), (May 1995), 2725-8.

Chen, H, et al., "Generation and evaluation of a high-growth reassortant H9N2 influenza A virus as a pandemic vaccine candidate", Vaccine, 21(17-18), (May 16, 2003), 1974-9.

Chen, Z., et al., "Influenza A Virus NS1 Protein Targets Poly(A)-Binding Protein II of the Cellular 3'-End Processing Machinery", The EMBO Journal, 18(8), (1999), 2273-2283.

Chevalie, Christophe, et al., "PB1-F2 Influenza A Virus Protein Adopts a B-Sheet Conformation and Forms Amyloid Fibers in Membrane Environments", The of Biological Chemistry, 285(17), (2010), 13233-13243.

Clarke, D. K., et al., "Rescue of Mumps Virus From cDNA", Journal of Virology, 74(10), (2000), 4831-4838.

Collins, P. L., et al., "Chapter 41—Parainfluenza Viruses", In: Fields Virology, edited by Fields, B. N., et al. (3rd Edition, 1996, Lippincott-Raven Publishers, Philadelphia, PA, 1205-1241.

Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad. Sci. USA, 92, (1995), 11563-11567.

Collins, P. L., "Rescue of Synthetic Analogs of Respiratory Syncytial Virus Genomic RNA and Effect of Truncations and Mutations on the Expression of a Foreign Reporter Gene", Proc. Natl. Acad. Sci. USA, 88, (1991), 9663-9667.

Conzelmann, K.-K., "Genetic Engineering of Animal RNA Viruses", Trends in Microbiology, 4(10), (1996), 386-393.

Conzelmann, K.-K., "Genetic manipulation of non-segmented negative-strand RNA viruses", Journal of General Virology, 77(Pt. 3), (Mar. 1996), 381-389.

Conzelmann, K.-K., "Nonsegmented Negative-Strand RNA Viruses: Genetics and Manipulation of Viral Genomes", Annu. Rev. Genet., 32, (1998), 123-162.

Conzelmann, K.-K., "Rescue of Synthetic Genomic RNA Analogs of Rabies Virus by Plasmid-Encoded Proteins", Journal of Virology, 68(2), (1994), 713-719.

De, B. P., et al., "Requirements and Functions of Vesicular Stomatitis Virus L and NS Proteins in the Transcription Process in Vitro", Biochemical and Biophysical Research Communications, 126(1), (1985), 40-49.

De, B. P., et al., "Rescue of synthetic analogs of genome RNA of human parainfluenza virus type 3", Virology, 196(1), (Sep. 1993), 344-348.

De, B. P., et al., "Reverse Genetics of Negative Strand RNA Viruses", Indian Journal of Biochemistry & Biophysics, 31, (1994), 367-375.

De Filette, Marina, et al., "An influenza A vaccine based on tetrameric ectodomain of matrix protein 2", J Biol Chem. 2008 ; 283 (17):, (Feb. 5, 2008), 11382-7.

De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.

De La Luna, S., et al., "Influenza Virus NS1 Protein Enhances the Rate of Translation Initiation of Viral mRNAs", Journal of Virology, 69(4), (1995), 2427-2435.

Desheva, J. A, et al., "Characterization of an influenza A H5N2 reassortant as a candidate for live-attenuated and inactivated vaccines against highly pathogenic H5N1 viruses with pandemic potential", Vaccine, (2006), 6859-6866.

Dimmock, Nigel J, et al., "In vivo antiviral activity: defective interfering virus protects better against virulent Influenza A virus than avirulent virus", Journal of General Virology 87, (Jan. 8, 2006), 1259-1265.

Dimock, K., et al., "Rescue of Synthetic Analogs of Genomic RNA and Replicative-Intermediate RNA of Human Parainfluenza Virus Type 3", Journal of Virology, 67(5), (1993), 2772-2778.

Dos Santos Afonso, Emmanuel, et al., "The generation of recombinant influenza A viruses expressing a PB2 fusion protein requires the conservation of a packaging signal overlapping the coding and noncoding regions at the 5V end of the PB2 segment", Virology, 341, (2005), 34-46.

Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.

Duff, K. C., et al., "The secondary structure of influenza A M2 transmembrane domain", FEBS Letters, 311 (3), (Oct. 1992), pp. 256-258.

Duff, K. C., et al., "The Transmembrane Domain of Influenza A M2 Protein Forms Amantadine-Sensitive Proton Channels in Planar Lipid Bilayers", Vilology, 190(1), (Sep. 1992), pp. 485-489.

Dunn, E. F., et al., "Transcription of a recombinant bunyavirus RNA template by transiently expressed bunyavirus proteins", Virology, 211(1), (1995), 133-143.

Durbin, A. P., et al., "Recovery of infectious human parainfluenza virus type 3 from cDNA", Virology, 235(2), (Sep. 1, 1997), 323-332.

Elliott, R. M., et al., "Rescue of Infectious Bunyavirus Entirely From Cloned cDNA", 10th International Conference on Negative Strand Virus, (Abstract No. 96), (1997), 1 pg.

Elliott, R. M., et al., "Some Highlights of Virus Research in 1990", Journal of General Virology, 72(Part 8), (1991), 1761-1779.

Emerson, S. U., et al., "Both NS And L Proteins Are Required for In Vitro RNA Synthesis by Vesicular Stomatitis Virus", Journal of Virology, 15(6), (1975), 1348-1356.

Enami, M., "An Influenza Virus Containing Nine Different RNA Segments", Virology, 185(1), (1991), 291-298.

Enami, M., et al., "High-Efficiency Formation of Influenza Virus Transfectants", Journal of Virology, 65(5), (1991), 2711-2713.

Enami, M., et al., "Introduction of Site-Specific Mutations Into the Genome of Influenza Virus", Proc. Natl. Acad. Sci. USA, 87, (1990), 3802-3805.

Fahey, J. L., "Status of Immune-Based Therapies in HIV Infection and Aids", Clinincal and Experimental Immunology, 88(1), (1992), 1-5.

Fan, J, et al., "Preclinical study of influenza virus A M2 peptide conjugate vaccines in mice, ferrets, and rhesus monkeys", Vaccine, 22, (2004), 2993-3003.

Fischer, W. B, et al., "Viral ion channels: structure and function.", Biochim Biophys Acta., 1561(1), (Mar. 19, 2002), 27-45.

Fleming, D. M, et al., "Comparison of the efficacy and safety of live attenuated cold-adapted influenza vaccine, trivalent, with trivalent inactivated influenza virus vaccine in children and adolescents with asthma", Pediatr Infect Dis J., 25(10), (2006), 860-869.

Fodor, E., et al., "Rescue of Influenza A Virus from Recombinant DNA", Journal of Virology, 73(11), XP002151487; ISSN:0022-538X, (Nov. 1999), 9679-9682.

Fortes, P., et al., "Influenza Virus NS1 Protein Inhibits Pre-mRNA Splicing and Blocks mRNA Nucleocytoplasmic Transport", The EMBO Journal, 13(3), (1994), 704-712.

(56) References Cited

OTHER PUBLICATIONS

Fujii, Ken, et al., "Importance of both the Coding and the Segment-Speci?c Noncoding Regions of the In?uenza A Virus NS Segment for Its Ef?cient", Journal of Virology, 79(6), (Mar. 2005), 3766-3774.

Gao, Qinshan, et al., "A Nine-Segment In?uenza A Virus Carrying Subtype H1 and H3 Hemagglutinins†", Journal of Virology, 84(16), (Aug. 2010), 8062-8071.

Gao, Qinshan, et al., "The In?uenza A Virus PB2, PA, NP, and M Segments Play a Pivotal Role during Genome Packaging", Journal of Virology, 86(13), Chou, (Jul. 2011), 043-7051.

Garcia-Sastre, A., et al., "Genetic Manipulation of Negative-Strand RNA Virus Genomes", Annu. Rev. Microbiol., 47, (1993), 765-790.

Garcin, D., et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.

Giddings, A M, et al., "The matrix protein of HIV-1 is not sufficient for assembly and release of virus-like particles", Virology, 248(1), (1998), 108-16.

Gotea, V, et al., "The functional relevance of somatic synonymous mutations in melanoma and other cancers", Pigment Cell & Melanoma Research, 28 issue 6, (Nov. 1, 2015), 673-686.

Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.

Grambas, S., et al., "Influence of amantadine resistance mutations on the pH regulatory function of the M2 protein of influenza A viruses", Virology, 191(2), (Dec. 1992), 541-549.

Grosfeld, H., et al., "RNA Replication by Respiratory Syncytial Virus (RSV) Is Directed by the N, P, and L Proteins; Transcription Also Occurs Under These Conditions but Requires RSV Superinfection for Efficient Synthesis of Full-Length mRNA", Journal of Virology, 69(9), (1995), 5677-5686.

Hai, Rong, et al., "Influenza B Virus NS1-Truncated Mutants: Live-Attenuated Vaccine Approach", Journal of Virology, 82(21), (2008), 10580-10590.

Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73 (4), (1999), 2921-2929.

Hatada, E., et al., "Binding of Influenza A Virus NS1 Protein to dsRNA in vitro", Journal of General Virology, 73, (1992), 3325-3329.

Hatta, M., et al., "The NB protein of influenza B virus is not necessary for virus replication in vitro", Journal of Virology, 77(10), (May 2003), 6050-6054.

Hay, A. J., et al., "The role of the M2 protein in influenza A virus infection", Proceedings of the International Conference on Options for the Control of Influenza, Courchevel, (1992), 281-288.

He, B., et al., "Recovery of infectious SV5 from cloned DNA and expression of a foreign gene", Virology, 237(2), (1997), 249-260.

Helenius, A., "Unpacking the Incoming Influenza Virus", Cell, 69, (May 1992), pp. 577-578.

Hevey, Michael, et al., "Marburg virus vaccines based upon alphavirus replicons protect guinea pigs and nonhuman primates", Virology, 251(1), (Nov. 10, 1998), 28-37.

Hiromoto, Y., et al., "Phylogenetic Analysis of the Three Polymerase Genes (PB1, PB2 and PA) of Influenza B Virus", Journal of General Virology, 81, (Apr. 2000), 929-937.

Hoffman, M. A., et al., "An Infectious Clone of Human Parainfluenza Virus Type 3", Journal of Virology, 71(6), (1997), 4272-4277.

Hoffmann, E., et al., "A DNA transfection system for generation of influenza A virus from eight plasmids", Proc Natl Acad Sci U S A., 97(11), (May 23, 2000), 6108-13.

Hoffmann, E., et al., "Ambisense Approach for the Generation of Influenza A Virus: vRNA and mRNA Synthesis from One Template", Virology, 267, (2000), 310-317.

Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.

Hoffmann, E., et al., "Rescue of Influenza B Virus from Eight Plasmids", Proceedings of the National Academy of Sciences of USA, National Academy of Science, 99(17), (Aug. 20, 2002), 11411-11416.

Holmes, E. C, et al., "Whole-Genome Analysis of Human Influenza A Virus Reveals Multiple Persistent Lineages and Reassortment Among Recent H3N2 Viruses", PLoS Biology, 3(9), (2005), 1579-1589.

Holsinger, L. J., et al., "Influenza A Virus M2 Ion Channel Protein: a Structure-Function Analysis", Journal of Virology, 68 (3), (1994), pp. 1551-1563.

Honda, Ayae, et al., "Differential Roles of Viral RNA and cRNA in Functional Modulation of the Influenza Virus RNA Polymerase", The Journal of Biological Chemistry, 276(33), (2001), 31179-31185.

Horimoto, T., et al., "Enhanced growth of seed viruses for H5N1 influenza vaccines", Virology, 366(1), (Sep. 15, 2007), 23-27.

Horimoto, T., et al., "Generation of Influenza A Viruses with Chimeric (Type A/B) Hemagglutinins", Journal of Virology, 77(14), (2003), 8031-8038.

Horimoto, T., et al., "The Development and Characterization of H5 Influenza Virus Vaccines Derived from a 2003 Human Isolate", Vaccine, 24(17), (2006), 3669-3676.

Huang, T.-S., et al., "Determination of Influenza Virus Proteins Required for Genome Replication", Journal of Virology, 64(11), (1990), 5669-5673.

Hunt, R., "Virology—Chapter Eight—Vaccines: Past Successes and Future Prospects", Microbiology and Immunology On-Line, http://www.med.sc.edu:85/lecture/vaccines.htm, (Observed Feb. 26, 2003), 15 pgs.

Isakova-Sivak, Irina, et al., "Characterization of Reverse Genetics-Derived Cold-Adapted Master Donor Virus A/Leningrad/134/17/57 (H2N2) and Reassortants with H5N1 Surface Genes in a Mouse Model", Clinical and Vaccine Immunology, 21(5), (May 2014), 722-731.

Ives, J. A., et al., "The H274Y mutation in the influenza A/H1N1 neuraminidase active site following oseltamivir phosphate treatment leave virus severely compromised both in vitro and in vivo.", Antiviral Research, 55(2), (2002), 307-317.

Iwatsuki-Horimoto, K., et al., "The cytoplasmic tail of the influenza A virus M2 protein plays a role in viral assembly.", J Virol., 80(11), (Jun. 2006), 5233-40.

Jackson, D., et al., "A reverse genetics approach for recovery of recombinant influenza B viruses entirely from cDNA.", J Virol., 76(22), (Nov. 2002), 11744-7.

Jasenosky, Luke D, et al., "Ebola Virus VP40-Induced Particle Formation and Association with the Lipid Bilayer", Journal of Virology, 75 (110, (Jun. 2001), 5205-5214.

Kaplan, G., et al., "In vitro Synthesis of Infectious Poliovirus RNA", Proc. Natl. Acad. Sci. USA, 82, (1985), 8824-8428.

Katinger, D., et al., "Attenuated Influenza Viruses as a Vector for Mucosal Immunization Against HIV-1", Vaccines, 97, Cold Spring Harbor, (1997), 315-319.

Kato, A., et al., "Initiation of Sendai Virus Multiplication From Transfected cDNA or RNA With Negative or Positive Sense", Genes to Cells, 1, (1996), 569-579.

Kawaoka, Y, et al., "Sequence requirements for cleavage activation of influenza virus hemagglutinin expressed in mammalian cells", Proc Natl Acad Sci., 85(2), (1988), 324-328.

Kawaoka, Y., "Mutant Cells With Altered Sialic Acid", U.S. Appl. No. 11/644,179, filed Dec. 22, 2006, 51 pgs.

Kimura, N., et al., "An In Vivo Study of the Replication Origin in the Influenza Virus Complementary RNA", The Journal of Biochemistry, 113(1), (1993), 88-92.

Kimura, N., et al., "Transcription of a Recombinant Influenza Virus RNA in Cells That Can Express the Influenza Virus RNA Polymerase and Nucleoprotein Genes", Journal of General Virology, 73, (1992), 1321-1328.

(56) References Cited

OTHER PUBLICATIONS

Kiseleva, et al., "Role of individual genes of the A-Leningrad/134/17/57 (H2N2) cold-adapted donor strain in manifestation of the temperature-sensitive phenotype of reassortant influenza A viruses", International Congress Series, vol. 1263, (2004), 547-550.
Kittel, Christian, et al., "Generation of an In?uenza A Virus Vector Expressing Biologically Active Human Interleukin-2 from the NS Gene Segment", Journal of Virology, 79(16), (Aug. 2005), 10672-10677.
Kobayashi, M., et al., "Reconstitution of Influenza Virus RNA Polymerase From Three Subunits Expressed Using Recombinant Baculovirus System", Virus Research, 22, (1992), 235-245.
Kochendoerfer, G. G, et al., "Total Chemical Synthesis of the Integral Membrane Protein Influenza A Virus M2: Role of its C-Terminal Domain in Tetramer Assembly", Biochemistry 38, (1999), 11905-11913.
Konarska, M. M., et al., "Structure of RNAs Replicated by the DNA-Dependent T7 RNA Polymerase", Cell, 63(2), (1990), 609-618.
Krystal, M., et al., "Expression of the Three Influenza Virus Polymerase Proteins in a Single Cell Allows Growth Complementation of Viral Mutants", Proc. Natl. Acad. Sci. USA, 83, (1986), 2709-2713.
Krystal, M., "Influenza B/Lee/40, hemagglutinin (seg 4), complete segment.", Database EM_VI E.B.I. Hinxton U.K., (Apr. 25, 1990).
Kunkel, T. A., "Rapid and Efficient Site-Specific Mutagenesis Without Phenotypic Selection", Proc. Natl. Acad. Sci. USA, 82, (1985), 488-492.
Lamb, Robert A., et al., "Chapter 20—Paramyxoviridae: The Viruses and Their Replication", In: Fundamental Virology, Fields, B. N., et al., editors, Lippincott-Raven (2nd Edition), (1996), 577-647.
Lawson, N. D., "Recombinant Vesicular Stomatitis Viruses From DNA", Proc. Natl. Acad. Sci. USA, 92(10), (1995), 4477-4481.
Lazarovits, et al., "Endocytosis of Chimeric Influenza Virus Hemaggulutinin Proteins That Lack a Cytoplasmic Recognition Feature for Coated Pits", The Journal of Cell Biology, vol. 134, No. 2, (1996), 339-348.
Lee, C. W, et al., "Generation of reassortant influenza vaccines by reverse genetics that allows utilization of a DIVA (Differentiating Infected from Vaccinated Animals) strategy for the control of avian influenza", Vaccine, vol. 22, (2004), 3175-3181.
Lee, Dong-Hun, et al., "Progress and hurdles in development of influenza virus-like particle vaccines for veterinary use", Korean Vaccine Society, (2014), 133-139.
Levis, R., et al., "Deletion Mapping of Sindbis Virus DI RNAs Derived From cDNAs Defines the Sequences Essential for Replication and Packaging", Cell, 44, (1986), 137-145.
Li, Y, et al., "Viral liposomes released from insect cells infected with recombinant baculovirus expressing the matrix protein of vesicular stomatitis virus", Journal of Virology, 67 (7), (1993), 4415-4420.
Liu, Bo, et al., "[Comparison of three methods in construction fusion gene of influenza A virus Nucleoprotein].", (English Abstract), Zhonghua Shi Yan He Lin Chuang Bing Du Xue Za Zhi, 26(1), 70-74, (Feb. 2012), 1 pg.
Lu, Xiuhua, et al., "Cross-protective immunity in mice induced by live-attenuated or inactivated vaccines against highly pathogenic influenza A (H5N1) viruses", Vaccine, 24(44-46), (2006), 6588-6593.
Luo, M., "Inhibitors of Influenza Virus Neuraminidase", Abstract No. WO296, from a paper presented at the Annual Meeting of the American Crystallographic Association, http://www.hwi.buffalo.edu/ACA/ACA98/abstracts/text/WO296.html, (Observed Feb. 27, 2003), 1 pg.
Luytjes, W., "Amplification, Expression, and Packaging of a Foreign Gene by Influenza Virus", Cell, 59(6), (1989), 1107-1113.
Manicassamy, Balaji, et al., "Analysis of in vivo dynamics of influenza virus infection in mice using a GFP reporter virus", Proc Natl Acad Sci. USA, 107(25), (2010), 11531-11536.
Manz, Benjamin, et al., "Disruption of the Viral Polymerase Complex Assembly as a Novel Approach to Attenuate Influenza A Virus", The Journal of Biological Chemistry, 286(10), (2011), 8414-8424.
Mark, A, et al., "Effect of Mutations and Deletions in a Bicistronic mRNA on the Synthesis of Influenza B Virus NB and NA Glycoproteins", Journal of Virology, vol. 77, No. 10, (May 2003), 6050-6054.
Matsuoka, et al., "Neuraminidase Stalk Length and Additional Glycosylation of the Hemagglutinin Influence the Virulence of Influenza H5N1 Viruses for Mice", Journal of Virology, vol. 83, No. 9 (2009), pp. 4704-4708.
McCown, M F, et al., "The influenza A virus M2 cytoplasmic tail is required for infectious virus production and efficient genome packaging.", J Virol., 79(6), (Mar. 2005), 3595-605.
McCown, M. F, et al., "Distinct domains of the influenza a virus M2 protein cytoplasmic tail mediate binding to the M1 protein and facilitate infectious virus production.", J Virol., 80(16), (Aug. 2006), 8178-89.
McKimm, J. L., et al., "Mutations in a Conserved Residue in the Influenza Virus Neuraminidase Active Site Decreases Sensitivity to Neu5Ac2en-Derived Inhibitors", Journal of Virology, 72(3), (1998), 2456-2462.
Mebatsion, Teshome, et al., "Budding of Rabies Virus Particles in the Absence of the Spike Glycoprotein", Cell, 84(6), (1996), 941-951.
Mebatsion, Teshome, et al., "Matrix Protein of Rabies Virus Is Responsible for the Assembly and Budding of Bullet-Shaped Particles and Interacts with the Transmembrane Spike Glycoprotein G", Journal of Virology, 73 (1), (Jan. 1999), 242/250.
Mena, I., "Rescue of a Synthetic Choramphenicol Acetyltransferase RNA into influenza Virus-Like Particles obtained from recombinant plasmids", Journal of Virology, 70(8), (1996), 5016-5024.
Mena, I., et al., "Synthesis of Biologically Active Influenza Virus Core Proteins Using a Vaccinia Virus-T7 RNA Polymerase Expression System", Journal of General Virology, 75, (1994), 2109-2114.
Mitnaul, et al., "The Cytoplasmic Tail of Influenza a Virus Neuraminidase (NA) Affects NA Incorporation into Virons, Viron Morphology, and Virulence in Mice but is not essential for Virus Replication", Journal of Virology, 70 (2), (1996), 873-879.
Monto, Arnold S, et al., "Comparative efficacy of inactivated and live attenuated influenza vaccines.", N Engl J Med., 361(13), (Sep. 24, 2009), 1260-7.
Moyer, S. A., et al., "Assembly and Transcription of Synthetic Vesicular Stomatitis Virus Nucleocapsids", Journal of Virology, 65(5), (1991), 2170-2178.
Murphy, Brian R, et al., "Virulence of Avian Influenza A Viruses for Squirrel Monkeys", Infection and Immunity 37 (3), (Sep. 1982), 1119-1126.
Muster, T., et al., "An Influenza A Virus Containing Influenza B Virus 5' and 3' Noncoding Regions on the Neuraminidase Gene is Attenuated in Mice", Proc. Natl. Acad. Sci. USA, 88, (1991), 5177-5181.
Naito, S., et al., "Function and Structure of RNA Polymerase From Vesicular Stomatitis Virus", The Journal of Biological Chemistry, 251(14), (1976), 4307-4314.
Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.
Neirynck, S., "A universal influenza A vaccine based on the extracellular domain of the M2 protein", Nature Medicine, 5 (10), (Oct. 1999), pp. 1157-1163.
Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.
Neumann, G., et al., "Generation of influenza A virus from cloned cDNAs—historical perspective and outlook for the new millenium.", Rev Med Virol., 12(1), XP002314285, (Jan.-Feb. 2002), 13-30.
Neumann, G., et al., "Generation of influenza A viruses entirely from cloned cDNAs", Proc. Natl. Acad. Sci. USA., 96(16), (1999), 9345-9350.

(56) References Cited

OTHER PUBLICATIONS

Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan. 2000), 547-551.

Neumann, G., et al., "RNA Polymerase I-Mediated Expression of Influenza Viral RNA Molecules", Virology, 202(1), (1994), 477-479.

Neumann, Gabriele, et al., "Reverse Genetics Demonstrates that Proteolytic Processing of the Ebola Virus Glycoprotein Is Not Essential for Replication in Cell Culture", Journal of Virology, 76 (1), (Jan. 2002), 406-410.

Noda, Takeshi, et al., "Three-dimensional analysis of ribonucleoprotein complexes in influenza A virus", Nature Communications, 3, (2012), 1-6.

Odagiri, T., et al., "Nucleotide Sequence of the PA Gene of Influenza A/WSN/33 (H1N1)", Nucleic Acids Research, 18 (3), Department of Virology, (Jan. 9, 1990).

Orkin, S. H, et al., "Report and Recommendations of the Panel to Assess the NIH Investment in Research on Gene Therapy", http://www.nih.gov/news/panelrep.html, (Dec. 7, 1995), 37 pgs.

Palese, P., et al., "47. Orthomyxoviridae: The Viruses and Their Replication", In: Fields Virology (5th Edition), (2007), 90 pgs.

Palese, P., "Negative-Strand RNA Viruses: Genetic Engineering and Applications", Proc. Natl. Acad. Sci. USA, 93(21), (1996), 11354-11358.

Park, Eun K., et al., "The M2 Ectodomain is important for its incorporation into influenza A virions", J. of Virology, vol. 72, No. 3, XP002196797, (Mar. 1998), 2449-2455.

Park, K. H., et al., "Rescue of a Foreign Gene by Sendai Virus", Proc. Natl. Acad. Sci. USA, 88, (1991), 5537-5541.

Pattnaik, A. K., et al., "Cells That Express All Five Proteins of Vesicular Stomatitis Virus From Cloned cDNAs Support Replication, Assembly, and Budding of Defective Interfering Particles", Proc. Natl. Acad. Sci. USA, 88(4), (1991), 1379-1383.

Peeters, B. P. H., et al., "Rescue of Newcastle Disease Virus From Cloned cDNA: Evidence That Cleavability of the Fusion Protein Is a Major Determinant for Virulence", Journal of Virology, 73(6), (1999), 5001-5009.

Pekosz, A., "Commentary—Reverse Genetics of Negative-Strand RNA Viruses: Closing the Circle", Proc. Natl. Acad. Sci. USA, 96, (1999), 8804-8806.

Pekosz, A., et al., "Influenza C virus CM2 integral membrane glycoprotein is produced from a polypeptide precursor by cleavage of an internal signal sequence", PNAS, vol. 95, XP002196653, (Oct. 1998), 13233-13238.

Percy, N., et al., "Expression of a Foreign Protein by Influenza A Virus", Journal of Virology, 68(7), (1994), 4486-4492.

Perez, Jasmine T., et al., "Unit 15G.4—Insertion of a GFP Reporter Gene in Influenza Virus", Curr Protoc Microbiol., (2013), 20 pgs.

Piller, S C., et al., "Vpr protein of human immunodeficiency virus type 1 forms cation-selective channels in planar lipid bilayers", PNAS, 93, (1996), 111-1115.

Ping, J, et al., "Development of high-yield influenza A virus vaccine viruses", Nature Communications, Retrieved from the Internet: <http://www.nature.com/article-assets/npg/ncomms/2015/150902/ncomms9148/extref/ncomms9148-s1.pdf>, (Sep. 2, 2015), 8148 pgs.

Pinto, L. H., et al., "Influenza Virus M2 Protein Has Ion Channel Activity", Cell, 69, (May 1992), pp. 517-528.

Plant, E P, et al., "Mutations to A/PuertoRico/8/34 PB1 gene improves seasonal reassortant influenza A virus growth kinetics", Vaccine, vol. 31, No. 1, (Dec. 1, 2012), 207-212 pgs.

Pleschka, S., et al., "A Plasmid-Based Reverse Genetics System for Influenza A Virus", Journal of Virology, 70(6), (1996), 4188-4192.

Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.

Qiu, Y., et al., "The Influenza Virus NS1 Protein Is a Poly(A)-Binding Protein That Inhibits Nuclear Export of mRNAs Containing Poly(A)", Journal of Virology, 68(4), (1994), 2425-2432.

Racaniello, V. R., et al., "Cloned Poliovirus Complimentary DNA Is Infectious in Mammalian Cells", Science, 214, (1981).

Radecke, F., et al., "Rescue of Measles Viruses From Cloned DNA", The EMBO Journal, 14(23), (1995), 5773-5784.

Radecke, F., et al., "Reverse Genetics Meets the Nonsegmented Negative-Strand RNA Viruses", Reviews in Medical Virology, 7, (1997), 49-63.

Roberts, A., et al., "Minireview—Recovery of Negative-Strand RNA Viruses From Plasmid DNAs: A Positive Approach Revitalizes a Negative Field", Virology, 247(1), (1998), 1-6.

Rose, J. K., "Positive Strands to the Rescue Again: A Segmented Negative-Strand RNA Virus Derived From Cloned cDNAs", Proc. Natl. Acad. Sci. USA, 94, (1996), 14998-15000.

Ruigrok, R W, et al., "Characterization of three highly purified influenza virus strains by electron microscopy", J Gen Virol 65 (Pt 4), (Apr. 1984), 799-802.

Ruigrok, R W, et al., "Structural Characterization and Membrane Binding Properties of the Matrix Protein VP40 of Ebola Virus", Journal of Molecular Biology, 300(1), (2000), 103-112.

Sansom, M. S., et al., "Influenza virus M2 Protein: a molecular modelling study of the ion channel", Protein Engineering, 6 (1), (1993), pp. 65-74.

Schickli, J. H, et al., "Plasmid-only Rescue of Influenza A Virus Vaccine Candidates", Philosophical Transactions of the Royal Society of London. Series B, Biological Sciences, 356(1416), (Dec. 29, 2001), 1965-1973.

Schlesinger, S., "RNA Viruses as Vectors for the Expression of Heterologous Proteins", Molecular Biotechnology, 3(2), (1995), 155-165.

Schnell, M. J., "Infectious Rabies Viruses From Cloned cDNA", The EMBO Journal, 13(18), (1994), 4195-4203.

Schnell, Matthias J, et al., "Requirement for a non-specific glycoprotein cytoplasmic domain sequence to drive efficient budding of vesicular stomatitis virus", EMBO Journal, 17 (5), (1998), 1289-1296.

Schotsaert, M, et al., "Universal M2 ectodomain-based influenza A vaccines: preclinical and clinical developments", Expert Rev Vaccines. Apr. 2009;8(4):, 499-508.

Seong, B. L., et al., "A New Method for Reconstituting Influenza Polymerase and RNA in Vitro: A Study of the Promoter Elements for cRNA and vRNA Synthesis in Vitro and Viral Rescue in Vivo", Virology, 186(1), (1992), 247-260.

Shinya, Kyoko, et al., "Characterization of a Neuraminidase-Deficient Influenza A Virus as a Potential Gene Delivery Vector and a Live Vaccine", Journal of Virology, 78(6), (2004), 3083-3088.

Sidhu, M. S., et al., "Rescue of Synthetic Measles Virus Minireplicons: Measles Genomic Termini Direct Efficient Expression and Propagation of a Reporter Gene", Virology, 208, (1995), 800-807.

Skehel, J. J., et al., "On the Mechanism of Inhibition of Influenza Virus Replication by Amantadine Hydrochloride", The Journal of General Virology, 38 (1), (1977), pp. 97-110.

Smeenk, et al., "Mutations in the Hemagglutinin and Matrix Genes of a Virulent Influenza Virus Variant, A/FM/1/47-MA, Control Different Stages in Pathogenesis", Virus Research 44, (1996), 79-95.

Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen", Journal of Virology, 69(10), (1995), 5969-5977.

Subbarao, K., et al., "Evaluation of a Genetically Modified Reassortant H5N1 Influenza A Virus Vaccine Candidate Generated by Plasmid-based Reverse Genetics", Virology, vol. 305(1), (Jan. 5, 2003), 192-200.

Sugrue, R. J., et al., "Specific structural alteration of the influenza haemagglutinin by amantadine", The EMBO Journal, 9 (11), (1990), pp. 3469-3476.

(56) References Cited

OTHER PUBLICATIONS

Sugrue, R. J., et al., "Structural Characteristics of the M2 Protein of Influenza A Viruses: Evidence That It Forms a Tetrameric Channel", Virology, 180, (1991), pp. 617-624.

Suguitan, A. L, et al., "Live, Attenuated Influenza A H5N1 Candidate Vaccines Provide Broad Cross-Protection in Mice and Ferrets", PLoS Med., 3(9), (2006), 1541-1555.

Sunstrom, N. A., et al., "Ion Channels formed by NB, an influenza B virus Protein", J. of Membrane Biology, vol. 150, XP002196654, (Dec. 1996), 127-132.

Sweet, T. M., et al., "Creation of amantadine resistant clones of influenza type A virus using a new transfection procedure.", J Virol Methods., 69(1-2), (Dec. 1997), 103-11.

Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.

Takeda, M., et al., "Influenza a virus M2 ion channel activity is essential for efficient replication in tissue culture.", J Virol., 76(3), (Feb. 2002), 1391-9.

Takeuchi, K., et al., "Influenza Virus M2 Protein Ion Channel Activity Stabilizes the Native Form of Fowl Plague Virus Hemagglutinin during Intracellular Transport", Journal of Virology, 68 (2), (Feb. 1994), pp. 911-919.

Tannock, G. A, et al., "Relative immunogenicity of the cold-adapted influenza virus A/AnnArbor/6/60 (A/AA/6/60-ca), recombinants of A/AA/6/60-ca, and parental strains with similar surface antigens.", Infect Immun., 43(2), (Feb. 1984), 457-62.

Taylor, J., et al., "Newcastle Disease Virus Fusion Protein Expressed in a Fowlpox Virus Recombinant Confers Protection in Chickens", Journal of Virology, 64(4), (1990), 1441-1450.

Tobler, K, "Effect of cytoplasmic tail truncations on the activity of the M(2) ion channel of influenza A virus", J Virol., (1999), 9695-701.

Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.

Verma, I. M, et al., "Gene Therapy—Promises, Problems and Prospects", Nature, 389, (Sep. 18, 1997), 239-242.

Voeten, J. T, et al., "Characterization of high-growth reassortant influenza A viruses generated in MDCK cells cultured in serum-free medium", Vaccine, vol. 17, (1999), 1942-1950.

Volchkov, Viktor E, et al., "Recovery of Infectious Ebola Virus from Complementary DNA: RNA Editing of the GP Gene and Viral Cytotoxicity", Science Magazine, 291, (Mar. 2001), 1965-1969.

Wagner, R., et al., "Interdependence of hemagglutinin glycosylation and neuraminidase as regulators of influenza virus growth: a study by reverse genetics", Journal of Virology, 74 (14), (Jul. 2000), 6316-6323.

Wang, C., et al., "Ion Channel Activity of Influenza A Virus M2 Protein: Characterization of the Amantadine Block", Journal of Virology, 67 (9), (Sep. 1993), pp. 5585-5594.

Wang, Wenlig, et al., "Robust Immunity and Heterologous Protection against Influenza in Mice Elicited by a Novel Recombinant NP-M2e Fusion Protein Expressed in E. coli", PLoS ONE 7(12): e52488, (Dec. 2012), 1-13.

Ward, C. D., et al., "Direct Measurement of the Poliovirus RNA Polymerase Error Frequency In Vitro", Journal of Virology, 62(2), (1988), 558-562.

Wareing, M. D, et al., "Immunogenic and isotype-specific responses to Russian and US cold-adapted influenza a vaccine donor strains A/Leningrad/134/17/57, A/Leningrad/134/47/57, and A/Ann Arbor/6/60 (H2N2) in mice.", J Med Virol., 65(1), (Sep. 2001), 171-7.

Watanabe, et al."", Journal of Virology 82, (2008), 2486-2492.

Watanabe, et al."", Journal of Virology 75, (2001), 5656-5662.

Watanabe, S., et al., "Influenza A Virus Lacking M2 Protein as a Live Attenuated Vaccine", Journal of Virology, 83(11), (2009), 5947-5950.

Watanabe, T., et al., "Influenza A virus can undergo multiple cycles of replication without M2 ion channel activity", J Virol., 75(12), (Jun. 2001), 5656-62.

Watanabe, T., et al., "Influenza A Virus with Defective M2 Ion Channel Activity as a Live Vaccine", Virology, 299(2), (Aug. 1, 2002), 266-270.

Watanabe, Tokiko, et al., "Exploitation of Nucleic Acid Packaging Signals to Generate a Novel In?uenza Virus-Based Vector Stably Expressing Two Foreign Genes", Journal of Virology, 77(19), (Oct. 2003), 10575-10583.

Wei, Hung-Ju, et al., "Fabrication of influenza virus-like particles using M2 fusion proteins for imaging single viruses and designing vaccines", Vaccine, 29, (2011), 7163-7172.

Whelan, S. P. J., et al., "Efficient Recovery of Infectious Vesicular Stomatitis Virus Entirely from cDNA Clones", Proc. Natl. Acad. Sci. USA, 92, (1995), 8388-8392.

Williams, Mark A., et al., "Effect of Mutations and Deletions in a Bicistronic mRNA on the Synthesis of Influenza B Virus NB and NA Glycoproteins", Journal of Virology, 63(1), (1989), 28-35.

Wilson, Julie A, et al., "Epitopes Involved in Antibody-Mediated Protection from Ebola Virus", Science, 287, (Mar. 2000), 1664-1666.

Winter, G., et al., "The use of synthetic oligodeoxynucleotide primers in cloning and sequencing segment 8 of influenza virus (A/PR/8/34)", Nucleic Acids Res., 9(2), (1981), 237-245.

Wu, Rui, et al., "A live bivalent influenza vaccine based on a H9N2 virus strain", Vaccine, 28, (2010), 673-680.

Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.

Yannarell, et al., "Factors affecting the yield of cold-adapted influenza virus vaccine", Journal of Virological Methods, vol. 64, (1997), 161-169.

Yu, Q., et al., "Functional cDNA Clones of the Human Respiratory Syncytial (RS) Virus N, P, and L Proteins Support Replication of RS Virus Genomic RNA Analogs and Define Minimal trans-Acting Requirements for RNA Replication", Journal of Virology, 69(4), (1995), 2412-2419.

Yusoff, K., et al., "Nucleotide Sequence Analysis of the L Gene of Newcastle Disease Virus: Homologies With Sendai and Vesicular Stomatitis Viruses", Nucleic Acids Research, 15(10), (1987), 3961-3976.

Zaghouani, H, et al., "Induction of Antibodies to the Envelope Protein of the Human Immunodeficiency Virus by Immunization With Monoclonal Anti-Idiotypes", Proc. Natl. Acad. Sci. USA, 88, (1991), 5645-5649.

Zaghouani, H., et al., "Cells Expressing an H Chain 1g Gene Carrying a Viral T Cell Epitope are Lysed by Specific Cytolytic T Cells", The Journal of Immunology, 148(11), (1992), 3604-3609.

Zebedee, S. L, et al., "Characterization of the Influenza Virus M2 Integral Membrane Protein and Expression at the Infected-Cell Surface from Cloned cDNA", Journal of Virology, 56(2), (Nov. 1985), 502-511.

Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.

Zobel, A., et al., "RNA Polymerase I Catalysed Transcription of Insert Viral cDNA", Nucleic Acids Research, 21(16), (1993), 3607-3614.

"International Application Serial No. PCT/US2017/018443, International Search Report dated May 22, 2017", 9 pgs.

"International Application Serial No. PCT/US2017/018443, Written Opinion dated May 22, 2017", 9 pgs.

Cao, S., et al., "Characterization of the Nucleocytoplasmic Shuttle of the Matrix Protein of Influenza B Virus", *Journal of Virology.*, 88(13), (Jul. 2014), 7464-7473.

Kim, H., et al., "Cold adaptation generates mutations associated with the growth of influenza B vaccine viruses", *Vaccine*, 33(43), (2015), 5786-5793.

(56) References Cited

OTHER PUBLICATIONS

Ping, J., et al., "Development of high-yield influenza B virus vaccine viruses", *Proc. Natl. Acad. Sci. USA*, 113(51), (2016), E8296-E8305, and 25 pgs of Supplemental Material.
GenBank ABL77178.1, (2006).
GenBank AAO15329.1, (2003).
GenBank ABL7718 6 .1, (2006).
GenBank AAT69443.1, (2006).
"U.S. Appl. No. 13/070,110 Response filed Feb. 14, 2017 to Final Office Action dated Sep. 14, 2016", 8 pgs.
"U.S. Appl. No. 13/070,110, Advisory Action dated Mar. 3, 2017", 5 pgs.
"U.S. Appl. No. 13/070,110, Response filed Feb. 14, 2017 to Final Office Action dated Sep. 14, 2016", 8 pgs.
"U.S. Appl. No. 14/745,236, Non Final Office Action dated Feb. 2, 2017", 14 pgs.
"U.S. Appl. No. 14/745,236, Response filed May 2, 2017 to Non Final Office Action dated Feb. 2, 2017", 10 pgs.
"U.S. Appl. No. 15/000,851, Non Final Office Action dated Jan. 26, 2017", 15 pgs.
"U.S. Appl. No. 15/436,245, Preliminary Amendment filed May 5, 2017", 3 pgs.
"Canadian Application Serial No. 2,525,953, Response filed Feb. 1, 2017 to Office Action dated Aug. 1, 2016", 28 pgs.
"European Application Serial No. 10777154.5, Office Action dated May 2, 2016", 6 pgs.
"European Application Serial No. 10777154.5, Response filed Sep. 8, 2016 to Office Action dated May 2, 2016", 69 pgs.
"GenBank ABL77187", (2006).
"Japanese Application Serial No. 2012-536963, Amendment and Argument filed Jun. 26, 2015 to Office Action dated Jan. 6, 2015", (w/ English Translation of Amended Claims), 12 pgs.
"Japanese Application Serial No. 2012-536963, Examiners Decision of Final Refusal dated Nov. 17, 2015", (w/ English Translation), 8 pgs.
"Norway Application Serial No. 20056074, Office Action dated Jan. 17, 2017", (English Translation), 5 pgs.
"Norway Application Serial No. 20056074, Office Action dated Apr. 25, 2017", (w English Translation), 3 pgs.
"Norway Application Serial No. 20056074, Office Action Response dated Apr. 1817", W/ English Claims, 27 Pgs.
"Polymerase PB2 [Influenza B virus (B/Hong Kong/330/2001)] GenBank ABL77188.1", (2006), 1 pg.

Chan, Winnie, et al., "The cold adapted and temperature sensitive influenza A/Ann Arbor/6/60 virus, the master donor virus for live attenuated influenza vaccines, has multiple defects in replication at the restrictive temperature", Virology, 380(2), (2008), 304-311.
Hickman, Danielle, et al., "An avian live attenuated master backbone for potential use in epidemic and pandemic influenza vaccines", Journal of General Virology, 89(Part 11), (2008), 2682-2690.
Kiseleva, Irina V, et al., "PB2 and PA genes control the expression of the temperature-sensitive phenotype of cold-adapted B/USSR/60/69 influenza master donor virus", Journal of General Virology, 91(4), (2010), 931-937.
Kovacova, Andrea, et al., "Sequence Similarities and Evolutionary Relationships of Influenza Vrus A Hemagglutinins", Virus Genes, 24(1), (2002), 57-63.
Lee, Jong-Soo, et al., "The Highly Conserved HA2 Protein of the Influenza A Virus Induces a Cross Protective Immune Response", Journal of Virological Methods, 194(1-2), (2013), 280-288.
Li, et al., "Genesis of a highly pathogenic and potentially pandemic H5N1 influenza virus in eastern Asia", (2004), 209-213 pgs.
Lugovtsev, V. Y., et al., "Genetic Composition and Mutational Pattern of Influenza B Viruses Adapted to Replication in Embryonated Eggs", GenBank: AAT69446.1, (2005), 1 pg.
"U.S. Appl. No. 13/070,110, Non Final Office Action dated Jul. 21, 2017", 14 pgs.
"U.S. Appl. No. 13/070,110, Response filed Jun. 20, 2017 to Advisory Action dated Mar. 3, 2017", 13 pgs.
"U.S. Appl. No. 14/745,236, Final Office Action dated Aug. 25, 2017", 16 pgs.
"U.S. Appl. No. 15/000,851, Response filed Jul. 26, 2017 to Non Final Office Action dated Jan. 26, 2017", 16 pgs.
"U.S. Appl. No. 15/203,581, Response filed Aug. 15, 2017 to Restriction Requirement dated Jun. 16, 2017", 8 pgs.
"U.S. Appl. No. 15/203,581, Restriction Requirement dated Jun. 16, 2017", 8 pgs.
"U.S. Appl. No. 15/593,039, Preliminary Amendment filed Jul. 25, 2017", 7 pgs.
"U.S. Appl. No. 15/593,039, Supplemental Preliminary Amendment filed Jul. 26, 2017", 4 pgs.
"Israel Application Serial No. 238584, Office Action dated Jul. 24, 2017", 2 pgs.
"Japanese Application Serial No. 2016-110879, Office Action dated May 30, 2017", (w/ English Translation), 7 pgs.
"Norway Application Serial No. 20056074, Response filed Jul. 25, 2017 to Office Action dated Apr. 25, 2017", (w/ English Translation of Amended Claims), 111 pgs.

FIG. 1

PB2                    PR8(Cambridge)

```
AGCGAAAGCAGGTCAATTATATTCAATATGGAAAGAATAAAAGAACTAAGAAATCTAATGTCGCAGTCTCGCACCCGCGAGATA
CTCACAAAAACCACCGTGGACCATATGGCCATAATCAAGAAGTACACATCAGGAAGACAGGAGAAGAACCCAGCACTTAGGATG
AAATGGATGATGGCAATGAAATATCCAATTACAGCAGACAAGAGGATAACGGAAATGATTCCTGAGAGAAATGAGCAAGGACAA
ACTTTTATGGAGTAAAATGAATGATGCCGGATCAGACCGAGTGATGGTATCACCTCTGGCTGTGACATGGTGGAATAGGAATGGA
CCAATGACAAATACAGTTCATTATCCAAAAATCTACAAAACTTATTTTGAAAGAGTCGAAAGGCTAAAGCATGGAACCTTTGGC
CCTGTCCATTTTAGAAACCAAGTCAAAATACGTCGGAGAGTTGACATAAATCCTGGTCATGCAGATCTCAGTGCCAAGGAGGCA
CAGGATGTAATCATGGAAGTTGTTTTCCCTAACGAAGTGGGAGCCAGATACTAACATCGGAATCGCAACTAACGATAACCAAA
GAGAAGAAAGAAGAACTCCAGGATTGCAAAATTTCTCCTTTGATGGTTGCATACATGTTGGAGAGAGAACTGGTCCGCAAAACG
AGATTCCTCCCAGTGGCTGGTGGACAAGCAGTGTGTACATTGAAGTGTTGCATTTGACTCAAGGAACATGCTGGGAACAGATG
TATACTCCAGGAGGGGAAGTGAAGAATGATGATGTTGATCAAAGCTTGATTATTGCTGCTAGGAACATAGTGAGAAGAGCTGCA
GTATCAGCAGACCCACTAGCATCTTTATTGGAGATGTGCCACAGCACACAGATTGGTGGAATTAGGATGGTAGACATCCTTAAG
CAGAACCCAACAGAAGAGCAAGCCGTGGATATATGCAAGGCTGCAATGGGACTGAGAATTAGCTCATCCTTCAGTTTTGGTGGA
TTCACATTTAAGAGAACAAGCGGATCATCAGTCAAGAGAGAGGAAGAGGTGCTTACGGGCAATCTTCAAACATTGAAGATAAGA
GTGCATGAGGGATCTGAAGAGTTCACAATGGTTGGGAGAAGAGCAACAGCCATACTCAGAAAAGCAACCAGGAGATTGATTCAG
CTGATAGTGAGTGGGAGAGACGAACAGTCGATTGCCGAAGCAATAATTGTGGCCATGGTATTTTCACAAGAGGATTGTATGATA
AAAGCAGTTAGAGGTGATCTGAATTTCGTCAATAGGGCGAATCAGCGACTGAATCCTATGCATCAACTTTTAAGACATTTTCAG
AAGGATGCGAAAGTGCTTTTTCAAAATTGGGGAGTTGAACCTATCGACAATGTGATGGAATGATTGGGATATTGCCCGACATG
ACTCCAAGCATCGAGATGTCAATGAGAGGAGTGAGAATCAGCAAAATGGGTGTAGATGAGTACTCCAGCACGGAGAGGGTAGTG
GTGAGCATTGACCGGTTCTTGAGAGTCAGGGACCAACGAGGAAATGTACTACTGTCTCCCGAGGAGGTCAGTGAAACACAGGGA
ACAGAGAAACTGACAATAACTTACTCATCGTCAATGATGTGGGAGATTAATGGTCCTGAATCAGTGTTGGTCAATACCTATCGA
TGGATCATCAGAAACTGGGAAACTGTTAAAATTCAGTGGTCCCAGAACCCTACAATGCTATACAATAAAATGGAATTTGAACCA
TTTCAGTCTTTAGTACCTAAGGCCATTAGAGGCCAATACAGTGGGTTTGTAAGAACTCTGTTCCAACAAATGAGGGATGTGCTT
GGGACATTTGATACCGCACAGATAATAAAACTTCTTCCCTTCGCAGCCGCTCCACCAAAGCAAAGTAGAATGCAGTTCTCCTCA
TTTACTGTGAATGTGAGGGGATCAGGAATGAGAATACTTGTAAGGGGCAATTCTCCTGTATTCAACTACAACAAGGCCACGAAG
AGACTCACAGTTCTCGGGAAAGGATGCTGGCACTTTAACCGAAGACCCAGATGAAGGCACAGCTGGAGTGGAGTCCGCTGTCTG
AGGGGATTCCTCATTCTGGGCAAAGAAGACAGGAGATATGGGCCAGCATTAAGCATCAATGAACTGAGCAACCTTGCGAAAGGA
GAGAAGGCTAATGTGCTAATTGGGCAAGGAGACGTGGTGTTGGTAATGAAACGAAAACGGGACTCTAGCATACTTACTGACAGC
CAGACAGCGACCAAAAGAATTCGGATGGCCATCAATTAGTGTCGAATAGTTTAAAAACGACCTTGTTTCTACT
```

(SEQ ID NO: 1)

PB1

```
AGCGAAAGCAGGCAAACCATTTGAATGGATGTCAATCCGACCTTACTTTTCTTAAAAGTGCCAGCACAAAATGCTATAAGCACA
ACTTTCCCTTATACCGGAGACCCTCCTTACAGCCATGGGACAGGAACAGGATACACCATGGATACTGTCAACAGGACACATCAG
TACTCAGAAAAGGGAAGATGGACAACAAACACCGAAACTGGAGCACCGCAACTCAACCCGATTGATGGGCCACTGCCAGAAGAC
AATGAACCAAGTGGTTATGCCCAAACAGATTGTGTATTGGAAGCAATGGCTTTCCTTGAGGAATCCCATCCTGGTATTTTTGAA
AACTCGTGTATTGAAACGATGGAGGTTGTTCAGCAAACACGAGTGGACAAGCTGACACAAGGCCGACAGACCTATGACTGGACT
TTAAATAGAAACCAGCCTGCTGCAACAGCATTGGCCAACACAATAGAAGTGTTCAGATCAAATGGCCTCACGGCCAATGAGTCA
GGAAGGCTCATAGACTTCCTTAAGGATGTAATGGAGTCAATGAAAAAAGAAGAAATGGGGATCACAACTCATTTTCAGAGAAAG
AGACGGGTGAGAGACAATATGACTAAGAAAATGATAACACAGAGAACAATAGGTAAAAGGAAACAGAGATTGAACAAAAGGGGT
TATCTAATTAGAGCATTGACCCTGAACAATAGACCAAAGATGCTGAGAGAGGAAGCTAAAACGGAGAGCAATTGCAACCCCA
GGGATGCAAATAAGGGGGTTTGTATACTTTGTTGAGACACTGGCAAGGAGTATATGTGAGAAACTTGAACAATCAGGGTTGCCA
GTTGGAGGCAATGAGAAGAAACAAAGTTGGCAAATGTTGTAAGGAAGATGATGACCAATTCTCAGGACACCGAACTTTCTTTC
ACCATCACTGGAGATAACACCAAATGGAACGAAAATCAGAATCCTCGGATGTTTTTGGCCATGATCACATATATGACCAGAAAT
CAGCCCGAATGGTTCAGAAATGTTCTAAGTATTGCTCCAATAATGTTCTCAAACAAAATGGCGAGACTGGGAAAAGGGTATATG
TTTGAGAGCAAGAGTATGAAACTTAGAACTCAAATACCTGCAGAAATGCTAGCAAGCATTGATTTGAAATATTTCAATGATTCA
ACAAGAAAGAAGATTGAAAAAATCCGACCGCTCTTAATAGAGGGGACTGCATCATTGAGCCCTGGAATGATGATGGGCATGTTC
AATATGTTAAGCACTGTATTAGGCGTCTCCATCCTGAATCTTGGACAAAAGAGATACACCAAGACTACTTACTGGTGGGATGGT
CTTCAATCCTCTCTGACGATTTTGCTCTGATTGTGAATGCACCCAATCATGAAGGGATTCAAGCCGGAGTCGACAGGTTTTATCGA
ACCTGTAAGCTACTTGGAATCAATATGAGCAAGAAAAAGTCTTACATAAACAGAACAGGTACATTTGAATTCACAAGTTTTTTC
TATCGTTATGGGTTTGTTGCCAATTTCAGCATGGAGCTTCCCAGTTTTGGGGTGTCTGGGATCAACGAGTCAGCGGACATGAGT
ATTGGAGTTACTGTCATCAAAAACAATATGATAAACAATGATCTTGGTCCAGCAACAGCTCAAATGGCCCTTCAGTTGTTCATC
AAAGATTACAGGTACACGTACCGATGCCATAGAGGTGACACACAAATACAAACCCGAAGATCATTTGAAATAAAAGAAACTGTGG
GAGCAAACCCGTTCCAAAGCTGGACGCTGTGGTCTCCGACGGAGCCCAAATTTATACAACATTAGAAATCTCCACATTCCTGAA
GTCTGCCTAAAATGGGAATTGATGGTGAGGATTACCAGGGGCGTTTATGCAACCCACTGAACCCATTTGTCAGCCATAAAGAA
ATTGAATCAATGAACAATGCAGTGATGATGCCAGCACATGGTCCAGCCAAAAACATGGAGTATGATGCTGTTGCAACAACACAC
TCCTGGATCCCCAAAAGAAATCGATCCATCTTGAATACAAGTCAAAGAGGAGTACTTGAAGATGAACAAATGTACCAAAGGTGC
TGCAATTTATTTGAAAAATTCTTCCCCAGCAGTTCATACAGAAGACCAGTCGGGATATCCAGTATGGTGGAGGCTATGGTTTCC
AGAGCCCGAATTGATGCACGGATTGATTTCGAATCTGGAAGGATAAAGAAGAGTTCACTGAGATCTGTTCC
ACCATTGAAGAGCTCAGACGGCAAAAATAGTGAATTTAGCTTGTCCTTCATGAAAAAATGCCTTGTTTCTACT
```

(SEQ ID NO: 10)

FIG. 1 (Continued)

PR8 (Cambridge)

PA

AGCGAAAGCAGGTACTGATTCAAAATGGAAGATTTTGTGCGACAATGCTTCAATCCGATGATTGTCGAGCTTGCGGAAAAAACA
ATGAAAGAGTATGGGGAGGACCTGAAAATCGAAACAAACAAATTTGCAGCAATATGCACTCACTTGGAAGTATGCTTCATGTAT
TCAGATTTTCCACTTCATCAATGAGCAAGGCGAGTCAATAATCGTAGAACTTGGTGATCCTAATGCACTTTTGAAGCACAGATTT
GAAATAATCGAGGGAAGAGATCGCACAATGGCCTGGACAGTAGTAAACAGTATTTGCAACACTACAGGGGCTGAGAAACCAAAG
TTTCTACCAGATTTGTATGATTACAAGGAAATAGATTCATCGAAATTGGAGTAACAAGGAGAGAAGTTCACATATACTATCTG
GAAAAGGCCAATAAAATTAAATCTGAGAAAACACACATCCACATTTTCTCGTTCACTGGGGAAGAAATGGCCACAAGGGCCGAC
TACACTCTCGATGAAGAAAGCAGGGCTAGGATCAAAACCAGGCTATTCACCATAAGACAAGAAATGGCCAGCAGGCCTCTGG
GATTCCTTTCGTCAGTCCGAGAGGGAGAAGAGACAATTGAAGAAAGGTTTGAAATCACAGGAACAATGCGCAAGCTTGCCGAC
CAAAGTCTCCCGCCGAACTTCTCCAGCCTTGAAAATTTTAGAGCCTATGTGGATGGATTCGAACCGAACGGCTACATTGAGGGC
AAGCTGTCTCAAATGTCCAAAGAAGTAAATGCTAGAATTGAACCTTTTTTTGAAAACAACACCACGACCACTTAGACTTCCGAAT
GGGCCTCCCTGTTCTCAGCGGTCCAAATTCCTGCTGATGGATGCCTTAAAATTGAGGACCCAAGTCATGAAGGAGAG
GGAATACCGCTATATGATGCAATCAAATGCATGAGAACATTCTTTGGATGGAAGGAACCCAATGTTGTTAAACCACACGAAAAG
GGAATAAATCCAAATTATCTTCTGTCATGGAAGCAAGTACTGGCAGAACTGCAGGACATTGAGAATGAGGAGAAAATTCCAAAG
ACTAAAAATATGAAAAAAACAAGTCAGCTAAAGTGGGCACTTGGTGAGAACATGGCACCAGAAAGGTAGACTTTGACGACTGT
AAAGATGTAGGTGATTTGAAGCAATATGATAGTGATGAACCAGAATTGAGGTCGCTTGCAAGTTGGATTCAGAATGAGTTCAAC
AAGGCATGCGAACTGCACAGATTCAAGCTGGATAGAGCTTGATGAGATTGAGAAGATGTGGCTCCAATTGAACACATTGCAAGC
ATGAGAAGGAATTATTTCACATCAGAGGTGTCTCACTGCAGAGCCACAGAATACATAATGAAGGGGGTGTACATCAATACTGCC
TTACTTAATGCATCTTGTGCAGCAATGGATGATTTCCAATTAATTCCAATGATAAGCAAGTGTAGAACTAAGGAGGGAAGGCGA
AAGACCAACTTGTATGGTTTCATCATAAAAGGAAGATCCCACTTAAGGAATGACACCGACGTGGTAAACTTTGTGAGCATGGAG
TTTTCTCTCACTGACCCAAGACTTGAACCACACAAATGGGAAGTACTGTGTTCTTGAGATAGGAGATATGCTTCTAAGAAGT
GCCATAGGCCAGGTTTCAAGGCCCATGTTCTTGTATGTGAGGACAAATGGAACCTCAAAAATTAAAATGAAATGGGGAATGGAG
ATGAGGCGTTGTCTCCTCCAGTCACTTCAACAAATTGAGAGTATGATTGAAGCTGAGTCCTCTGTCAAAGAGAAAGACATGACC
AAAGAGTTCTTTGAGAACAAATCAGAAACATGGCCCATTGGAGAGTCTCCCAAAGGAGTGGAGGAAAGTTCCATTGGGAAGGTC
TGCAGGACTTTATTAGCAAAGTCGGTATTTAACAGCTTGTATGCATCTCCACAACTAGAAGGATTTTCAGCTGAATCAAGAAAA
CTGCTTCTTATCGTTCAGGCTCTTAGGGACAATCTGGAACCTGGGACCTTTGATCTTGGGGGCTATATGAAGCAATTGAGGAG
TGCCTAATTAATGATCCCTGGGTTTTGCTTAATGCTTCTTGGTTCAACTCCTTCCTTACACATGCATTGAGTTAGTTGTGGCAG
TGCTACTATTTGCTATCCATACTGTCCAAAAAGTACCTTGTTTCTACT
(SEQ ID NO. 12)

NP

AGCAAAAGCAGGGTAGATAATCACTCACTGAGTGACATCAAAATCATGGCGTCCCAAGGCACCAAACGGTCTTACGAACAGATG
GAGACTGATGGAGAACGCCAGAATGCCACTGAAATCAGAGCATCCGTCGGAAAAATGATTGGTGGAATTGGACGATTCTACATC
CAAATGTGCACAGAACTTAAACTCAGTGATTATGAGGGACGGTTGATCCAAAACAGCTTAACAATAGAGAGAATGGTGCTCTCT
GCTTTTGACGAAAGGAGAAATAAATACCTGGAAGAACATCCCAGTGCGGGGAAAGATCCTAAGAAAACTGGAGGACCTATATAC
AGAAGAGTAAACGGAAAGTGGATGAGAGAACTCATCCTTTATGACAAAGAAGAAATAAGGCGAATCTGGCGCCAAGCTAATAAT
GGTGACGATGCAACGGCTGGTCTGACTCACATGATGATCTGGCATTCCAATTTGAATGATGCAACTTATCAGAGGACAAGGGCT
CTTGTTCGCACCGGAATGGATCCCAGGATGTGCTCTCTGATGCAAGGTTCAACTCTCCCTAGGAGGTCTGGAGCCGCAGGTGCT
GCAGTCAAAGGAGTTGGAACAATGGTGATGGAATTGGTCAGGATGATCAAACGTGGGATCAATGATCGGAACTTCTGGAGGGGT
GAGAATGGACGAAAAACAAGAATTGCTTATGAAAGAATGTGCAACATTCTCAAAGGGAAATTTCAAACTGCTGCACAAAAAGCA
ATGATGGATCAAGTGAGAGAGAGCCGGAACCCAGGGAATGCTGAGTTCGAAGATCTCACTTTTCTAGCACGGTCTGCACTCATA
TTGAGAGGGTCGGTTGCTCACAAGTCCTGCCTGCCTGCCTGTGTGTATGGACCTGCCGTAGCCAGTGGGTACGACTTTGAAGA
GAGGGATACTCTCTAGTCGGAATAGACCCTTTCAGACTGCTTCAAAACAGCCAAGGTGTACAGCCTAATCAGACCAAATGAGAAT
CCAGCACACAAGAGTCAACTGGTGTGGATGGCATGCCATTCTGCCGCATTTGAAGATCTAAGAGTATTGAGCTTCATCAAAGGG
ACGAAGGTGGTCCCAAGAGGGAAGCTTTCCAACTAGAGGAGTTCAAATTGCTTCCAATGAAAATATGGAAGACTATGGAATCAAGT
ACACTTGAACTGAAGAGCAGGTACTGGGCCATAAGGACCAGAAGTGGAGGAAACACCAATCAACAGAGGGCATCTGCGGGCCAA
ATCAGCATACAACCTACGTTCTCAGTACAGAGAAATCTCCCTTTTGACAGAACAACCGTTATGGCAGCATTCACTGGGAATACA
GAGGGAGAACATCTGACATGAGGACCGAAATCATAAGGATGATGGAAAGTGCAAGACCAGAAGATGTGTCTTTCCAGGGGCGG
GGAGTCTTCGAGCTCTCGGACGAAAAGGCAGCGAGCCCGATCGTGCCTTCCTTTGACATGAGTAATGAAGGATCTTATTTCTTC
GGAGACAATGCAGAGGAGTACGACAATTAAAGAAAAATACCCTTGTTTCTACT
(SEQ ID NO. 13)

M

AGCAAAAGCAGGTAGATATTGAAAGATGAGTCTTCTAACCGAGGTCGAAACGTACGTTCTCTCTATCATCCCGTCAGGCCCCCT
CAAAGCCGAGATCGCACAGAGACTTGAAGATGTCTTTGCAGGGAAGAACACCGATCTTGAGGTTCTCATGGAATGGCTAAAGAC
AAGACCAATCCTGTCACCTCTGACTAAGGGGATTTTAGGATTTGTGTTCACGCTCACCGTGCCCAGTGAGCGAGGACTGCAGCG
TAGACGCTTTGTCCAAAATGCCCTTAATGGGAACGGGGATCCAAATAACATGGACAAAGCAGTTAAACTGTATAGGAAGCTCAA
GAGGGAGATAACATTCCATGGGGCCAAAGAAATCTCACTCAGTTATTCTGCTGGTGCACTTGCCAGTTGTATGGGCCTCATATA
CAACAGGATGGGGGCTGTGACCACTGAAGTGGCATTTGGCCTGGTATGTGCAACCTGTGAACAGATTGCTGACTCCCAGCATCG

FIG. 1 (Continued)

PR8(Cambridge)
GTCTCATAGGCAAATGGTGACAACAACCAACCCACTAATCAGACATGAGAACAGAATGGTTTTAGCCAGCACTACAGCTAAGGC
TATGGAGCAAATGGCTGGATCGAGTGAGCAAGCAGCAGAGGCCATGGAGGTTGCTAGTCAGGCTAGGCAAATGGTGCAAGCGAT
GAGAACCATTGGGACTCATCCTAGCTCCAGTGCTGGTCTGAAAAATGATCTTCTTGAAAATTTGCAGGCCTATCAGAAACGAAT
GGGGGTGCAGATGCAACGGTTCAAGTGATCCTCTCGCTATTGCCGCAAATATCATTGGGATCTTGCACTTGATATTGTGGATTC
TTGATCGTCTTTTTTTTCAAATGCATTTACCGTCGCTTTAAATACGGACTGAAAGGAGGGCCTTCTACGGAAGGAGTGCCAAAGT
CTATGAGGGAAGAATATCGAAAGGAACAGCAGAGTGCTGTGGATGCTGACGATGGTCATTTTGTCAGCATAGAGCTGGAGTAAA
AAACTACCTTGTTTCTACT

SEQ ID NO: 14

NS

AGCAAAAGCAGGGTGACAAAGACATAATGGATCCAAACACTGTGTCAAGCTTTCAGGTAGATTGCTTTCTTTGGCATGTCCGCA
AACGAGTTGCAGACCAAGAACTAGGTGATGCCCCATTCCTTGATCGGCTTCGCCGAGATCAGAAATCCCTAAGAGGAAGGGGCA
GCACTCTTGGTCTGGACATCGAGACAGCCACACGTGCTGGAAAGCAGATAGTGGAGCGGATTCTGAAAGAAGAATCCGATGAGG
CACTTAAAATGACCATGGCCTCTGTACCTGCGTCGCGTTACCTAACCGACATGACTCTTGAGGAAATGTCAAGGGAATGGTCCA
TGCTCATACCCAAGCAGAAAGTGGCAGGCCCTCTTTGTATCAGAATGGACCAGGCGATCATGGATAAAAACATCATACTGAAAG
CGAACTTCAGTGTGATTTTTGACCGGCTGGAGACTCTAATATTGCTAAGGGCTTTCACCGAAGAGGGAGCAATTGTTGGCGAAA
TTTCACCATTGCCTTCTCTTCCAGGACATACTGCTGAGGATGTCAAAAATGCAGTTGGAGTCCTCATCGGAGGACTTGAATGGA
ATGATAACACAGTTCGAGTCTCTGAAACTCTACAGAGATTCGCTTGGAGAAGCAGTAATGAGAATGGGAGACCTCCACTCACTC
CAAAACAGAAACGAGAAATGGCGGGAACAATTAGGTCAGAAGTTTGAAGAAATAAGATGGTTGATTGAAGAAGTGAGACACAAA
CTGAAGGTAACAGAGAATAGTTTTGAGCAAATAACATTTATGCAAGCCTTACATCTATTGCTTGAAGTGGAGCAAGAGATAAGA
ACTTTCTCATTTCAGCTTATTTAATAATAAAAAACACCCTTGTTTCTACT

SEQ ID NO: 15

Figure 3 Summary of HA assay of 1434 individual clones

| Groups | Numbers of clone | Fold change | % |
|---|---|---|---|
| WT HA titer = $2^7$ | - | - | - |
| HA titer = $2^{>9-9.5}$ | 8 | >4 | 0.6% |
| HA titer = $2^{>8.5-9}$ | 23 | >2.8 - 4 | 1.6% |
| HA titer = $2^{7-8.5}$ | 748 | 1 - 2.8 | 52.2% |
| HA titer < $2^7$ | 655 | <1 | 45.6% |
| Total | 1434 | - | 100% |

Figure 4 Recombinant viruses generated from dominant mutations

| Viruses | HA | NA | Gene backbone | | | | | | Virus stock titer | |
|---|---|---|---|---|---|---|---|---|---|---|
| | | | PB2 | PB1 | PA | NP | M | NS | 2 | Pfu/ml |
| WT | | | PR8-wt | PR8-wt | PR8-wt | PR8-wt | PR8-wt | PR8-wt | 7 | 3.0E+07 |
| 1 | Indo/NC /09 delHA | Indo/NC /09 NA | M202L F323L | M507V V644A | | I116L | | K55E | 9~9.5 | 2.0E+08 |
| 2 | | | M202L F323L | Q247H | R401K | | | T49A | 9 | 1.0E+08 |
| 3 | | | I504V | M507V V644A | I550L | R74K N417D | | K55E | 8~8.5 | 5.7E+07 |
| 4 | | | I505V | E112G | I550L | R74K | | S161T | 9 | 1.6E+08 |
| 5 | | | M202L F323L | E112G | | | | S161T | 8.5 | 1.3E+08 |
| 6 | | | M66R | M40I G180W | | R74K | | S161T | 8~8.5 | 2.3E+07 |

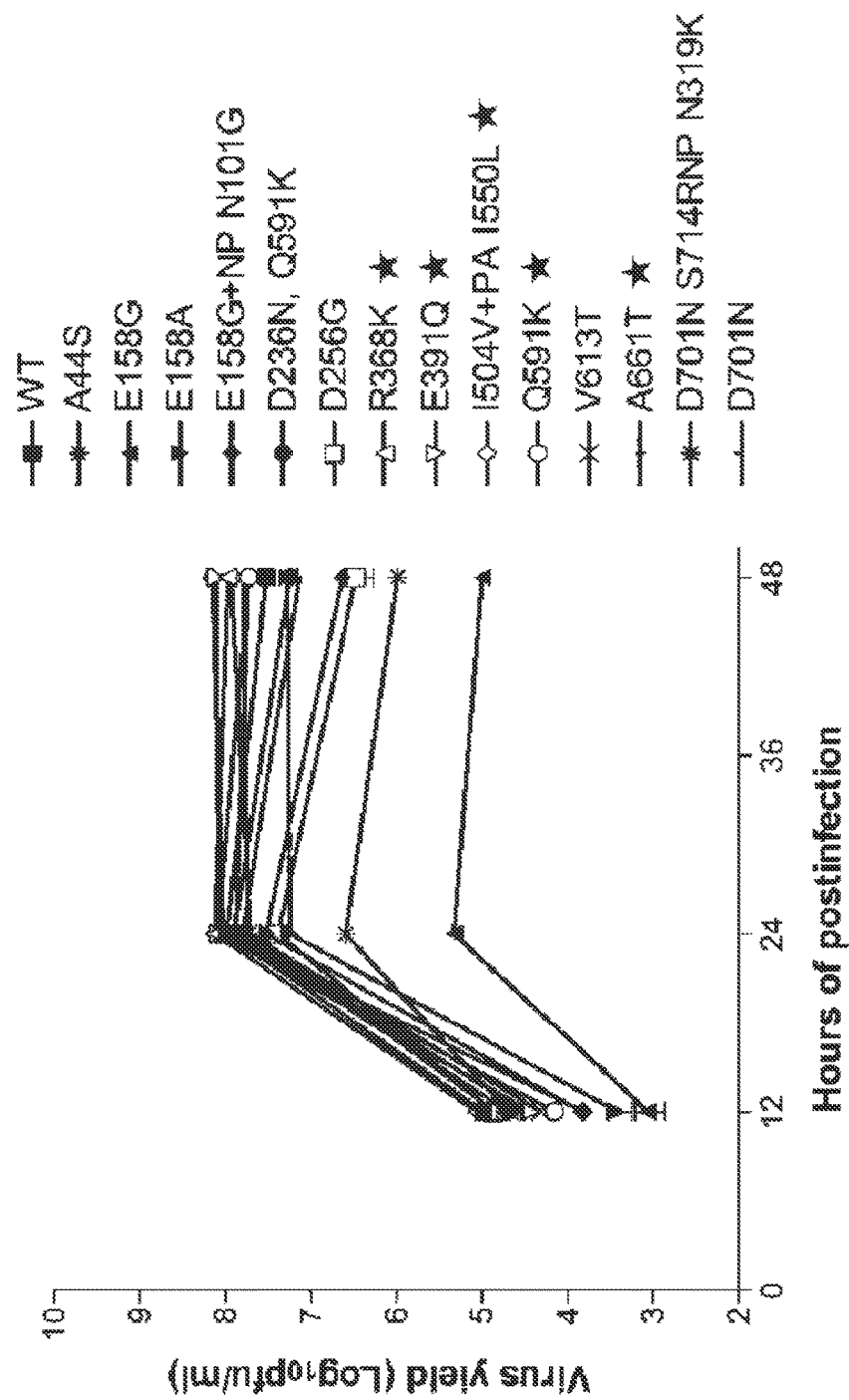

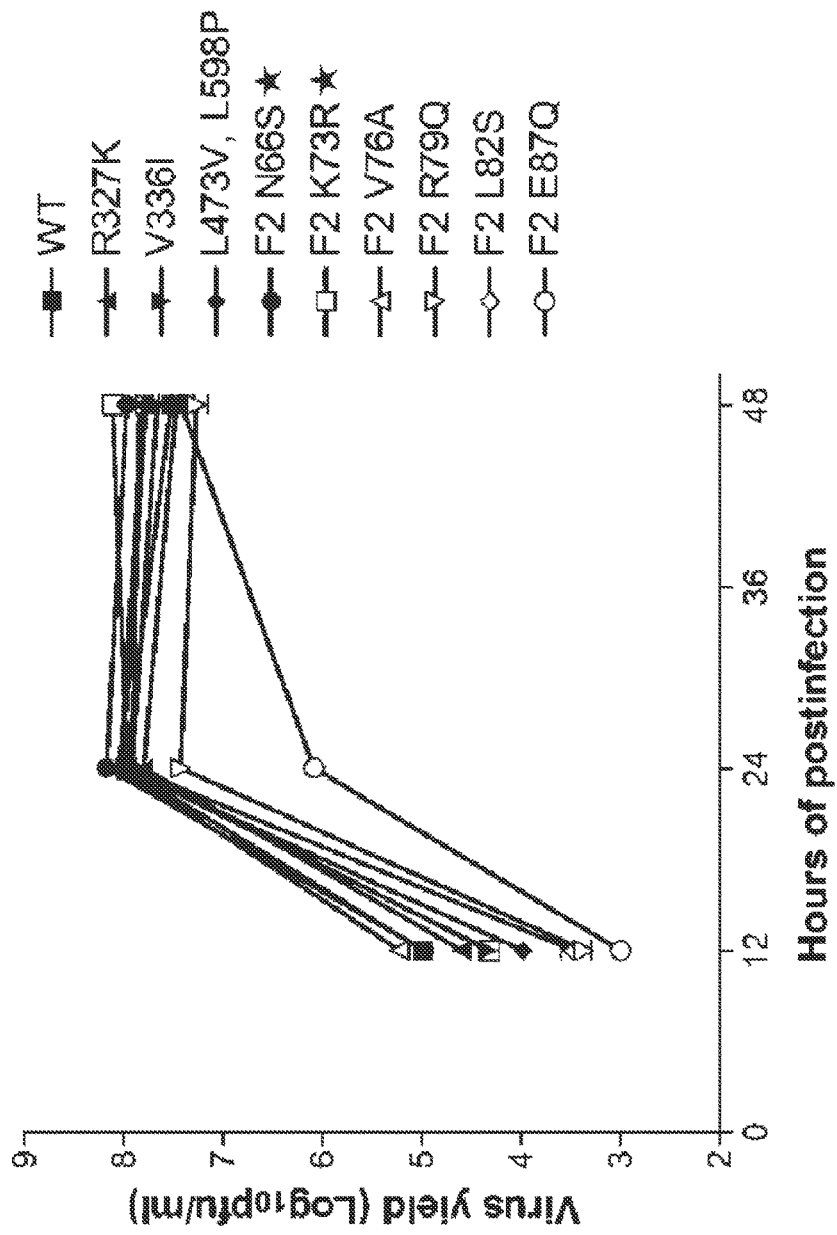

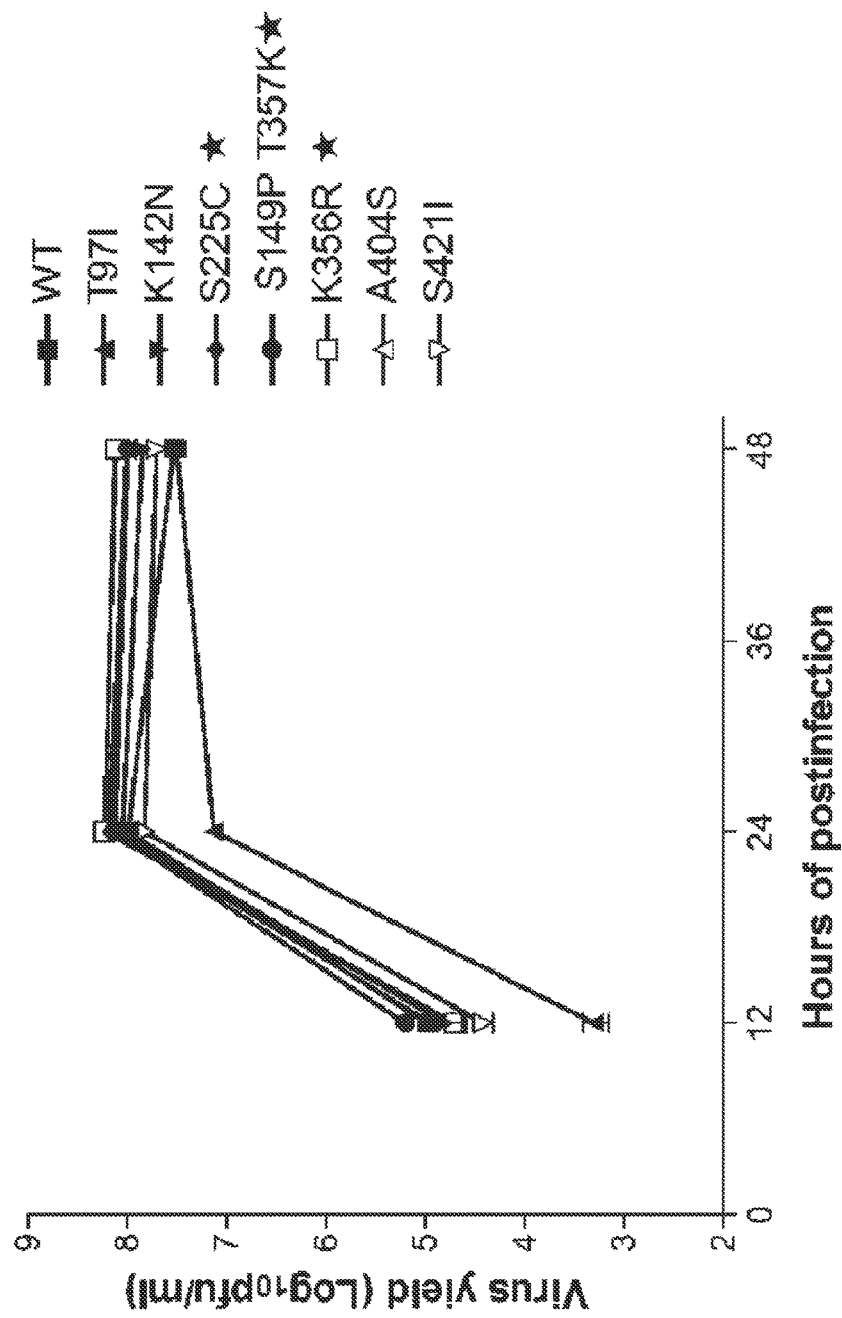

Figure 5D NP, M and NS1 mutants

Figure 6 Confirmed high replicative mutations

| Gene | Screened from viruses libraries | Described in literature |
|---|---|---|
| PB2 | M202L, F323L, I504V, M66R | A44S, E158G, E158A, D236N, D256G, R368K, E391Q, I504V, Q591K, V613T, A661T, D701N, D701N, S714R |
| PB1 | M507V, V644A, V644A, R54L, Q247H, E112G, M40I, G180W, I667T, M714T | R327K, V336I, L473V, L598P |
| PB1 F2 | - | N66S, K73R, V76A, R79Q, L82S, E87Q |
| PA | F105C, R401K | T97I, K142N, S225C, S149PP, T357K, K356R, A404S, S421I |
| NP | R293M, I116L, N224I, R74K, R74K, N417D | R293K, R305K, E372D, R422K, T442A, D455E, I109V, N101G, N319K |
| M | P90S | V97A, Y100H, V97A, Y100H |
| NS | A30P, T49A, R140Q, S161T, A223E | K55E |

Figure 7A Recombinant viruses generated by RGS

| Virus # | HA | NA | Gene backbone | | | | | | | Virus stock titer | |
|---|---|---|---|---|---|---|---|---|---|---|---|
| | | | PB2 | PB1 | PA | NP | M | NS | $2^n$ | Pfu/ml |
| wt | Inda/NC/09 delHA | Indo/NC/09 NA | wt | wt | wt | wt | wt | wt | 7 | 3.0E+07 |
| 1 | | | M202L F323L | M507V V644A | | I116L | | K55E | 9~9.5 | 2.0E+08 |
| 4 | | | M202L F323L | M507V V644A | K356R | T442A | V97A Y100H | K55E | 10~10.5 | 1.6E+08 |
| 36 | | | I504V | E112G | I550L | I112L | Y100H | R140Q | 9.5 | 1.3E+08 |
| 38 | | | M202L F323L | M507V V644A | | I116L | Y100H | K55E | 10~10.5 | 2.3E+08 |
| HY-#17 | | | I504V | E112G | S225C | R74K N417D | V97A Y100H | K55E | 9.5~10 | 5.8E+08 |
| HY-#61 | | | M202L F323L | Q247H | K142N | R74K | V97A Y100H | K55E | 10~10.5 | 2.0E+08 |
| HY-#26 | | | M202L F323L | M40L G180W | S225C | R422K | V97A Y100H | K55E | 10 | 3.0E+08 |

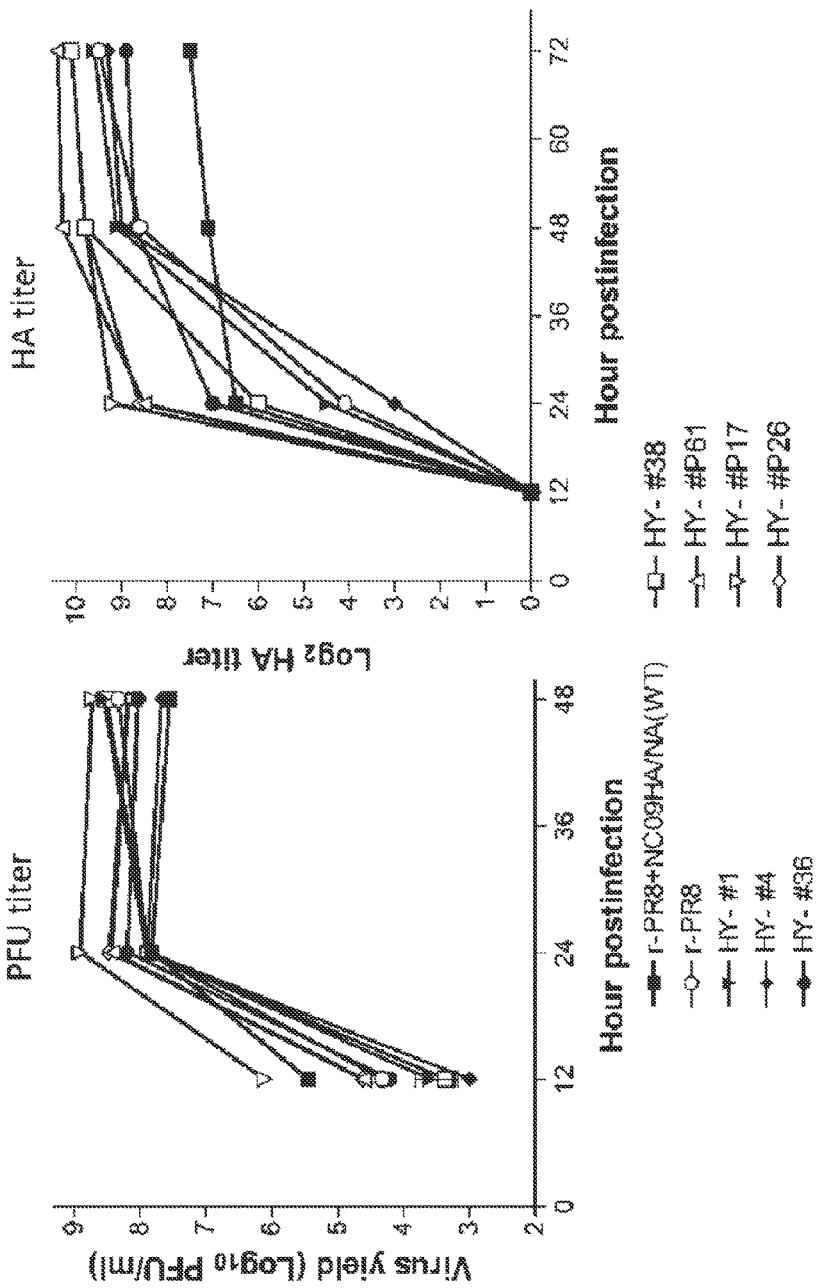

Total viral protein yield: 4.2 fold

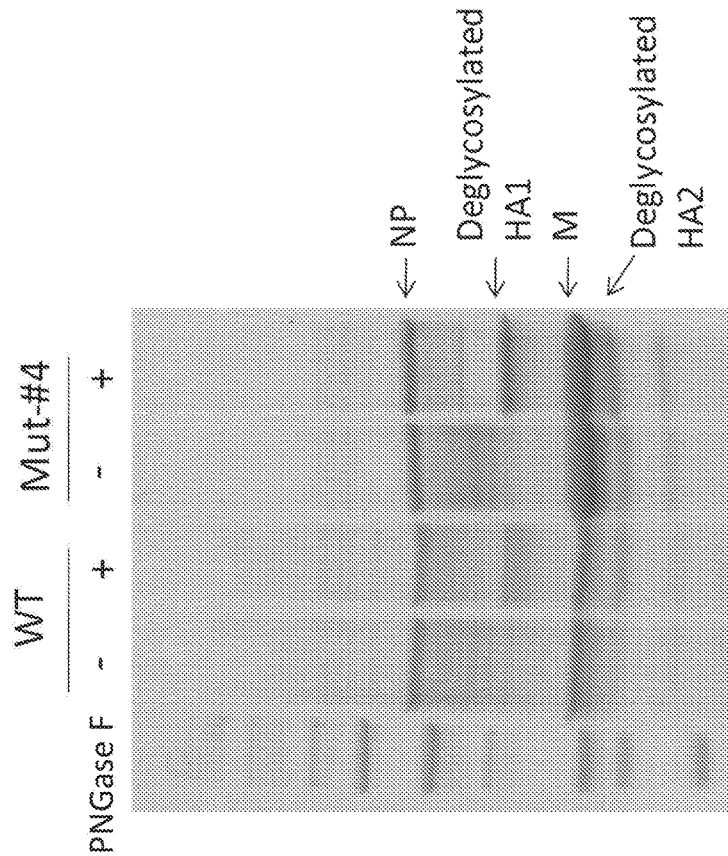

Figure 9A Wild type VS. mutant

| # | HA | NA | Gene backbone | | | | | | Virus stock titer

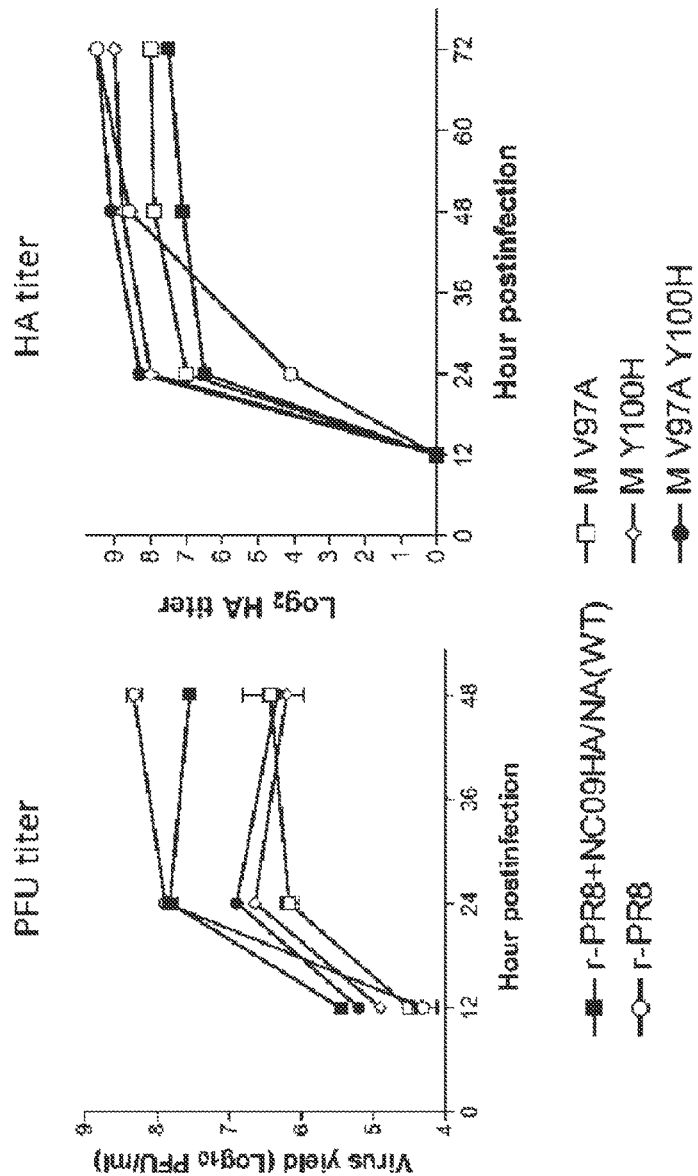

Figure 10A Codons usage frequency of Canis familiaris

*Canis familiaris* [gbmam]: 11094 CDS's (5089501 codons)

fields: [triplet] [amino acid] [fraction] [frequency: per thousand] ([number])

| | | | | | | |
|---|---|---|---|---|---|---|
| UUU F 0.41 17.1 ( 86940) | UCU S 0.18 13.0 ( 77333) | UAU Y 0.40 11.5 ( 64564) | UGU C 0.42 10.1 ( 53658) |
| UUC F 0.59 24.4 (136711) | UCC S 0.24 18.4 (102999) | UAC Y 0.60 17.5 ( 97864) | UGC C 0.58 13.8 ( 77233) |
| UUA L 0.06 5.8 ( 32270) | UCA S 0.13 9.8 ( 54667) | UAA * 0.27 0.6 ( 325) | UGA * 0.53 1.1 ( 642) |
| UUG L 0.12 11.8 ( 66270) | UCG S 0.06 4.0 ( 25844) | UAG * 0.21 0.5 ( 254) | UGG W 1.00 13.0 ( 77040) |
| | | | |
| CUU L 0.12 11.7 ( 65233) | CCU P 0.27 15.6 ( 87133) | CAU H 0.39 9.0 ( 50399) | CGU R 0.07 3.9 ( 21630) |
| CUC L 0.22 21.8 (122224) | CCC P 0.35 20.4 (114220) | CAC H 0.61 14.1 ( 78886) | CGC R 0.20 10.6 ( 59433) |
| CUA L 0.06 6.3 ( 35444) | CCA P 0.23 14.6 ( 81571) | CAA Q 0.25 11.0 ( 61490) | CGA R 0.11 5.6 ( 31550) |
| CUG L 0.43 42.8 (238966) | CCG P 0.12 7.0 ( 38923) | CAG Q 0.75 32.6 (182464) | CGG R 0.21 11.0 ( 61322) |
| | | | |
| AUU I 0.32 15.5 ( 86562) | ACU T 0.22 12.3 ( 68960) | AAU N 0.43 16.5 ( 92533) | AGU S 0.14 10.8 ( 60299) |
| AUC I 0.53 25.7 (143911) | ACC T 0.39 21.4 (119790) | AAC N 0.57 24.0 (134104) | AGC S 0.25 18.8 (105595) |
| AUA I 0.15 7.2 ( 40177) | ACA T 0.26 14.2 ( 79722) | AAA K 0.40 22.2 (124104) | AGA R 0.20 10.5 ( 58877) |
| AUG M 1.00 22.7 (127170) | ACG T 0.13 7.2 ( 40003) | AAG K 0.60 33.4 (189663) | AGG R 0.21 11.1 ( 62288) |
| | | | |
| GUU V 0.11 9.3 ( 51809) | GCU A 0.25 17.3 ( 96408) | GAU D 0.43 19.7 (110183) | GGU G 0.16 11.3 ( 62983) |
| GUC V 0.27 17.2 ( 96407) | GCC A 0.44 30.3 (169277) | GAC D 0.57 26.2 (146653) | GGC G 0.35 24.2 (135130) |
| GUA V 0.10 6.5 ( 36469) | GCA A 0.20 13.7 ( 76533) | GAA E 0.40 26.4 (147760) | GGA G 0.24 16.9 ( 94655) |
| GUG V 0.48 31.0 (173660) | GCG A 0.11 7.9 ( 44313) | GAG E 0.60 40.3 (225522) | GGG G 0.25 17.4 ( 97180) |

Coding GC 53.18% 1st letter GC 55.35% 2nd letter GC 41.92% 3rd letter GC 62.27%
Genetic code: 1: Standard

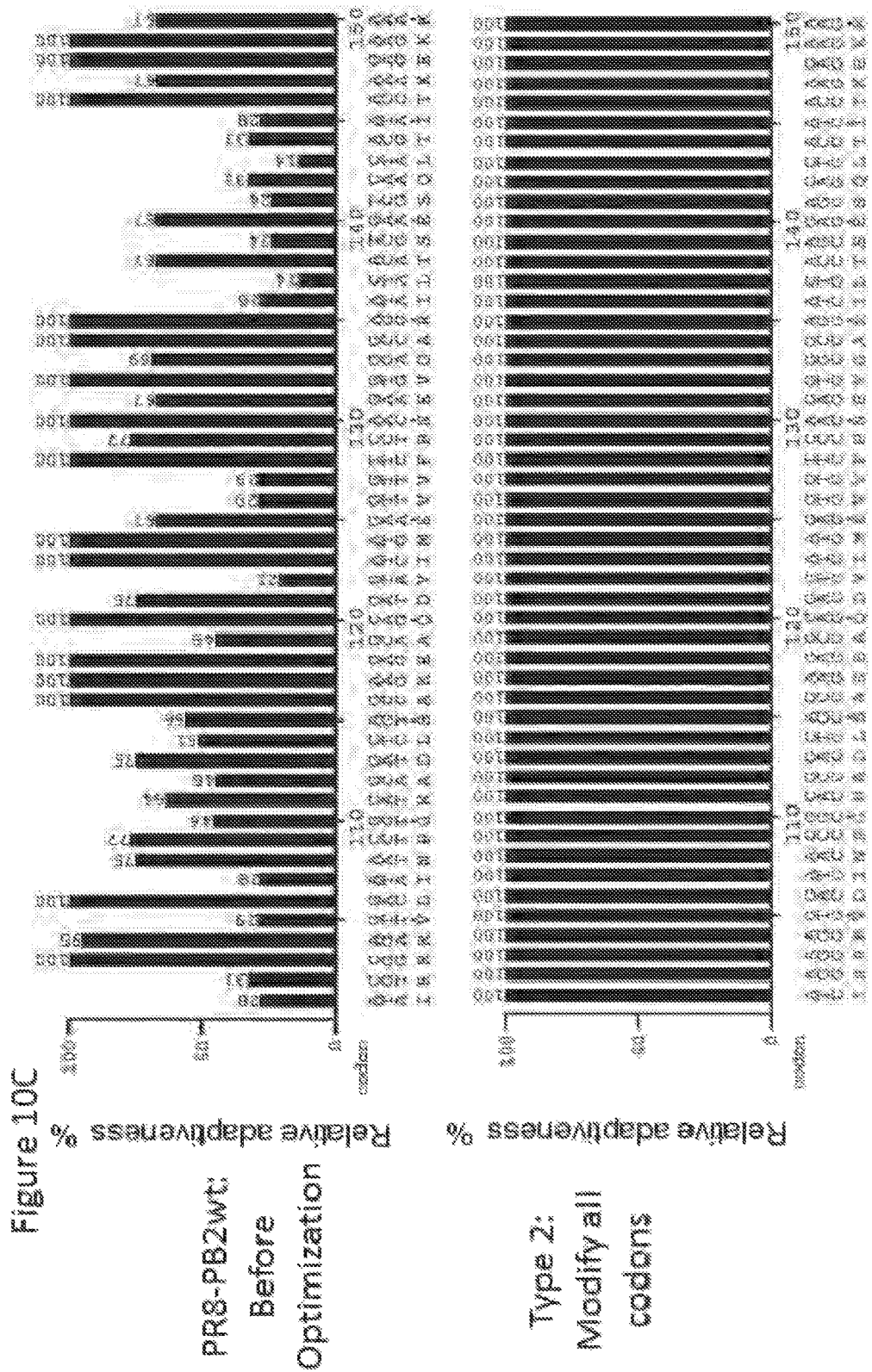

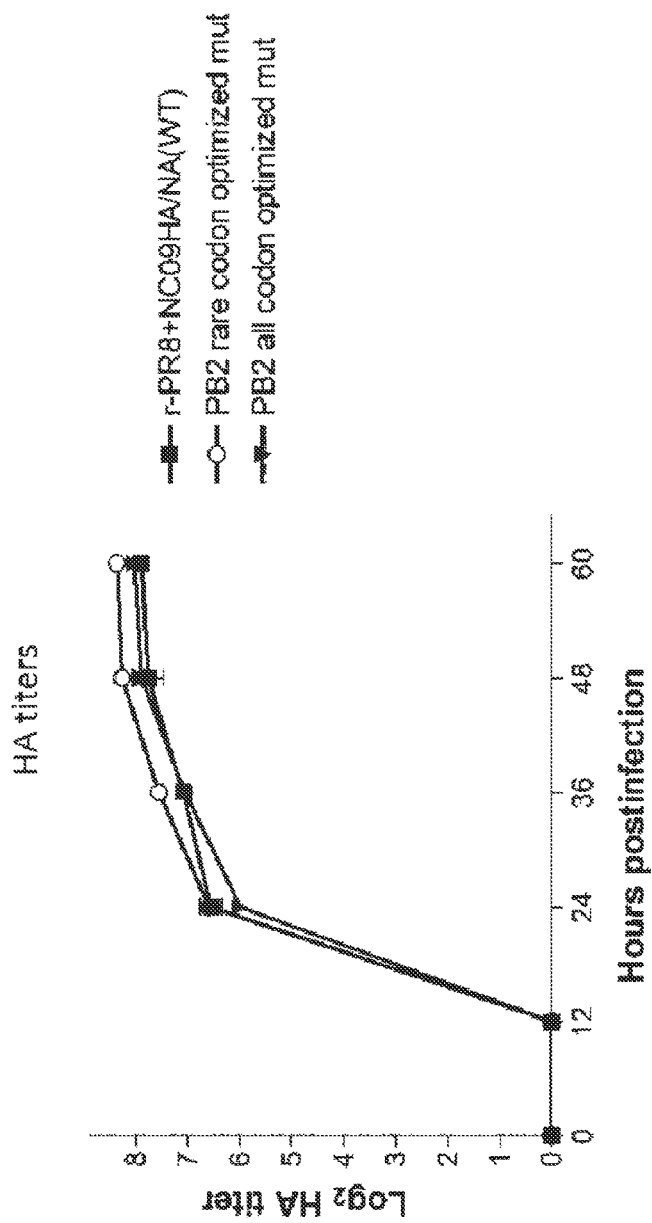
Figure 10D Growth kinetics in MDCK cells

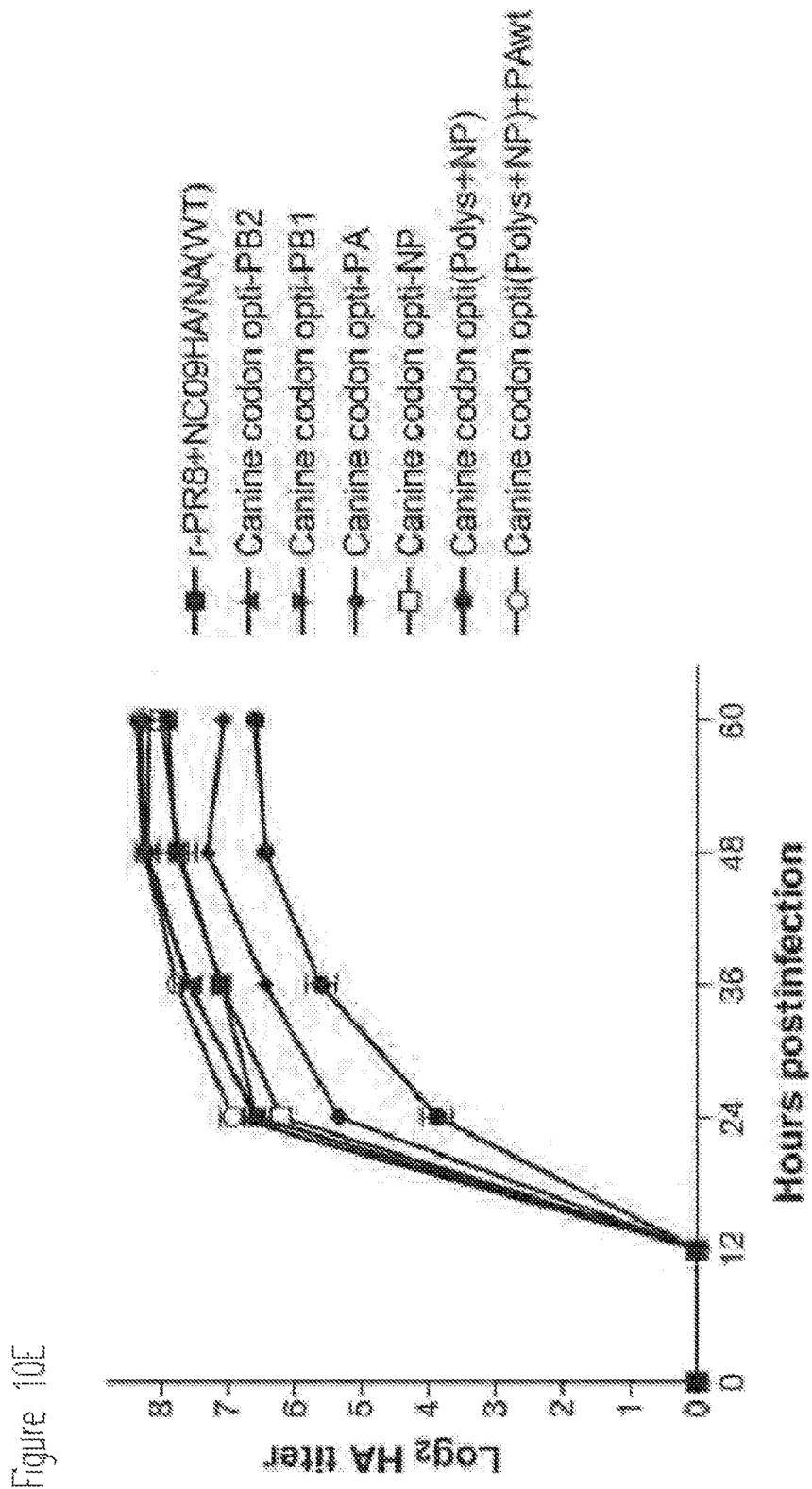

AGCGAAAGCAGGTCAATTATATTCAATATGGAAAGAATAAAAGAACTACGAAATCTAATGTCGCAGTCTCGCACCCGCGA

GATACTCACAAAAACCACCGTGGACCATATGGCCATAATCAAGAAGTACACATCAGGAAGACAGGAGAAGAACCCAGCAC

TTAGGATGAAATGGATGATGGCAATGAAATATCCAATTACAGCAGACAAGAGGATAACGGAAATGATTCCTGAGAGAAAT

GAGCAAGGACAAACTTTATGGAGTAAAATGAATGATGCCGGATCAGACCGAGTGATGGTATCACCTCTGGCTGTGACATG

GTGGAATAGGAATGGACCAATAACAAATACAGTTCATTATCCAAAAATCTACAAAACTTATTTTGAAAGAGTCGAAAGGC

TAAAGCATGGAACCTTTGGCCCTGTCCATTTTAGAAACCAAGTCAAAATACGTCGGAGAGTTGACATAAATCCTGGTCAT

GCAGATCTCAGTGCCAAGGAGGCACAGGATGTAATCATGGAAGTTGTTTTCCCTAACGAAGTGGGAGCCAGGATACTAAC

ATCGGAATCGCAACTAACGATAACCAAAGAGAAGAAAGAAGAACTCCAGGATTGCAAAATTTCTCCTTTGATGGTTGCAT

ACATGTTGGAGAGAGAACTGGTCCGCAAAACGAGATTCCTCCCAGTGGCTGGTGGAACAAGCAGTGTGTACATTGAAGTG

TTGCATTTGACTCAAGGAACATGCTGGGAACAGATGTATACTCCAGGAGGGGAAGTGAGGAATGATGATGTTGATCAAAG

CTTGATTATTGCTGCTAGGAACATAGTGAGAAGAGCTGCAGTATCAGCAGATCCACTAGCATCTTTATTGGAGATGTGCC

ACAGCACACAGATTGGTGGAATTAGGATGGTAGACATCCTTAGGCAGAACCCAACAGAAGAGCAAGCCGTGGATATATGC

AAGGCTGCAATGGGACTGAGAATTAGCTCATCCTTCAGTTTTGGTGGATTCACATTTAAGAGAACAAGCGGATCATCAGT

CAAGAGAGAGGAAGAGGTGCTTACGGGCAATCTTCAAACATTGAAGATAAGAGTGCATGAGGGATATGAAGAGTTCACAA

TGGTTGGGAGAAGAGCAACAGCCATACTCAGAAAAGCAACCAGGAGATTGATTCAGCTGATAGTGAGTGGGAGAGACGAA

CAGTCGATTGCCGAAGCAATAATTGTGGCCATGGTATTTTCACAAGAGGATTGTATGATAAAAGCAGTCAGAGGTGATCT

GAATTTCGTCAATAGGGCGAATCAACGATTGAATCCTATGCATCAACTTTTAAGACATTTTCAGAAGGATGCGAAAGTGC

TTTTTCAAAATTGGGGAGTTGAACCTATCGACAATGTGATGGGAATGATTGGGATATTGCCCGACATGACTCCAAGCATC

GAGATGTCAATGAGAGGAGTGAGAATCAGCAAAATGGGTGTAGATGAGTACTCCAGCACGGAGAGGGTAGTGGTGAGCAT

TGACCGTTTTTTGAGAATCCGGGACCAACGAGGAAATGTACTACTGTCTCCCGAGGAGGTCAGTGAAACACAGGGAACAG

AGAAACTGACAATAACTTACTCATCGTCAATGATGTGGGAGATTAATGGTCCTGAATCAGTGTTGGTCAATACCTATCAA

TGGATCATCAGAAACTGGGAAACTGTTAAAATTCAGTGGTCCCAGAACCCTACAATGCTATACAATAAAATGGAATTTGA

ACCATTTCAGTCTTTAGTACCTAAGGCCATTAGAGGCCAATACAGTGGGTTTGTAAGAACTCTGTTCCAACAAATGAGGG

ATGTGCTTGGGACATTTGATACCGCACAGATAATAAAACTTCTTCCCTTCGCAGCCGCTCCACCAAAGCAAAGTAGAATG

CAGTTCTCCTCATTTACTGTGAATGTGAGGGGATCAGGAATGAGAATACTTGTAAGGGGCAATTCTCCTGTATTCAACTA

TAACAAGGCCACGAAGAGACTCACAGTTCTCGGAAAGGATGCTGGCACTTTAACTGAAGACCCAGATGAAGGCACAGCTG

GAGTGGAGTCCGCTGTTCTGAGGGGATTCCTCATTCTGGGCAAAGAAGACAAGAGATATGGGCCAGCACTAAGCATCAAT

GAACTGAGCAACCTTGCGAAAGGAGAGAAGGCTAATGTGCTAATTGGGCAAGGAGACGTGGTGTTGGTAATGAAACGGAA

ACGGGACTCTAGCATACTTACTGACAGCCAGACAGCGACCAAAAGAATTCGGATGGCCATCAATTAGTGTCGAATAGTTT

AAAAACGACCTTGTTTCTACT (SEQ ID NO:3)

FIG. 10F (Continued)

Canine codon optimized PR8-PB2:

AGCGAAAGCAGGTCAATTATATTCAATATGGAAAGAATAAAAGAACTACGAAATCTAATGTCGCAGTCTCGCACCCGCGA
GATACTCACAAAAACCACCGTGGACCATATGGCCATAATCAAGAAGTACACATCAGGAAGACAGGAGAAGAACCCAGCAC
TGAGGATGAAATGGATGATGGCAATGAAATATCCAATTACAGCAGACAAGAGGATCACCGAAATGATTCCTGAGAGAAAT
GAGCAGGGACAGACTCTGTGGAGTAAAATGAATGATGCCGGATCAGACCGAGTGATGGTGTCACCTCTGGCTGTGACATG
GTGGAATAGGAATGGACCAATCACAAATACAGTGCATTATCCAAAAATCTACAAAACTTATTTTGAAAGAGTCGAAAGGC
TGAAGCATGGAACCTTTGGCCCTGTCCATTTTAGAAACCAGGTCAAAATCCGGCGGAGAGTGGACATCAATCCTGGTCAT
GCAGATCTCAGTGCCAAGGAGGCACAGGATGTGATCATGGAAGTGGTGTTCCCTAACGAAGTGGGAGCCAGGATTCTGAC
ATCCGAATCCCAGCTGACCATTACCAAAGAGAAGAAAGAAGAACTCCAGGATTGCAAAATTTCTCCTCTGATGGTGGCAT
ACATGCTGGAGAGAGAACTGGTCCGCAAAACAAGATTCCTCCCAGTGGCTGGTGGAACAAGCAGTGTGTACATTGAAGTG
CTGCATCTGACTCAGGGAACATGCTGGGAACAGATGTATACTCCAGGAGGGGAAGTGAGGAATGATGATGTGGATCAGAG
CCTGATTATTGCTGCTAGGAACATTGTGAGAAGAGCTGCAGTGTCAGCAGATCCACTGGCATCTCTGCTGGAGATGTGCC
ACAGCACACAGATTGGTGGAATTAGGATGGTGGACATCCTGAGGCAGAACCCAACAGAAGAGCAGGCCGTGGATATTTGC
AAGGCTGCAATGGGACTGAGAATTAGCTCATCCTTCAGTTTTGGTGGATTCACATTTAAGAGAACAAGCGGATCATCAGT
CAAGAGAGAGGAAGAGGTGCTGACCGGCAATCTGCAGACACTGAAGATCAGAGTGCATGAGGGATATGAAGAGTTCACAA
TGGTGGGGAGAAGAGCAACAGCCATCCTCAGAAAAGCAACCAGGAGACTGATTCAGCTGATCGTGAGTGGGAGAGACGAA
CAGTCCATTGCCGAAGCAATTATTGTGGCCATGGTGTTTTCACAGGAGGATTGTATGATTAAAGCAGTCAGAGGTGATCT
GAATTTCGTCAATAGGGCCAATCAGCGACTGAATCCTATGCATCAGCTGCTGAGACATTTTCAGAAGGATGCCAAAGTGC
TGTTTCAGAATTGGGGAGTGGAACCTATCGACAATGTGATGGGAATGATTGGGATCCTGCCCGACATGACTCCAAGCATC
GAGATGTCAATGAGAGGAGTGAGAATCAGCAAAATGGGTGTGGATGAGTACTCCAGCACCGAGAGGGTCGTGGTGAGCAT
TGACAGATTTCTGAGAATCCGGGACCAGCGAGGAAATGTGCTCCTGTCTCCCGAGGAGGTCAGTGAAACACAGGGAACAG
AGAAACTGACAATTACTTACTCATCCTCAATGATGTGGGAGATTAATGGTCCTGAATCAGTGCTGGTCAATACCTATCAG
TGGATCATCAGAAACTGGGAAACTGTGAAAATTCAGTGGTCCCAGAACCCTACAATGCTGTACAATAAAATGGAATTTGA
ACCATTTCAGTCTCTGGTGCCTAAGGCCATTAGAGGCCAGTACAGTGGGTTTGTGAGAACTCTGTTCCAGCAGATGAGGG
ATGTGCTGGGGACATTTGATACCGCACAGATTATTAAACTGCTGCCCTTCGCAGCCGCTCCACCAAAGCAGAGTAGAATG
CAGTTCTCCTCATTTACTGTGAATGTGAGGGGATCAGGAATGAGAATCCTGGTGAGGGGCAATTCTCCTGTGTTCAACTA
TAACAAGGCCACCAAGAGACTCACAGTGCTCGGAAAGGATGCTGGCACTCTGACTGAAGACCCAGATGAAGGCACAGCTG
GAGTGGAGTCCGCTGTGCTGAGGGGATTCCTCATTCTGGGCAAAGAAGACAAGAGATATGGGCCAGCACTGAGCATCAAT
GAACTGAGCAACCTGGCCAAAGGAGAGAAGGCTAATGTGCTAATTGGGCAAGGAGACGTGGTGTTGGTAATGAAACGGAA
ACGGGACTCTAGCATACTTACTGACAGCCAGACAGCGACCAAAAGAATTCGGATGGCCATCAATTAGTGTCGAATAGTTT
AAAAACGACCTTGTTTCTACT (SEQ ID NO:13)

AGCGAAAGCAGGCAAACCATTTGAATGGATGTCAATCCGACCTTACTTTTCTTAAAAGTGCCAGCACAAAATGCTATAAG

CACAACTTTCCCTTATACTGGAGACCCTCCTTACAGCCATGGGACAGGAACAGGATACACCATGGATACTGTCAACAGGA

CACATCAGTACTCAGAAAAGGGAAGATGGACAACAAACACCGAAACTGGAGCACCGCAACTCAACCCGATTGATGGGCCA

CTGCCAGAAGACAATGAACCAAGTGGTTATGCCCAAACAGATTGTGTATTGGAGGCGATGGCTTTCCTTGAGGAATCCCA

TCCTGGTATTTTTGAAAACTCGTGTATTGAAACGATGGAGGTTGTTCAGCAAACACGAGTAGACAAGCTGACACAAGGCC

GACAGACCTATGACTGGACTCTAAATAGAAACCAACCTGCTGCAACAGCATTGGCCAACACAATAGAAGTGTTCAGATCA

AATGGCCTCACGGCCAATGAGTCTGGAAGGCTCATAGACTTCCTTAAGGATGTAATGGAGTCAATGAACAAAGAAGAAAT

GGGGATCACAACTCATTTTCAGAGAAAGAGACGGGTGAGAGACAATATGACTAAGAAAATGATAACACAGAGAACAATGG

GTAAAAAGAAGCAGAGATTGAACAAAAGGAGTTATCTAATTAGAGCATTGACCCTGAACACAATGACCAAAGATGCTGAG

AGAGGGAAGCTAAAACGGAGAGCAATTGCAACCCCAGGGATGCAAATAAGGGGGTTTGTATACTTTGTTGAGACACTGGC

AAGGAGTATATGTGAGAAACTTGAACAATCAGGGTTGCCAGTTGGAGGCAATGAGAAGAAAGCAAAGTTGGCAAATGTTG

TAAGGAAGATGATGACCAATTCTCAGGACACCGAACTTTCTTTCACCATCACTGGAGATAACACCAAATGGAACGAAAAT

CAGAATCCTCGGATGTTTTTGGCCATGATCACATATATGACCAGAAATCAGCCCGAATGGTTCAGAAATGTTCTAAGTAT

TGCTCCAATAATGTTCTCAAACAAAATGGCGAGACTGGGAAAAGGGTATATGTTTGAGAGCAAGAGTATGAAACTTAGAA

CTCAAATACCTGCAGAAATGCTAGCAAGCATCGATTTGAAATATTTCAATGATTCAACAAGAAAGAAGATTGAAAAAATC

CGACCGCTCTTAATAGAGGGGACTGCATCATTGAGCCCTGGAATGATGATGGGCATGTTCAATATGTTAAGCACTGTATT

AGGCGTCTCCATCCTGAATCTTGGACAAAAGAGATACACCAAGACTACTTACTGGTGGGATGGTCTTCAATCCTCTGACG

ATTTTGCTCTGATTGTGAATGCACCCAATCATGAAGGGATTCAAGCCGGAGTCGACAGGTTTTATCGAACCTGTAAGCTA

CTTGGAATCAATATGAGCAAGAAAAGTCTTACATAAACAGAACAGGTACATTTGAATTCACAAGTTTTTTCTATCGTTA

TGGGTTTGTTGCCAATTTCAGCATGGAGCTTCCCAGTTTTGGGGTGTCTGGGATCAACGAGTCAGCGGACATGAGTATTG

GAGTTACTGTCATCAAAAACAATATGATAAACAATGATCTTGGTCCAGCAACAGCTCAAATGGCCCTTCAGTTGTTCATC

AAAGATTACAGGTACACGTACCGATGCCATATAGGTGACACACAAATACAAACCCGAAGATCATTTGAAATAAAGAAACT

GTGGGAGCAAACCCGTTCCAAAGCTGGACTGCTGGTCTCCGACGGAGGCCCAAATTTATACAACATTAGAAATCTCCACA

TTCCTGAAGTCTGCCTAAAATGGGAATTGATGGATGAGGATTACCAGGGGCGTTTATGCAACCCACTGAACCCATTTGTC

AGCCATAAAGAAATTGAATCAATGAACAATGCAGTGATGATGCCAGCACATGGTCCAGCCAAAAACATGGAGTATGATGC

TGTTGCAACAACACACTCCTGGATCCCCAAAAGAAATCGATCCATCTTGAATACAAGTCAAAGAGGAGTACTTGAGGATG

AACAAATGTACCAAAGGTGCTGCAATTTATTTGAAAAATTCTTCCCCAGCAGTTCATACAGAAGACCAGTCGGGATATCC

AGTATGGTGGAGGCTATGGTTTCCAGAGCCCGAATTGATGCACGGATTGATTTCGAATCTGGAAGGATAAAGAAGAAGA

GTTCACTGAGATCATGAAGATCTGTTCCACCATTGAAGAGCTCAGACGGCAAAAATAGTGAATTTAGCTTGTCCTTCATG

AAAAAAATGCCTTGTTTCTACT (SEQ ID NO:2)

FIG. 10F (Continued)

Canine codon optimized PR8 PB1:

AGCGAAAGCAGGCAAACCATTTGAATGGATGTCAATCCGACCTTACTTTTCTTAAAAGTGCCAGCACAAAATGCTATAAG

CACAACTTTCCCTTATACTGGAGACCCTCCTTACAGCCATGGGACAGGAACAGGATACACCATGGATACTGTCAACAGGA

CACATCAGTACTCAGAAAAGGGAAGATGGACAACAAACACCGAAACTGGAGCACCGCAACTCAACCCGATTGATGGGCCA

CTGCCAGAAGACAATGAACCAAGTGGTTATGCCCAAACAGATTGTGTATTGGAGGCGATGGCTTTCCTTGAGGAATCCCA

TCCTGGTATTTTTGAAAACTCGTGTATTGAAACGATGGAGGTTGTTCAGCAAACACGAGTGGACAAGCTGACACAGGGCC

GACAGACCTATGACTGGACTCTGAATAGAAACCAGCCTGCTGCAACAGCACTGGCCAACACAATCGAAGTGTTCAGATCA

AATGGCCTCACCGCCAATGAGTCTGGAAGGCTCATCGACTTCCTGAAGGATGTGATGGAGTCAATGAACAAAGAAGAAAT

GGGGATCACAACTCATTTTCAGAGAAAGAGACGGGTGAGAGACAATATGACTAAGAAAATGATTACACAGAGAACAATGG

GTAAAAAGAAGCAGAGACTGAACAAAAGGAGTTATCTGATTAGAGCACTGACCCTGAACACAATGACCAAAGATGCTGAG

AGAGGGAAGCTGAAACGGAGAGCAATTGCAACCCCAGGGATGCAGATTAGGGGGTTTGTGTACTTTGTGGAGACACTGGC

AAGGAGTATTTGTGAGAAACTGGAACAGTCAGGGCTGCCAGTGGGAGGCAATGAGAAGAAAGCAAAGCTGGCAAATGTGG

TGAGGAAGATGATGACCAATTCTCAGGACACCGAACTGTCTTTCACCATCACTGGAGATAACACCAAATGGAACGAAAAT

CAGAATCCTCGGATGTTTCTGGCCATGATCACATATATGACCAGAAATCAGCCCGAATGGTTCAGAAATGTGCTGAGTAT

TGCTCCAATTATGTTCTCAAACAAAATGGCCAGACTGGGAAAAGGGTATATGTTTGAGAGCAAGAGTATGAAACTGAGAA

CTCAGATTCCTGCAGAAATGCTGGCAAGCATCGATCTGAAATATTTCAATGATTCAACAAGAAAGAAGATTGAAAAAATC

CGACCCCTCCTGATTGAGGGGACTGCATCACTGAGCCCTGGAATGATGATGGGCATGTTCAATATGCTGAGCACTGTGCT

GGGCGTCTCCATCCTGAATCTGGGACAGAAGAGATACACCAAGACTACTTACTGGTGGGATGGTCTGCAGTCCTCTGACG

ATTTTGCTCTGATTGTGAATGCACCCAATCATGAAGGGATTCAGGCCGGAGTCGACAGGTTTTATCGAACCTGTAAGCTG

CTGGGAATCAATATGAGCAAGAAAAAGTCTTACATCAACAGAACAGGTACATTTGAATTCACAAGTTTTTTCTATCGCTA

TGGGTTTGTGGCCAATTTCAGCATGGAGCTGCCCAGTTTTGGGGTGTCTGGGATCAACGAGTCAGCCGACATGAGTATTG

GAGTGACTGTCATCAAAAACAATATGATCAACAATGATCTGGGTCCAGCAACAGCTCAGATGGCCCTGCAGCTGTTCATC

AAAGATTACAGGTACACCTACCGATGCCATATCGGTGACACACAGATTCAGACCCGAAGATCATTTGAAATCAAGAAACT

GTGGGAGCAGACCCGCTCCAAAGCTGGACTGCTGGTCTCCGACGGAGGCCCAAATCTGTACAACATTAGAAATCTCCACA

TTCCTGAAGTCTGCCTGAAATGGGAACTGATGGATGAGGATTACCAGGGGCGCCTGTGCAACCCACTGAACCCATTTGTC

AGCCATAAAGAAATTGAATCAATGAACAATGCAGTGATGATGCCAGCACATGGTCCAGCCAAAAACATGGAGTATGATGC

TGTGGCAACAACACACTCCTGGATCCCCAAAAGAAATCGATCCATCCTGAATACAAGTCAGAGAGGAGTGCTGGAGGATG

AACAGATGTACCAGAGGTGCTGCAATCTGTTTGAAAAATTCTTCCCCAGCAGTTCATACAGAAGACCAGTCGGGATCTCC

AGTATGGTGGAGGCTATGGTGTCCAGAGCCCGAATTGATGCACGGATTGATTTCGAATCTGGAAGGATCAAGAAAGAAGA

GTTCACTGAGATCATGAAGATCTGTTCCACCATTGAAGAGCTCAGACGGCAAAAATAGTGAATTTAGCTTGTCCTTCATG

AAAAAATGCCTTGTTTCTACT (SEQ ID NO:12)

AGCGAAAGCAGGTACTGATCCAAAATGGAAGATTTTGTGCGACAATGCTTCAATCCGATGATTGTCGAGCTTGCGGAAAA
AACAATGAAAGAGTATGGGGAGGACCTGAAAATCGAAACAAACAAATTTGCAGCAATATGCACTCACTTGGAAGTATGCT
TCATGTATTCAGATTTTCACTTCATCAATGAGCAAGGCGAGTCAATAATCGTAGAACTTGGTGATCCAAATGCACTTTTG
AAGCACAGATTTGAAATAATCGAGGGAAGAGATCGCACAATGGCCTGGACAGTAGTAAACAGTATTTGCAACACTACAGG
GGCTGAGAAACCAAAGTTTCTACCAGATTTGTATGATTACAAGGAGAATAGATTCATCGAAATTGGAGTAACAAGGAGAG
AAGTTCACATATACTATCTGGAAAAGGCCAATAAAATTAAATCTGAGAAAACACACATCCACATTTTCTCGTTCACTGGG
GAAGAAATGGCCACAAAGGCAGACTACACTCTCGATGAAGAAAGCAGGGCTAGGATCAAAACCAGACTATTCACCATAAG
ACAAGAAATGGCCAGCAGAGGCCTCTGGGATTCCTTTCGTCAGTCCGAGAGAGGAGAAGAGACAATTGAAGAAAGGTTTG
AAATCACAGGAACAATGCGCAAGCTTGCCGACCAAAGTCTCCCGCCGAACTTCTCCAGCCTTGAAAATTTTAGAGCCTAT
GTGGATGGATTCGAACCGAACGGCTACATTGAGGGCAAGCTGTCTCAAATGTCCAAAGAAGTAAATGCTAGAATTGAACC
TTTTTTGAAAACAACACCACGACCACTTAGACTTCCGAATGGGCCTCCCTGTTCTCAGCGGTCCAAATTCCTGCTGATGG
ATGCCTTAAAATTAAGCATTGAGGACCCAAGTCATGAAGGAGAGGGAATACCGCTATATGATGCAATCAAATGCATGAGA
ACATTCTTTGGATGGAAGGAACCCAATGTTGTTAAACCACACGAAAAGGGAATAAATCCAAATTATCTTCTGTCATGGAA
GCAAGTACTGGCAGAACTGCAGGACATTGAGAATGAGGAGAAAATTCCAAAGACTAAAAATATGAAGAAAACAAGTCAGC
TAAAGTGGGCACTTGGTGAGAACATGGCACCAGAAAAGGTAGACTTTGACGACTGTAAAGATGTAGGTGATTTGAAGCAA
TATGATAGTGATGAACCAGAATTGAGGTCGCTTGCAAGTTGGATTCAGAATGAGTTTAACAAGGCATGCGAACTGACAGA
TTCAAGCTGGATAGAGCTCGATGAGATTGGAGAAGATGTGGCTCCAATTGAACACATTGCAAGCATGAGAAGGAATTATT
TCACATCAGAGGTGTCTCACTGCAGAGCCACAGAATACATAATGAAGGGAGTGTACATCAATACTGCCTTGCTTAATGCA
TCTTGTGCAGCAATGGATGATTTCCAATTAATTCCAATGATAAGCAAGTGTAGAACTAAGGAGGGAAGGCGAAAGACCAA
CTTGTATGGTTTCATCATAAAAGGAAGATCCCACTTAAGGAATGACACCGACGTGGTAAACTTTGTGAGCATGGAGTTTT
CTCTCACTGACCCAAGACTTGAACCACATAAATGGGAGAAGTACTGTGTTCTTGAGATAGGAGATATGCTTATAAGAAGT
GCCATAGGCCAGGTTTCAAGGCCCATGTTCTTGTATGTGAGAACAAATGGAACCTCAAAAATTAAAATGAAATGGGGAAT
GGAGATGAGGCGTTGCCTCCTCCAGTCACTTCAACAAATTGAGAGTATGATTGAAGCTGAGTCCTCTGTCAAAGAGAAAG
ACATGACCAAAGAGTTCTTTGAGAACAAATCAGAAACATGGCCCATTGGAGAGTCCCCCAAAGGAGTGGAGGAAAGTTCC
ATTGGGAAGGTCTGCAGGACTTTATTAGCAAAGTCGGTATTCAACAGCTTGTATGCATCTCCACAACTAGAAGGATTTTC
AGCTGAATCAAGAAAACTGCTTCTTATCGTTCAGGCTCTTAGGGACAACCTGGAACCTGGGACCTTTGATCTTGGGGGGC
TATATGAAGCAATTGAGGAGTGCCTGATTAATGATCCCTGGGTTTTGCTTAATGCTTCTTGGTTCAACTCCTTCCTTACA
CATGCATTGAGTTAGTTGTGGCAGTGCTACTATTTGCTATCCATACTGTCCAAAAAAGTACCTTGTTTCTACT (SEQ ID NO:1)

FIG. 10F (Continued)

Canine codon optimized PR8 PA:

AGCGAAAGCAGGTACTGATCCAAAATGGAAGATTTTGTGCGACAATGCTTCAATCCGATGATTGTCGAGCTTGCGGAAAA
AACAATGAAAGAGTATGGGGAGGACCTGAAAATCGAAACAAACAAATTTGCAGCAATATGCACTCACTTGGAAGTATGCT
TCATGTATTCAGATTTTCACTTCATCAATGAGCAAGGCGAGTCAATAATCGTAGAACTTGGTGATCCAAATGCACTTTTG
AAGCACAGATTTGAAATAATCGAGGGAAGAGATCGCACAATGGCCTGGACAGTAGTAAACAGTATTTGCAACACTACAGG
GGCTGAGAAACCAAAGTTTCTACCAGATTTGTATGATTACAAGGAGAATAGATTCATCGAAATTGGAGTAACAAGGAGAG
AAGTTCACATATACTATCTGGAAAAGGCCAATAAAATTAAATCTGAGAAAACACACATCCACATTTTCTCGTTCACTGGG
GAAGAAATGGCCACAAAGGCAGACTACACTCTCGATGAAGAAAGCAGGGCTAGGATCAAAACCAGACTATTCACCATAAG
ACAAGAAATGGCCAGCAGAGGCCTCTGGGATTCCTTTCGTCAGTCCGAGAGAGGAGAAGAGACAATTGAAGAAAGGTTTG
AAATCACAGGAACAATGCGCAAGCTTGCCGACCAAAGTCTCCCGCCGAACTTCTCCAGCCTTGAAAATTTTAGAGCCTAT
GTGGATGGATTCGAACCGAACGGCTACATTGAGGGCAAGCTGTCTCAAATGTCCAAAGAAGTAAATGCTAGAATTGAACC
TTTTCTGAAAACAACACCACGACCACTGAGACTGCCCAATGGGCCTCCCTGTTCTCAGCGGTCCAAATTCCTGCTGATGG
ATGCCCTGAAACTGAGCATTGAGGACCCAAGTCATGAAGGAGAGGGAATTCCCCTGTATGATGCAATCAAATGCATGAGA
ACATTCTTTGGATGGAAGGAACCCAATGTGGTGAAACCACACGAAAAGGGAATCAATCCAAATTATCTGCTGTCATGGAA
GCAGGTGCTGGCAGAACTGCAGGACATTGAGAATGAGGAGAAAATTCCAAAGACTAAAAATATGAAGAAAACAAGTCAGC
TGAAGTGGGCACTGGGTGAGAACATGGCACCAGAAAAGGTGGACTTTGACGACTGTAAAGATGTGGGTGATCTGAAGCAG
TATGATAGTGATGAACCAGAACTGAGGTCCCTGGCAAGTTGGATTCAGAATGAGTTTAACAAGGCATGCGAACTGACAGA
TTCAAGCTGGATTGAGCTCGATGAGATTGGAGAAGATGTGGCTCCAATTGAACACATTGCAAGCATGAGAAGGAATTATT
TCACATCAGAGGTGTCTCACTGCAGAGCCACAGAATACATCATGAAGGGAGTGTACATCAATACTGCCCTGCTGAATGCA
TCTTGTGCAGCAATGGATGATTTCCAGCTGATTCCAATGATCAGCAAGTGTAGAACTAAGGAGGGAAGGCGAAAGACCAA
CCTGTATGGTTTCATCATCAAAGGAAGATCCCACCTGAGGAATGACACCGACGTGGTGAACTTTGTGAGCATGGAGTTTT
CTCTCACTGACCCAAGACTGGAACCACATAAATGGGAGAAGTACTGTGTGCTGGAGATTGGAGATATGCTGATCAGAAGT
GCCATTGGCCAGGTGTCAAGGCCCATGTTCCTGTATGTGAGAACAAATGGAACCTCAAAAATTAAAATGAAATGGGGAAT
GGAGATGAGGCGCTGCCTCCTCCAGTCACTGCAGCAGATTGAGAGTATGATTGAAGCTGAGTCCTCTGTCAAAGAGAAAG
ACATGACCAAAGAGTTCTTTGAGAACAAATCAGAAACATGGCCCATTGGAGAGTCCCCCAAAGGAGTGGAGGAAAGTTCC
ATTGGGAAGGTCTGCAGGACTCTGCTGGCAAAGTCCGTGTTCAACAGCCTGTATGCATCTCCACAGCTGGAAGGATTTTC
AGCTGAATCAAGAAAACTGCTGCTGATCGTGCAGGCTCTGAGGGACAACCTGGAACCTGGGACCTTTGATCTGGGGGGGC
TGTATGAAGCAATTGAGGAGTGCCTGATTAATGATCCCTGGGTGCTGCTGAATGCTTCTTGGTTCAACTCCTTCCTTACA
CATGCATTGAGTTAGTTGTGGCAGTGCTACTATTTGCTATCCATACTGTCCAAAAAAGTACCTTGTTTCTACT (SEQ ID NO:11)

AGCAAAAGCAGGGTAGATAATCACTCACTGAGTGACATCAAAATCATGGCGTCTCAAGGCACCAAACGATCTTACGAACA
GATGGAGACTGATGGAGAACGCCAGAATGCCACTGAAATCAGAGCATCCGTCGGAAAAATGATTGGTGGAATTGGACGAT
TCTACATCCAAATGTGCACCGAACTCAAACTCAGTGATTATGAGGGACGGTTGATCCAAAACAGCTTAACAATAGAGAGA
ATGGTGCTCTCTGCTTTTGACGAAAGGAGAAATAAATACCTTGAAGAACATCCCAGTGCGGGGAAAGATCCTAAGAAAAC
TGGAGGACCTATATACAGGAGAGTAAACGGAAAGTGGATGAGAGAACTCATCCTTTATGACAAAGAAGAAATAAGGCGAA
TCTGGCGCCAAGCTAATAATGGTGACGATGCAACGGCTGGTCTGACTCACATGATGATCTGGCATTCCAATTTGAATGAT
GCAACTTATCAGAGGACAAGAGCTCTTGTTCGCACCGGAATGGATCCCAGGATGTGCTCTCTGATGCAAGGTTCAACTCT
CCCTAGGAGGTCTGGAGCCGCAGGTGCTGCAGTCAAAGGAGTTGGAACAATGGTGATGGAATTGGTCAGAATGATCAAAC
GTGGGATCAATGATCGGAACTTCTGGAGGGGTGAGAATGGACGAAAAACAAGAATTGCTTATGAAAGAATGTGCAACATT
CTCAAAGGGAAATTTCAAACTGCTGCACAAAAAGCAATGATGGATCAAGTGAGAGAGAGCCGGAACCCAGGGAATGCTGA
GTTCGAAGATCTCACTTTTCTAGCACGGTCTGCACTCATATTGAGAGGGTCGGTTGCTCACAAGTCCTGCCTGCCTGCCT
GTGTGTATGGACCTGCCGTAGCCAGTGGGTACGACTTTGAAAGGGAGGGATACTCTCTAGTCGGAATAGACCCTTTCAGA
CTGCTTCAAAACAGCCAAGTGTACAGCCTAATCAGACCAAATGAGAATCCAGCACACAAGAGTCAACTGGTGTGGATGGC
ATGCCATTCTGCCGCATTTGAAGATCTAAGAGTATTAAGCTTCATCAAAGGGACGAAGGTGCTCCCAAGAGGGAAGCTTT
CCACTAGAGGAGTTCAAATTGCTTCCAATGAAAATATGGAGACTATGGAATCAAGTACACTTGAACTGAGAAGCAGGTAC
TGGGCCATAAGGACCAGAAGTGGAGGAAACACCAATCAACAGAGGGCATCTGCGGGCCAAATCAGCATACAACCTACGTT
CTCAGTACAGAGAAATCTCCCTTTTGACAGAACAACCATTATGGCAGCATTCAATGGGAATACAGAGGGGAGAACATCTG
ACATGAGGACCGAAATCATAAGGATGATGGAAAGTGCAAGACCAGAAGATGTGTCTTTCCAGGGGCGGGGAGTCTTCGAG
CTCTCGGACGAAAAGGCAGCGAGCCCGATCGTGCCTTCCTTTGACATGAGTAATGAAGGATCTTATTTCTTCGGAGACAA
TGCAGAGGAGTACGACAATTAAAGAAAAATACCCTTGTTTCTACT (SEQ ID NO:4)

FIG. 10F (Continued)

Canine codon optimized NP:

AGCAAAAGCAGGGTAGATAATCACTCACTGAGTGACATCAAAATCATGGCGTCTCAAGGCACCAAACGATCTTACGAACA
GATGGAGACTGATGGAGAACGCCAGAATGCCACTGAAATCAGAGCATCCGTCGGAAAAATGATTGGTGGAATTGGACGAT
TCTACATCCAGATGTGCACCGAACTCAAACTCAGTGATTATGAGGGACGGCTGATCCAGAACAGCCTGACAATCGAGAGA
ATGGTGCTCTCTGCTTTTGACGAAAGGAGAAATAAATACCTGGAAGAACATCCCAGTGCCGGGAAAGATCCTAAGAAAAC
TGGAGGACCTATCTACAGGAGAGTGAACGGAAAGTGGATGAGAGAACTCATCCTGTATGACAAAGAAGAAATCAGGCGAA
TCTGGCGCCAGGCTAATAATGGTGACGATGCAACCGCTGGTCTGACTCACATGATGATCTGGCATTCCAATCTGAATGAT
GCAACTTATCAGAGGACAAGAGCTCTGGTGCGCACCGGAATGGATCCCAGGATGTGCTCTCTGATGCAGGGTTCAACTCT
CCCTAGGAGGTCTGGAGCCGCAGGTGCTGCAGTCAAAGGAGTGGGAACAATGGTGATGGAACTGGTCAGAATGATCAAAA
GAGGGATCAATGATCGGAACTTCTGGAGGGGTGAGAATGGACGAAAAACAAGAATTGCTTATGAAAGAATGTGCAACATT
CTCAAAGGGAAATTTCAGACTGCTGCACAGAAAGCAATGATGGATCAGGTGAGAGAGAGCCGGAACCCAGGGAATGCTGA
GTTCGAAGATCTCACTTTTCTGGCACGGTCTGCACTCATCCTGAGAGGGTCCGTGGCTCACAAGTCCTGCCTGCCTGCCT
GTGTGTATGGACCTGCCGTGGCCAGTGGGTACGACTTTGAAAGGGAGGGATACTCTCTGGTCGGAATTGACCCTTTCAGA
CTGCTGCAGAACAGCCAGGTGTACAGCCTGATCAGACCAAATGAGAATCCAGCACACAAGAGTCAGCTGGTGTGGATGGC
ATGCCATTCTGCCGCATTTGAAGATCTGAGAGTGCTGAGCTTCATCAAAGGGACCAAGGTGCTCCCAAGAGGGAAGCTGT
CCACTAGAGGAGTGCAGATTGCTTCCAATGAAAATATGGAGACTATGGAATCAAGTACACTGGAACTGAGAAGCAGGTAC
TGGGCCATCAGGACCAGAAGTGGAGGAAACACCAATCAGCAGAGGGCATCTGCCGGCCAGATCAGCATTCAGCCTACCTT
CTCAGTGCAGAGAAATCTCCCTTTTGACAGAACAACCATTATGGCAGCATTCAATGGGAATACAGAGGGGAGAACATCTG
ACATGAGGACCGAAATCATCAGGATGATGGAAAGTGCAAGACCAGAAGATGTGTCTTTCCAGGGGCGGGGAGTCTTCGAG
CTCTCGGACGAAAAGGCAGCGAGCCCGATCGTGCCTTCCTTTGACATGAGTAATGAAGGATCTTATTTCTTCGGAGACAA
TGCAGAGGAGTACGACAATTAAAGAAAAATACCCTTGTTTCTACT (SEQ ID NO:14)

Figure 11 A Nucleotide mutation in position 4 of each gene of PR8 and Indo/NC/09.

| Genes | Position 4 of vRNA |
|---|---|
| PR8 PB2 | C |
| PR8 PB1 | C |
| PR8 PA | C |
| PR8 NP | U |
| PR8 M | U |
| PR8 NS | U |
| Inda/NC/09 HA | U |
| Inda/NC/09 NA | U |

Figure 11B All 3'C4U mutant

| Genes | Position 4 of vRNA | |
|---|---|---|
| PR8 PB2 | | U |
| PR8 PB1 | | U |
| PR8 PA | | U |
| PR8 NP | | U |
| PR8 M | | U |
| PR8 NS | | U |
| Inda/NC/09 HA | | U |
| Inda/NC/09 NA | | U |

Figure 11C Growth kinetics of 3' C4U mutant

Figure 12

HA
atgaacactcaaatcctggtattcgctctgattgcgatcattccaacaaatgcagacaaaatctgcctcggacatcatgccgtgtcaaacggaaccaaagtaaa
cacattaactgaaagaggagtggaagtcgtcaatgcaactgaaacagtggaacgaacaaacatccccaggatctgctcaaaagggaaaaggacagttgacc
tcggtcaatgtggactcctggggacaatcactggaccacctcaatgtgaccaattcctagaattttcagccgatttaattattgagaggcgagaaggaagtgatg
tctgttatcctggggaaattcgtgaatgaagaagctctgaggcaaattctcagagaatcaggcggaattgacaaggaagcaatgggattcacatacagtggaat
aagaactaatggagcaaccagtgcatgtaggagatcaggatcttcattctatgcagaaatgaaatggctcctgtcaaacacagataatgctgcattcccgcaga
tgactaagtcatatataaaaatacaagaaaaagcccagctctaatagtatggggdatccatcattccgtatcaactgcagagcaaaccaagctatatgggagtgg
aaacaaactggtgacagttggggagttctaattatcaacaatcttttgtaccgagtccaggagcgagaccacaagttaatggtctatctggaagaattgactttcat
tggctaatgctaaatcccaatgatacagtcactttcagtttcaatggggctttcatagctccagaccgtgcaagcttcctgagaggaaaatctatgggaatccag
agtggagtacaggttgatgccaattgtgaaggggactgctatcatagtggaggacaataataagtaacttgccatttcagaacatagatagcagggcagttg
gaaaatgtccgagatatgttaagcaaaggagtctgctgctagcaacagggatgaagaatgttcctgagattcaaagggaagaggcctatttggtgctatagc
gggtttcattgaaaatggatgggaaggcctaattgatggttggtatgtttcagacaccagaatgcacagggagagggaactgctgcagattacaaagcact
caatcggcaattgatcaaataacaggaaaattaaaccggcttatagaaaaaaccaaccaacaatttgagttgatagacaatgaattcaatgaggtagagaag
caaatcggtaatgtgataaattggaccagagattctataacagaagtgtggtcatacaatgctgaactcttggtagcaatggagaaccagcatacaattgatct
ggctgattcagaaatggacaaactgtacgaacgagtgaaaagacagctgagagagaatgctgaagaagatggcactggttgctttgaaatatttcacaagtgt
gatgatgactgtatggccagtattagaaataacacctatgatcacagcaaatacagggaagaggcaatgcaaaatagaatacagattgacccagtcaaacta
agcagcggctacaaagatgtgatactttggtttagcttcggggcatcatgtttcat

FIG. 12 CONT

EGKILKWESLTGTAKHIEECSCYGERTGITCTCRDNWQGSNRPVIQIDPVAMTHTSQYICSPVLTDNPRPNDPNIGKCNDPYPG
NNNNGVKGFSYLDGANTWLGRTISTASRSGYEMLKVPNALTDDRSKPIQGQTIVLNADWSGYSGSFMDYWAEGDCYRACFY
VELIRGRPKEDKVWWTSNSIVSMCSSTEFLGQWNWPDGAKIEYFL (SEQ ID NO:20)

HA
atgaacactcaaatcctggtattcgctctgattgcgatcattccaacaaatgcagacaaaatctgcctcggacatcatgctgtgtcaaacggaaccaaagtaaa
cacattaactgaaagaggagtggaagtcgtcaatgcaactgaaacagtggaacgaacaaacatccccaggatctgctcaaaagggaaaaggacagttgacc
tcggtcaatgtggactcctggggacaatcactggaccacctcaatgtgaccaattcctagaattttcagccgatttaattattgagaggcgagaaggaagtgatg
tctgttatcctgggaaattcgtgaatgaagaagctctgaggcaaattctcagagaatcaggcggaattgacaaggaagcaatgggattcacatacagtggaat
aagaactaatggagcaaccagttcatgtaggagatcaggatcttcattctatgcagaaatgaaatggctcctgtcaaacacagataatgctgcattcccgcaga
tgactaagtcatataaaaatacaagaaaaaacccagctctaatagtatggggatccatcattccggatcaactgcagagcaaaccaagctatatgggagtgg
aaacaaactggtgacagttggggagttctaattatcaacaatcttttgtaccgagtccgggagcgagaacacaagttaatggtcaatctggaagaattgacttca
ttggctaatgctaaatcccaatgatacagtcacttcagtttcaatggggcttcatagctccagaccgtgcaagcttcctgagaggaaaatctatgggaatccag
agtggagtacaggttgatgccgattgtgaaggggactgctattatagtggaggacaataataagtaacttgccattcagaacatagatagcagggcagttgg
aaaatgtccgagatatgttaagcaaaggagtctgctgctagcaacagggatgaagaatgttcctgagattccaaagggaagaggcctatttggtgctatagcg
ggtttcattgaaaatggatgggaaggcctaattgatggttggtatggtttcagacaccagaatgcacaggagagggaactgctgcagattacaaaagcactc
aatcggcaattgatcaaataacaggaaaattaaaccggcttatagaaaaaaccaaccaacaatttgagttgatagacaatgaattcactgaggtagagaagc
aaatcggtaatgtgataaaattggaccagagattctataacagaagtgtggtcatacaatgctgaactcttggtagcaatggagaaccagcatacaatigatctg
gctgattcagaaatggacaaactgtacgaacgagtgaaaagacagctgagagagaatgctgaagaagatggcactggttgctttgaaatatttcacaagtgtg
atgatgactgtatggccagcattagaaataacacctatgatcacagcaaatacagggaagaggcaatgcaaaatagaatacagattgacccagtcaaactaa
gcagcggctacaaagatgtgatactttggtttagcttcggggcatcatgtttcatacttctagccattgcaatgggccttgtcttcatatgtgtaaagaatggaaac
atgcggtgcactatttgtatataa (SEQ ID NO:21)

MNTQILVFALIAIIPTNADKICLGHHAVSNGTKVNTLTERGVEVVNATETVERTNIPRICSKGKRTVDLGQCGLLGTITGPPQCDQ
FLEFSADLIIERREGSDVCYPGKFVNEEALRQILRESGGIDKEAMGFTYSGIRTNGATSSCRRSGSSFYAEMKWLLSNTDNAAFP
QMTKSYKNTRKNPALIVWGIHHSGSTAEQTKLYGSGNKLVTVGSSNYQQSFVPSPGARTQVNGQSGRIDFHWLMLNPNDTV
TFSFNGAFIAPDRASFLRGKSMGIQSGVQVDADCEGDCYYSGGTIISNLPFQNIDSRAVGKCPRYVKQRSLLLATGMKNVPEIP
KGRGLFGAIAGFIENGWEGLIDWYGFRHQNAQGEGTAADYKSTQSAIDQITGKLNRLIEKTNQQFELIDNEFTEVEKQIGNVI
NWTRDSITEVWSYNAELLVAMENQHTIDLADSEMDKLYERVKRQLRENAEEDGTGCFEIFHKCDDDCMASIRNNTYDHSKYR
EEAMQNRIQIDPVKLSSGYKDVILWFSFGASCFLLAIAMGLVFICVKNGNMRCTICI (SEQ ID NO:22)

NA
atgaatccaaatcagaagattctatgcacttcagccactgctatcataataggcgcaatcgcagtactcattggaatagcaaacctaggattgaacataggact
gcatctaaaaccgagctgcaattgctcacactcacaacctgaaacaaccaacacaagccaaacaataataaacaactattataatgaaacaaacatcaccaa
catccaaatggaagagagaacaagcaggaatttcaataacttaactaaagggctctgtactataaattcatggcacatatatgggaaagacaatgcggtaaga
attggagagagctcggatgttttagtcacaagagaaccctatgtttcatgcgacccagatgaatgcaggttctatgctctcagccaaggaacaacaatcagagg
aaaacactcaaacggaacaatacacgataggtccagtatcgcgccctgataagctggccactatcatcaccgcccacagtgtacaacagcagggtggaatg
cattgggtggtcaagtactagttgccatgatggcaaatccaggatgtcaaatgtatatcaggaccaaacaacaatgcatctgcagtagtatggtacaacagaa
ggcctgttgcagaaattaacacatgggcccgaaacatactaagaacacaggaaatgtgtatgccacaacggcgtatgcccagtagtgttcaccgatgg
gtctgccactggacctgcagacacaagaatatatattttaaagaggggaaaatattgaaatgggagtctctgactggaactgctaagcatatattgaagaatgct
catgttacggggaacgaacaggaattacctgcacatgcaaggacaattggcagggctcaaatagaccagtgattcagatagatccagtagcaatgacacaca
ctagtcagtatatatgcagtcctgttcttacagacaatccccgaccgaatgacccaaatataggtaagtgtaatgaccccttatccaggtaataataacaatggag
tcaagggattctcatacctggatggggctaacacttggctaggaggacaataagcacagcctcgaggtctggatacgagatgttaaaagtgccaaatgcatt
gacagatgatagatcaaagccccattcaaggtcagacaattgtattaaacgctgactggagtggttacagtggatctttcatggactattgggctgaggggact
gctatcgagcgtgtttttatgtggaattgatacgtggaagacccaaggaggataagtgtggtggaccagcaatagtatagtatcgatgtgttccagtacagaat
tcctgggacaatggaactggcctgatggggctaaaatagagtacttcctctaa (SEQ ID NO:23)

MNPNQKILCTSATAIIIGAIAVLIGIANLGLNIGLHLKPSCNCSHSQPETTNTSQTIINNYYNETNITNIQMEERTSRNFNNLTKGL
CTINSWHIYGKDNAVRIGESSDVLVTREPYVSCDPDECRFYALSQGTTIRGKHSNGTIHDRSQYRALISWPLSSPPTVYNSRVECI
GWSSTSCHDGKSRMSICISGPNNNASAVVWYNRRPVAEINTWARNILRTQESECVCHNGVCPVVFTDGSATGPADTRIYYFK

FIG. 12 CONT

EGKILKWESLTGTAKHIEECSCYGERTGITCTCKDNWQGSNRPVIQIDPVAMTHTSQYICSPVLTDNPRPNDPNIGKCNDPYPG
NNNNGVKGFSYLDGANTWLGRTISTASRSGYEMLKVPNALTDDRSKPIQGQTIVLNADWSGYSGSFMDYWAEGDCYRACFY
VELIRGRPKEDKVWWTSNSIVSMCSSTEFLGQWNWPDGAKIEYFL (SEQ ID NO:24)

Figure 13A Construct chimeric HA &NA to increase virus replication

Chimeric HA: 3' NCR SignalP — Ectodomain — TM — Tail — 5' NCR, 1775bp
positions: 1, 18, 531, 556, 565

Chimeric NA #1: 3' NCR — TM — Stalk — Ectodomain — 5' NCR, 1458bp
positions: 7, 38, 87

Chimeric NA #2: 3' NCR — TM — Stalk — Ectodomain — 5' NCR, 1413bp
positions: 7, 38, 71

Legend:
- A/PR/8/34 NA
- A/Goose/GD/1/96 NA: long stalk, 20 aa longer than Indo/NC/09 NA.
- A/CK/Indo/NC/09 NA

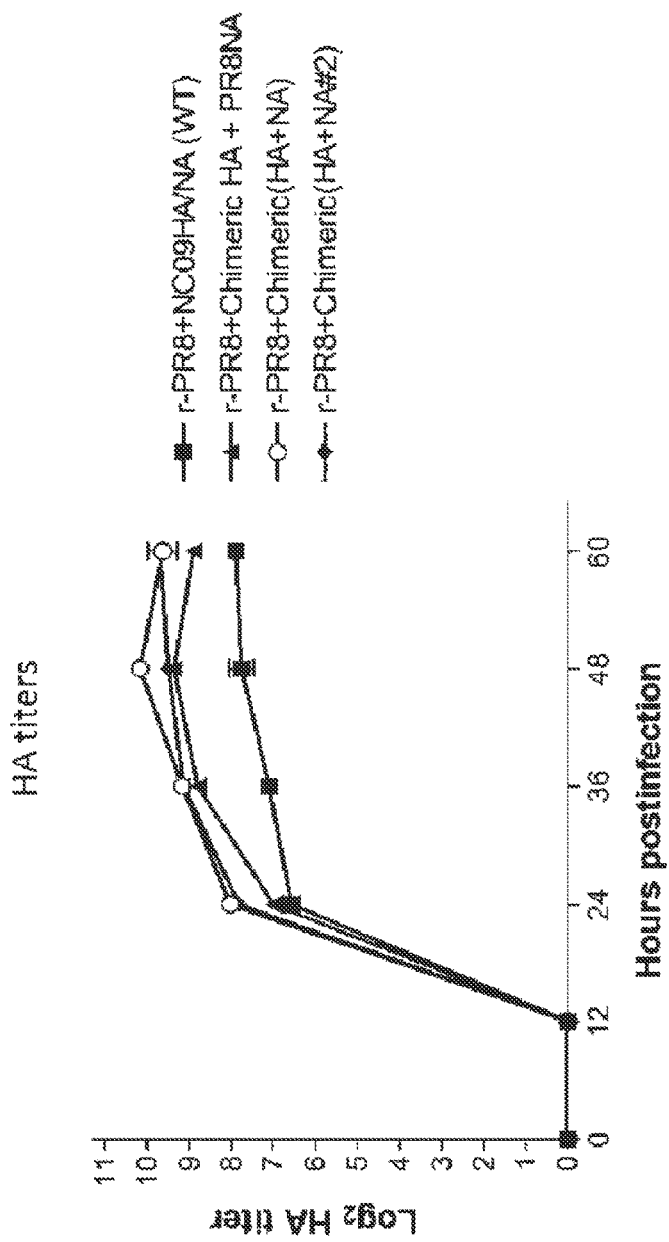
Figure 13B Growth kinetics in MDCK cells

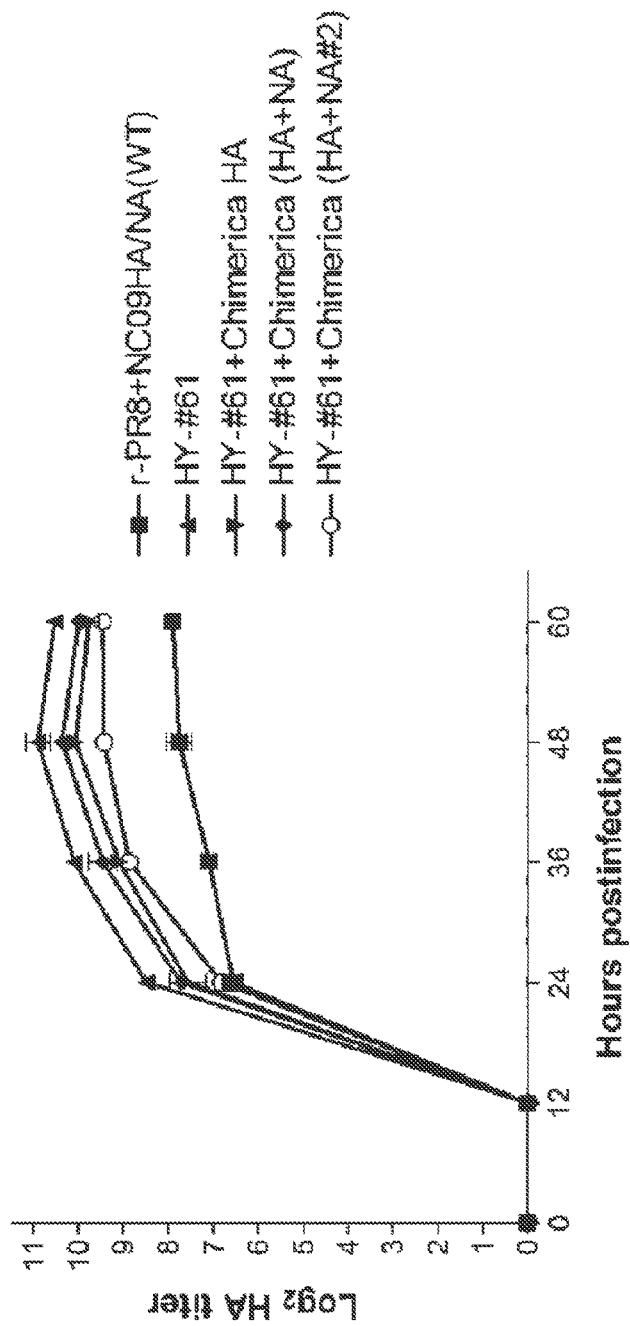

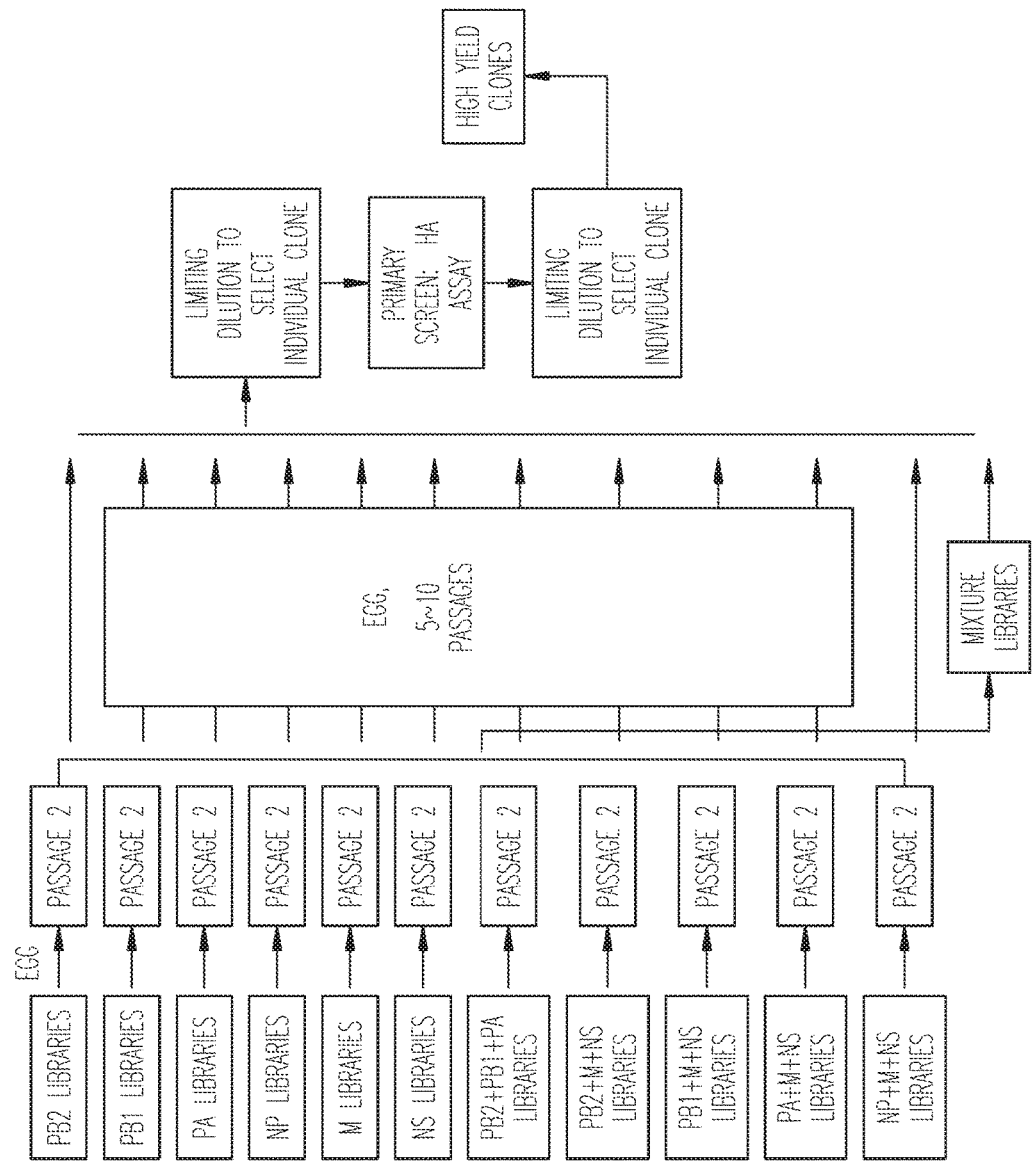
Figure 15 Schematic diagram of screening high growth mutations in eggs.

Figure 16 Summary of HA assay of individual clones purified from Vero cells

| Groups | Numbers of clone | Fold change | % |
|---|---|---|---|
| WT HA titer = $2^{6.5}$ | 5 | - | 2.3% |
| HA titer = $2^{>9-9.5}$ | 16 | >5.6 | 7.4% |
| HA titer = $2^{>8-9}$ | 91 | >2.8-5.6 | 42.2% |
| HA titer = $2^{6.5-8}$ | 80 | 1 - 2.8 | 37.0% |
| HA titer < $2^{6.5}$ | 24 | <1 | 11.1% |
| Total | 216 | - | 100% |

Figure 17Recombinant viruses generated with different PR8 backbone mutants.

| # | Del-HA & NA genes | PB2 | PB1 | PA | NP | M | NS |
|---|---|---|---|---|---|---|---|
| WT | CK/Indo/NC/09 | WT | WT | WT | WT | WT | WT |
| HY-1 | | I504V | M40L G180W | R401K | I116L | WT | A30P R118K |
| HY-2 | | E391Q | | I30T E31K K142N | R74K S377N | WT | S161T |
| HY-3 | | I504V | | K142N | I116L | V97A Y100H | V136M S161T |
| HY-4 | | M202L F323L | | K356R | I116L | V97A Y100H | K55E |
| HY-5 | | | | K356R | R422L | WT | K55E |

Flow chart of high yield candidate vaccine viruses in MDCK and Vero cells

```
┌─────────────────────┐      ┌─────────────────────┐
│ Generate PR8        │      │ Test mutations      │
│ internal gene       │      │ described in the    │
│ random mutant       │      │ literature to       │
│ virus libraries     │      │ increase virus      │
└─────────────────────┘      │ replication and     │
          │                  │ polymerase activity │
          │ Consecutively    │ in cell culture     │
          │ passage 12       └─────────────────────┘
          │ times in MDCK cells         │
          ▼                             ▼
┌─────────────────────┐      ┌─────────────────────┐
│ Plaque purification,│      │ 14 high growth      │
│ then HA assay to    │      │ mutations were      │
│ identify high HA    │      │ confirmed           │
│ titer clones        │      └─────────────────────┘
└─────────────────────┘                 │
          │                             │
          ▼                             │
┌─────────────────────┐                 │
│ Sequencing to       │                 │
│ confirm high HA     │                 │
│ titer mutations     │                 │
└─────────────────────┘                 │
                    │                   │
                    └─────────┬─────────┘
                              ▼
                  ┌─────────────────────┐
                  │ Mix these mutations,│
                  │ select high growth  │
                  │ variant             │
                  └─────────────────────┘
                      │              │
         ┌────────────┘              └────────────┐
         ▼                                         ▼
┌─────────────────────┐     Or        ┌─────────────────────┐
│ Introduce canine    │               │ Promoter C4U        │
│ codon optimized     │               │ mutations           │
│ internal genes      │               │                     │
└─────────────────────┘               └─────────────────────┘
         │                                         │
         ▼                                         ▼
       MDCK                                       Vero
```

HIGH TITER RECOMBINANT INFLUENZA VIRUSES WITH ENHANCED REPLICATION IN MDCK OR VERO CELLS OR EGGS

CROSS-REFERENCE TO RELATED APPLICATIONS

This application claims the benefit of the filing date of U.S. application Ser. No. 61/846,460, filed on Jul. 15, 2013, the disclosure of which is incorporated by reference herein.

STATEMENT OF GOVERNMENT RIGHTS

This invention was made with government support under AI070010 and HHSN266200700010C awarded by the National Institutes of Health. The government has certain rights in the invention.

BACKGROUND

Influenza is a major respiratory disease in some mammals including horses and is responsible for substantial morbidity and economic losses each year. In addition, influenza virus infections can cause severe systemic disease in some avian species, leading to death. The segmented nature of the influenza virus genome allows for reassortment of segments during virus replication in cells infected with two or more influenza viruses. The reassortment of segments, combined with genetic mutation and drift, can give rise to a myriad of divergent strains of influenza virus over time. The new strains exhibit antigenic variation in their hemagglutinin (HA) and/or neuraminidase (NA) proteins, and in particular the gene coding for the HA protein has a high rate of variability. The predominant current practice for the prevention of flu is vaccination. As the influenza HA protein is the major target antigen for the protective immune responses of a host to the virus and is highly variable, the isolation of influenza virus and the identification and characterization of the HA antigen in viruses associated with recent outbreaks is important for vaccine production. Based on prevalence and prediction, a vaccine is designed to stimulate a protective immune response against the predominant and expected influenza virus strains (Park et al., 2004).

There are three general types of influenza viruses, Type A, Type B and Type C, which are defined by the absence of serological crossreactivity between their internal proteins. Influenza Type A viruses are further classified into subtypes based on antigenic and genetic differences of their glycoproteins, the HA and NA proteins. Most of all the known HA and NA subtypes (H1 to H17 and N1 to N10) have been isolated from aquatic birds, which are though to act as a natural reservoir for influenza. The H1N1 pandemic virus caused a pandemic in 2009. The first vaccine candidates tested in 2009 did not grow to high titers, demonstrating the need to develop vaccine virus backbones that confer efficient replication to vaccine virus candidates.

SUMMARY OF THE INVENTION

Mutations that increase the replicative ability of viruses in cell culture and/or embryonated chicken eggs are useful to amplify influenza viruses and to establish robust influenza vaccine platforms. Currently, most influenza vaccines are generated in embryonated chicken eggs. Influenza vaccines generated in MDCK cells are now approved for human use in the U.S. and in Europe, and influenza vaccines derived from Vero cells are approved for human use in Europe. Virus libraries possessing random mutations in the 'internal' viral genes (i.e., all viral genes except those encoding the viral surface glycoproteins HA and NA) of a vaccine virus isolate, e.g., UW-PR8, were generated and passaged in MDCK cells. The identified mutations result in higher virus titers in MDCK cells (and may also increase virus titers in Vero cells and/or embryonated chicken eggs), allowing more efficient influenza virus growth and more cost-effective vaccine production. Moreover, previously described mutations increased the replicative ability of UW-PR8 vaccine backbone virus. In addition to mutations in the coding regions of the six internal gene segments, mutations in non-coding regions were observed to increase viral titers, including promoter mutations, for instance, C-to-U mutations at position 4 from the 3' end of the PB2, PB1, and/or PA vRNA segments. The resulting sequences may be also codon-usage optimized, e.g., optimized for expression in mammalian cells such as canine cells or primate cells, or avian cells, e.g., chicken embryos. The mutations can be used in various combinations, with results influenced by the cell line (or egg) in use and the desired level of improvement in the replication of the virus.

The invention provides isolated recombinant, e.g., reassortant, influenza viruses with selected amino acid residues at one or more specified positions in one or more gene segments for PA, PB1, PB2, NP, M (encoding M1 and M2 proteins), and/or NS (encoding NS1 and NS2 proteins), e.g., in selected amino acid residues at specified positions of PB1, PB2 and NS1; PA, PB1, PB2, NP and NS1; PB1, PB2, NP, M, and NS1; PA, PB1, PB2, NP and NS1; or PA, PB1, PB2, NP, M, and NS1, and including HA and NA genes/proteins of interest, e.g., from annual and pandemic strains, which viruses are produced more efficiently and cost-effectively via cell culture (in MDCK or Vero cells) or in embryonated chicken eggs. In one embodiment, the recombinant reassortant influenza virus has an amino acid residue at position 142 in PA that results in enhanced growth in cells including MDCK cells. Vero cells or eggs relative to a corresponding virus with, for instance, a lysine at position 142 in PA, i.e., the residue at position 142 in PA in the PA gene segment in the recombinant influenza virus is not lysine but is a residue that is correlated with enhanced replication in MDCK cells, Vero cells or eggs, as well as optionally selected amino acid residues at one or more specified positions in PB1, PB2, NP, M1 and/or NS1. In one embodiment, the recombinant reassortant influenza virus has an amino acid residue at position 142 in PA that results in enhanced interaction with one or more host proteins in MDCK cells, Vero cells or eggs relative to a corresponding virus with, for instance, a lysine at position 142 in PA. In one embodiment, the recombinant reassortant influenza virus has an asparagine or glutamine at position 142 in PA as well as optionally selected amino acid residues at one or more specified positions in PB1, PB2, NP, M1 and/or NS1. In one embodiment, the recombinant reassortant influenza virus has an amino acid residue at position 247 in PB1 that results in enhanced growth in cells including MDCK cells, Vero cells or eggs relative to a corresponding virus with, for instance, a glutamine at position 247 in PB1, i.e., the residue at position 247 in PB1 in the PB1 gene segment in the recombinant influenza virus is not glutamine but is a residue that is correlated with enhanced replication in MDCK cells, Vero cells or eggs, as well as optionally selected amino acid residues at one or more specified positions PA, PB2, NP, M1 and/or NS1 which have are described herein. In one embodiment, the recombinant reassortant influenza virus has an amino acid residue at position 247 in PB1 that results in enhanced interaction with one or more host proteins in MDCK cells, Vero cells or eggs relative to a corresponding virus with, for instance, a glutamine at position 247 in PB1. In one embodiment, the recombinant reassortant influenza virus has a histidine, arginine or lysine at position 247 in PB1 as well as optionally selected amino acid residues at one or more specified positions PA, PB2, NP, M1 and/or NS1 which are described herein. In one embodiment, the recombinant reassortant influenza virus has an amino acid residue at position 202 and/or position 323 in PB2 that results in enhanced growth in cells including MDCK cells, Vero cells or eggs relative to a corresponding virus with, for instance, a methionine at position 202 or a phenylalanine at position 323 in PB2, i.e., the residue at position 202 and/or 323 in PB2 in the PB2 gene segment in the recombinant influenza virus is not methionine or phenylalanine but is a residue that is correlated with enhanced replication in MDCK cells, Vero cells or eggs, as well as optionally selected amino acid residues at one or more specified positions PA, PB1, NP, M1 and/or NS which are described herein. In one embodiment, the recombinant reassortant influenza virus has an amino acid residue at position 323 in PB2 that results in an altered cap binding interaction relative to a corresponding virus with, for instance, a phenylalanine at position 323 in PB2. In one embodiment, the recombinant reassortant influenza virus has a leucine, alanine, threonine, valine, isoleucine, or glycine, at position 202 and/or position 323 in PB2 as well as optionally selected amino acid residues at one or more specified positions PA, PB1, NP, M1 and/or NS which are described herein. In one embodiment, the recombinant reassortant influenza virus has an amino acid residue at position 74 in NP that results in enhanced growth in cells including MDCK cells, Vero cells or eggs relative to a corresponding virus with, for instance, an arginine at position 74 in NP, i.e., the residue at position 74 in NP in the NP gene segment in the recombinant influenza virus is not arginine but is a residue that is correlated with enhanced replication in MDCK cells, Vero cells or eggs, as well as optionally selected amino acid residues at one or more specified positions PA, PB1, PB2, M1 and/or NS which are described herein. In one embodiment, the recombinant reassortant influenza virus has an amino acid residue at position 74 in NP that may alter folding, stability and/or interaction with other viral or host proteins relative to a corresponding virus with, for instance, an arginine at position 74 in NP. In one embodiment, the recombinant reassortant influenza virus has a lysine or histidine at position 74 in NP as well as optionally selected amino acid residues at one or more specified positions PA, PB1, PB2, M1 and/or NS which are described herein. In one embodiment, the recombinant reassortant influenza virus has an amino acid residue at position 97 and/or position 100 in M1 that results in enhanced growth in cells including MDCK cells, Vero cells or eggs relative to a corresponding virus with, for instance, a valine at position 97 or a tyrosine at position 100 in M1, i.e., the residue at position 97 and/or 100 in M1 in the M gene segment in the recombinant influenza virus is not valine or tyrosine, respectively, but is a residue that is correlated with enhanced replication in MDCK cells, Vero cells or eggs, as well as selected amino acid residues at one or more specified positions PA, PB1, PB2, NP and/or NS1 which are described herein. In one embodiment, the recombinant reassortant influenza virus has an amino acid residue at position 97 in M1 that may alter dimerization relative to a corresponding virus with, for instance, a valine at position 97 in M1. In one embodiment, the recombinant reassortant influenza virus has an amino acid residue at position 100 in M1 that may alter virus assembly relative to a corresponding virus with, for instance, a tyrosine at position 100 in M1. In one embodiment, the recombinant reassortant influenza virus has a leucine, threonine, isoleucine, alanine, or glycine, at position 97 and/or a lysine, arginine, or histidine at position 100 in M1 as well as selected amino acid residues at one or more specified positions PA, PB1, PB2, NP and/or NS1 which are described herein. In one embodiment, the recombinant reassortant influenza virus has an amino acid residue at position 55 in NS1 that results in enhanced growth in cells including MDCK cells, Vero cells or eggs relative to a corresponding virus with, for instance, a lysine at position 55 in NS1 as well as selected amino acid residues at one or more specified positions PA, PB1, PB2, NP and/or M1 which are described herein. In one embodiment, the recombinant reassortant influenza virus has an asparagine, aspartic acid, glutamic acid or glutamine at position 55 in NS1 as well as selected amino acid residues at one or more specified positions PA, PB1, PB2, NP and/or M1 which are described herein. In one embodiment, the invention provides an isolated recombinant reassortant influenza virus having six "internal" gene segments from a vaccine influenza virus with two or more of the selected amino acid residues at specified positions described herein, and a NA gene segment selected from a first influenza virus isolate, and a HA gene segment from the same isolate or a different isolate.

In one embodiment, the influenza virus of the invention is a recombinant influenza virus having two or more of selected amino acid residues at specified positions in one or more gene segments for PA, PB1, PB2, NP, M1, and/or NS1, which can be employed with HA and NA genes of interest. In one embodiment, the recombinant reassortant influenza virus has an amino acid residue at position 142 in PA that results in enhanced growth in MDCK cells, Vero cells or eggs relative to a corresponding virus with, for instance, a lysine at position 142 in PA; an amino acid residue at position 247 in PB1 that results in enhanced growth in MDCK cells, Vero cells or eggs relative to a corresponding virus with, for instance, a glutamine at position 247 in PB1; an amino acid residue at position 202 and/or position 323 in PB2 that results in enhanced growth in MDCK cells, Vero cells or eggs relative to a corresponding virus with, for instance, a methionine at position 202 or a phenylalanine at position 323 in PB2; an amino acid residue at position 74 in NP that results in enhanced growth in MDCK cells, Vero cells or eggs relative to a corresponding virus with, for instance, a arginine at position 74 in NP; an amino acid residue at position 97 and/or position 100 in M1 that results in enhanced growth in MDCK cells, Vero cells or eggs relative to a corresponding virus with, for instance, a valine at position 97 or a tyrosine at position 100 in M1; or an amino acid residue at position 55 in NS1 that results in enhanced growth in MDCK cells, Vero cells or eggs relative to a corresponding virus with, for instance, a lysine at position 55 in NS1, or combinations thereof.

In one embodiment, the influenza virus of the invention is a recombinant influenza virus having two or more of selected amino acid residues at specified positions in one or more gene segments for PA, PB1, PB2, NP, M1, and/or NS1, which can be employed with HA and NA genes of interest. In one embodiment, the recombinant reassortant influenza virus has two or more of a lysine at position 142 in PA; a glutamine at position 247 in PB1; a leucine at position 202 and/or at position 323 in PB2; a lysine at position 74 in NP; an alanine at position 97 and an histidine at position 100 in M1; or a glutamic acid at position 55 in NS1.

The invention provides isolated recombinant, e.g., reassortant, influenza viruses with selected amino acid residues at one or more specified positions in one or more gene segments for PA, PB1, PB2, NP, M1, and/or NS1, e.g., in selected amino acid residues at specified positions PB1, PB2 and NS; PB1, PB2, NP and NS; PA, PB1, PB2, NP and NS; PB1, PB2, NP, M and NS; or PA, PB1, PB2, NP, M, and NS, that include one or more of the characteristic residues described herein. In one embodiment, the recombinant reassortant influenza virus has an amino acid residue at position 105 and/or 401 in PA that results in enhanced growth in cells, e.g., MDCK cells, relative to a corresponding virus with, for instance, a phenylalanine or arginine at position 105 or 401, respectively, in PA. In one embodiment, the recombinant reassortant influenza virus has an amino acid residue at position 40, 54, 59, 62, 63, 66 (F2), 73 (F2), 75, 76, 78, 79, 80, 112, 180, 327, 507, 624, 644, 667, 694, 695, 697, 699, 700, 701, 702, 705, 713, and/or 714 in PB1 that results in enhanced growth in cells, e.g., MDCK cells, relative to a corresponding virus with, for instance, a methionine, arginine, threonine, glycine, alanine, asparagine, lysine, glutamic acid, aspartic acid, glutamic acid, proline, serine, glutamic acid, glycine, isoleucine, methionine, leucine, valine, isoleucine, asparagine, leucine, glutamic acid, phenyalanine, phenylalanine, proline, serine, tyrosine, serine or methionine, at position 40, 54, 59, 62, 63, 66 (F2), 73 (F2), 75, 76, 78, 79, 80, 112, 180, 504, 507, 624, 644, 667, 694, 695, 697, 699, 700, 701, 702, 705, 713, or 714, respectively, in PB1. In one embodiment, the recombinant reassortant influenza virus has an amino acid residue at position 57, 58, 59, 61, 66, 202, 323, 368, 391, 504, 591, 677, 678, or 679 in PB2 that results in enhanced growth in cells, e.g., MDCK cells, relative to a corresponding virus with, for instance, an isoleucine, threonine, alanine, lysine, methionine, methionine, phenylalanine, arginine, glutamic acid, isoleucine, glutamine, glutamic acid, aspartic acid or phenylalanine, at position 57, 58, 59, 61, 66, 202, 323, 368, 391, 504, 591, 677, 678 or 679, respectively, in PB2. In one embodiment, the recombinant reassortant influenza virus has an amino acid residue at position 116, 224, 293, 371, 417, 422 or 442 in NP that results in enhanced growth in cells, e.g., MDCK cells, relative to a corresponding virus with, for instance, a leucine, asparagine, arginine, methionine, aspartic acid, arginine or threonine, at position 116, 224, 293, 371, 417, 422, or 442, respectively, in NP. In one embodiment, the recombinant reassortant influenza virus has an amino acid residue at position 90 in M1 that results in enhanced growth in cells relative to a corresponding virus with, for instance, a serine at position 90 in M1. In one embodiment, the recombinant reassortant influenza virus has an amino acid residue at position 30, 49, 140, 161 or 223 in NS1 that results in enhanced growth in MDCK cells relative to a corresponding virus with, for instance, a proline, alanine, glutamine, threonine or glutamic acid, respectively, at position 30, 49, 140, 161 or 223, respectively, in NS1. IN one embodiment, the recombinant reassortant influenza virus does not have a valine at residue 504 in PB2 and a leucine at residue 550 in PA.

In one embodiment, the influenza virus of the invention is a recombinant influenza virus having a particular amino acid residue at specified positions in one, two, three or more of PA, PB1, PB2, NP, M1 and/or NS1 and having an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, such as a polypeptide with a residue other than K142, S225, K356 or I550 in PA; other than E112, Q247, M507 or V644 in PB1; other than M202, F323 or I504 in PB2; other than R74, I112, I116, T442, or N417 in NP; other than V97 and/or Y100 in M1; and/or other than R140 or K55 in NS. The residue other than the specified residue may be conservative substitution. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: threonine-valine-leucine-isoleucine-alanine; phenylalanine-tyrosine; lysine-arginine; alanine-valine; glutamic-aspartic; and asparagine-glutamine.

In one embodiment, the influenza virus of the invention is a recombinant influenza virus having a particular amino acid residue at specified positions in one or more of PA, PB1, PB2, NP, M1 and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, such as a polypeptide with a residue that is a conservative substitution relative to M202 in PB2, R74 in NP, and/or V97 in M1.

In one embodiment, the influenza virus of the invention is a recombinant influenza virus having a particular amino acid residue at specified positions in PA, PB1, PB2, NP, M1 and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, e.g., a polypeptide with a residue that is a non-conservative substitution relative to K142 in PA, Q247 in PB1, M202, F323 or I504 in PB2, R74 I112, I116, J442 or N417 in NP, V97 and/or Y100 in M1, and/or K55 or R140 in NS1.

In one embodiment, the influenza virus of the invention is a recombinant influenza virus having a particular amino acid residue at specified positions in PA, PB1, PB2, NP, M1 and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, e.g., a PB2 gene segment with a residue other than isoleucine and that is a conservative substitution for isoleucine at residue 504; a PB1 gene segment with a non-conservative substitution for E112; a PA gene segment with a substitution for S225; a NP gene segment with a conservative substitution for R74 and N417; a M gene segment with a conservative substitution for V97 and a non-conservative substitution for Y100; and a NS gene segment with a non-conservative substitution for K55.

In one embodiment, the influenza virus of the invention is a recombinant influenza virus having a particular amino acid residue at specified positions in PA, PB1, PB2, NP, M1 and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, e.g., a PB2 gene segment with a non-conservative substitution for M202 and F323; a PB1 gene segment with a non-conservative substitution for Q247; a PA gene segment with a non-conservative substitution for K142; a NP gene segment with a conservative substitution for R74; a M gene segment with a conservative substitution for V97 and a non-conservative substitution for Y100; and a NS gene segment with a conservative substitution for K55E.

In one embodiment, the influenza virus of the invention is a recombinant influenza virus having a particular amino acid residue at specified positions in PA, PB1, PB2, NP, M1 and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 or 10-15, e.g., a PB2 segment with a conservative substitution for I504; a PB1 segment with a conservative substitution for M40L and a non-conservative substitution for G180; a PA segment with a conservative substitution for R401; a NP segment with a conservative substitution for I116; a NS gene segment with a conservative substitution for A30 or R118.

In one embodiment, the influenza virus of the invention is a recombinant influenza virus having a particular amino acid residue at specified positions in one or more of PA, PB1, PB2, NP, M1 and/or NS1 and an amino acid sequence with at least 80%, e.g., 90%, 92%, 95%, 97% or 99%, including any integer between 80 and 99, contiguous amino acid sequence identity to a corresponding polypeptide encoded by one of SEQ ID Nos. 1-6 or 10-15, such as a polypeptide with a residue that is a non-conservative substitution relative to K142 in PA, Q247 in PB1, F323 in PB2, Y100 in M1, and/or K55 in NS1. In one embodiment, the amino acid residue that is replaced has an aliphatic side chain, amide-containing side chain, basic side chain, or sulfur containing side chain and the replacement of an aromatic side chain or acidic side chain (a nonconservative substitution). In one embodiment, the recombinant influenza virus has a residue that is a neutral or positively charged residue that is replaced with a polar or negatively charged residue.

Also included are any combination of the selected amino acid residues at specified positions described herein.

Gene segments for of PA, PB1, PB2, NP, M and/or NS that have the residues at the specified positions may be combined with a gene segment for HA, e.g., H1, H2, H3, H4, H5, H6, H7, H8, H9, H10, H11, H12, H13, H14, H15, H16, or H17 and a gene segment for NA, e.g., N1, N2, N3, N4, N5, N6, N7, N8, N9, or N10, and any combination of HA and NA, to provide the reassortant vaccine viruses of the invention. In one embodiment, the HA is H1, H5 or H7. In one embodiment the NA is N1 or N9. In one embodiment, the HA gene segment in the reassortant virus is heterologous to the gene segments for PA, PB1, PB2, NP, M and NS. In one embodiment, the NA gene segment in the reassortant virus is heterologous to the gene segments for PA, PB1, PB2, NP, M and NS. In one embodiment, the HA gene segment in the reassortant virus has gene segments for PA, PB1, PB2, NP, M and NS from one influenza virus isolate or strain ("parent"), or a variant thereof, e.g., one with gene segments encoding influenza virus proteins with at least 95%, 96%, 97%, 98%, 99%, or 99.5% amino acid sequence identity, or having 1, 2, 5, 10, or 20 substitutions relative, to sequences in a parent influenza virus isolate or strain. In one embodiment, the parent strain has gene segments with sequences corresponding to SEQ ID Nos. 1-6 or 10-15. In one embodiment, the HA gene segment in the reassortant virus is a chimeric HA gene segment, e.g., a chimera of heterologous HA ectodomain sequences linked to HA signal peptide sequences and/or HA transmembrane domain sequences from the HA gene segment of the parent isolate or strain, or variant thereof. In one embodiment, the NA gene segment in the isolated recombinant virus is a chimeric NA gene segment e.g., a chimera of heterologous NA ectodomain sequences linked to NA transmembrane domain sequences from the NA gene segment of the parent isolate or strain, or variant thereof, and/or stalk sequences from the parent isolate or strain, or variant thereof. In one embodiment, the NA gene segment in the isolated recombinant virus is a chimeric NA gene segment e.g., a chimera of heterologous NA ectodomain sequences linked to NA transmembrane domain sequences from the NA gene segment of the parent isolate or strain, or variant thereof, and/or stalk sequences from a second isolate or strain, or variant thereof. In one embodiment, the isolated recombinant virus has a heterologous HA gene segment, a heterologous NA gene segment, a chimeric HA gene segment, a chimeric NA gene segment, or any combination thereof. The nucleic acid sequences employed to prepare vRNA may be ones that introduce the residues at the specified positions via recombinant methodology or may be selected as having the residues at the specified positions.

A/Puerto Rico/8/34 (H1N1), "PR8," virus serves as the genetic backbone for generation of inactivated influenza vaccines. Occasionally, vaccine strains based on PR8 backbone replicate to relatively low titers in eggs and cell culture resulting in delayed vaccine production and vaccine shortage. To determine if high yield vaccine strain backbones for propagation in MDCK cells, chicken eggs and Vero cells can be prepared to supply the demand of seasonal flu and highly pathogenic pandemic viruses, various mutagenesis strategies were employed. For example, PR8 backbone random mutant libraries were screened for high replicative mutants, e.g., by introducing random mutations to internal PR8 genes by error prone PCR, introducing mutations that confer high replication and high polymerase activity, and optimizing PR8 internal gene via codon bias. In another approach, the HA gene was optimized to increase virus replication and HA content, e.g., by optimizing the HA promoter to generate a strong promoter, optimizing the HA noncoding region, and/or optimizing the HA signal peptide.

As described herein, an influenza virus isolate useful as a vaccine virus (e.g., A/Puerto Rico/8/34, "PR8," including a specific isolate such as UW-PR8) to carry heterologous gene segments for NA and/or HA, was serially passaged in MDCK cells, e.g., about 10-12-times although fewer passages may be employed, to obtain virus with enhanced replication in those cells. In one embodiment, viruses obtained after serial passage which have enhanced replication, have titers that are at least 1 or 2 logs higher than viruses that were not serially passaged. In one embodiment, viruses obtained after serial passage had substitutions in two or more internal gene segments relative to the parent virus.

Thus, for vaccine viruses that are to be grown or passaged in cells in culture, e.g., MDCK or Vero cells or eggs, selection of sequences with, or replacement of, the disclosed residues at the specified positions in one or more of PA, PB1, PB2, NP, M1 and/or NS1, that confer enhanced growth of the virus in cultured cells when employed with HA and NA sequences of interest, can result in significantly higher viral titers. Thus, the invention provides a method to select for influenza viruses with enhanced replication in cell culture. The method includes providing cells suitable for influenza vaccine production; serially culturing one or more influenza virus isolates in the cells; and isolating serially cultured virus with enhanced growth relative to the one or more isolates prior to serial culture. In one embodiment, the cells are canine or primate, e.g., human or monkey, cells.

In one embodiment, the influenza virus of the invention is a recombinant influenza virus having two or more of selected amino acid residues at specified positions in one or more of PA, PB1, PB2, NP, M1, and/or NS1, which can be employed with HA and NA genes of interest. In one embodiment, the recombinant reassortant influenza virus has an asparagine or glutamine at position 142 in PA, a cysteine at position 225, an arginine or histidine at position 356 in PA, or a leucine, valine, threonine, or glycine at position 550 in PA; a histidine, arginine or lysine at position 247 in PB1, a valine, leucine, isoleucine, threonine, alanine or glycine at position 507 in PB1 and/or an alanine, glycine, leucine or isoleucine at position 644 in PB1; a leucine, alanine, valine, isoleucine, glycine, or threonine at position 202 and/or position 323 in PB2, or a valine, leucine, glycine, threonine, or alanine at position 504 in PB2; a lysine or a histidine at position 74 in NP or a leucine, valine, glycine or alanine at position 112, 116 or 442 in NP; a leucine, isoleucine, alanine, glycine, or threonine, at position 97 and/or a lysine, arginine or histidine position 100 in M1; or an asparagine, aspartic acid, glutamic acid or glutamine at position 55 or glutamine or asparagine at position 140 in NS1.

The invention provides a plurality of influenza virus vectors of the invention, e.g., those useful to prepare reassortant viruses including 6:1:1 reassortants, 6:2 reassortants and 7:1 reassortants. A 6:1:1 reassortant within the scope of the present invention is an influenza virus with 6 internal gene segments from a vaccine virus, a NA gene segment from a different (second) viral isolate, and a HA gene segment from a third isolate; a 6:2 reassortant within the scope of the present invention is an influenza virus with 6 internal gene segments from a vaccine virus, and a NA gene segment and a HA gene segment from a different (second) viral isolate; and a 7:1 reassortant within the scope of the present invention is an influenza virus with 6 internal gene segments and a NA gene segment from a vaccine virus, and a HA gene segment from a different viral source than the vaccine virus, or an influenza virus with 6 internal gene segments and a HA gene segment from the vaccine virus, and a NA gene segment is from a different viral source than the vaccine virus.

In one embodiment of the invention, the plurality includes vectors for vRNA production selected from a vector comprising a promoter operably linked to an influenza virus PA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising a promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a operably linked to an influenza virus NS DNA linked to a transcription termination sequence. In one embodiment, the DNAs for vRNA production of PB1, PB2, PA, NP, M, and NS, have sequences from an influenza virus that replicates to high titers in cultured mammalian cells such as MDCK cells, Vero cells or PER.C6® cells and also optionally embryonated eggs, and/or from a vaccine virus, e.g., one that does not cause significant disease in humans. The DNA for vRNA production of NA may be from any NA, e.g., any of N1-N10, and the DNA for vRNA production of HA may be from any HA, e.g., H1-H17. In one embodiment, the DNAs for vRNA production may be for an influenza B or C virus. The DNAs for vRNA production of NA and HA may be from different strains or isolates (6:1:1 reassortants) or from the same strain or isolate (6:2 reassortants), or the NA may be from the same strain or isolate as that for the internal genes (7:1 reassortant). The plurality also includes vectors for mRNA production selected from a vector encoding influenza virus PA, a vector encoding influenza virus PB1, a vector encoding influenza virus PB2, and a vector encoding influenza virus NP, and optionally one or more vectors encoding NP, NS, M, e.g., M1 and M2, HA or NA. The vectors encoding viral proteins may further include a transcription termination sequence.

Viruses that may provide the internal genes for reassortants within the scope of the invention include viruses that have high titers in MDCK cells, e.g., titers of at least about $10^5$ PFU/mL, e.g., at least $10^6$ PFU/mL, $10^7$ PFU/mL or $10^8$ PFU/mL; high titers in embryonated eggs, e.g., titers of at least about $10^7$ EID$_{50}$/mL, e.g., at least $10^8$ EID$_{50}$/mL, $10^9$ EID$_{50}$/mL or $10^{10}$ EID$_{50}$/mL; high titers in cells such as MDCK cells, e.g., titers of at least about $10^7$ PFU/mL, e.g., at least $10^8$ PFU/mL, or high titers in two of more of those host cells.

In one embodiment, the titers of the reassortant viruses of the invention in cells such as MDCK cells or Vero cells may be over 1 log, 2 logs, 3 logs, or greater, than titers of the corresponding virus without particular residues at the specified positions.

Other reassortants with internal genes from other PR8 isolates or vaccine viruses may be employed in recombinant reassortant viruses of the invention. In particular, 5:1:2 reassortants having UW-PR8 PB1, PB2, PA, NP, and M ("5") and PR8(Cam) NS ("1"); 6:1:1 reassortants having UW-PR8 NA, PB1, PB2, PA, NP, and M ("6") and PR8 (Cam) NS ("1"); and 7:1 reassortants having UW-PR8 PB1, PB2, PA, NP, M, NA, and NS ("7") may be employed.

In one embodiment, the DNAs for the internal genes for PB1, PB2, PA, NP, M, and NS encode proteins with substantially the same activity as a corresponding polypeptide encoded by one of SEQ ID NOs:1-6 or 10-15. As used herein, "substantially the same activity" includes an activity that is about 0.1%, 1%, 10%, 30%, 50%, 90%, e.g., up to 100% or more, or detectable protein level that is about 80%, 90% or more, the activity or protein level, respectively, of the corresponding full-length polypeptide. In one embodiment, the nucleic acid a sequence encoding a polypeptide which is substantially the same as, e.g., having at least 80%, e.g., 90%, 92%, 95%, 97%, 98%, or 99%, including any integer between 80 and 99, contiguous amino acid sequence identity to, a polypeptide encoded by one of SEQ ID NOs:1-6 or 10-15. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of SEQ ID NOs:1-6 or 10-15 and, in one embodiment, also encodes a polypeptide having at least 80%, e.g., 90%, 92%, 95%, 97%, 98%, or 99%, including any integer between 80 and 99, contiguous amino acid sequence identity to a polypeptide encoded by one of SEQ ID NOs:1-6 or 10-15. In one embodiment, the influenza virus polypeptide has one or more, for instance, 2, 5, 10, 15, 20 or more, conservative amino acids substitutions, e.g., conservative substitutions of up to 10% or 20% of 2, 5, 10, 15, 20 or more, of a combination of conservative and non-conservative amino acids substitutions, e.g., conservative substitutions of up to 10% or 20% of the residues, or relative to a polypeptide encoded by one of SEQ IS NOs:1-6 or 10-15, and has a characteristic residue in two or more of PA, PB1, PB2, NP, M1, and/or NS1 the residues, relative to a polypeptide encoded by one of SEQ ID NOs:1-6 or 10-15, and has a characteristic residue in two or more of the gene segments for PA, PB1, PB2, NP, M1, and/or NS1, e.g., there is an asparagine or glutamine at position 142 in PA; a histidine, arginine or lysine at position 247 in PB1; a leucine, alanine, valine, isoleucine, glycine, or serine at position 202 and/or position 323 in PB2; a lysine or a histidine at position 74 in NP; a leucine, isoleucine, alanine, glycine, or serine at position 202 and/or a lysine, arginine, or histidine position 100 in M1; or an asparagine, aspartic acid, glutamic acid or glutamine at position 44 in NS1. In one embodiment, the influenza virus polypeptide has one or more, for instance, 2, 3, 4, 5, 6, 7 or 8 conservative and/or nonconservative amino acid substitutions, relative to a polypeptide encoded by one of SEQ ID NOs:1-6 or 10-15, e.g., those in virus isolates 1, 4, 36, 38, P17, P25 or P61 in Table 4.

The invention thus includes the use of isolated and purified vectors or plasmids, which express or encode influenza virus proteins, or express or encode influenza vRNA, both native and recombinant vRNA. The vectors comprise influenza cDNA, e.g., influenza A (e.g., any influenza A gene including any of the 16 HA or 9 NA subtypes), B or C DNA (see Fields *Virology* (Fields et al. (eds.), Lippincott, Williams and Wickens (2006), which is specifically incorporated by reference herein). Any suitable promoter or transcription termination sequence may be employed to express a protein or peptide, e.g., a viral protein or peptide, a protein or peptide of a nonviral pathogen, or a therapeutic protein or peptide.

A composition or plurality of vectors of the invention may also comprise a heterologous gene or open reading frame of interest, e.g., a foreign gene encoding an immunogenic peptide or protein useful as a vaccine or in gene replacement, for instance, may encode an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes. Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA corresponding to the heterologous sequences of the vector.

The promoter in a vector for vRNA production may be a RNA polymerase I promoter, a RNA polymerase II promoter, a RNA polymerase III promoter, a T7 promoter, or a T3 promoter, and optionally the vector comprises a transcription termination sequence such as a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, the RNA polymerase I promoter is a human RNA polymerase I promoter.

The promoter or transcription termination sequence in a vRNA or virus protein expression vector may be the same or different relative to the promoter or any other vector. In one embodiment, the vector or plasmid which expresses influenza vRNA comprises a promoter suitable for expression in at least one particular host cell, e.g., avian or mammalian host cells such as canine, feline, equine, bovine, ovine, or primate cells including human cells, or for expression in more than one host.

In one embodiment, at least one vector for vRNA comprises a RNA polymerase II promoter linked to a ribozyme sequence linked to viral coding sequences linked to another ribozyme sequences, optionally linked to a RNA polymerase II transcription termination sequence. In one embodiment, at least 2, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same.

In one embodiment, the invention provides a plurality of influenza virus vectors for a reassortant, comprising a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA linked to a transcription termination sequence, wherein the DNAs for PB1, PB2, PA, NP, NS, and M are from one or more influenza vaccine seed viruses and contain two or more of the characteristic residues at the specified position(s); and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2. In one embodiment, at least one vector comprises sequences corresponding to those encoding PB1, PB2, PA, NP, M, or NS, or a portion thereof, having substantially the same activity as a corresponding polypeptide encoded by one of SEQ ID NOs:1-6 or 10-15, e.g., a sequence encoding a polypeptide with at least 80%, e.g., 85%, 90%, 92%, 95%, 98%, 99% or 100%, including any integer between 80 and 100, amino acid identity to a polypeptide encoded by one of SEQ ID NOs:1-6 or 10-15. Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus M2 cDNA linked to a transcription termination sequence.

A plurality of the vectors of the invention may be physically linked or each vector may be present on an individual plasmid or other, e.g., linear, nucleic acid delivery vehicle. In one embodiment, each vRNA production vector is on a separate plasmid. In one embodiment, each mRNA production vector is on a separate plasmid.

The invention also provides a method to prepare influenza virus. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as well as a host cell contacted with the plurality of vectors or virus of the invention. In another embodiment, the invention includes contacting the cell with one or more vectors, either vRNA or protein production vectors, prior to other vectors, either vRNA or protein production vectors. In one embodiment, the promoter for vRNA vectors employed in the method is a RNA polymerase I promoter, a RNA polymerase II promoter, a RNA polymerase III promoter, a T3 promoter or a T7 promoter. In one embodiment, the RNA polymerase I promoter is a human RNA polymerase I promoter. In one embodiment, each vRNA vector employed in the method is on a separate plasmid. In one embodiment, the vRNA vectors employed in the method are on one plasmid or on two or three different plasmids. In one embodiment, each mRNA vector employed in the method is on a separate plasmid. In one embodiment, the mRNA vectors for PA, PB1, PB2 and NP employed in the method are on one plasmid or on two or three different plasmids.

In one embodiment, the invention provides a method to select for influenza viruses with enhanced replication in cell culture. The method includes providing cells suitable for influenza vaccine production; serially culturing one or more influenza virus isolates in the cells; and isolating serially cultured virus with enhanced growth relative to the one or more isolates prior to serial culture. In one embodiment, the cells are rodent or primate cells.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors). Thus, a virus for use in medical therapy (e.g., for a vaccine or gene therapy) is provided.

The invention also provides isolated viral polypeptides, and methods of preparing and using recombinant virus of the invention. The methods include administering to a host organism, e.g., a mammal, an effective amount of the influenza virus of the invention, e.g., an inactivated virus preparation, optionally in combination with an adjuvant and/or a carrier, e.g., in an amount effective to prevent or ameliorate infection of an animal such as a mammal by that virus or an antigenically closely related virus. In one embodiment, the virus is administered intramuscularly while in another embodiment, the virus is administered intranasally. In some dosing protocols, all doses may be administered intramuscularly or intranasally, while in others a combination of intramuscular and intranasal administration is employed. The vaccine may further contain other isolates of influenza virus including recombinant influenza virus, other pathogen(s), additional biological agents or microbial components, e.g., to form a multivalent vaccine. In one embodiment, intranasal vaccination, for instance containing with inactivated influenza virus, and a mucosal adjuvant may induce virus-specific IgA and neutralizing antibody in the nasopharynx as well as serum IgG.

The influenza virus of the invention may employed with other anti-virals, e.g., amantadine, rimantadine, and/or neuraminidase inhibitors, e.g., may be administered separately in conjunction with those anti-virals, for instance, administered before, during and/or after.

BRIEF DESCRIPTION OF THE FIGURES

FIG. 1. Nucleotide sequence for PR8(Cambridge) genes (SEQ ID NOs:10-15).

FIG. 3. Number of clones with random mutations having specified HA titers.

FIG. 4. Titers of clones having selected mutations.

Figure 5D:
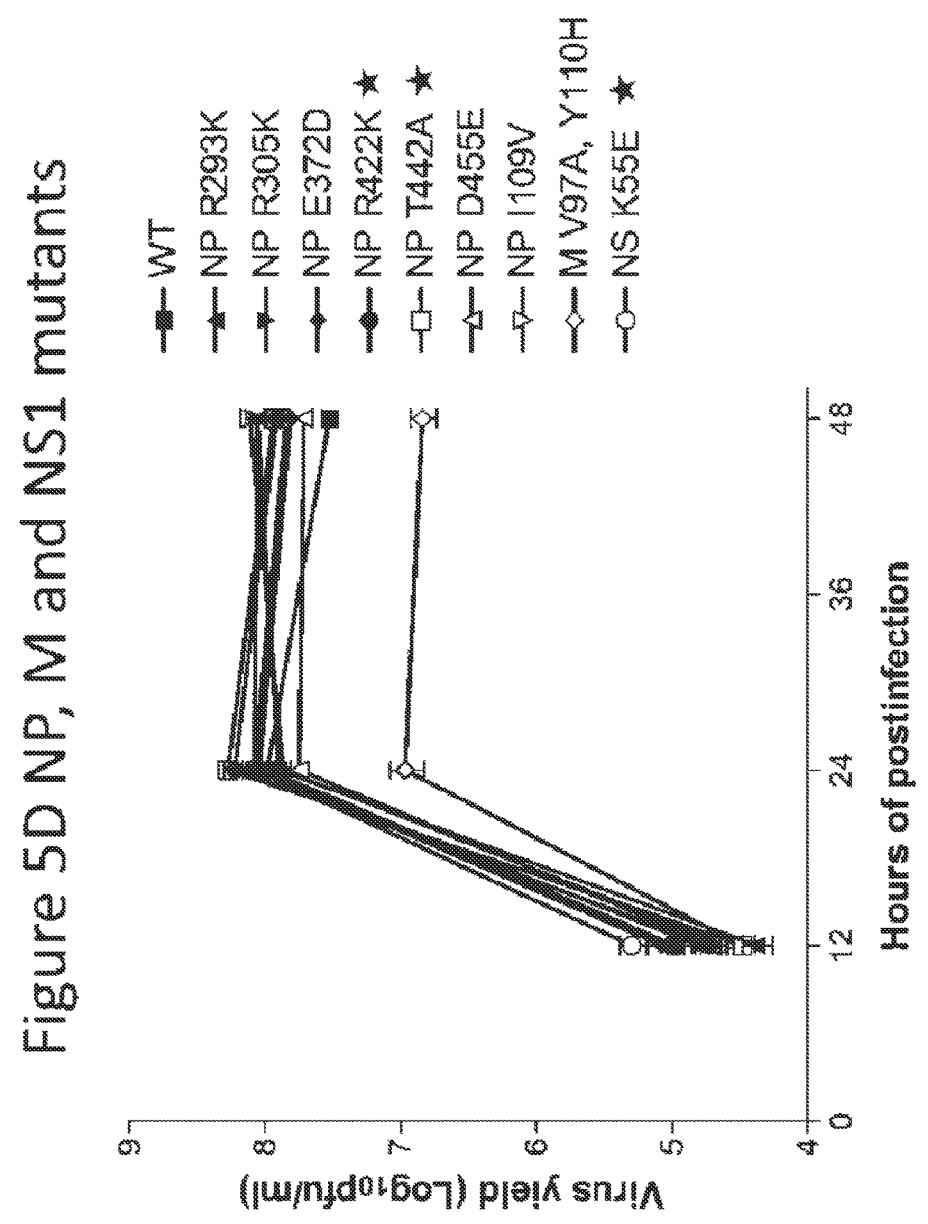

FIGS. 5A-D. Growth curves of UW-PR8 viruses possessing previously identified mutations in PB2 (A), PB1 (B), PA (C), and NP, M or NS1 (D).

FIG. 6. Summary of mutations that confer high replicative property in MDCK cells.

FIGS. 7A-B. A) Virus stocks were tested for HA titers (in 2") and virus titers (in PFU/mL). B) Growth curves in MDCK cells.

FIGS. 8A-C. A) HA titer of wild type (UW-PR8) and clone #4. B) Viral protein for wild type (UW-PR8) and #4. C) SDS-PAGE analysis of viral proteins of wild type and #4.

FIGS. 9A-B. A) Comparison of titers of wild type virus (UW-PR8) and high replicative virus with mutations in M1. B) Growth kinetics of wild type virus (UW-PR8) and high replicative virus with mutations in M1.

FIGS. 10A-F. A) Codon usage table for canines. B) Relative adaptiveness of wild type (UW-PR8) and "rare" codon optimized PB2 viruses. C) Relative adaptiveness of wild type (UW-PR8) and "all" codon optimized PB2 viruses. D) Growth kinetics of PB2 codon optimized viruses.

E) Growth kinetics of viruses with codon optimized PB2, PB1, PA, or NP gene segment or combinations of segments.

F) Sequence of PB2, PB1, PA and NP gene segments of UW-PR8 (SEQ ID Nos. 3, 2, 1 and 4, respectively), and sequence of canine codon-usage optimized PB2, PB1, PA and NP gene segments of UW-PR8 (SEQ ID Nos. 25, 26, 27 and 28, respectively).

Figure 11C:
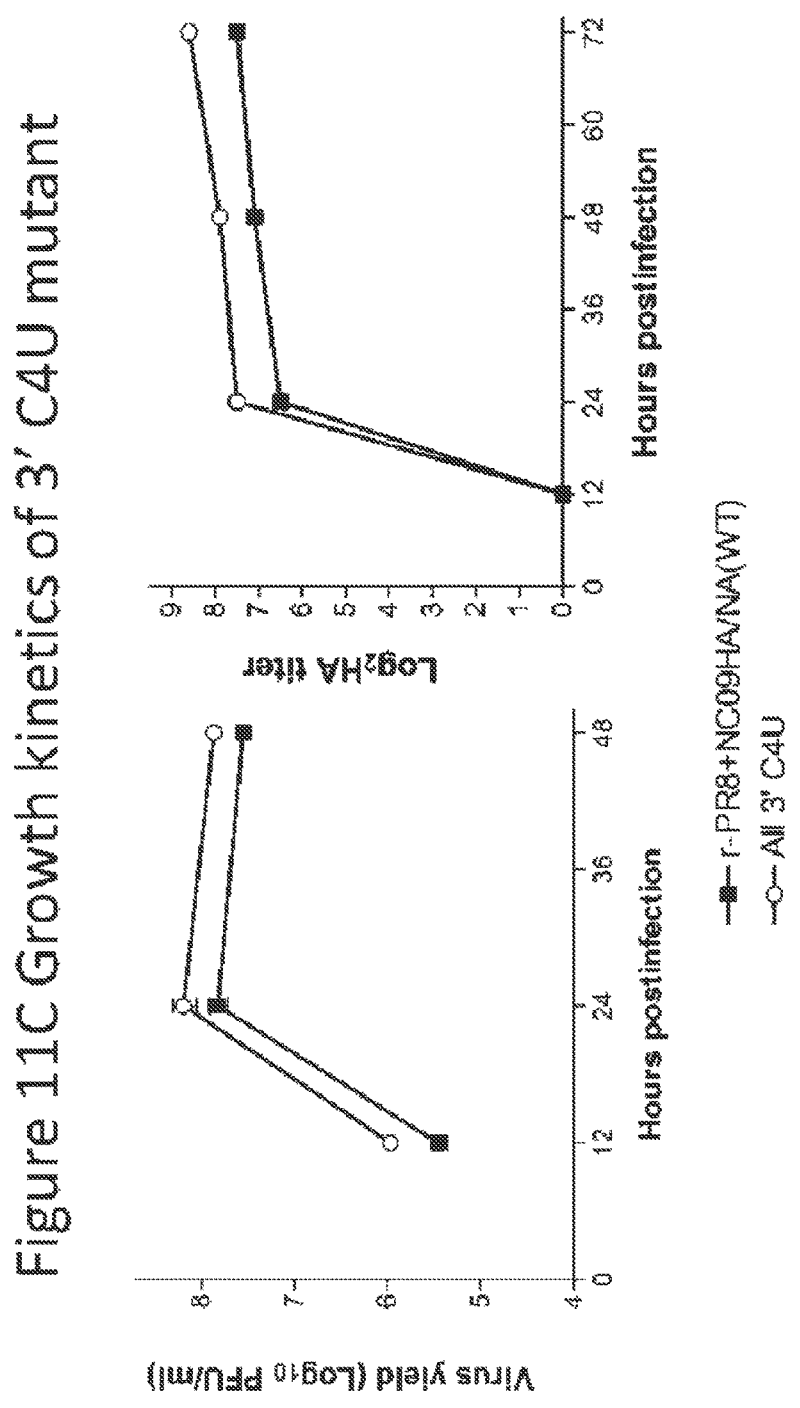

FIGS. 11A-C. A) Nucleotide position 4 of each gene of PR8 and Indo/NC/09. B) All 3'C4U mutant. C) Growth kinetics of a recombinant UW-PR8 virus encoding 'C' at position 4 of the PB2, PB1, and PA genes (black), and a mutant encoding 'U' at position 4 of all eight segments (red).

FIG. 12. Nucleotide and amino acid sequences for H7 and N9 which are exemplary sequences for use with the internal gene segment sequences disclosed herein useful to provide high titer influenza viruses for vaccines (SEQ ID NOs: 17-24)

FIGS. 13A-B. A) Schematic of chimeric HA and NA genes to increase virus titer. B) Growth kinetics of chimeric viruses.

Figure 14B:
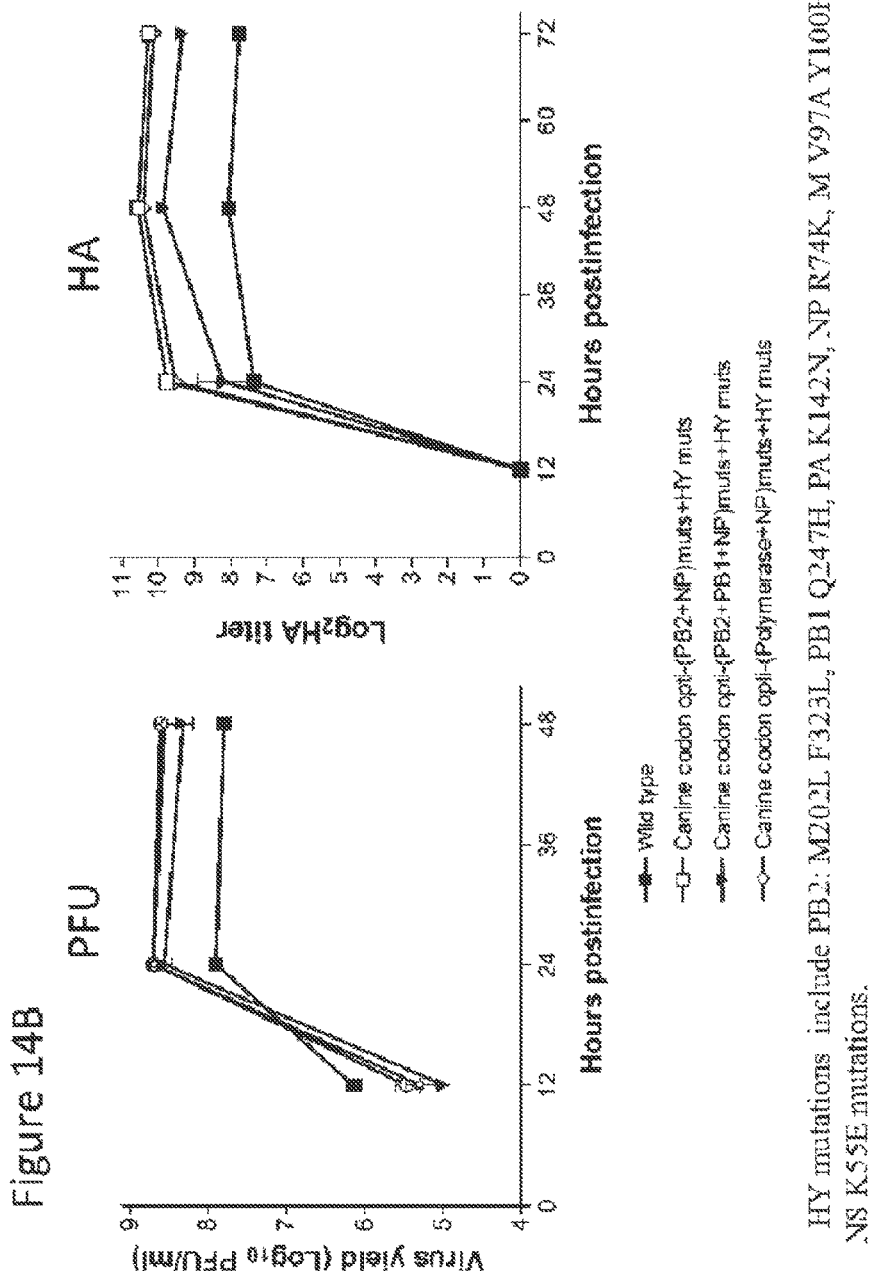

FIGS. 14A-B. A) Growth kinetics of viruses with combinations of mutations. B) PFU and HA titers of viruses with combinations of mutations.

FIG. 15. Screening in eggs.

FIG. 16. HA titers of 216 clones isolated from Vero cells.

FIG. 17. Recombinant viruses generated with different PR8 backbone mutations.

Figure 18B:
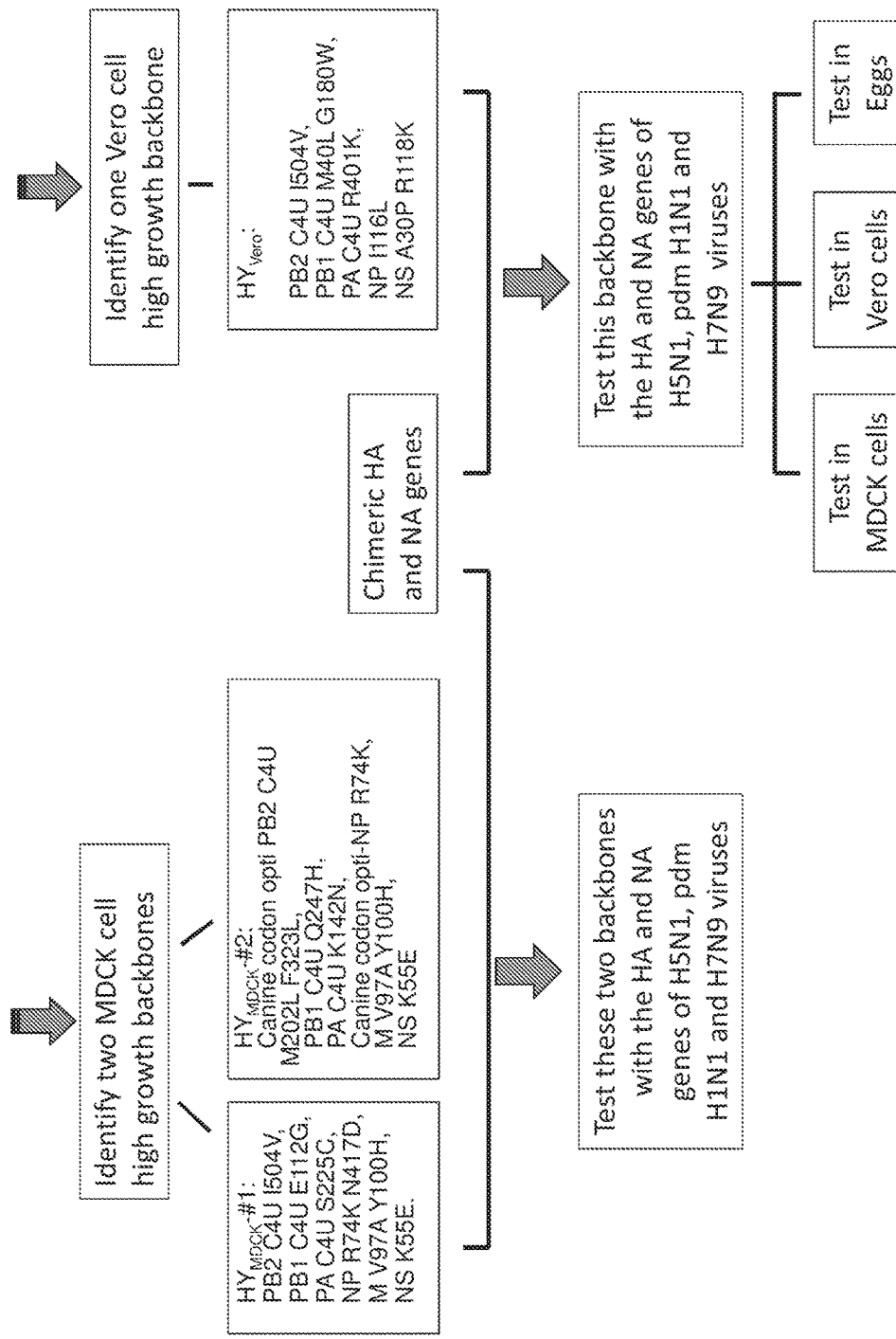

FIGS. 18A-B Overview of generation of viruses with enhanced growth in MDCK cells and Vero cells.

DETAILED DESCRIPTION

Definitions

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, a "heterologous" influenza virus gene or gene segment is from an influenza virus source that is different than a majority of the other influenza viral genes or gene segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information (http://www.ncbi.nlm.nih.gov/). The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5, N=-4, and a comparison of both strands. For amino acid sequences, the BLASTP program may use as defaults a wordlength (W) of 3, an expectation (E) of 10, and the BLOSUM62 scoring matrix. See http://www.ncbi.nlm.nih.gov. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Influenza Virus Structure and Propagation

Influenza A viruses possess a genome of eight single-stranded negative-sense viral RNAs (vRNAs) that encode at least ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cRNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein with ion channel activity but has BM2 and has a gene segment with both NA and NB sequences. Influenza C virus has only seven gene segments.

Cell Lines that can be Used in the Present Invention

Any cell, e.g., any avian or mammalian cell, such as a human, e.g., 293T or PER.C6® cells, or canine, e.g., MDCK, bovine, equine, feline, swine, ovine, rodent, for instance mink, e.g., MvLu1 cells, or hamster, e.g., CHO cells, or non-human primate, e.g., Vero cells, including mutant cells, which supports efficient replication of influenza virus can be employed to isolate and/or propagate influenza viruses. Isolated viruses can be used to prepare a reassortant virus. In one embodiment, host cells for vaccine production are continuous mammalian or avian cell lines or cell strains. A complete characterization of the cells to be used, may be conducted so that appropriate tests for purity of the final product can be included. Data that can be used for the characterization of a cell includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. In one embodiment, the passage level, or population doubling, of the host cell used is as low as possible.

In one embodiment, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity may be tested in cells that are at the same passage level as those used for vaccine production. The virus may be purified by a process that has been shown to give consistent results, before vaccine production (see, e.g., World Health Organization, 1982).

Virus produced by the host cell may be highly purified prior to vaccine or gene therapy formulation. Generally, the purification procedures result in extensive removal of cellular DNA and other cellular components, and adventitious agents. Procedures that extensively degrade or denature DNA may also be used.

Influenza Vaccines

A vaccine of the invention includes an isolated recombinant influenza virus of the invention, and optionally one or more other isolated viruses including other isolated influenza viruses, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (laver & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines. Inactivated influenza virus vaccines are provided by inactivating replicated virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines. Live, attenuated influenza virus vaccines, such as those including a recombinant virus of the invention can be used for preventing or treating influenza virus infection. Attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions of the present invention, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 μg, e.g., 30 to 100 μg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water.

Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein. Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-$\alpha$, interferon-$\beta$, interferon-$\gamma$, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition of the present invention may confer resistance to one or more pathogens, e.g., one or more influenza virus strains, by either passive immunization or active immunization. In active immunization, an attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present invention, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{15}$, e.g., $10^3$-$10^{12}$, plaque forming units (PFU)/kg, or any range or value therein. The dose of inactivated vaccine may range from about 0.1 to 1000, e.g., 30 to 100 µg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 30 to 100 µg or any range or value therein, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount, e.g., 1-50 µg or any range or value therein, or the amount recommended by the U.S. Public Heath Service (PHS), which is usually 15 µg per component for older children (greater than or equal to 3 years of age), and 7.5 µg per component for children less than 3 years of age. The quantity of NA can also be standardized, however, this glycoprotein can be labile during the processor purification and storage (Kendal et al., 1980; Kerr et al., 1975). Each 0.5-ml dose of vaccine may contains approximately 1-50 billion virus particles, and preferably 10 billion particles.

Exemplary Embodiments

In one embodiment, the invention provides an isolated recombinant influenza virus having PA, PB1, PB2, NP, NS, and M gene segments from a first influenza vaccine virus isolate, a heterologous influenza virus NA gene segment, and a heterologous HA gene segment, wherein two or more of the PA, PB1, PB2, NP, NS, and M gene segments have selected amino acid residues at positions 30, 31, 105, 142, 149, 225, 356, 357, 401, and/or 550 in PA; positions 40, 54, 59, 62, 63, 75, 76, 78, 79, 80, 112, 180, 247, 327, 507, 624, 644, 667, 694, 695, 697, 699, 700, 701, 702, 705, 713, and/or 714 in PB1; positions 57, 58, 59, 61, 66, 202, 323, 368, 391, 504, 591, 677, 678, and/or 679, in PB2; positions 74, 112, 116, 224, 293, 371, 377, 417, 422 or 442 in NP; positions 90, 97 and/or 100 in M1; or positions 30, 49, 55, 118, 140, 161 and/or 223 in NS1. In one embodiment, the isolated virus has 142N, 225C, 356R, or 550L in PA; has one or more of 112G, 247H, 507V, or 644A in PB1; has one or more of 202L, 323L or 504V in PB2; has one or more of 74K, 112L, 116L, 417D, or 442A in NP; 97A and/or 100H in M1; and/or 55E and/or 140Q in NS1, or combinations thereof, e.g., has at least one of 202L and/or 323L in PB2, 247H in PB1 or 74K in NP and optionally at least one of 142N in PA1, 55K in NS1 or 97A and/or 100H in M1 or has at least one of 202L and/or 323L in PB2, 247H in PB1 or 74K in NP and at least one of 142N in PA1, 55K in NS1 or 97A and/or 100H in M1. In one embodiment, the virus has at least one of 202L and/or 323L in PB2, 247H in PB1 or 74K in NP and optionally at least one of 142N in PA1, 55K in NS1 or 97A and/or 100H in M1. In one embodiment, the virus has at least one of 202L and/or 323L in PB2, 247H in PB1 or 74K in NP and at least one of 142N in PA1, 55K in NS1 or 97A and/or 100H in M1. In one embodiment, the isolated virus has 202L and/or 323L in PB2, and optionally has 247H in PB1 and optionally 74K in NP. In one embodiment, the isolated virus has 247H in PB1 and optionally 74K in NP. In one embodiment, the isolated virus has 40I, 40L, 112G, 180W, 247H, 507V, or 644A in PB1 and optionally has 202L and/or 323L in PB2, and optionally has 74K, 112L, 116L, 377N, 417D, or 422L in NP, and optionally has 30P, 118K, 161T or 140Q in NS1, and optionally has 142N, 225C, 356R, 401K, or 550L in PA. In one embodiment, the isolated virus has 40I, 40L, 112G, 180W, 247H, 507V, or 644A in PB1. In one embodiment, the isolated virus has 202L and/or 323L in PB2. In one embodiment, the isolated virus has 74K, 112L, 116L, 377N, 417D, or 422L in NP. In one embodiment, the isolated virus has 30P, 118K, 161T or 140Q in NS1. In one embodiment, the isolated virus has 142N, 225C, 356R, 401K, or 550L in PA. In one embodiment, the selected amino acid residues at specified positions in the PA is/are at position(s) 97, 105, 142, 149, 225, 356, 357, 401, 404, and/or 421. In one embodiment, the selected amino acid residues at specified positions in the PB1 is/are at position(s) 12, 40, 54, 59, 62, 63, 66, 75, 76, 78, 79, 80, 180, 247, 507, 624, 644, 694, 695, 697, 699, 700, 701, 705, 713, 714, and/or 762. In one embodiment, the selected amino acid residues at specified positions in the PB2 is/are at position(s) 57, 58, 59, 61, 66, 202, 243, 323, 504, 677, 678, and/or 679. In one embodiment, the selected amino acid residues at specified positions in the NP is/are at position(s) 74, 112, 116, 224, 293, 417, and/or 442. In one embodiment, the selected amino acid residues at specified positions in the M1 is/are at position(s) 90, 97, and/or 100. In one embodiment, the selected amino acid residues at specified positions in the NS1 is/are at position(s) 49, 30, 55, 161, and/or 223. In one embodiment, the selected amino acid residues at specified positions in the PA is/are at position(s) 97, 105, 142, 149, 225, 356, 357, 401, 404, and/or 421; and optionally the selected amino acid residues at specified positions in the PB1 is/are at position(s) 12, 40, 54, 59, 62, 63, 66, 75, 76, 78, 79, 80, 180, 247, 507, 624, 644, 694, 695, 697, 699, 700, 701, 705, 713, 714, and/or 762, in any combination with the selected residues for PA; and optionally the selected amino acid residues at specified positions in the PB2 is/are at position(s) 57, 58, 59, 61, 66, 202, 243, 323, 504, 677, 678, and/or 679 in any combination with the selected residues for PA and/or PB1; and optionally the selected amino acid residues at specified positions in the NP is/are at position(s) 74, 112, 116, 224, 293, 417, and/or 442 any combination with the selected residues for PA, PB1 and/or PB2; and optionally the selected amino acid residues at specified positions in the M1 is/are at position(s) 90, 97, and/or 100 any combination with the selected residues for PA, PB1, PB2, and/or NP; and optionally the selected amino acid residues at specified positions in the NS1 is/are at position(s) 49, 30, 55, 161, and/or 223, or in any combination with the selected residues for PA, PB1, PB2, NP, and/or M1.

For any of the exemplary viruses disclosed above, in one embodiment, the PA, PB1, PB2, NP, NS, and M gene segments comprise sequences for at least one of the following: a PB1 having the amino acid sequence encoded by SEQ ID NO:2 or PB1 with at least 95% amino acid sequence identity to the PB1 encoded by SEQ ID NO:2; a PB2 having the amino acid sequence encoded by SEQ ID NO:3 or PB2 with at least 95% amino acid sequence identity to the PB2 encoded by SEQ ID NO:3; a PA having the amino acid sequence encoded by SEQ ID NO:1 or PA with at least 95% amino acid sequence identity to the PA encoded by SEQ ID NO:1; a NP having the amino acid sequence encoded by SEQ ID NO:4 or NP with at least 95% amino acid sequence identity to the NP encoded by SEQ ID NO:4; a M having the amino acid sequence encoded by SEQ ID NO:5 or M with at least 95% amino acid sequence identity to the M encoded by SEQ ID NO:5; or a NS having the amino acid sequence encoded by SEQ ID NO:6 or NS with at least 95% amino acid sequence identity to the NS encoded by SEQ ID NO:6, or the PA, PB1, PB2, NP, NS, and M gene segments comprise sequences for at least one of the following: a PB1 having the amino acid sequence encoded by SEQ ID NO:10 or PB1 with at least 95% amino acid sequence identity to the PB1 encoded by SEQ ID NO:10; a PB2 having the amino acid sequence encoded by SEQ ID NO:11 or PB2 with at least 95% amino acid sequence identity to the PB2 encoded by SEQ ID NO:11; a PA having the amino acid sequence encoded by SEQ ID NO:12 or PA with at least 95% amino acid sequence identity to the PA encoded by SEQ ID NO:12; a NP having the amino acid sequence encoded by SEQ ID NO:13 or NP with at least 95% amino acid sequence identity to the NP encoded by SEQ ID NO:13; a M having the amino acid sequence encoded by SEQ ID NO:14 or M with at least 95% amino acid sequence identity to the M encoded by SEQ ID NO:14; or a NS having the amino acid sequence encoded by SEQ ID NO:15 or NS with at least 95% amino acid sequence identity to the NS encoded by SEQ ID NO:15.

For any of the exemplary viruses disclosed above, in one embodiment, at least one of the PA, PB1, PB2, NP, NS, and M gene segments has a C to U promoter mutation.

Any of the isolated viruses disclosed herein may be employed in a vaccine.

In one embodiment, the invention provides a plurality of influenza virus vectors for preparing a reassortant. In one embodiment, the plurality includes a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production of NA has sequences for a heterologous NA, and wherein the HA DNA in the vector for vRNA production of HA has sequences for a heterologous HA, 30, 31, 105, 142, 149, 225, 356, 357, 401, and/or 550 in PA; 40, 54, 59, 62, 63, 75, 76, 78, 79, 80, 112, 180, 247, 327, 507, 624, 644, 667, 694, 695, 697, 699, 700, 701, 702, 705, 713, or 714 and/or 247 in PB1; 57, 58, 59, 61, 66, 202, 323, 368, 391, 504, 591, 677, 678, or 679, 202 and/or 323 in PB2; 74, 112, 116, 224, 293, 371, 377, 417, 422 and/or 442 in NP; 90, 97 and/or 100 in M1; or 30, 49, 55, 118, 140, 161 and/or 223 in NS; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2. In one embodiment, the PB1, PB2, PA, NP, NS, and M DNAs in the vectors for vRNA production have a sequence corresponding to one that encodes a polypeptide having at least 95% amino acid sequence identity to a corresponding polypeptide encoded by SEQ ID NOs:1-6 or 10-15. In one embodiment, the promoter for vRNA vectors is a RNA polymerase I promoter, a RNA polymerase II promoter, a RNA polymerase III promoter, a T3 promoter or a T7 promoter. In one embodiment, the NA is N9. In one embodiment, the HA is H7. In one embodiment, the PA, PB1, PB2, NP, NS, and/or M gene segments has/have a promoter C to a mutation.

In one embodiment, the invention provides a method to prepare influenza virus. The method includes contacting a cell with: a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production of NA has sequences for a heterologous NA, and wherein the HA DNA in the vector for vRNA production of HA has sequences for a heterologous HA, 30, 31, 105, 142, 149, 225, 356, 357, 401, and/or 550 in PA; 40, 54, 59, 62, 63, 75, 76, 78, 79, 80, 112, 180, 247, 327, 507, 624, 644, 667, 694, 695, 697, 699, 700, 701, 702, 705, 713, and/or 714 and/or 247 in PB1; 57, 58, 59, 61, 66, 202, 323, 368, 391, 504, 591, 677, 678, and/or 679, 202 and/or 323 in PB2; 74, 112, 116, 224, 293, 371, 377, 417, 422 and/or 442 in NP; 90, 97 and/or 100 in M1; or 30, 49, 55, 118, 140, 161 or 223 in NS; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2; in an amount effective to yield infectious influenza virus. In one embodiment, the cell is an avian cell or a mammalian cell, e.g., a Vero cell, a human cell or a MDCK cell. In one embodiment, the PB1, PB2, PA, NP, NS, and M DNAs in the vectors for vRNA productions have a sequence that corresponds to one that encodes a polypeptide having at least 95% amino acid sequence identity to a corresponding polypeptide encoded by SEQ ID NOs:1-6 or 10-15. In one embodiment, the method includes isolating the virus. In one embodiment, at least one of PA, PB1, or PB2 gene segments has a C to U promoter mutation.

Further provided is a vector for vRNA or mRNA expression of influenza virus PA having at least 95% amino acid sequence identity to a polypeptide encoded by SEQ ID NO:1 and having a threonine at position 30, a lysine at position 31, cysteine at position 105 or a lysine at position 401; a vector for vRNA or mRNA expression of influenza virus PB1 having at least 95% amino acid sequence identity to a polypeptide encoded by SEQ ID NO:2 and having a leucine at position 40, an alanine or isoleucine at position 54, glycine at position 112, histidine at position 247, valine at position 507, alanine at position 644, or cysteine at position 713; a vector for vRNA or mRNA expression of PB2 having at least 95% amino acid sequence identity to a polypeptide encoded by SEQ ID NO:3 and a leucine at position 202 and/or 323; a vector for vRNA or mRNA expression of influenza virus NP having at least 95% amino acid sequence identity to a polypeptide encoded by SEQ ID NO:4 and having a lysine at position 74, leucine at position 116, isoleucine at position 224, lysine at position 293, asparagine at position 377, or aspartic acid at position 417; a vector for vRNA or mRNA expression of influenza virus NS1 having at least 95% amino acid sequence identity to a NS1 polypeptide encoded by SEQ ID NO:6 and having a proline at position 30, alanine at position 49, lysine at position 118, glutamine at position 140, threonine at position 161, or glutamic acid at position 223; and a vector for vRNA or RNA expression of influenza virus M1 having at least 95% amino acid sequence identity to a M1 polypeptide encoded by SEQ ID NO:5 and having a serine at position 90.

The invention will be described by the following nonlimiting examples.

Example 1

Methods

Cells and Viruses 293T human embryonic kidney cells are maintained in Dulbecco's modified Eagle's minimal essential medium (DMEM) with 10% fetal calf serum and antibiotics. Madin-Darby canine kidney (MDCK) cells are grown in MEM with 5% newborn calf serum and antibiotics. African green monkey Vero WCB cells, which had been established after biosafety tests for use in human vaccine production (Sugawara et al., 2002), are maintained in serum-free VP-SFM medium (GIBCO-BRL) with antibiotics. Cells are maintained at 37° C. in 5% $CO_2$. A WHO-recommended vaccine seed virus is NIBRG-14.

Construction of Plasmids and Reverse Genetics

To generate reassortants of influenza A viruses, a plasmid-based reverse genetics (Neumann et al., 1999) is used. The full-length cDNAs were cloned into a plasmid under control of the human polymerase I promoter and the mouse RNA polymerase I terminator (PolI plasmids).

A previously produced series of PolI constructs, derived from A/WSN/33 (H5N1; WSN) or PR8 strains is used, for reverse genetics (Horimoto et al., 2006; Neumann et al., 1999). The World Health Organization (WHO) recommends A/Puerto Rico/8/34 (H1N1; PR8) as a donor virus, because of its safety in humans (Wood & Robertson, 2004; Webby & Webster, 2003).

Plasmids expressing WSN or PR8 NP, PA, PB1, or PB2 under control of the chicken actin, e.g., beta-actin, promoter are used for all reverse genetics experiments (Horimoto et al., 2006; Neumann et al., 1999). Briefly, PolI plasmids and protein expression plasmids are mixed with a transfection reagent, Trans-IT 293T (Panvera), incubated at room temperature for 15 minutes, and then added to 293T cells. Transfected cells are incubated in Opti-MEM I (GIBCO-BRL) for 48 hours. For reverse genetics in Vero WCB cells, an electroporator (Amaxa) is used to transfect the plasmid mixtures according to the manufacturer's instructions. Sixteen hours after transfection, freshly prepared Vero WCB cells were added onto the transfected cells and TPCK-trypsin (1 µg/mL) is added to the culture 6 hours later. Transfected cells are incubated in serum-free VP-SFM for a total of 4 days. Supernatants containing infectious viruses are harvested, and may be biologically cloned by limiting dilution.

A recombinant virus having the HA and NA genes from A/Hong Kong/213/2003 (H5N1) and the remainder of the type A influenza virus genes from PR8(UW) was prepared. The titer of the recombinant virus was $10^{10.67}$ $EID_{50}$/mL, and the HA titer was 1:1600

TABLE 1

| Virus possessing PR8 genes together with the following HA and NA genes | HA titer (HAU/mL) in each dilition | | | | | | |
|---|---|---|---|---|---|---|---|
| | 10-2 | 10-3 | 10-4 | 10-5 | 10-6 | 10-7 | 10-8 |
| WSN-HA NA | 160 | 40 | 40 | 320 | 40 | 640 | <1 |
| HK-HAavir NA | 400 | 800 | 400 | 400 | 400 | 800 | <1 |

The sequences of PR8 (UW) genes are as follows:

PA (SEQ ID NO: 1)

```
AGCGAAAGCA GGTACTGATC CAAAATGGAA GATTTTGTGC GACAATGCTT CAATCCGATG
ATTGTCGAGC TTGCGGAAAA AACAATGAAA GAGTATGGGG AGGACCTGAA AATCGAAACA
AACAAATTTG CAGCAATATG CACTCACTTG GAAGTATGCT TCATGTATTC AGATTTTCAC
TTCATCAATG AGCAAGGCGA GTCAATAATC GTAGAACTTG GTGATCCAAA TGCACTTTTG
AAGCACAGAT TTGAAATAAT CGAGGGAAGA GATCGCACAA TGGCCTGGAC AGTAGTAAAC
AGTATTTGCA ACACTACAGG GGCTGAGAAA CCAAAGTTTC TACCAGATTT GTATGATTAC
AAGGAGAATA GATTCATCGA AATTGGAGTA ACAAGGAGAG AAGTTCACAT ATACTATCTG
GAAAAGGCCA ATAAAATTAA ATCTGAGAAA ACACACATCC ACATTTTCTC GTTCACTGGG
GAAGAAATGG CCACAAAGGC AGACTACACT CTCGATGAAG AAAGCAGGGC TAGGATCAAA
ACCAGACTAT TCACCATAAG ACAAGAAATG GCCAGCAGAG GCCTCTGGGA TTCCTTTCGT
CAGTCCGAGA GAGGAGAAGA GACAATTGAA GAAAGGTTTG AAATCACAGG AACAATGCGC
AAGCTTGCCG ACCAAAGTCT CCCGCCGAAC TTCTCCAGCC TTGAAAATTT TAGAGCCTAT
GTGGATGGAT TCGAACCGAA CGGCTACATT GAGGGCAAGC TGTCTCAAAT GTCCAAAGAA
GTAAATGCTA GAATTGAACC TTTTTTGAAA ACAACACCAC GACCACTTAG ACTTCCGAAT
GGGCCTCCCT GTTCTCAGCG GTCCAAATTC CTGCTGATGG ATGCCTTAAA ATTAAGCATT
GAGGACCCAA GTCATGAAGG AGAGGGAATA CCGCTATATG ATGCAATCAA ATGCATGAGA
ACATTCTTTG GATGGAAGGA ACCCAATGTT GTTAAACCAC ACGAAAAGGG AATAAATCCA
AATTATCTTC TGTCATGGAA GCAAGTACTG GCAGAACTGC AGGACATTGA GAATGAGGAG
AAAATTCCAA AGACTAAAAA TATGAAGAAA ACAAGTCAGC TAAAGTGGGC ACTTGGTGAG
AACATGGCAC CAGAAAAGGT AGACTTTGAC GACTGTAAAG ATGTAGGTGA TTTGAAGCAA
TATGATAGTG ATGAACCAGA ATTGAGGTCG CTTGCAAGTT GGATTCAGAA TGAGTTTAAC
AAGGCATGCG AACTGACAGA TTCAAGCTGG ATAGAGCTCG ATGAGATTGG AGAAGATGTG
GCTCCAATTG AACACATTGC AAGCATGAGA AGGAATTATT TCACATCAGA GGTGTCTCAC
TGCAGAGCCA CAGAATACAT AATGAAGGGA GTGTACATCA ATACTGCCTT GCTTAATGCA
TCTTGTGCAG CAATGGATGA TTTCCAATTA ATTCCAATGA TAAGCAAGTG TAGAACTAAG
GAGGGAAGGC GAAAGACCAA CTTGTATGGT TTCATCATAA AAGGAAGATC CCACTTAAGG
AATGACACCG ACGTGGTAAA CTTTGTGAGC ATGGAGTTTT CTCTCACTGA CCCAAGACTT
GAACCACATA AATGGGAGAA GTACTGTGTT CTTGAGATAG GAGATATGCT TATAAGAAGT
GCCATAGGCC AGGTTTCAAG GCCCATGTTC TTGTATGTGA GAACAAATGG AACCTCAAAA
ATTAAAATGA AATGGGGAAT GGAGATGAGG CGTTGCCTCC TCCAGTCACT TCAACAAATT
GAGAGTATGA TTGAAGCTGA GTCCTCTGTC AAAGAGAAAG ACATGACCAA AGAGTTCTTT
GAGAACAAAT CAGAAACATG GCCCATTGGA GAGTCCCCCA AAGGAGTGGA GGAAAGTTCC
ATTGGGAAGG TCTGCAGGAC TTTATTAGCA AAGTCGGTAT TCAACAGCTT GTATGCATCT
CCACAACTAG AAGGATTTTC AGCTGAATCA AGAAAACTGC TTCTTATCGT TCAGGCTCTT
AGGGACAACC TGGAACCTGG GACCTTTGAT CTTGGGGGGC TATATGAAGC AATTGAGGAG
TGCCTGATTA ATGATCCCTG GGTTTTGCTT AATGCTTCTT GGTTCAACTC CTTCCTTACA
CATGCATTGA GTTAGTTGTG GCAGTGCTAC TATTTGCTAT CCATACTGTC CAAAAAAGTA
CCTTGTTTCT ACT
```

PB1

-continued (SEQ ID NO: 2)

```
AGCGAAAGCA GGCAAACCAT TTGAATGGAT GTCAATCCGA CCTTACTTTT CTTAAAAGTG

CCAGCACAAA ATGCTATAAG CACAACTTTC CCTTATACTG GAGACCCTCC TTACAGCCAT

GGGACAGGAA CAGGATACAC CATGGATACT GTCAACAGGA CACATCAGTA CTCAGAAAAG

GGAAGATGGA CAACAAACAC CGAAACTGGA GCACCGCAAC TCAACCCGAT TGATGGGCCA

CTGCCAGAAG ACAATGAACC AAGTGGTTAT GCCCAAACAG ATTGTGTATT GGAGGCGATG

GCTTTCCTTG AGGAATCCCA TCCTGGTATT TTTGAAAACT CGTGTATTGA AACGATGGAG

GTTGTTCAGC AAACACGAGT AGACAAGCTG ACACAAGGCC GACAGACCTA TGACTGGACT

CTAAATAGAA ACCAACCTGC TGCAACAGCA TTGGCCAACA CAATAGAAGT GTTCAGATCA

AATGGCCTCA CGGCCAATGA GTCTGGAAGG CTCATAGACT TCCTTAAGGA TGTAATGGAG

TCAATGAACA AAGAAGAAAT GGGGATCACA ACTCATTTTC AGAGAAAGAG ACGGGTGAGA

GACAATATGA CTAAGAAAAT GATAACACAG AGAACAATGG GTAAAAAGAA GCAGAGATTG

AACAAAAGGA GTTATCTAAT TAGAGCATTG ACCCTGAACA CAATGACCAA AGATGCTGAG

AGAGGGAAGC TAAAACGGAG AGCAATTGCA ACCCCAGGGA TGCAAATAAG GGGGTTTGTA

TACTTTGTTG AGACACTGGC AAGGAGTATA TGTGAGAAAC TTGAACAATC AGGGTTGCCA

GTTGGAGGCA ATGAGAAGAA AGCAAAGTTG GCAAATGTTG TAAGGAAGAT GATGACCAAT

TCTCAGGACA CCGAACTTTC TTTCACCATC ACTGGAGATA ACACCAAATG GAACGAAAAT

CAGAATCCTC GGATGTTTTT GGCCATGATC ACATATATGA CCAGAAATCA GCCCGAATGG

TTCAGAAATG TTCTAAGTAT TGCTCCAATA ATGTTCTCAA ACAAAATGGC GAGACTGGGA

AAAGGGTATA TGTTTGAGAG CAAGAGTATG AAACTTAGAA CTCAAATACC TGCAGAAATG

CTAGCAAGCA TCGATTTGAA ATATTTCAAT GATTCAACAA GAAAGAAGAT TGAAAAAATC

CGACCGCTCT AATAGAGGG GACTGCATCA TTGAGCCCTG AATGATGAT GGGCATGTTC

AATATGTTAA GCACTGTATT AGGCGTCTCC ATCCTGAATC TTGGACAAAA GAGATACACC

AAGACTACTT ACTGGTGGGA TGGTCTTCAA TCCTCTGACG ATTTTGCTCT GATTGTGAAT

GCACCCAATC ATGAAGGGAT TCAAGCCGGA GTCGACAGGT TTTATCGAAC CTGTAAGCTA

CTTGGAATCA ATATGAGCAA GAAAAAGTCT TACATAAACA GAACAGGTAC ATTTGAATTC

ACAAGTTTTT TCTATCGTTA TGGGTTTGTT GCCAATTTCA GCATGGAGCT TCCCAGTTTT

GGGGTGTCTG GATCAACGA GTCAGCGGAC ATGAGTATTG GAGTTACTGT CATCAAAAAC

AATATGATAA ACAATGATCT TGGTCCAGCA ACAGCTCAAA TGGCCCTTCA GTTGTTCATC

AAAGATTACA GGTACACGTA CCGATGCCAT ATAGGTGACA CACAAATACA AACCCGAAGA

TCATTTGAAA TAAAGAAACT GTGGGAGCAA ACCCGTTCCA AAGCTGGACT GCTGGTCTCC

GACGGAGGCC CAAATTTATA CAACATTAGA AATCTCCACA TTCCTGAAGT CTGCCTAAAA

TGGGAATTGA TGGATGAGGA TTACCAGGGG CGTTTATGCA ACCCACTGAA CCCATTTGTC

AGCCATAAAG AAATTGAATC AATGAACAAT GCAGTGATGA TGCCAGCACA TGGTCCAGCC

AAAAACATGG AGTATGATGC TGTTGCAACA ACACACTCCT GGATCCCCAA AGAAATCGA

TCCATCTTGA TACAAGTCA AAGAGGAGTA CTTGAGGATG AACAAATGTA CCAAAGGTGC

TGCAATTTAT TTGAAAAATT CTTCCCCAGC AGTTCATACA GAAGACCAGT CGGGATATCC

AGTATGGTGG AGGCTATGGT TTCCAGAGCC CGAATTGATG CACGGATTGA TTTCGAATCT
```

```
GGAAGGATAA AGAAAGAAGA GTTCACTGAG ATCATGAAGA TCTGTTCCAC CATTGAAGAG

CTCAGACGGC AAAAATAGTG AATTTAGCTT GTCCTTCATG AAAAAATGCC TTGTTTCTAC

T
```

PB2

(SEQ ID NO: 3)

```
AGCGAAAGCA GGTCAATTAT ATTCAATATG GAAAGAATAA AGAACTACG AAATCTAATG

TCGCAGTCTC GCACCCGCGA GATACTCACA AAAACCACCG TGGACCATAT GGCCATAATC

AAGAAGTACA CATCAGGAAG ACAGGAGAAG AACCCAGCAC TTAGGATGAA ATGGATGATG

GCAATGAAAT ATCCAATTAC AGCAGACAAG AGGATAACGG AAATGATTCC TGAGAGAAAT

GAGCAAGGAC AAACTTTATG GAGTAAAATG AATGATGCCG GATCAGACCG AGTGATGGTA

TCACCTCTGG CTGTGACATG GTGGAATAGG AATGGACCAA TAACAAATAC AGTTCATTAT

CCAAAAATCT ACAAAACTTA TTTTGAAAGA GTCGAAAGGC TAAAGCATGG AACCTTTGGC

CCTGTCCATT TTAGAAACCA AGTCAAAATA CGTCGGAGAG TTGACATAAA TCCTGGTCAT

GCAGATCTCA GTGCCAAGGA GGCACAGGAT GTAATCATGG AAGTTGTTTT CCCTAACGAA

GTGGGAGCCA GGATACTAAC ATCGGAATCG CAACTAACGA TAACCAAAGA GAAGAAAGAA

GAACTCCAGG ATTGCAAAAT TTCTCCTTTG ATGGTTGCAT ACATGTTGGA GAGAGAACTG

GTCCGCAAAA CGAGATTCCT CCCAGTGGCT GGTGGAACAA GCAGTGTGTA CATTGAAGTG

TTGCATTTGA CTCAAGGAAC ATGCTGGGAA CAGATGTATA CTCCAGGAGG GGAAGTGAGG

AATGATGATG TTGATCAAAG CTTGATTATT GCTGCTAGGA ACATAGTGAG AAGAGCTGCA

GTATCAGCAG ATCCACTAGC ATCTTTATTG GAGATGTGCC ACAGCACACA GATTGGTGGA

ATTAGGATGG TAGACATCCT TAGGCAGAAC CCAACAGAAG AGCAAGCCGT GGATATATGC

AAGGCTGCAA TGGGACTGAG AATTAGCTCA TCCTTCAGTT TTGGTGGATT CACATTTAAG

AGAACAAGCG GATCATCAGT CAAGAGAGAG GAAGAGGTGC TTACGGGCAA TCTTCAAACA

TTGAAGATAA GAGTGCATGA GGGATATGAA GAGTTCACAA TGGTTGGGAG AAGAGCAACA

GCCATACTCA GAAAAGCAAC CAGGAGATTG ATTCAGCTGA TAGTGAGTGG GAGAGACGAA

CAGTCGATTG CCGAAGCAAT AATTGTGGCC ATGGTATTTT CACAAGAGGA TTGTATGATA

AAAGCAGTCA GAGGTGATCT GAATTTCGTC AATAGGGCGA ATCAACGATT GAATCCTATG

CATCAACTTT TAAGACATTT TCAGAAGGAT GCGAAAGTGC TTTTTCAAAA TTGGGGAGTT

GAACCTATCG ACAATGTGAT GGGAATGATT GGGATATTGC CCGACATGAC TCCAAGCATC

GAGATGTCAA TGAGGAGAGT GAGAATCAGC AAAATGGGTG TAGATGAGTA CTCCAGCACG

GAGAGGGTAG TGGTGAGCAT TGACCGTTTT TTGAGAATCC GGGACCAACG AGGAAATGTA

CTACTGTCTC CCGAGGAGGT CAGTGAAACA CAGGGAACAG AGAAACTGAC AATAACTTAC

TCATCGTCAA TGATGTGGGA GATTAATGGT CCTGAATCAG TGTTGGTCAA TACCTATCAA

TGGATCATCA GAAACTGGGA AACTGTTAAA ATTCAGTGGT CCCAGAACCC TACAATGCTA

TACAATAAAA TGGAATTTGA ACCATTTCAG TCTTTAGTAC CTAAGGCCAT TAGAGGCCAA

TACAGTGGGT TTGTAAGAAC TCTGTTCCAA CAAATGAGGG ATGTGCTTGG ACATTTGAT

ACCGCACAGA TAATAAAACT TCTTCCCTTC GCAGCCGCTC CACCAAAGCA AAGTAGAATG

CAGTTCTCCT CATTTACTGT GAATGTGAGG GGATCAGGAA TGAGAATACT TGTAAGGGGC

AATTCTCCTG TATTCAACTA TAACAAGGCC ACGAAGAGAC TCACAGTTCT CGGAAAGGAT

GCTGGCACTT TAACTGAAGA CCCAGATGAA GGCACAGCTG GAGTGGAGTC CGCTGTTCTG

AGGGGATTCC TCATTCTGGG CAAAGAAGAC AAGAGATATG GGCCAGCACT AAGCATCAAT
```

-continued

GAACTGAGCA ACCTTGCGAA AGGAGAGAAG GCTAATGTGC TAATTGGGCA AGGAGACGTG

GTGTTGGTAA TGAAACGGAA ACGGGACTCT AGCATACTTA CTGACAGCCA GACAGCGACC

AAAAGAATTC GGATGGCCAT CAATTAGTGT CGAATAGTTT AAAAACGACC TTGTTTCTAC

T

NP (SEQ ID NO: 4)
AGCAAAAGCA GGGTAGATAA TCACTCACTG AGTGACATCA AAATCATGGC GTCTCAAGGC

ACCAAACGAT CTTACGAACA GATGGAGACT GATGGAGAAC GCCAGAATGC CACTGAAATC

AGAGCATCCG TCGGAAAAAT GATTGGTGGA ATTGGACGAT TCTACATCCA AATGTGCACC

GAACTCAAAC TCAGTGATTA TGAGGGACGG TTGATCCAAA ACAGCTTAAC AATAGAGAGA

ATGGTGCTCT CTGCTTTTGA CGAAAGGAGA AATAAATACC TTGAAGAACA TCCCAGTGCG

GGGAAAGATC CTAAGAAAAC TGGAGGACCT ATATACAGGA GAGTAAACGG AAAGTGGATG

AGAGAACTCA TCCTTTATGA CAAAGAAGAA ATAAGGCGAA TCTGGCGCCA AGCTAATAAT

GGTGACGATG CAACGGCTGG TCTGACTCAC ATGATGATCT GGCATTCCAA TTTGAATGAT

GCAACTTATC AGAGGACAAG AGCTCTTGTT CGCACCGGAA TGGATCCCAG GATGTGCTCT

CTGATGCAAG GTTCAACTCT CCCTAGGAGG TCTGGAGCCG CAGGTGCTGC AGTCAAAGGA

GTTGGAACAA TGGTGATGGA ATTGGTCAGA ATGATCAAAC GTGGGATCAA TGATCGGAAC

TTCTGGAGGG GTGAGAATGG ACGAAAAACA AGAATTGCTT ATGAAAGAAT GTGCAACATT

CTCAAAGGGA AATTTCAAAC TGCTGCACAA AAAGCAATGA TGGATCAAGT GAGAGAGAGC

CGGAACCCAG GGAATGCTGA GTTCGAAGAT CTCACTTTTC TAGCACGGTC TGCACTCATA

TTGAGAGGGT CGGTTGCTCA CAAGTCCTGC CTGCCTGCCT GTGTGTATGG ACCTGCCGTA

GCCAGTGGGT ACGACTTTGA AAGGGAGGGA TACTCTCTAG TCGGAATAGA CCCTTTCAGA

CTGCTTCAAA ACAGCCAAGT GTACAGCCTA ATCAGACCAA ATGAGAATCC AGCACACAAG

AGTCAACTGG TGTGGATGGC ATGCCATTCT GCCGCATTTG AAGATCTAAG AGTATTAAGC

TTCATCAAAG GGACGAAGGT GCTCCCAAGA GGGAAGCTTT CCACTAGAGG AGTTCAAATT

GCTTCCAATG AAAATATGGA GACTATGGAA TCAAGTACAC TTGAACTGAG AAGCAGGTAC

TGGGCCATAA GGACCAGAAG TGGAGGAAAC ACCAATCAAC AGAGGGCATC TGCGGGCCAA

ATCAGCATAC AACCTACGTT CTCAGTACAG AGAAATCTCC CTTTTGACAG AACAACCATT

ATGGCAGCAT TCAATGGGAA TACAGAGGGG AGAACATCTG ACATGAGGAC CGAAATCATA

AGGATGATGG AAAGTGCAAG ACCAGAAGAT GTGTCTTTCC AGGGGCGGGG AGTCTTCGAG

CTCTCGGACG AAAAGGCAGC GAGCCCGATC GTGCCTTCCT TTGACATGAG TAATGAAGGA

TCTTATTTCT TCGGAGACAA TGCAGAGGAG TACGACAATT AAAGAAAAAT ACCCTTGTTT

CTACT

M (SEQ ID NO: 5)
AGCAAAAGCA GGTAGATATT GAAAGATGAG TCTTCTAACC GAGGTCGAAA CGTACGTACT

CTCTATCATC CCGTCAGGCC CCCTCAAAGC CGAGATCGCA CAGAGACTTG AAGATGTCTT

TGCAGGGAAG AACACCGATC TTGAGGTTCT CATGGAATGG CTAAAGACAA GACCAATCCT

GTCACCTCTG ACTAAGGGGA TTTTAGGATT TGTGTTCACG CTCACCGTGC CCAGTGAGCG

AGGACTGCAG CGTAGACGCT TTGTCCAAAA TGCCCTTAAT GGGAACGGGG ATCCAAATAA

CATGGACAAA GCAGTTAAAC TGTATAGGAA GCTCAAGAGG GAGATAACAT TCCATGGGGC

CAAAGAAATC TCACTCAGTT ATTCTGCTGG TGCACTTGCC AGTTGTATGG GCCTCATATA

CAACAGGATG GGGGCTGTGA CCACTGAAGT GGCATTTGGC CTGGTATGTG CAACCTGTGA

-continued

```
ACAGATTGCT GACTCCCAGC ATCGGTCTCA TAGGCAAATG GTGACAACAA CCAATCCACT

AATCAGACAT GAGAACAGAA TGGTTTTAGC CAGCACTACA GCTAAGGCTA TGGAGCAAAT

GGCTGGATCG AGTGAGCAAG CAGCAGAGGC CATGGAGGTT GCTAGTCAGG CTAGACAAAT

GGTGCAAGCG ATGAGAACCA TTGGGACTCA TCCTAGCTCC AGTGCTGGTC TGAAAAATGA

TCTTCTTGAA AATTTGCAGG CCTATCAGAA ACGAATGGGG GTGCAGATGC AACGGTTCAA

GTGATCCTCT CACTATTGCC GCAAATATCA TTGGGATCTT GCACTTGACA TTGTGGATTC

TTGATCGTCT TTTTTTCAAA TGCATTTACC GTCGCTTTAA ATACGGACTG AAAGGAGGGC

CTTCTACGGA AGGAGTGCCA AAGTCTATGA GGGAAGAATA TCGAAAGGAA CAGCAGAGTG

CTGTGGATGC TGACGATGGT CATTTTGTCA GCATAGAGCT GGAGTAAAAA ACTACCTTGT

TTCTACT
```

NS (SEQ ID NO: 6)
```
AGCAAAAGCA GGGTGACAAA AACATAATGG ATCCAAACAC TGTGTCAAGC TTTCAGGTAG

ATTGCTTTCT TTGGCATGTC CGCAAACGAG TTGCAGACCA AGAACTAGGC GATGCCCCAT

TCCTTGATCG GCTTCGCCGA GATCAGAAAT CCCTAAGAGG AAGGGGCAGT ACTCTCGGTC

TGGACATCAA GACAGCCACA CGTGCTGGAA AGCAGATAGT GGAGCGGATT CTGAAAGAAG

AATCCGATGA GGCACTTAAA ATGACCATGG CCTCTGTACC TGCGTCGCGT TACCTAACTG

ACATGACTCT TGAGGAAATG TCAAGGGACT GGTCCATGCT CATACCCAAG CAGAAAGTGG

CAGGCCCTCT TTGTATCAGA ATGGACCAGG CGATCATGGA TAAGAACATC ATACTGAAAG

CGAACTTCAG TGTGATTTTT GACCGGCTGG AGACTCTAAT ATTGCTAAGG GCTTTCACCG

AAGAGGGAGC AATTGTTGGC GAAATTTCAC CATTGCCTTC TCTTCCAGGA CATACTGCTG

AGGATGTCAA AAATGCAGTT GGAGTCCTCA TCGGAGGACT TGAATGGAAT GATAACACAG

TTCGAGTCTC TGAAACTCTA CAGAGATTCG CTTGGAGAAG CAGTAATGAG AATGGGAGAC

CTCCACTCAC TCCAAAACAG AAACGAGAAA TGGCGGGAAC AATTAGGTCA GAAGTTTGAA

GAAATAAGAT GGTTGATTGA AGAAGTGAGA CACAAACTGA AGATAACAGA GAATAGTTTT

GAGCAAATAA CATTTATGCA AGCCTTACAT CTATTGCTTG AAGTGGAGCA AGAGATAAGA

ACTTTCTCGT TTCAGCTTAT TTAGTACTAA AAAACACCCT TGTTTCTACT
```

HA (SEQ ID NO: 7)
```
AGCAAAAGCAGGGGAAAATAAAAACAACCAAAATGAAGGCAAACCTACTGGTCCTGTTATGTGCACTTG

CAGCTGCAGATGCAGACACAATATGTATAGGCTACCATGCGAACAATTCAACCGACACTGTTGACACAG

TACTCGAGAAGAATGTGACAGTGACACACTCTGTTAACCTGCTCGAAGACAGCCACAACGGAAAACTAT

GATTAAAAGGAATAGCCCCACTACAATTGGGGAAATGTAACATCGCCGGATGGCTCTTGGGAAACCCAG

GTAAATGCGACCCACTGCTTCCAGTGAGATCATGGTCCTACATTGTAGAAACACCAAACTCTGAGAATG

GAATATGTTATCCAGGAGATTTCATCGACTATGAGGAGCTGAGGGAGCAATTGAGCTCAGTGTCATCAT

TCGAAAGATTCGAAATATTTCCCAAAGAAAGCTCATGGCCCAACCACAACACAAACGGAGTAACGGCAG

CATGCTCCCATGAGGGGAAAAGCAGTTTTTACAGAAATTTGCTATGGCTGACGGAGAAGGAGGGCTCAT

ACCCAAAGCTGAAAAATTCTTATGTGAACAAAAAGGGAAAGAAGTCCTTGTACTGTGGGTATTCATC

ACCCGCCTAACAGTAAGGAACAACAGAATCTCTATCAGAATGAAAATGCTTATGTCTCTGTAGTGACTT

CAAATTATAACAGGAGATTTACCCCGGAAATAGCAGAAAGACCCAAAGTAAGAGATCAAGCTGGGAGGA

TGAACTATTACTGGACCTTGCTAAAACCCGGAGACACAATAATATTTGAGGCAAATGGAAATCTAATAG

CACCAATGTATGCTTTCGCACTGAGTAGAGGCTTTGGGTCCGGCATCATCACCTCAAACGCATCAATGC
```

-continued

```
ATGAGTGTAACACGAAGTGTCAAACACCCCTGGGAGCTATAAACAGCAGTCTCCCTTACCAGAATATAC

ACCCAGTCACAATAGGAGAGTGCCCAAAATACGTCAGGAGTGCCAAATTGAGGATGGTTACAGGACTAA

GGAACATTCCGTCCATTCAATCCAGAGGTCTATTTGGAGCCATTGCCGGTTTTATTGAAGGGGGATGGA

CTGGAATGATAGATGGATGGTATGGTTATCATCATCAGAATGAACAGGGATCAGGCTATGCAGCGGATC

AAAAAAGCACACAAAATGCCATTAACGGGATTACAAACAAGGTGAACACTGTTATCGAGAAAATGAACA

TTCAATTCACAGCTGTGGGTAAAGAATTCAACAAATTAGAAAAAAGGATGGAAAATTTAAATAAAAAAG

TTGATGATGGATTTCTGGACATTTGGACATATAATGCAGAATTGTTAGTTCTACTGGAAAATGAAAGGA

CTCTGGATTTCCATGACTCAAATGTGAAGAATCTGTATGAGAAAGTAAAAAGCCAATTAAAGAATAATG

CCAAAGAAATCGGAATGGATGTTTTGAGTTCTACCACAAGTGTGACAATGAATGCATGGAAAGTGTAA

GAAATGGGACTTATGATTATCCCAAATATTCAGAAGAGTCAAAGTTGAACAGGGAAAAGGTAGATGGAG

TGAAATTGGAATCAATGGGATCTATCAGATTCTGGCGATCTACTCAACTGTCGCCAGTTCACTGGTGC

TTTTGGTCTCCCTGGGGGCAATCAGTTTCTGGATGTGTTCTAATGGATCTTTGCAGTGCAGAATATGCA

TCTGAGATTAGAATTTCAGAGATATGAGGAAAAACACCCTTGTTTCTACT
```

NA
                                              (SEQ ID NO: 8)
```
AGCAAAAGCAGGGGTTTAAAATGAATCCAAATCAGAAAATAATAACCATTGGATCAATCTGTCTGGTAGT

CGGACTAATTAGCCTAATATTGCAAATAGGGAATATAATCTCAATATGGATTAGCCATTCAATTCAAACT

GGAAGTCAAAACCATACTGGAATATGCAACCAAAACATCATTACCTATAAAAATAGCACCTGGGTAAAGG

ACACAACTTCAGTGATATTAACCGGCAATTCATCTCTTTGTCCCATCCGTGGGTGGGCTATATACAGCAA

AGACAATAGCATAAGAATTGGTTCCAAAGGAGACGTTTTTGTCATAAGAGAGCCCTTTATTTCATGTTCT

CACTTGGAATGCAGGACCTTTTTTCTGACCCAAGGTGCCTTACTGAATGACAAGCATTCAAGTGGGACTG

TTAAGGACAGAAGCCCTTATAGGGCCTTAATGAGCTGCCCTGTCGGTGAAGCTCCGTCCCCGTACAATTC

AAGATTTGAATCGGTTGCTTGGTCAGCAAGTGCATGTCATGATGGCATGGGCTGGCTAACAATCGGAATT

TCAGGTCCAGATAATGGAGCAGTGGCTGTATTAAAATACAACGGCATAATAACTGAAACCATAAAAAGTT

GGAGGAAGAAAATATTGAGGACACAAGAGTCTGAATGTGCCTGTGTAAATGGTTCATGTTTTACTATAAT

GACTGATGGCCCGAGTGATGGGCTGGCCTCGTACAAAATTTTCAAGATCGAAAAGGGGAAGGTTACTAAA

TCAATAGAGTTGAATGCACCTAATTCTCACTATGAGGAATGTTCCTGTTACCCTGATACCGGCAAAGTGA

TGTGTGTGTGCAGAGACAATTGGCATGGTTCGAACCGGCCATGGGTGTCTTTCGATCAAAACCTGGATTA

TCAAATAGGATACATCTGCAGTGGGGTTTTCGGTGACAACCCGCGTCCCGAAGATGGAACAGGCAGCTGT

GGTCCAGTGTATGTTGATGGAGCAAACGGAGTAAAGGGATTTTCATATAGGTATGGTAATGGTGTTTGGA

TAGGAAGGACCAAAAGTCACAGTTCCAGACATGGGTTTGAGATGATTTGGGATCCTAATGGATGGACAGA

GACTGATAGTAAGTTCTCTGTGAGGCAAGATGTTGTGGCAATGACTGATTGGTCAGGGTATAGCGGAAGT

TTCGTTCAACATCCTGAGCTGACAGGGCTAGACTGTATGAGGCCGTGCTTCTGGGTTGAATTAATCAGGG

GACGACCTAAAGAAAAAACAATCTGGACTAGTGCGAGCAGCATTTCTTTTTGTGGCGTGAATAGTGATAC

TGTAGATTGGTCTTGGCCAGACGGTGCTGAGTTGCCATTCAGCATTGACAAGTAGTCTGTTCAAAAAACT

CCTTGTTTCTACT
```

High-titer A/PR/8/34 (H1N1, PR8(UW)) virus grows 10 times better than other A/PR/8/34 PR8 strains in eggs ($10^{10}$ EID$_{50}$/mL; HA titer:1:8,000). Thus, replacement of the HA and NA genes of PR8(UW) with those of a currently circulating strain of influenza virus results in a vaccine strain that can be safely produced, and validates the use of PR8 (UW) as a master vaccine strain.

Genes that contribute to different growth properties between PR8(UW) and PR8 (Cambridge), which provides the non-HA and -NA genes of the NIBRG-14 vaccine strain (FIG. 1), were determined. Higher titers in eggs were obtained when the majority of internal genes were from PR8(UW). Highest titers were with the M gene segment of PR8(UW) and the NS gene of PR8 (Cambridge). The NS gene in PR8(UW) has a K (lysine) at residue 55 while the NS gene in PR8(Cam) has a E (glutamic acid). The polymerase subunit (PA, PB1, and PB2) and NP genes of PR8(UW) enhanced the growth of an H5N1 vaccine seed virus in chicken embryonated eggs, and the NS gene of PR8(Cambridge) enhanced the growth of an H5N1 vaccine seed virus in chicken embryonated eggs. A tyrosine (Y) at position 360 in PB2 of PR8(UW) likely contributes to the high growth rate of that virus in MDCK cells.

Example 2

To develop an high-yield A/PR/8/34 (H1N1; PR8) virus backbone for growth of vaccine virus in specific host cells, random mutagenesis of the internal genes of PR8(HG) (PR8UW) was conducted. Random mutations were introduced into the UW-PR8 (Example 1) internal genes by error-prone PCR, after which plasmid libraries were prepared that possessed the random mutations in an individual UW-PR8 internal gene. Then virus libraries (PR8/H5N1) were generated that possessed random mutations in an individual UW-PR8 internal gene, along with the other wild type internal genes and the NA and 'detoxified' HA genes of A/chicken/Indonesia/NC/09 (H5N1) virus (Table 1), to generate "6+2" recombinant viruses. Consecutive passages of the virus in MDCK cells were employed to select for variants with high-growth properties.

TABLE 1

Virus libraries generated

| | | Internal genes | | Titer of |
|---|---|---|---|---|
| Number | Gene library | Other internal genes | HA + NA | virus library (pfu/ml) |
| Control | | PR8 wild type | NC/09/H5N1 | $3 \times 10^6$ |
| 1 | PB2 | 5 UW-PR8 genes | NC/09/H5N1 | $2.1 \times 10^2$ |

TABLE 1-continued

Virus libraries generated

| | | Internal genes | | Titer of |
|---|---|---|---|---|
| Number | Gene library | Other internal genes | HA + NA | virus library (pfu/ml) |
| 2 | PB1 | 5 UW-PR8 genes | NC/09/H5N1 | $1.6 \times 10^5$ |
| 3 | PA | 5 UW-PR8 genes | NC/09/H5N1 | $7 \times 10^3$ |
| 4 | NP | 5 UW-PR8 genes | NC/09/H5N1 | $1.5 \times 10^3$ |
| 5 | M | 5 UW-PR8 genes | NC/09/H5N1 | $1 \times 10^6$ |
| 6 | NS | 5 UW-PR8 genes | NC/09/H5N1 | $1.8 \times 10^6$ |
| 7 | PB2 + PB1 + PA | 3UW-PR8 genes | NC/09/H5N1 | 75 |
| 8 | PB2 + PB1 + PA + NP | 2UW-PR8 genes | NC/09/H5N1 | 33 |
| 9 | PB2 + NS | 4UW-PR8 genes | NC/09/H5N1 | $2 \times 10^2$ |
| 10 | M + NS | 4UW-PR8 genes | NC/09/H5N1 | $5.7 \times 10^5$ |

Figure 2:
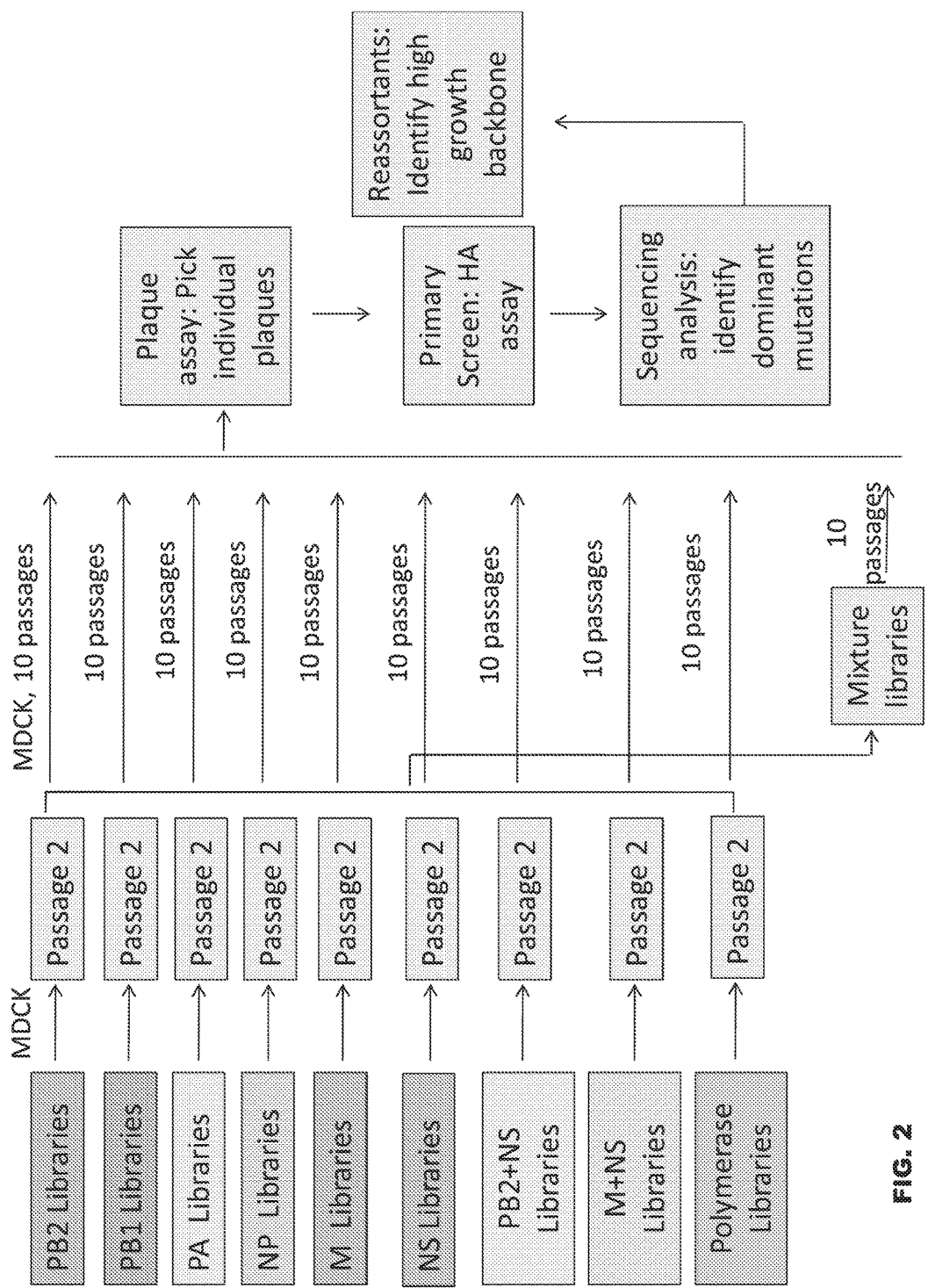
FIG. 2: Overview of library passages and the identification of high-yield candidates.

Virus libraries were passaged 12 times in MDCK cells or, after 2 passages, the libraries were mixed and 10 more passages were carried out (FIG. 2).

After 10 to about 12 consecutive passages in MDCK cells, plaque assays were performed and over 1,400 individual plaques were picked. FIG. 3 shows the numbers of clones with various HA titers. Growth enhancing mutations included: PB2: M202L, F323L, I504V, PB1: E112G, V644A, NP: R74K, N417D, I116L, and NS: S161T. FIG. 4 provides the titers of recombinant viruses generated from selected mutations.

36 viruses with the highest HA titers from the random mutagenesis libraries were sequenced (Table 2)

TABLE 2

Sequences of viruses with the highest HA titers

| Clone # | Library | HA titer ($2^n$) | PB2 | PB1 | PA | HA (H3 numbering) | NP | NA | M | NS |
|---|---|---|---|---|---|---|---|---|---|---|
| WT | | 7 | | | | | | | | |
| 329 | Mix | 9 | M202L F323L | | | L182V | | | | |
| 154 | Mix | 8.5~9 | M202L F323L | | | L182V | | | | |
| 347 | Mix | 9 | M202L F323L | | | L182V | | | | |
| 94 | Mix | 8.5 | M202L F323L | | | F252I | | I116L | L55S | |
| 1045 | Mix | 9 | M202L F323L | V644A | | F252I | | | | |
| 965 | Mix | 8.5~9 | M202L F323L | | F105C | V184I | | | P90S | |
| 50 | Mix | 8.5 | M202L F323L | | | M148I (HA2) | R293M | | | |
| 1005 | Mix | 9~9.5 | M202L F323L | V644A | R401K | M148I (HA2) | | | | T49A |
| 134 | Mix | 8.5 | M202L F323L | | | | | | | A223E |
| 387 | Mix | 9 | M202L F323L | M507V V644A | | | | | | |
| 852 | Mix | 9~9.5 | M202L F323L M243I | R54I | | | | | | |
| 981 | Mix | 8.5~9 | M202L F323L | Q247H | | | | | | |
| 993 | Mix | 8.5~9 | M202L F323L | | | | N224I | | | |
| 1043 | Mix | 8.5~9 | I504V | | | | L182V | R75K | | |
| 398 | Mix | 8.5 | I504V | | | | L182V | R74K, N417D | | A30P |
| 1007 | Mix | 8.5 | I504V | V644A | | | F252I | M371V | | |
| 1042 | Mix | 8.5~9 | I504V | E75V D76G E78P | | | F252I | R74K | | |

TABLE 2-continued

Sequences of viruses with the highest HA titers

| Clone # | Library | HA titer (2ⁿ) | PB2 | PB1 | PA | HA (H3 numbering) | NP | NA | M | NS |
|---|---|---|---|---|---|---|---|---|---|---|
| | | | | | P79V | | | | | |
| | | | | | S80G | | | | | |
| | | | | | V644A | | | | | |
| | | | | | E697P | | | | | |
| | | | | | F699L | | | | | |
| | | | | | F700L | | | | | |
| | | | | | P701H | | | | | |
| | | | | | S702R | | | | | |
| | | | | | Y705T | | | | | |
| 999 | Mix | 8.5~9 | | I504V | | M148I (HA2) | R74K, N417D | | | |
| 1014 | Mix | 8.5 | | I504V | T59I G62X A63P V644A N694K L695T | M148I (HA2) | R74K, N417D | A265V | | |
| 1016 | Mix | 8.5~9 | | I504V | | M148I (HA2) | | | | |
| 540 | PB1 | 8.5 | | E112G | | K162E | | | | S161T |
| 548 | PB1 | 8.5~9 | | E112G L624V | | K162E | | | | S161T |
| 191 | PB1 | 8~8.5 | | E112G | | | | | | |
| 571 | PB1 | 9~9.5 | | E112G | | | | | | |
| 572 | PB1 | 8.5 | | E112G | | | | | | |
| 573 | PB1 | 8.5 | | E112G | | | | | | |
| 1404 | PB1 | 8.5 | | I57V T58G A59V K61Q E677D D678E P679M | E112G S713C | | | | | |
| 1408 | PB1 | 8.5 | | M40I G180W | | | | | | S161T |
| 582 | PB1 | 8.5~9 | | M40L, G180W | | | | | | S161T |
| 545 | PB1 | 8.5 | | M40L, G180W | | K121E (HA2) | | | | |
| 543 | PB1 | 8.5 | | I667T | | | | | | |
| 219 | PB1 | 9 | | I667T, M714T | | K162E | | | | |
| 344 | Mix | 8.5~9 | M66R | | | L182V | | | | |
| 312 | Mix | 8.5~9 | | | | L182V | | I116L | | R140Q |
| 320 | Mix | 8.5 | | | | L182V | | | | |
| 209 | PB1 | 8.5~9 | | R54I | | E136D, Q179L, A194V | | | | |

In a second approach, potentially growth-enhancing mutations described in the literature were introduced into the background of UW-PR8 virus (see Table 3 for virus stock titers) and tested for replicative ability. FIGS. 5A-D show growth curves for various viruses.

TABLE 3

UW-PR8 viruses possessing mutation(s) identified in the literature

| Gene | Mutation(s) | Virus stock titer (Pfu/ml) |
|---|---|---|
| WT | — | $2 \times 10^7$ |
| PB2 | A44S | $4.5 \times 10^7$ |
| | E158G | $3.2 \times 10^4$ |
| | E158G + NP N101G | $7.5 \times 10^4$ |
| | E158A | $8.3 \times 0^6$ |
| | D253N + Q591K | $8.3 \times 10^6$ |
| | D256G | $2.8 \times 10^7$ |
| | R368K | $3.1 \times 10^7$ |
| | E391Q | $1.4 \times 10^8$ |
| | I504V + PA I550L | $1.1 \times 10^8$ |
| | Q591K | $4.4 \times 10^7$ |
| | V613T | $1.8 \times 10^7$ |
| | A661T | $2.2 \times 10^7$ |
| | D701N + S714R + NP N319K | $1 \times 10^6$ |
| | D701N | $2.1 \times 10^7$ |
| PB1 | R327K | $1.3 \times 10^7$ |
| | V336I | $2.3 \times 10^7$ |
| | L473V + L598P | $3.9 \times 10^6$ |
| PB1F2 | F2 N66S | $1.6 \times 10^8$ |
| | F2 K73R | $1.1 \times 10^8$ |
| | F2 V76A | $4.4 \times 10^7$ |
| | F2 R79Q | $6.2 \times 10^6$ |
| | F2 L82S | $2.7 \times 10^7$ |
| | F2 E87Q | $1.5 \times 10^6$ |

TABLE 3-continued

UW-PR8 viruses possessing mutation(s) identified in the literature

| Gene | Mutation(s) | Virus stock titer (Pfu/ml) |
|---|---|---|
| PA | T97I | $1.6 \times 10^7$ |
|  | K142N | $3.3 \times 10^7$ |
|  | S225C | $6.7 \times 10^7$ |
|  | S149P + T357K | $3.4 \times 10^8$ |
|  | K356R | $8.5 \times 10^7$ |
|  | A404S | $5.2 \times 10^7$ |
|  | S421I | $2.7 \times 10^7$ |
| NP | R293K | $4.7 \times 10^7$ |
|  | R305K | $7.2 \times 10^7$ |
|  | E372D | $2.2 \times 10^7$ |
|  | R422K | $1.3 \times 10^8$ |
|  | T442A | $5 \times 10^7$ |
|  | D455E | $2.2 \times 10^7$ |
|  | I109V | $3.9 \times 10^7$ |
| M | V97A + Y100H | $1.4 \times 10^7$ |
| NS1 | K55E | $1.6 \times 10^7$ |

In a third approach, candidates from approaches 1 and 2 were combined and HA titers and PFU/mL determined (Table 4).

TABLE 4

High-growth candidates identified in approaches 1 and 2 were tested in various combinations.

| # | HA | NA | PB2 | PB1 | PA | NP | M | NS | HA ($2^n$) | Pfu/ml |
|---|---|---|---|---|---|---|---|---|---|---|
| WT | Indo/NC/09 (detoxified) | Indo/NC/09 | UW-PR8 | UW-PR8 | UW-PR8 | UW-PR8 | UW-PR8 | UW-PR8 | 7 | 3.00E+07 |
| 1 |  |  | M202L F323L | M507V V644A |  | I116L |  | K55E | 9~9.5 | 2.00E+08 |
| 2 |  |  | M202L F323L | R54I |  | N224I |  | K55E | 5 | 1.00E+05 |
| 3 |  |  | M202L F323L | Q247H | R401K |  |  | T49A | 9 | 1.00E+08 |
| 4 |  |  | M202L F323L | M507V V644A | K356R | T442A | V97A Y100H | K55E | 10~10.5 | 1.60E+08 |
| 5 |  |  | I504V | M507V V644A | I550L | R74K N417D |  | K55E | 8~8.5 | 5.70E+07 |
| 6 |  |  | I504V | M507V V644A | I550L | R74K N417D | V97A Y100H | K55E | 9~9.5 | 4.40E+07 |
| 7 |  |  | I505V | E112G | I550L | R74K |  | S161T | 9 | 1.60E+08 |
| 8 |  |  | M202L F323L | I667T M714T |  | I116L |  | R140Q | <1 | <1E3 |
| 9 |  |  | M202L F323L | E112G |  |  |  | S161T | 8.5 | 1.30E+08 |
| 10 |  |  | M66R | M40I G180W |  | R74K |  | S161T | 8~8.5 | 2.30E+07 |
| 12 |  |  | R368K | PB1 F2 N66S | K356R | R422K |  | K55E | 5.5 | 9.00E+02 |
| 13 |  |  | E391Q | R327K | S149P T357K | R293K |  |  | 3 | 1.60E+06 |
| 14 |  |  | Q591K | PB1 F2 K73R | S225C | R422K |  | K55E | 7.5 | 2.00E+07 |
| 23 |  |  |  |  |  |  | V97A |  | 8.5~9 | 1.50E+07 |
| 24 |  |  |  |  |  |  | Y100H |  | 9 | 2.90E+07 |
| 25 | NCR 15-19nt mut[1] | Indo/NC/09 | M202L F323L | M507V V644A | K356R | R422K | V97A Y100H | K55E | 9.5~10 | 7.50E+07 |
| 26 | Indo/NC/09 (detoxified) | Indo/NC/09 |  |  |  |  |  | A30P | 6.5~7 | 1.00E+07 |
| 27 |  |  |  |  |  |  |  | T49A | 6.5~7 | 2.00E+07 |
| 28 |  |  |  |  |  |  |  | R140Q | 8 | 4.00E+07 |
| 29 |  |  |  |  |  |  |  | S161T | 7~7.5 | 1.40E+07 |
| 30 |  |  |  |  |  |  |  | A223E | 7.5 | 1.00E+07 |
| 31 |  |  |  | I667T M714T |  |  |  |  | 3.5 | 4.00E+05 |
| 32 | NCR 15-19nt mut | UW-PR8 | M202L F323L | V644A | K356R | T442A | Y100H | K55E | 7~7.5 | 4.30E+06 |
| 33 | Indo/NC/09 (detoxified) | Indo/NC/09 | M202L F323L | E112G | K356R | R74K | Y100H | K55E | 9~9.5 | 7.00E+07 |
| 34 | NCR 15-19nt mut | UW-PR8 | I504V | M507V V644A |  |  | V97A Y100H | K55E | 7 | 2.00E+05 |
| 35 | Indo/NC/09 (detoxified) | Indo/NC/09 | M202L F323L | M507V V644A | R401K | T442A | Y100H | R140Q | 9 | 3.20E+07 |
| 36 |  |  | I504V | E112G | I550L | I112L | Y100H | R140Q | 9.5 | 1.30E+08 |
| 37 |  |  | M202L F323L | E112G | S149P T357K | T442A | Y100H | K55E | 0 | 0.00E+00 |
| 38 |  |  | M202L F323L | M507V V644A |  | I116L | Y100H | K55E | 10.1 | 2.30E+00 |

TABLE 4-continued

High-growth candidates identified in approaches 1 and 2 were tested in various combinations.

| # | HA | NA | PB2 | PB1 | PA | NP | M | NS | HA (2") | Pfu/ml |
|---|----|----|-----|-----|-----|-----|-----|-----|---------|--------|
| 39 | | | M202L F323L | M507V V644A | K356R | T442A | Y100H | K55E | 9.8 | 1.00E+08 |
| 40 | | | I504V | M507V V644A | I550L | T442A | Y100H | K55E | 9.2 | 6.00E+07 |
| 41 | | | I504V | I112G | I550L | R74K | Y100H | K55E | 9.2 | 7.50E+07 |
| P17 | | | I504V | E112G | S225C | R74K N417D | V97A Y100H | K55E | 9.5~10 | 5.80E+08 |
| P26 | | | M202L F323L | M40L G180W | S225C | R422K | V97A Y100H | K55E | 10 | 3.00E+08 |
| P61 | | Indo/NC/ 09 NA P263T[2] | M202L F323L | Q247H | K142N | R74K | V97A Y100H | K55E | 10~10.5 | 2.00E+08 |

Figures 8A, 8B:
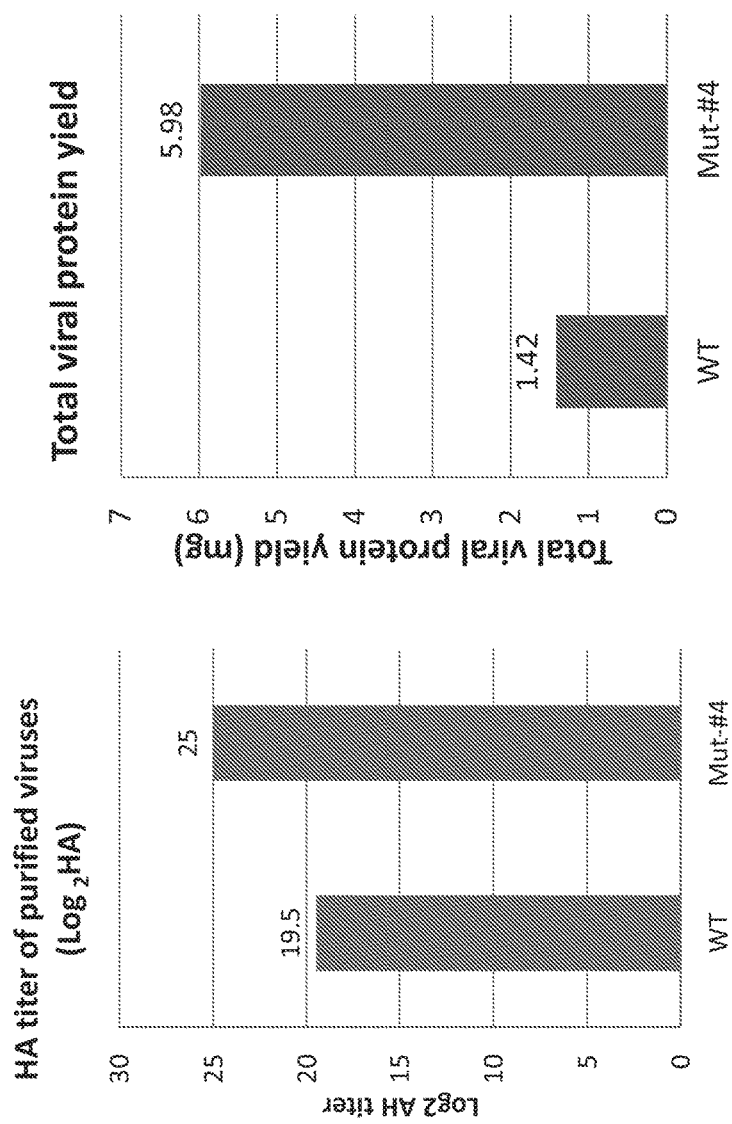

[1]Mutation in the HA gene noncoding region; [2] A P263T mutation was detected in the NA protein of this virus clone As shown in Table 4, several recombinant viruses were identified that replicated better than wild type, such as #1, #4, #36, #38, P17, P16, and P61. To identify the growth characteristics of these viruses, growth kinetics in MDCK cells were determined (FIG. 7). For one candidate, virus was purified on sucrose gradients and HA content and viral total protein evaluated. FIG. 8A shows HA titer of wild type (UW-PR8) and #4, FIG. 8B shows viral protein for wild type (UW-PR8) and #4, and FIG. 8BC is a SDS-PAGE analysis of viral proteins of wild type (UW-PR8) and #4. Further analysis demonstrated that viruses possessing the V97A/Y100H mutations in M1 yielded higher HA titers than the parental virus, although the virus titer was lower (see FIGS. 9A-B). The V97A/Y100H mutations in M1 may result in particles with a larger surface into which more HA protein can be incorporated. Since inactivated influenza viruses are dosed based on their HA content, variants with high HA content are attractive vaccine candidates.

To identify mutations in the influenza promoter region that provide for enhanced replication, viruses possessing a 'U' at position 4 at the 3' end of all eight vRNA segments were prepared in the UW-PR8 PA, PB1 and PB2 internal genes (the UW-PR8 PB2, PB1, and PA segments possess a 'C' at position 4). The growth curves of the resulting viruses are shown in FIG. 11C.

Viruses possessing combinations of promoter mutations and amino acid changes were prepared and titers determined (Table 5).

TABLE 5

Virus titers of high-growth candidates.

| Viruses | HA | NA | PB2 | PB1 | PA | NP | M | NS | HA (2") | pfu/ml |
|---------|----|----|-----|-----|-----|-----|-----|-----|---------|--------|
| Control | WT | WT | WT | WT | WT | WT | WT | WT | 7 | 3.0E+07 |
| 1 | WT | WT | 3'C4U | 3'C4U | 3'C4U | R74K | V97A | K55E | 10.5 | 2.2E+09 |
| 2 | 3' G3A U5C C8U & 5' U3C A8G | | M202L F323L | Q247H | K142N | | Y100H | | 8.5~9 | 5.6E+07 |
| 3 | NCR 15-19nt mut | | | | | | | | 9~9.5 | 1.4E+09 |
| 4 | 3' G3A U5C C8U & 5' U3C A8G & NCR 15-19nt mut | | | | | | | | 7 | 7.0E+07 |

Figure 10B:
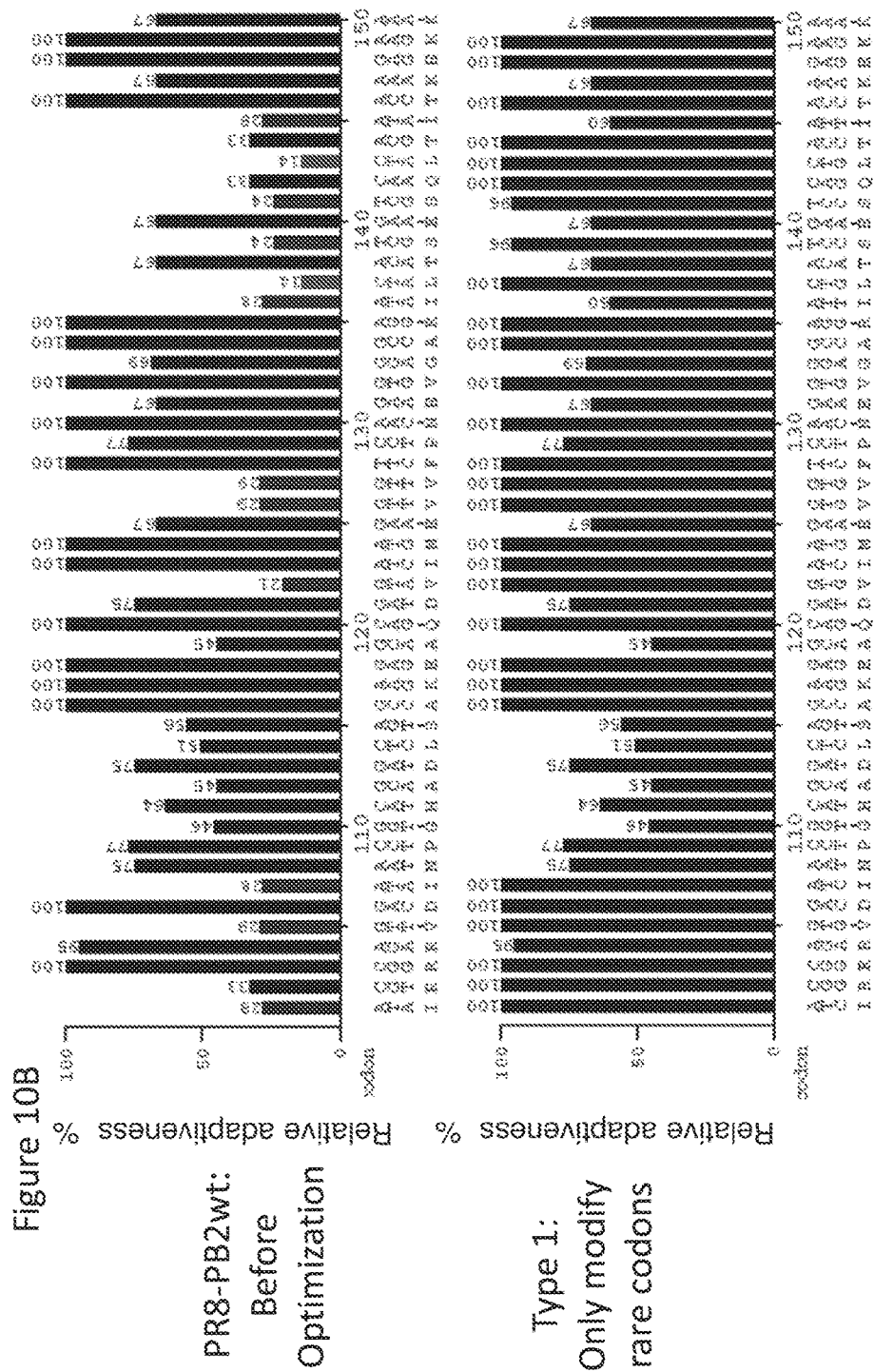

Codon usage optimization was also conducted. Alteration of codons may increase protein expression but could also alter RNA structure and stability. For example, codon usage optimization of the PB2 gene segment was performed to reflect the codon usage in canine cells (since MDCK cells are of canine origin) (FIG. 10A), while leaving the packaging signals (located at the 5' and 3' ends of the vRNA) unaltered. In one approach, codon optimization was performed for all codons in the 'internal' region of the PB2 gene (FIG. 10C) and in another approach, codon optimization was performed for so-called 'rare' codons (FIG. 10B) (used at significantly lower frequency compared to the codon used most frequently for a given amino acid) (see SEQ ID NO: 13 in FIG. 10F). Analyses were carried out using the "Graphical Codon Usage Analyser" (www.gcua.de). The titers of those viruses are shown in Table 6 (see also FIGS. 10B-C).

TABLE 6

Titers of viruses encoding codon-optimized PB2 genes.

| Virus | Gene backbone | | | | | | | | Virus stock titer | |
|---|---|---|---|---|---|---|---|---|---|---|
| | HA | NA | PB2 | PB1 | PA | NP | M | NS | HA (2$^n$) | pfu/ml |
| Wild type | WT | WT | WT | WT | WT | WT | WT | WT | 7~7.5 | 3.5E+07 |
| PB2 codon optimization-1 | WT | WT | Rare codon optimized PB2 | WT | WT | WT | WT | WT | 9 | 2.1E+08 |
| PB2 codon optimization-2 | WT | WT | All Codon optimized PB2 | WT | WT | WT | WT | WT | 3 | 9.0E+05 |

Optimization of rare codons in PB2 resulted in increased titers compared to wild type virus (UW-PR8) (see FIG. 10D). Other gene segments were codon optimized and titers of viruses with those segments or combinations of optimized segments were determined (FIG. 10E).

In another approach to increase virus titer in MDCK cells, chimeric HA and NA genes were prepared (FIG. 13A) and titers of viruses having those genes were determined (FIG. 13B).

Viruses with combinations of the above-mentioned mutations (high growth backbone mutations, promoter mutations, chimeric HA and NA genes and canine codon optimization) were prepared and growth kinetics, PFU and HA titers of those viruses were determined (see FIG. 14). An exemplary set of backbone mutations are canine codon opti-PB2+C4U+M202L, F323L; PB1: C4U+Q247H; PA: C4U+K142N; NP: Canine codon opti-NP+R74K; M: V97A, Y100H; and NS: K55E.

Any of the mutations described herein, or any combination thereof, may be combined with, for instance, seasonal H1N1 and H3N2, H3N2 Variant, PdmH1N1, H5N1, H7N9 or H9N2, or other clades or candidate vaccine strains. For example, HA and NA genes from A/California/04/2009(pdm H1N1) were combined with the six internal genes of UW-PR/8 to generate "6+2" recombinant viruses. Eleven virus libraries were generated and passaged 10 times in eggs. Three rounds of limiting dilution were performed to screen for high growth mutants (FIG. 15). In one embodiment, a variant with high growth properties in MDCK cells has a PB2 gene segment with a promoter mutation (C4U) and a mutation that results in I504V (relative to the parental virus); a PB1 gene segment with a promoter mutation (C4U) and a mutation that results in E112G; a PA gene segment with a promoter mutation (C4U) and a mutation that results in S225C; a NP gene segment with mutations that result in R74K and N417D; a M gene segment with mutations that result in V97A and Y100H; and a NS gene segment with a mutation that results in K55E, where optionally the sequence of one or more gene segments, e.g., the NP gene segment, is modified to include canine codon optimized codons. In one embodiment, a variant with high growth properties in MDCK cells has a canine codon optimized PB2 gene segment with a promoter mutation (C4U) and mutations that result in M202L and F323L; a PB1 gene segment with a promoter mutation (C4U) and a mutation that results in Q247H; a PA gene segment with a promoter mutation (C4U) and a mutation that results in K142N; a canine codon optimized NP gene segment with a mutation that results in R74K; a M gene segment with mutations that result in V97A Y100H; and a NS gene segment with a mutation that results in K55E.

Similar experiments were conducted in Vero cells, e.g., after about 3 to 5 passages in Vero cells, using clones with high replicative properties in MDCK cells (see FIG. 16). FIG. 17 shows 5 viruses likely to have high replicative properties in Vero cells. In one embodiment, a PR8(UW) variant with high-growth properties in Vero cells has the following mutations that may be used in various combinations to increase the replicative ability of PR8(UW) virus: PB2 segment: C4U (promoter mutation), I504V (amino acid change); PB1 segment: C4U (promoter mutation); M40L (amino acid change), G180W (amino acid change); PA segment: C4U (promoter mutation), R401K (amino acid change); NP segment: I116L (amino acid change); NS segment: A30P (amino acid change in NS1), or R118K (amino acid change in NS1).

REFERENCES

Avery's Drug Treatment: Principles and Practice of Clinical Pharmacology and Therapeutics, 3rd edition, ADIS Press, Ltd., Williams and Wilkins, Baltimore, Md. (1987).
Aymard-Henry et al., Virology: A Practical Approach, Oxford IRL Press, Oxford, 119-150 (1985).
Bachmeyer, Intervirology, 5:260 (1975).
Berkow et al., eds., The Merck Manual, 16th edition, Merck & Co., Rahway, N.J. (1992).
Hatta et al., Science, 293:1840 (2001).
Horimoto et al., J. Virol., 68:3120 (1994).
Horimoto et al., Vaccine, 24:3669 (2006).
Keitel et al., in Textbook of Influenza, eds. Nickolson, K. G., Webster, R. G., and Hay, A. (Blackwell, Oxford), pp. 373-390 (1998).

Laver & Webster, *Virology,* 69:511 (1976).
Neumann et al., *Adv. Virus Res.,* 53:265 (1999).
Neumann et al., *J. Gen. Virol.,* 83:2635 (2002).
Neumann et al., *J. Virol.,* 71:9690 (1997).
Neumann et al., *Proc. Natl. Acad. Sci. USA,* 96:9345 (1999).
Neumann et al., *Virology,* 287:243 (2001).
Osol (ed.), *Remington's Pharmaceutical Sciences,* Mack Publishing Co., Easton, Pa. 1324-1341 (1980).
Sugawara et al., *Biologicals,* 30:303 (2002).
Webby & Webster et al., *Science,* 302:1519 (2003).
Wood & Robertson, *Nat. Rev. Microbiol.,* 2:842 (2004).
World Health Organization TSR No. 673 (1982).
World Health Organization. Confirmed human cases of avian influenza A (H5N1). http://www.who.int/csr/disease/avian_influenza/country/en/index.html All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method to prepare influenza virus, comprising: contacting a cell with:
one or more vectors for vRNA or cRNA production of PA, PB1, PB2, NP, NS, M, NA, and HA viral segments, wherein the one or more vectors comprise a promoter operably linked to DNA for the viral segments linked to a transcription termination sequence, wherein the DNA for the NA viral segment for vRNA or cRNA production of NA has sequences for a heterologous NA, and wherein the DNA for the HA viral segment in the vector for vRNA or cRNA production of HA has sequences for a heterologous HA, wherein two or more of the PA, PB1, PB2, NP, NS, and M viral segments have sequences that are capable of encoding a PA protein, PB1 protein, PB2 protein, NP protein, NS1 protein, or M2 protein, respectively, having selected amino acid residues at positions 30, 31, 105, 142, 149, 225, 356, 357, 401, and/or 550 in the PA protein: 40, 54, 59, 62, 63, 75, 76, 78, 79, 80, 112, 180, 247, 327, 507, 624, 644, 667, 694, 695, 697, 699, 700, 701, 702, 705, 713, and/or 714 and/or 247 in the PB1 protein: 57, 58, 59, 61, 66, 202, 323, 368, 391, 504, 591, 677, 678, and/or 679, 202 and/or 323 in the PB2 protein: 74, 112, 116, 224, 293, 371, 377, 417, 422 and/or 442 in the NP protein: 90, 97 and/or 100 in M1 protein in the M viral segment; or 30, 49, 55, 118, 140, 161 or 223 in NS1 protein in the NS viral segment, wherein the selected amino acid residue when present in the, influenza viral protein in an influenza virus enhances replication relative to an influenza virus having an amino acid residue in a corresponding influenza virus protein encoded by SEQ ID NOs.: 1 to 6 or 10 to 16, wherein if the selected residue is in the PA protein, the position and the selected residue include 142N, 225C, 356R, 401K, or 550L, wherein if the selected residue is in the PB1 protein, the position and the selected residue include 40I/L 112G, 180W, 247H 507V, or 644A, wherein if the selected residue is in the PB2 protein, the position and the selected residue include 180W, 202L, 504 V or 323L, wherein if the selected residue is in the NP protein, the position and the selected residue include 74K, 112L, 116L, 377N, 417D, or 422L, wherein if the selected residue is in the NS1 protein, the position and the selected residue include 30P, 118K, 161T or 140Q, and wherein if the selected residue is in the M1 protein, the position and the selected residue include 97A or 100H; and one or more vectors for mRNA production comprising a promoter operably linked to a DNA segment encoding influenza virus PA, PB1, PB2 and NP viral segments and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2; in an amount effective to yield infectious influenza virus.

2. The method of claim 1 wherein the cell is an avian cell.

3. The method of claim 1 wherein the cell is a mammalian cell.

4. The method of claim 1 wherein the cell is a Vero cell, a human cell or a MDCK cell.

5. The method of claim 1 wherein the PB1, PB2, PA, NP, NS, and M DNAs in the vectors for vRNA productions have a sequence that corresponds to one that encodes a polypeptide having at least 95% amino acid sequence identity to a corresponding polypeptide encoded by SEQ ID NOs:1-6 or 10-15.

6. The method of claim 1 further comprising isolating the virus.

7. The method of claim 1 wherein at least one of PA, PB1, or PB2 viral segments has a C to U promoter mutation.

8. The method of claim 1 wherein selected position and residue in PA comprises 142N, 225C, 356R, or 550L; wherein the selected position and residue in PB1 comprises 112G, 247H, 507V, or 644A: wherein the selected position and residue in PB2 comprises 202L, 323L or 504V; wherein the selected position and residue in NP comprises 74K, 112L, 116L, 417D, or 442A; wherein the selected position and residue in M1 comprises 97A and/or 100H; and/or wherein the selected position and residue in NS1 comprises 55E and/or 140Q in NS1, or combinations thereof.

9. The method of claim 1 wherein the selected position and residue in PB2 comprises 202L and/or 323; wherein the selected position and residue in PB1 comprises 247H; or wherein the selected position and residue in NP comprises 74K.

10. The method of claim 1 wherein the selected position and residue in PB1 comprises 40I, 40L, 112G, 180W, 247H, 507V, or 644A; wherein the selected position and residue in PB2 comprises 202L and/or 323L; wherein the selected position and residue in NP comprises 74K, 112L, 116L, 377N, 417D, or 422L; wherein the selected position and residue in NS1 comprises 30P, 118K, 161T or 140Q; and/or wherein the selected position and residue in PA comprises 142N, 225C, 356R, 401K, or 550L.

11. The method of claim 1 wherein the NA viral segment and the HA viral segment are from the same influenza virus isolate.

12. The method of claim 1 wherein the PA, PB1, PB2, NP, NS, and M viral segments comprise sequences for at least one of the following: a PB1 having the amino acid sequence encoded by SEQ ID NO:2 or PB1 with at least 95% amino acid sequence identity to the PB1 encoded by SEQ ID NO:2; a PB2 having the amino acid sequence encoded by SEQ ID NO:3 or PB2 with at least 95% amino acid sequence identity to the PB2 encoded by SEQ ID NO:3; a PA having the amino acid sequence encoded by SEQ ID NO:1 or PA with at least 95% amino acid sequence identity to the PA encoded by SEQ ID NO: 1; a NP having the amino acid sequence encoded by SEQ ID NO:4 or NP with at least 95% amino acid sequence identity to the NP encoded by SEQ ID NO:4; a M having the amino acid sequence encoded by SEQ ID NO:5 or M with at least 95% amino acid sequence identity to the M encoded by SEQ ID NO:5; or a NS having the amino acid sequence encoded by SEQ ID NO:6 or NS with at least 95% amino acid sequence identity to the NS encoded by SEQ ID NO:6 or wherein the PA, PB1, PB2, NP, NS, and M viral segments comprise sequences for at least one of the following: a PB1 having the amino acid sequence encoded by SEQ ID NO:10 or PB1 with at least 95% amino acid sequence identity to the PB1 encoded by SEQ ID NO:10; a PB2 having the amino acid sequence encoded by SEQ ID NO:11 or PB2 with at least 95% amino acid sequence identity to the PB2 encoded by SEQ ID NO: 11; a PA having the amino acid sequence encoded by SEQ ID NO:12 or PA with at least 95% amino acid sequence identity to the PA encoded by SEQ ID NO:12; a NP having the amino acid sequence encoded by SEQ ID NO:13 or NP with at least 95% amino acid sequence identity to the NP encoded by SEQ ID NO:13; a M having the amino acid sequence encoded by SEQ ID NO:14 or M with at least 95% amino acid sequence identity to the M encoded by SEQ ID NO:14; or a NS having the amino acid sequence encoded by SEQ ID NO:15 or NS with at least 95% amino acid sequence identity to the NS encoded by SEQ ID NO:15.

13. The method of claim 1 wherein the selected position and residue in PB2 comprises 504V; wherein the selected position and residue in PB1 comprises 40L or 180W; wherein the selected position and residue in PA comprises 401K; wherein the selected position and residue in NP comprises 116L; and/or wherein the selected position and residue in NS1 comprises A30P or R118K.

14. The method of claim 1 wherein the selected position and residue in PB2 comprises 504V; wherein the selected position and residue in PB1 comprises 112G; wherein the selected position and residue in PA comprises 225C; wherein the selected position and residue in NP comprises 74K or 417D; wherein the selected position and residue in M1 comprises 97A and/or 100H; and/or wherein the selected position and residue in NS comprises 55E.

15. The method of claim 1 wherein at least one of the PA, PB1, PB2, NP, NS, and M viral segments has a C to U promoter mutation.

16. The method of claim 1 wherein the at least two viral segments with the selected amino acid residues are selected from the group consisting of the PA viral segment, the PB1 viral segment, the PB2 viral segment or the NP viral segment.

17. The method of claim 1 wherein at least three of the PA viral segment, the PB1 viral segment, the PB2 viral segment or the NP viral segment have one of the selected amino acid residues.

* * * * *

SEQUENCE LISTING

```
<160> NUMBER OF SEQ ID NOS: 28

<210> SEQ ID NO 1
<211> LENGTH: 2233
<212> TYPE: DNA
<213> ORGANISM: Influenza A

<400> SEQUENCE: 1
agcgaaagca ggtactgatc caaaatggaa gattttgtgc gacaatgctt caatccgatg      60
attgtcgagc ttgcggaaaa aacaatgaaa gagtatgggg aggacctgaa aatcgaaaca     120
aacaaatttg cagcaatatg cactcacttg gaagtatgct tcatgtattc agattttcac     180
ttcatcaatg agcaaggcga gtcaataatc gtagaacttg gtgatccaaa tgcacttttg     240
aagcacagat ttgaaataat cgagggaaga gatcgcacaa tggcctggac agtagtaaac     300
agtatttgca acactacagg ggctgagaaa ccaaagtttc taccagattt gtatgattac     360
aaggagaata gattcatcga aattggagta acaaggagag aagttcacat atactatctg     420
gaaaaggcca ataaaattaa atctgagaaa acacacatcc acattttctc gttcactggg     480
gaagaaatgg ccacaaaggc agactacact ctcgatgaag aaagcagggc taggatcaaa     540
accagactat tcaccataag acaagaaatg gccagcagag gcctctggga ttcctttcgt     600
cagtccgaga gaggagaaga gacaattgaa gaaaggtttg aaatcacagg aacaatgcgc     660
aagcttgccg accaaagtct cccgccgaac ttctccagcc ttgaaaattt tagagcctat     720
gtggatggat tcgaaccgaa cggctacatt gagggcaagc tgtctcaaat gtccaaagaa     780
gtaaatgcta gaattgaacc ttttttgaaa acaacaccac gaccacttag acttccgaat     840
gggcctccct gttctcagcg gtccaaattc ctgctgatga tgcctttaaa attaagcatt     900
gaggacccaa gtcatgaagg agagggaata ccgctatatg atgcaatcaa atgcatgaga     960
acattctttg gatggaagga acccaatgtt gttaaaccac acgaaaaggg aataaatcca    1020
aattatcttc tgtcatggaa gcaagtactg gcagaactgc aggacattga gaatgaggag    1080
aaaattccaa agactaaaaa tatgaagaaa acaagtcagc taaagtgggc acttggtgag    1140
aacatggcac cagaaaaggt agactttgac gactgtaaag atgtaggtga tttgaagcaa    1200
tatgatagtg atgaaccaga attgaggtcg cttgcaagtt ggattcagaa tgagtttaac    1260
aaggcatgcg aactgacaga ttcaagctgg atagagctcg atgagattgg agaagatgtg    1320
gctccaattg aacacattgc aagcatgaga aggaattatt tcacatcaga ggtgtctcac    1380
tgcagagcca cagaatacat aatgaaggga gtgtacatca atactgcctt gcttaatgca    1440
tcttgtgcag caatggatga tttccaatta attccaatga taagcaagtg tagaactaag    1500
gagggaaggc gaaagaccaa cttgtatggt ttcatcataa aaggaagatc ccacttaagg    1560
aatgacaccg acgtggtaaa ctttgtgagc atggagtttt ctctcactga cccaagactt    1620
```

-continued

| | |
|---|---|
| gaaccacata aatgggagaa gtactgtgtt cttgagatag agatatgct tataagaagt | 1680 |
| gccataggcc aggttttcaag gcccatgttc ttgtatgtga aacaaatgg aacctcaaaa | 1740 |
| attaaaatga aatggggaat ggagatgagg cgttgcctcc tccagtcact tcaacaaatt | 1800 |
| gagagtatga ttgaagctga gtcctctgtc aaagagaaag acatgaccaa agagttcttt | 1860 |
| gagaacaaat cagaaacatg gcccattgga gagtccccca aggagtgga ggaaagttcc | 1920 |
| attgggaagg tctgcaggac tttattagca aagtcggtat tcaacagctt gtatgcatct | 1980 |
| ccacaactag aaggattttc agctgaatca agaaaactgc ttcttatcgt tcaggctctt | 2040 |
| agggacaacc tggaacctgg gacctttgat cttggggggc tatatgaagc aattgaggag | 2100 |
| tgcctgatta atgatccctg ggttttgctt aatgcttctt ggttcaactc cttccttaca | 2160 |
| catgcattga gttagttgtg gcagtgctac tatttgctat ccatactgtc caaaaaagta | 2220 |
| ccttgtttct act | 2233 |

<210> SEQ ID NO 2
<211> LENGTH: 2340
<212> TYPE: DNA
<213> ORGANISM: Influenza A

<400> SEQUENCE: 2

| | |
|---|---|
| agcgaaagca ggcaaaccat ttgaatggat gtcaatccga ccttactttt cttaaaagtg | 60 |
| ccagcacaaa atgctataag cacaactttc ccttatactg gagaccctcc ttacagccat | 120 |
| gggacaggaa caggatacac catggatact gtcaacagga cacatcagta ctcagaaaag | 180 |
| ggaagatgga caacaaacac cgaaactgga gcaccgcaac tcaacccgat tgatgggcca | 240 |
| ctgccagaag acaatgaacc aagtggttat gcccaaacag attgtgtatt ggaggcgatg | 300 |
| gctttccttg aggaatccca tcctggtatt tttgaaaact cgtgtattga aacgatggag | 360 |
| gttgttcagc aaacacgagt agacaagctg acacaaggcc gacagaccta tgactggact | 420 |
| ctaaatagaa accaacctgc tgcaacagca ttggccaaca caatagaagt gttcagatca | 480 |
| aatggcctca cggccaatga gtctggaagg ctcatagact tccttaagga tgtaatggag | 540 |
| tcaatgaaca agaagaaat ggggatcaca actcattttc agagaaagag acgggtgaga | 600 |
| gacaatatga ctaagaaaat gataacacag agaacaatgg gtaaaaagaa gcagagattg | 660 |
| aacaaaagga gttatctaat tagagcattg accctgaaca caatgaccaa agatgctgag | 720 |
| agagggaagc taaaacggag agcaattgca accccaggga tgcaaataag ggggtttgta | 780 |
| tactttgttg agacactggc aaggagtata tgtgagaaac ttgaacaatc agggttgcca | 840 |
| gttggaggca atgagaagaa agcaaagttg gcaaatgttg taaggaagat gatgaccaat | 900 |
| tctcaggaca ccgaactttc tttcaccatc actggagata acaccaaatg aacgaaaat | 960 |
| cagaatcctc ggatgttttt ggccatgatc acatatatga ccagaaatca gcccgaatgg | 1020 |
| ttcagaaatg ttctaagtat tgctccaata atgttctcaa acaaaatggc gagactggga | 1080 |
| aaagggtata tgtttgagag caagagtatg aaacttagaa ctcaaatacc tgcagaaatg | 1140 |
| ctagcaagca tcgatttgaa atatttcaat gattcaacaa gaagaagat tgaaaaaatc | 1200 |
| cgaccgctct aatagaggg gactgcatca ttgagccctg aatgatgat gggcatgttc | 1260 |
| aatatgttaa gcactgtatt aggcgtctcc atcctgaatc ttggacaaaa gagatacacc | 1320 |
| aagactactt actggtggga tggtcttcaa tcctctgacg attttgctct gattgtgaat | 1380 |
| gcacccaatc atgaagggat tcaagccgga gtcgacaggt tttatcgaac ctgtaagcta | 1440 |

```
cttggaatca atatgagcaa gaaaaagtct tacataaaca gaacaggtac atttgaattc   1500
acaagttttt tctatcgtta tgggtttgtt gccaatttca gcatggagct tcccagtttt   1560
ggggtgtctg ggatcaacga gtcagcggac atgagtattg gagttactgt catcaaaaac   1620
aatatgataa acaatgatct tggtccagca acagctcaaa tggcccttca gttgttcatc   1680
aaagattaca ggtacacgta ccgatgccat ataggtgaca cacaaataca aacccgaaga   1740
tcatttgaaa taaagaaact gtgggagcaa acccgttcca aagctggact gctggtctcc   1800
gacggaggcc caaatttata caacattaga aatctccaca ttcctgaagt ctgcctaaaa   1860
tgggaattga tggatgagga ttaccagggg cgtttatgca acccactgaa cccatttgtc   1920
agccataaag aaattgaatc aatgaacaat gcagtgatga tgccagcaca tggtccagcc   1980
aaaaacatgg agtatgatgc tgttgcaaca acacactcct ggatccccaa aagaaatcga   2040
tccatcttga tacaagtcaa agaggagtac ttgaggatga acaaatgtac caaaggtgct   2100
gcaatttatt tgaaaaattc ttccccagca gttcatacag aagaccagtc gggatatcca   2160
gtatggtgga ggctatggtt tccagagccc gaattgatgc acggattgat ttcgaatctg   2220
gaaggataaa gaaagaagag ttcactgaga tcatgaagat ctgttccacc attgaagagc   2280
tcagacggca aaaatagtga atttagcttg tccttcatga aaaaatgcct tgtttctact   2340
```

<210> SEQ ID NO 3
<211> LENGTH: 2341
<212> TYPE: DNA
<213> ORGANISM: Influenza A

<400> SEQUENCE: 3

```
agcgaaagca ggtcaattat attcaatatg gaaagaataa aagaactacg aaatctaatg     60
tcgcagtctc gcacccgcga gatactcaca aaaaccaccg tggaccatat ggccataatc    120
aagaagtaca catcaggaag acaggagaag aacccagcac ttaggatgaa atggatgatg    180
gcaatgaaat atccaattac agcagacaag aggataacgg aaatgattcc tgagagaaat    240
gagcaaggac aaactttatg gagtaaaatg aatgatgccg gatcagaccg agtgatggta    300
tcacctctgg ctgtgacatg gtggaatagg aatggaccaa taacaaatac agttcattat    360
ccaaaaatct acaaaactta ttttgaaaga gtcgaaaggc taaagcatgg aacctttggc    420
cctgtccatt ttagaaacca agtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
gaactccagg attgcaaaat ttctcctttg atggttgcat acatgttgga gagagaactg    660
gtccgcaaaa cgagattcct cccagtggct ggtggaacaa gcagtgtgta cattgaagtg    720
ttgcatttga ctcaaggaac atgctgggaa cagatgtata ctccaggagg ggaagtgagg    780
aatgatgatg ttgatcaaag cttgattatt gctgctagga acatagtgag aagagctgca    840
gtatcagcag atccactagc atctttattg gagatgtgcc acagcacaca gattggtgga    900
attaggatgg tagacatcct taggcagaac ccaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggcaa tcttcaaaca   1080
ttgaagataa gagtgcatga gggatatgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
```

| | |
|---|---|
| aaagcagtca gaggtgatct gaatttcgtc aataggcga atcaacgatt gaatcctatg | 1320 |
| catcaacttt taagacattt tcagaaggat gcgaaagtgc tttttcaaaa ttggggagtt | 1380 |
| gaacctatcg acaatgtgat gggaatgatt gggatattgc ccgacatgac tccaagcatc | 1440 |
| gagatgtcaa tgagaggagt gagaatcagc aaaatgggtg tagatgagta ctccagcacg | 1500 |
| gagagggtag tggtgagcat tgaccgtttt ttgagaatcc gggaccaacg aggaaatgta | 1560 |
| ctactgtctc ccgaggaggt cagtgaaaca cagggaacag agaaactgac aataacttac | 1620 |
| tcatcgtcaa tgatgtggga gattaatggt cctgaatcag tgttggtcaa tacctatcaa | 1680 |
| tggatcatca gaaactggga aactgttaaa attcagtggt cccagaaccc tacaatgcta | 1740 |
| tacaataaaa tggaatttga accatttcag tctttagtac taaggccat tagaggccaa | 1800 |
| tacagtgggt ttgtaagaac tctgttccaa caaatgaggg atgtgcttgg gacatttgat | 1860 |
| accgcacaga taataaaact tcttcccttc gcagccgctc caccaaagca aagtagaatg | 1920 |
| cagttctcct catttactgt gaatgtgagg ggatcaggaa tgagaatact tgtaaggggc | 1980 |
| aattctcctg tattcaacta taacaaggcc acgaagagac tcacagttct cggaaaggat | 2040 |
| gctggcactt taactgaaga cccagatgaa ggcacagctg gagtggagtc cgctgttctg | 2100 |
| aggggattcc tcattctggg caaagaagac aagagatatg gccagcact aagcatcaat | 2160 |
| gaactgagca accttgcgaa aggagagaag gctaatgtgc taattgggca aggagacgtg | 2220 |
| gtgttggtaa tgaaacggaa acgggactct agcatactta ctgacagcca gacagcgacc | 2280 |
| aaaagaattc ggatggccat caattagtgt cgaatagttt aaaaacgacc ttgtttctac | 2340 |
| t | 2341 |

<210> SEQ ID NO 4
<211> LENGTH: 1565
<212> TYPE: DNA
<213> ORGANISM: Influenza A

<400> SEQUENCE: 4

| | |
|---|---|
| agcaaaagca gggtagataa tcactcactg agtgacatca aaatcatggc gtctcaaggc | 60 |
| accaaacgat cttacgaaca gatggagact gatggagaac gccagaatgc cactgaaatc | 120 |
| agagcatccg tcggaaaaat gattggtgga attggacgat tctacatcca aatgtgcacc | 180 |
| gaactcaaac tcagtgatta tgagggacgg ttgatccaaa acagcttaac aatagagaga | 240 |
| atggtgctct ctgcttttga cgaaaggaga aataaatacc ttgaagaaca tcccagtgcg | 300 |
| gggaaagatc taagaaaac tggaggacct atatacagga gagtaaacgg aaagtggatg | 360 |
| agagaactca tcctttatga caaagaagaa ataaggcgaa tctggcgcca agctaataat | 420 |
| ggtgacgatg caacggctgg tctgactcac atgatgatct ggcattccaa tttgaatgat | 480 |
| gcaacttatc agaggacaag agctcttgtt cgcaccggaa tggatcccag gatgtgctct | 540 |
| ctgatgcaag gttcaactct ccctaggagg tctgagccg caggtgctgc agtcaaagga | 600 |
| gttggaacaa tggtgatgga attggtcaga atgatcaaac gtgggatcaa tgatcggaac | 660 |
| ttctggaggg gtgagaatgg acgaaaaaca agaattgctt atgaaagaat gtgcaacatt | 720 |
| ctcaaaggga aatttcaaac tgctgcacaa aaagcaatga tggatcaagt gagagagagc | 780 |
| cggaacccag ggaatgctga gttcgaagat ctcactttc tagcacggtc tgcactcata | 840 |
| ttgagagggt cggttgctca caagtcctgc ctgcctgcct gtgtgtatgg acctgccgta | 900 |
| gccagtgggt acgactttga aagggaggga tactctctag tcggaataga cccttttcaga | 960 |

| | |
|---|---|
| ctgcttcaaa acagccaagt gtacagccta atcagaccaa atgagaatcc agcacacaag | 1020 |
| agtcaactgg tgtggatggc atgccattct gccgcatttg aagatctaag agtattaagc | 1080 |
| ttcatcaaag ggacgaaggt gctcccaaga gggaagcttt ccactagagg agttcaaatt | 1140 |
| gcttccaatg aaaatatgga gactatgaa tcaagtacac ttgaactgag aagcaggtac | 1200 |
| tgggccataa ggaccagaag tggaggaaac accaatcaac agagggcatc tgcgggccaa | 1260 |
| atcagcatac aacctacgtt ctcagtacag agaaatctcc cttttgacag aacaaccatt | 1320 |
| atggcagcat tcaatgggaa tacagagggg agaacatctg catgaggac cgaaatcata | 1380 |
| aggatgatgg aaagtgcaag accagaagat gtgtctttcc aggggcgggg agtcttcgag | 1440 |
| ctctcggacg aaaaggcagc gagcccgatc gtgccttcct ttgacatgag taatgaagga | 1500 |
| tcttatttct tcggagacaa tgcagaggag tacgacaatt aaagaaaaat acccttgttt | 1560 |
| ctact | 1565 |

```
<210> SEQ ID NO 5
<211> LENGTH: 1027
<212> TYPE: DNA
<213> ORGANISM: Influenza A

<400> SEQUENCE: 5
```

| | |
|---|---|
| agcaaaagca ggtagatatt gaaagatgag tcttctaacc gaggtcgaaa cgtacgtact | 60 |
| ctctatcatc ccgtcaggcc ccctcaaagc cgagatcgca cagagacttg aagatgtctt | 120 |
| tgcagggaag aacaccgatc ttgaggttct catggaatgg ctaaagacaa gaccaatcct | 180 |
| gtcacctctg actaaggga ttttaggatt tgtgttcacg ctcaccgtgc ccagtgagcg | 240 |
| aggactgcag cgtagacgct ttgtccaaaa tgcccttaat gggaacgggg atccaaataa | 300 |
| catggacaaa gcagttaaac tgtataggaa gctcaagagg gagataacat tccatggggc | 360 |
| caaagaaatc tcactcagtt attctgctgg tgcacttgcc agttgtatgg gcctcatata | 420 |
| caacaggatg ggggctgtga ccactgaagt ggcatttggc ctggtatgtg caacctgtga | 480 |
| acagattgct gactcccagc atcggtctca taggcaaatg gtgacaacaa ccaatccact | 540 |
| aatcagacat gagaacagaa tggttttagc cagcactaca gctaaggcta tggagcaaat | 600 |
| ggctggatcg agtgagcaag cagcagaggc catggaggtt gctagtcagg ctagacaaat | 660 |
| ggtgcaagcg atgagaacca ttgggactca tcctagctcc agtgctggtc tgaaaaatga | 720 |
| tcttcttgaa aatttgcagg cctatcagaa acgaatgggg gtgcagatgc aacggttcaa | 780 |
| gtgatcctct cactattgcc gcaaatatca ttgggatctt gcacttgaca ttgtggattc | 840 |
| ttgatcgtct ttttttcaaa tgcatttacc gtcgctttaa atacggactg aaaggagggc | 900 |
| cttctacgga aggagtgcca agtctatga gggaagaata tcgaaaggaa cagcagagtg | 960 |
| ctgtggatgc tgacgatggt cattttgtca gcatagagct ggagtaaaaa actaccttgt | 1020 |
| ttctact | 1027 |

```
<210> SEQ ID NO 6
<211> LENGTH: 890
<212> TYPE: DNA
<213> ORGANISM: Influenza A

<400> SEQUENCE: 6
```

| | |
|---|---|
| agcaaaagca gggtgacaaa aacataatgg atccaaacac tgtgtcaagc tttcaggtag | 60 |
| attgctttct ttggcatgtc cgcaaacgag ttgcagacca agaactaggc gatgccccat | 120 |
| tccttgatcg gcttcgccga gatcagaaat ccctaagagg aagggcagt actctcggtc | 180 |

```
tggacatcaa gacagccaca cgtgctggaa agcagatagt ggagcggatt ctgaaagaag    240
aatccgatga ggcacttaaa atgaccatgg cctctgtacc tgcgtcgcgt tacctaactg    300
acatgactct tgaggaaatg tcaagggact ggtccatgct catacccaag cagaaagtgg    360
caggccctct ttgtatcaga atggaccagg cgatcatgga taagaacatc atactgaaag    420
cgaacttcag tgtgattttt gaccggctgg agactctaat attgctaagg ctttcaccg     480 aagagggagc aattgttggc gaaatttcac cattgccttc tcttccagga catactgctg    540
aggatgtcaa aaatgcagtt ggagtcctca tcggaggact gaatggaat gataacacag     600 ttcgagtctc tgaaactcta cagagattcg cttggagaag cagtaatgag aatgggagac    660
ctccactcac tccaaaacag aaacgagaaa tggcgggaac aattaggtca gaagtttgaa    720
gaaataagat ggttgattga agaagtgaga cacaaactga agataacaga gaatagtttt    780
gagcaaataa catttatgca agccttacat ctattgcttg aagtggagca agagataaga    840
actttctcgt ttcagcttat ttagtactaa aaaacaccct tgtttctact               890

<210> SEQ ID NO 7
<211> LENGTH: 1775
<212> TYPE: DNA
<213> ORGANISM: Influenza A

<400> SEQUENCE: 7
agcaaaagca ggggaaaata aaaacaacca aaatgaaggc aaacctactg gtcctgttat      60
gtgcacttgc agctgcagat gcagacacaa tatgtatagg ctaccatgcg aacaattcaa    120
ccgacactgt tgacacagta ctcgagaaga atgtgacagt gacacactct gttaacctgc    180
tcgaagacag ccacaacgga aaactatgta ttaaaaagg aatagcccca ctacaattgg    240
ggaaatgtaa catcgccgga tggctcttgg gaaacccaga atgcgaccca ctgcttccag    300
tgagatcatg gtcctacatt gtagaaacac caaactctga atggaata tgttatccag     360 gagatttcat cgactatgag gagctgaggg agcaattgag ctcagtgtca tcattcgaaa    420
gattcgaaat atttcccaaa gaaagctcat ggcccaacca caacacaaac ggagtaacgg    480
cagcatgctc ccatgagggg aaaagcagtt tttacagaaa tttgctatgg ctgacggaga    540
aggagggctc atacccaaag ctgaaaaatt cttatgtgaa caaaaaaggg aaagaagtcc    600
ttgtactgtg gggtattcat cacccgccta acagtaagga caacagaat ctctatcaga    660 atgaaaatgc ttatgtctct gtagtgactt caaattataa caggagattt accccggaaa    720
tagcagaaag acccaaagta agagatcaag ctggaggat gaactattac tggaccttgc    780
taaaacccgg agacacaata atatttgagg caaatggaaa tctaatagca ccaatgtatg    840 cttttcgcact gagtagaggc tttgggtccg gcatcatcac ctcaaacgca tcaatgcatg    900
agtgtaacac gaagtgtcaa acaccctgg gagctataaa cagcagtctc ccttaccaga    960
atatacaccc agtcacaata ggagagtgcc caaaatacgt caggagtgcc aaattgagga   1020
tggttacagg actaaggaac attccgtcca ttcaatccag aggtctattt ggagccattg   1080
ccggttttat tgaaggggga tggactggaa tgatagatgg atggtatggt tatcatcatc   1140
agaatgaaca gggatcaggc tatgcagcgg atcaaaaaag cacacaaaat gccattaacg   1200
ggattacaaa caaggtgaac actgttatcg agaaaatgaa cattcaattc acagctgtgg   1260
gtaaagaatt caacaaatta gaaaaaagga tggaaatttt aataaaaaa gttgatgatg   1320 gatttctgga catttggaca tataatgcag aattgttagt tctactggaa aatgaaagga   1380
```

| ctctggattt | ccatgactca | aatgtgaaga | atctgtatga | gaaagtaaaa | agccaattaa | 1440 |
| agaataatgc | caaagaaatc | ggaaatggat | gttttgagtt | ctaccacaag | tgtgacaatg | 1500 |
| aatgcatgga | aagtgtaaga | aatgggactt | atgattatcc | caaatattca | gaagagtcaa | 1560 |
| agttgaacag | ggaaaaggta | gatggagtga | aattggaatc | aatggggatc | tatcagattc | 1620 |
| tggcgatcta | ctcaactgtc | gccagttcac | tggtgctttt | ggtctccctg | ggggcaatca | 1680 |
| gtttctggat | gtgttctaat | ggatctttgc | agtgcagaat | atgcatctga | gattagaatt | 1740 |
| tcagagatat | gaggaaaaac | acccttgttt | ctact | | | 1775 |

<210> SEQ ID NO 8
<211> LENGTH: 1413
<212> TYPE: DNA
<213> ORGANISM: Influenza A

<400> SEQUENCE: 8

| agcaaaagca | ggggtttaaa | atgaatccaa | atcagaaaat | aataaccatt | ggatcaatct | 60 |
| gtctggtagt | cggactaatt | agcctaatat | tgcaaatagg | gaatataatc | tcaatatgga | 120 |
| ttagccattc | aattcaaact | ggaagtcaaa | accatactgg | aatatgcaac | caaaacatca | 180 |
| ttacctataa | aaatagcacc | tgggtaaagg | acacaacttc | agtgatatta | accggcaatt | 240 |
| catctctttg | tcccatccgt | gggtgggcta | tatacagcaa | agacaatagc | ataagaattg | 300 |
| gttccaaagg | agacgttttt | gtcataagag | agcccttta  | ttcatgttct | cacttggaat | 360 |
| gcaggacctt | ttttctgacc | caaggtgcct | tactgaatga | caagcattca | agtgggactg | 420 |
| ttaaggacag | aagcccttat | agggccttaa | tgagctgccc | tgtcggtgaa | gctccgtccc | 480 |
| cgtacaattc | aagatttgaa | tcggttgctt | ggtcagcaag | tgcatgtcat | gatggcatgg | 540 |
| gctggctaac | aatcggaatt | tcaggtccag | ataatggagc | agtggctgta | ttaaaataca | 600 |
| acggcataat | aactgaaacc | ataaaaagtt | ggaggaagaa | aatattgagg | acacaagagt | 660 |
| ctgaatgtgc | ctgtgtaaat | ggttcatgtt | ttactataat | gactgatggc | ccgagtgatg | 720 |
| ggctggcctc | gtacaaaatt | ttcaagatcg | aaaaggggaa | ggttactaaa | tcaatagagt | 780 |
| tgaatgcacc | taattctcac | tatgaggaat | gttcctgtta | ccctgatacc | ggcaaagtga | 840 |
| tgtgtgtgtg | cagagacaat | tggcatggtt | cgaaccggcc | atgggtgtct | ttcgatcaaa | 900 |
| acctggatta | tcaaataggg | tacatctgca | gtggggtttt | cggtgacaac | ccgcgtcccg | 960 |
| aagatggaac | aggcagctgt | ggtccagtgt | atgttgatgg | agcaaacgga | gtaaagggat | 1020 |
| tttcatatag | gtatggtaat | ggtgtttgga | taggaaggac | caaaagtcac | agttccagac | 1080 |
| atgggtttga | gatgatttgg | gatcctaatg | gatggacaga | gactgatagt | aagttctctg | 1140 |
| tgaggcaaga | tgttgtggca | atgactgatt | ggtcagggta | tagcggaagt | ttcgttcaac | 1200 |
| atcctgagct | gacagggcta | gactgtatga | ggccgtgctt | ctgggttgaa | ttaatcaggg | 1260 |
| gacgacctaa | agaaaaaaca | atctggacta | gtgcgagcag | catttctttt | tgtggcgtga | 1320 |
| atagtgatac | tgtagattgg | tcttggccag | acggtgctga | gttgccattc | agcattgaca | 1380 |
| agtagtctgt | tcaaaaaact | ccttgtttct | act | | | 1413 |

<210> SEQ ID NO 9

<400> SEQUENCE: 9

000

<210> SEQ ID NO 10

<211> LENGTH: 2341
<212> TYPE: DNA
<213> ORGANISM: Influenza A

<400> SEQUENCE: 10
agcgaaagca ggcaaaccat ttgaatggat gtcaatccga ccttactttt cttaaaagtg 60
ccagcacaaa atgctataag cacaactttc ccttataccg gagaccctcc ttacagccat 120
gggacaggaa caggatacac catggatact gtcaacagga cacatcagta ctcagaaaag 180
ggaagatgga caacaaacac cgaaactgga gcaccgcaac tcaacccgat tgatgggcca 240
ctgccagaag acaatgaacc aagtggttat gcccaaacag attgtgtatt ggaagcaatg 300
gctttccttg aggaatccca tcctggtatt tttgaaaact cgtgtattga aacgatggag 360
gttgttcagc aaacacgagt agacaagctg acacaaggcc gacagaccta tgactggact 420
ttaaatagaa accagcctgc tgcaacagca ttggccaaca caatagaagt gttcagatca 480
aatggcctca cggccaatga gtcaggaagg ctcatagact tccttaagga tgtaatggag 540
tcaatgaaaa aagaagaaat ggggatcaca actcattttc agagaaagag acgggtgaga 600
gacaatatga ctaagaaaat gataacacag agaacaatag gtaaaaggaa acagagattg 660
aacaaaaggg gttatctaat tagagcattg accctgaaca caatgaccaa agatgctgag 720
agagggaagc taaaacggag agcaattgca accccaggga tgcaaataag ggggtttgta 780
tactttgttg agacactggc aaggagtata tgtgagaaac ttgaacaatc agggttgcca 840
gttggaggca atgagaagaa agcaaagttg gcaaatgttg taaggaagat gatgaccaat 900
tctcaggaca ccgaactttc tttcaccatc actggagata acaccaaatg gaacgaaaat 960
cagaatcctc ggatgttttt ggccatgatc acatatatga ccagaaatca gcccgaatgg 1020
ttcagaaatg ttctaagtat tgctccaata atgttctcaa acaaaatggc gagactggga 1080
aaagggtata tgtttgagag caagagtatg aaacttagaa ctcaaatacc tgcagaaatg 1140
ctagcaagca ttgatttgaa atatttcaat gattcaacaa gaaagaagat tgaaaaaatc 1200
cgaccgctct taatagaggg gactgcatca ttgagccctg gaatgatgat gggcatgttc 1260
aatatgttaa gcactgtatt aggcgtctcc atcctgaatc ttggacaaaa gagatacacc 1320
aagactactt actggtggga tggtcttcaa tcctctgacg attttgctct gattgtgaat 1380
gcacccaatc atgaagggat tcaagccgga gtcgacaggt tttatcgaac ctgtaagcta 1440
cttggaatca atatgagcaa gaaaaagtct tacataaaca gaacaggtac atttgaattc 1500
acaagttttt tctatcgtta tgggtttgtt gccaatttca gcatggagct tcccagtttt 1560
ggggtgtctg ggatcaacga gtcagcggac atgagtattg gagttactgt catcaaaaac 1620
aatatgataa acaatgatct tggtccagca acagctcaaa tggcccttca gttgttcatc 1680
aaagattaca ggtacacgta ccgatgccat agaggtgaca cacaaataca aacccgaaga 1740
tcatttgaaa taaagaaact gtgggagcaa acccgttcca aagctggact gctggtctcc 1800
gacggaggcc caaatttata caacattaga aatctccaca ttcctgaagt ctgcctaaaa 1860
tgggaattga tggatgagga ttaccagggg cgtttatgca acccactgaa cccatttgtc 1920
agccataaag aaattgaatc aatgaacaat gcagtgatga tgccagcaca tggtccagcc 1980
aaaaacatgg agtatgatgc tgttgcaaca acacactcct ggatccccaa aagaaatcga 2040
tccatcttga atacaagtca aagaggagta cttgaagatg aacaaatgta ccaaaggtgc 2100
tgcaatttat ttgaaaaatt cttccccagc agttcataca gaagaccagt cgggatatcc 2160
agtatggtgg aggctatggt ttccagagcc cgaattgatg cacggattga tttcgaatct 2220

-continued

| | |
|---|---|
| ggaaggataa agaaagaaga gttcactgag atcatgaaga tctgttccac cattgaagag | 2280 |
| ctcagacggc aaaaatagtg aatttagctt gtccttcatg aaaaaatgcc ttgtttctac | 2340 |
| t | 2341 |

<210> SEQ ID NO 11
<211> LENGTH: 2341
<212> TYPE: DNA
<213> ORGANISM: Influenza A

<400> SEQUENCE: 11

| | |
|---|---|
| agcgaaagca ggtcaattat attcaatatg gaaagaataa agaactaag aaatctaatg | 60 |
| tcgcagtctc gcacccgcga gatactcaca aaaccaccg tggaccatat ggccataatc | 120 |
| aagaagtaca catcaggaag acaggagaag aacccagcac ttaggatgaa atggatgatg | 180 |
| gcaatgaaat atccaattac agcagacaag aggataacgg aaatgattcc tgagagaaat | 240 |
| gagcaaggac aaactttatg gagtaaaatg aatgatgccg gatcagaccg agtgatggta | 300 |
| tcacctctgg ctgtgacatg gtggaatagg aatggaccaa tgacaaatac agttcattat | 360 |
| ccaaaaatct acaaaactta ttttgaaaga gtcgaaaggc taaagcatgg aacctttggc | 420 |
| cctgtccatt ttagaaacca agtcaaaata cgtcggagag ttgacataaa tcctggtcat | 480 |
| gcagatctca gtgccaagga ggcacaggat gtaatcatgg aagttgtttt ccctaacgaa | 540 |
| gtgggagcca ggatactaac atcggaatcg caactaacga taaccaaaga gaagaaagaa | 600 |
| gaactccagg attgcaaaat ttctcctttg atggttgcat acatgttgga gagagaactg | 660 |
| gtccgcaaaa cgagattcct cccagtggct ggtggaacaa gcagtgtgta cattgaagtg | 720 |
| ttgcatttga ctcaaggaac atgctgggaa cagatgtata ctccaggagg gaagtgaag | 780 |
| aatgatgatg ttgatcaaag cttgattatt gctgctagga acatagtgag aagagctgca | 840 |
| gtatcagcag acccactagc atctttattg gagatgtgcc acagcacaca gattggtgga | 900 |
| attaggatgg tagacatcct taagcagaac ccaacagaag agcaagccgt ggatatatgc | 960 |
| aaggctgcaa tgggactgag aattagctca tccttcagtt ttggtggatt cacatttaag | 1020 |
| agaacaagcg gatcatcagt caagagagag gaagaggtgc ttacgggcaa tcttcaaaca | 1080 |
| ttgaagataa gagtgcatga gggatctgaa gagttcacaa tggttgggag aagagcaaca | 1140 |
| gccatactca gaaaagcaac caggagattg attcagctga tagtgagtgg gagagacgaa | 1200 |
| cagtcgattg ccgaagcaat aattgtggcc atggtatttt cacaagagga ttgtatgata | 1260 |
| aaagcagtta gaggtgatct gaatttcgtc aataggcga atcagcgact gaatcctatg | 1320 |
| catcaacttt taagacattt tcagaaggat gcgaaagtgc ttttttcaaaa ttggggagtt | 1380 |
| gaacctatcg acaatgtgat gggaatgatt ggatattgc ccgacatgac tccaagcatc | 1440 |
| gagatgtcaa tgagaggagt gagaatcagc aaaatgggtg tagatgagta ctccagcacg | 1500 |
| gagagggtag tggtgagcat tgaccggttc ttgagagtca gggaccaacg aggaaatgta | 1560 |
| ctactgtctc ccgaggaggt cagtgaaaca caggggaacag agaaactgac aataacttac | 1620 |
| tcatcgtcaa tgatgtggga gattaatggt cctgaatcag tgttggtcaa tacctatcaa | 1680 |
| tggatcatca gaaactggga aactgttaaa attcagtggt cccagaaccc tacaatgcta | 1740 |
| tacaataaaa tggaatttga accatttcag tctttagtac ctaaggccat tagaggccaa | 1800 |
| tacagtgggt ttgtaagaac tctgttccaa caaatgaggg atgtgcttgg acatttgat | 1860 |
| accgcacaga taataaaact tcttcccttc gcagccgctc caccaaagca agtagaatg | 1920 |

| | |
|---|---|
| cagttctcct catttactgt gaatgtgagg ggatcaggaa tgagaatact tgtaagggc | 1980 |
| aattctcctg tattcaacta caacaaggcc acgaagagac tcacagttct cggaaaggat | 2040 |
| gctggcactt taaccgaaga cccagatgaa ggcacagctg gagtggagtc cgctgttctg | 2100 |
| aggggattcc tcattctggg caaagaagac aggagatatg gccagcatt aagcatcaat | 2160 |
| gaactgagca accttgcgaa aggagagaag gctaatgtgc taattgggca aggagacgtg | 2220 |
| gtgttggtaa tgaaacgaaa acgggactct agcatactta ctgacagcca gacagcgacc | 2280 |
| aaaagaattc ggatggccat caattagtgt cgaatagttt aaaaacgacc ttgtttctac | 2340 |
| t | 2341 |

<210> SEQ ID NO 12
<211> LENGTH: 2233
<212> TYPE: DNA
<213> ORGANISM: Influenza A

<400> SEQUENCE: 12

| | |
|---|---|
| agcgaaagca ggtactgatt caaaatggaa gattttgtgc gacaatgctt caatccgatg | 60 |
| attgtcgagc ttgcggaaaa acaatgaaa gagtatgggg aggacctgaa atcgaaaca | 120 |
| aacaaatttg cagcaatatg cactcacttg gaagtatgct tcatgtattc agatttccac | 180 |
| ttcatcaatg agcaaggcga gtcaataatc gtagaacttg gtgatcctaa tgcactttg | 240 |
| aagcacagat ttgaaataat cgagggaaga gatcgcacaa tggcctggac agtagtaaac | 300 |
| agtatttgca acactacagg ggctgagaaa ccaaagtttc taccagattt gtatgattac | 360 |
| aaggaaaata gattcatcga aattggagta acaaggagaa agttcacat atactatctg | 420 |
| gaaaaggcca ataaaattaa atctgagaaa acacacatcc acattttctc gttcactggg | 480 |
| gaagaaatgg ccacaaggc cgactacact ctcgatgaag aaagcagggc taggatcaaa | 540 |
| accaggctat tcaccataag acaagaaatg gccagcagag gcctctggga ttcctttcgt | 600 |
| cagtccgaga gaggagaaga gacaattgaa gaaaggtttg aaatcacagg aacaatgcgc | 660 |
| aagcttgccg accaaagtct cccgccgaac ttctccagcc ttgaaaattt tagagcctat | 720 |
| gtggatggat tcgaaccgaa cggctacatt gagggcaagc tgtctcaaat gtccaaagaa | 780 |
| gtaaatgcta gaattgaacc ttttttgaaa acaacaccac gaccacttag acttccgaat | 840 |
| gggcctccct gttctcagcg gtccaaattc ctgctgatgg atgccttaaa attaagcatt | 900 |
| gaggacccaa gtcatgaagg agagggaata ccgctatatg atgcaatcaa atgcatgaga | 960 |
| acattctttg gatggaagga acccaatgtt gttaaaccac acgaaaaggg aataaatcca | 1020 |
| aattatcttc tgtcatggaa gcaagtactg gcagaactgc aggacattga gaatgaggag | 1080 |
| aaaattccaa agactaaaaa tatgaaaaaa acaagtcagc taaagtgggc acttggtgag | 1140 |
| aacatggcac cagaaaaggt agactttgac gactgtaaag atgtaggtga tttgaagcaa | 1200 |
| tatgatagtg atgaaccaga attgaggtcg cttgcaagtt ggattcagaa tgagttcaac | 1260 |
| aaggcatgcg aactgacaga ttcaagctgg atagagcttg atgagattgg agaagatgtg | 1320 |
| gctccaattg aacacattgc aagcatgaga aggaattatt tcacatcaga ggtgtctcac | 1380 |
| tgcagagcca cagaatacat aatgaagggg gtgtacatca atactgcctt acttaatgca | 1440 |
| tcttgtgcag caatggatga tttccaatta attccaatga taagcaagtg tagaactaag | 1500 |
| gagggaaggc gaaagaccaa cttgtatggt tcatcataa aaggaagatc ccacttaagg | 1560 |
| aatgacaccg acgtggtaaa ctttgtgagc atggagtttt ctctcactga cccaagactt | 1620 |
| gaaccacaca atgggagaa gtactgtgtt cttgagatag gagatatgct tctaagaagt | 1680 |

```
gccataggcc aggtttcaag gcccatgttc ttgtatgtga ggacaaatgg aacctcaaaa    1740
attaaaatga atggggaat ggagatgagg cgttgtctcc tccagtcact tcaacaaatt    1800
gagagtatga ttgaagctga gtcctctgtc aaagagaaag acatgaccaa agagttcttt    1860
gagaacaaat cagaaacatg gcccattgga gagtctccca aaggagtgga ggaaagttcc    1920
attgggaagg tctgcaggac tttattagca aagtcggtat ttaacagctt gtatgcatct    1980
ccacaactag aaggattttc agctgaatca agaaaactgc ttcttatcgt tcaggctctt    2040
agggacaatc tggaacctgg gacctttgat cttgggggc tatatgaagc aattgaggag    2100
tgcctaatta atgatccctg gttttgctt aatgcttctt ggttcaactc cttccttaca    2160
catgcattga gttagttgtg gcagtgctac tatttgctat ccatactgtc caaaaaagta    2220
ccttgtttct act    2233
```

<210> SEQ ID NO 13
<211> LENGTH: 1565
<212> TYPE: DNA
<213> ORGANISM: Influenza A

<400> SEQUENCE: 13

```
agcaaaagca gggtagataa tcactcactg agtgacatca aaatcatggc gtcccaaggc      60
accaaacggt cttacgaaca gatggagact gatggagaac gccagaatgc cactgaaatc     120
agagcatccg tcggaaaaat gattggtgga attggacgat tctacatcca aatgtgcaca     180
gaacttaaac tcagtgatta tgagggacgg ttgatccaaa acagcttaac aatagagaga     240
atggtgctct ctgcttttga cgaaaggaga aataaatacc tggaagaaca tcccagtgcg     300
gggaaagatc ctaagaaaac tggaggacct atatacagaa gagtaaacgg aaagtggatg     360
agagaactca tcctttatga caagaagaa ataaggcgaa tctggcgcca agctaataat     420
ggtgacgatg caacggctgg tctgactcac atgatgatct ggcattccaa tttgaatgat     480
gcaacttatc agaggacaag ggctcttgtt cgcaccggaa tggatcccag gatgtgctct     540
ctgatgcaag gttcaactct ccctaggagg tctggagccg caggtgctgc agtcaaagga     600
gttggaacaa tggtgatgga attggtcagg atgatcaaac gtgggatcaa tgatcggaac     660
ttctggaggg gtgagaatgg acgaaaaaca agaattgctt atgaaagaat gtgcaacatt     720
ctcaaaggga aatttcaaac tgctgcacaa aaagcaatga tggatcaagt gagagagagc     780
cggaacccag ggaatgctga gttcgaagat ctcactttc tagcacggtc tgcactcata     840
ttgagagggt cggttgctca caagtcctgc ctgcctgcct gtgtgtatgg acctgccgta     900
gccagtgggt acgactttga aagagggga tactctctag tcggaataga ccctttcaga     960
ctgcttcaaa acagccaagt gtacagccta atcagaccaa atgagaatcc agcacacaag    1020
agtcaactgg tgtggatggc atgccattct gccgcatttg aagatctaag agtattgagc    1080
ttcatcaaag gacgaaggt ggtcccaaga gggaagcttt ccactagagg agttcaaatt    1140
gcttccaatg aaaatatgga gactatggaa tcaagtacac ttgaactgag aagcaggtac    1200
tgggccataa ggaccagaag tggaggaaac accaatcaac agagggcatc tgcgggccaa    1260
atcagcatac aacctacgtt ctcagtacag agaaatctcc cttttgacag aacaccgtt    1320 atggcagcat tcactgggaa tacagagggg agaacatctg acatgaggac cgaaatcata    1380
aggatgatgg aaagtgcaag accagaagat gtgtctttcc aggggcgggg agtcttcgag    1440
ctctcggacg aaaaggcagc gagcccgatc gtgccttcct ttgacatgag taatgaagga    1500
```

```
tcttatttct tcggagacaa tgcagaggag tacgacaatt aaagaaaaat acccttgttt    1560
ctact                                                                1565

<210> SEQ ID NO 14
<211> LENGTH: 1027
<212> TYPE: DNA
<213> ORGANISM: Influenza A

<400> SEQUENCE: 14
agcaaaagca ggtagatatt gaaagatgag tcttctaacc gaggtcgaaa cgtacgttct      60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggaacgggg atccaaataa    300
catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg ggggctgtga ccactgaagt ggcatttggc ctggtatgtg caacctgtga    480
acagattgct gactcccagc atcggtctca taggcaaatg gtgacaacaa ccaacccact    540
aatcagacat gagaacagaa tggttttagc cagcactaca gctaaggcta tggagcaaat    600
ggctggatcg agtgagcaag cagcagaggc catggaggtt gctagtcagg ctaggcaaat    660
ggtgcaagcg atgagaacca ttgggactca tcctagctcc agtgctggtc tgaaaaatga    720
tcttcttgaa aatttgcagg cctatcagaa acgaatgggg gtgcagatgc aacggttcaa    780
gtgatcctct cgctattgcc gcaaatatca ttgggatctt gcacttgata ttgtggattc    840
ttgatcgtct tttttcaaa tgcatttacc gtcgctttaa atacgactg aaaggagggc    900 cttctacgga aggagtgcca aagtctatga gggaagaata tcgaaggaa cagcagagtg    960 ctgtggatgc tgacgatggt cattttgtca gcatagagct ggagtaaaaa actaccttgt   1020
ttctact                                                             1027

<210> SEQ ID NO 15
<211> LENGTH: 890
<212> TYPE: DNA
<213> ORGANISM: Influenza A

<400> SEQUENCE: 15
agcaaaagca gggtgacaaa gacataatgg atccaaacac tgtgtcaagc tttcaggtag     60
attgctttct ttggcatgtc cgcaaacgag ttgcagacca gaactaggt gatgccccat    120 tccttgatcg gcttcgccga gatcagaaat ccctaagagg aagggggcagc actcttggtc    180 tggacatcga gacagccaca cgtgctggaa agcagatagt ggagcggatt ctgaaagaag    240
aatccgatga ggcacttaaa atgaccatgg cctctgtacc tgcgtcgcgt tacctaaccg    300
acatgactct tgaggaaatg tcaagggaat ggtccatgct catacccaag cagaaagtgg    360
caggccctct ttgtatcaga atggaccagg cgatcatgga taaaaacatc atactgaaag    420
cgaacttcag tgtgatttttt gaccggctgg agactctaat attgctaagg ctttcaccg    480 aagagggagc aattgttggc gaatttcac cattgccttc tcttccagga catactgctg    540
aggatgtcaa aaatgcagtt ggagtcctca tcggaggact tgaatggaat gataacacag    600
ttcgagtctc tgaaactcta cagagattcg cttggagaaa cagtaatgag aatgggagac    660
ctccactcac tccaaaacag aaacgagaaa tggcgggaac aattaggtca gaagtttgaa    720
```

```
gaaataagat ggttgattga agaagtgaga cacaaactga aggtaacaga gaatagtttt    780
gagcaaataa catttatgca agccttacat ctattgcttg aagtggagca agagataaga    840
actttctcat ttcagcttat ttaataataa aaaacaccct tgtttctact              890
```

<210> SEQ ID NO 16

<400> SEQUENCE: 16

000

<210> SEQ ID NO 17
<211> LENGTH: 1683
<212> TYPE: DNA
<213> ORGANISM: Influenza A

<400> SEQUENCE: 17

```
atgaacactc aaatcctggt attcgctctg attgcgatca ttccaacaaa tgcagacaaa     60
atctgcctcg acatcatgc cgtgtcaaac ggaaccaaag taaacacatt aactgaaaga    120
ggagtggaag tcgtcaatgc aactgaaaca gtggaacgaa caaacatccc caggatctgc    180
tcaaaaggga aaaggacagt tgacctcggt caatgtggac tcctggggac aatcactgga    240
ccacctcaat gtgaccaatt cctagaattt tcagccgatt taattattga gaggcgagaa    300
ggaagtgatg tctgttatcc tgggaaattc gtgaatgaag aagctctgag gcaaattctc    360
agagaatcag gcggaattga caaggaagca atgggattca catacagtgg aataagaact    420
aatgagcaa ccagtgcatg taggagatca ggatcttcat tctatgcaga aatgaaatgg    480
ctcctgtcaa acacagataa tgctgcattc ccgcagatga ctaagtcata taaaaataca    540
agaaaaagcc cagctctaat agtatggggg atccatcatt ccgtatcaac tgcagagcaa    600
accaagctat atgggagtgg aaacaaactg gtgacagttg ggagttctaa ttatcaacaa    660
tcttttgtac cgagtccagg agcgagacca caagttaatg gtctatctgg aagaattgac    720
tttcattggc taatgctaaa tcccaatgat acagtcactt tcagtttcaa tgggggctttc    780
atagctccag accgtgcaag cttcctgaga ggaaaatcta tgggaatcca gagtggagta    840
caggttgatg ccaattgtga agggggactgc tatcatagtg gagggacaat aataagtaac    900
ttgccatttc agaacataga tagcagggca gttggaaaat gtccgagata tgttaagcaa    960
aggagtctgc tgctagcaac agggatgaag aatgttcctg agattccaaa gggaagaggc   1020
ctatttggtg ctatagcggg tttcattgaa atggatgggg aaggcctaat tgatggttgg   1080
tatggtttca gacaccagaa tgcacaggga gagggaactg ctgcagatta caaaagcact   1140
caatcggcaa ttgatcaaat aacaggaaaa ttaaaccggc ttatagaaaa aaccaaccaa   1200
caatttgagt tgatagacaa tgaattcaat gaggtagaga agcaaatcgg taatgtgata   1260
aattggacca gagattctat aacagaagtg tggtcataca atgctgaact cttggtagca   1320
atggagaacc agcatacaat tgatctggct gattcagaaa tggacaaact gtacgaacga   1380
gtgaaaagac agctgagaga gaatgctgaa gaagatggca ctggttgctt tgaaatattt   1440
cacaagtgtg atgatgactg tatggccagt attagaaata caccatgat cacagcaaa   1500
tacagggaag aggcaatgca aaatagaata cagattgacc cagtcaaact aagcagcggc   1560
tacaaagatg tgatactttg gtttagcttc ggggcatcat gtttcatact tctagccatt   1620
gtaatgggcc ttgtcttcat atgtgtaaag aatggaaaca tgcggtgcac tatttgtata   1680
taa                                                                 1683
```

<210> SEQ ID NO 18
<211> LENGTH: 560
<212> TYPE: PRT
<213> ORGANISM: Influenza A

<400> SEQUENCE: 18

```
Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
    210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
```

| | | 370 | | | 375 | | | 380 | | | |
|---|---|---|---|---|---|---|---|---|---|---|---|

Asp Gln Ile Thr Gly Lys Leu Asn Arg Leu Ile Glu Lys Thr Asn Gln
385                    390                    395                    400

Gln Phe Glu Leu Ile Asp Asn Glu Phe Asn Glu Val Glu Lys Gln Ile
                  405                    410                    415

Gly Asn Val Ile Asn Trp Thr Arg Asp Ser Ile Thr Glu Val Trp Ser
                420                    425                    430

Tyr Asn Ala Glu Leu Leu Val Ala Met Glu Asn Gln His Thr Ile Asp
        435                    440                    445

Leu Ala Asp Ser Glu Met Asp Lys Leu Tyr Glu Arg Val Lys Arg Gln
450                    455                    460

Leu Arg Glu Asn Ala Glu Asp Gly Thr Gly Cys Phe Glu Ile Phe
465                    470                    475                    480

His Lys Cys Asp Asp Cys Met Ala Ser Ile Arg Asn Asn Thr Tyr
                485                    490                    495

Asp His Ser Lys Tyr Arg Glu Glu Ala Met Gln Asn Arg Ile Gln Ile
        500                    505                    510

Asp Pro Val Lys Leu Ser Ser Gly Tyr Lys Asp Val Ile Leu Trp Phe
515                    520                    525

Ser Phe Gly Ala Ser Cys Phe Ile Leu Leu Ala Ile Val Met Gly Leu
        530                    535                    540

Val Phe Ile Cys Val Lys Asn Gly Asn Met Arg Cys Thr Ile Cys Ile
545                    550                    555                    560

<210> SEQ ID NO 19
<211> LENGTH: 1398
<212> TYPE: DNA
<213> ORGANISM: Influenza A

<400> SEQUENCE: 19

| | | | | |
|---|---|---|---|---|
| atgaatccaa atcagaagat tctatgcact tcagccactg ctatcataat aggcgcaatc | | | | 60 |
| gcagtactca ttggaatagc aaacctagga ttgaacatag gactgcatct aaaaccgggc | | | | 120 |
| tgcaattgct cacactcaca acctgaaaca accaacacaa gccaaacaat aataaacaac | | | | 180 |
| tattataatg aaacaaacat caccaacatc caaatggaag agagaacaag caggaatttc | | | | 240 |
| aataacttaa ctaaagggct ctgtactata aattcatggc acatatatgg aaagacaat | | | | 300 |
| gcagtaagaa ttggagagag ctcggatgtt ttagtcacaa gagaacccta tgtttcatgc | | | | 360 |
| gacccagatg aatgcaggtt ctatgctctc agccaaggaa caacaatcag agggaaacac | | | | 420 |
| tcaaacggaa caatacacga taggtcccag tatcgcgccc tgataagctg ccactatca | | | | 480 |
| tcaccgccca cagtgtacaa cagcagggtg gaatgcattg ggtggtcaag tactagttgc | | | | 540 |
| catgatggca atccaggat gtcaatatgt atatcaggac caaacaacaa tgcatctgca | | | | 600 |
| gtagtatggt acaacagaag gcctgttgca gaaattaaca tgggcccg aaacatacta | | | | 660 |
| agaacacagg aatctgaatg tgtatgccac aacggcgtat gcccagtagt gttcaccgat | | | | 720 |
| gggtctgcca ctggacctgc agacacaaga atatactatt ttaaagaggg gaaaatattg | | | | 780 |
| aaatgggagt ctctgactgg aactgctaag catattgaag aatgctcatg ttacgggaa | | | | 840 |
| cgaacaggaa ttacctgcac atgcagggac aattggcagg ctcaaataag accagtgatt | | | | 900 |
| cagatagacc cagtagcaat gacacacact agtcaatata tatgcagtcc tgttcttaca | | | | 960 |
| gacaatcccc gaccgaatga cccaaatata ggtaagtgta atgacccta tccaggtaat | | | | 1020 |
| aataacaatg gagtcaaggg attctctata ctggatgggg ctaacacttg gctagggagg | | | | 1080 |

-continued

```
acaataagca cagcctcgag gtctggatac gagatgttaa aagtgccaaa tgcattgaca    1140
gatgatagat caaagcccat tcaaggtcag acaattgtat taaacgctga ctggagtggt    1200
tacagtggat cttccatgga ctattgggct gaaggggact gctatcgagc gtgttttat     1260 gtggagttga tacgtggaag acccaaggaa gataaagtgt ggtggaccag caatagtata    1320
gtatcgatgt gttccagtac agaattcctg ggacaatgga actggcctga tggggctaaa    1380
atagagtact cctctaa                                                   1398
```

<210> SEQ ID NO 20
<211> LENGTH: 465
<212> TYPE: PRT
<213> ORGANISM: Influenza A

<400> SEQUENCE: 20

```
Met Asn Pro Asn Gln Lys Ile Leu Cys Thr Ser Ala Thr Ala Ile Ile
 1               5                  10                  15

Ile Gly Ala Ile Ala Val Leu Ile Gly Ile Ala Asn Leu Gly Leu Asn
             20                  25                  30

Ile Gly Leu His Leu Lys Pro Gly Cys Asn Cys Ser His Ser Gln Pro
         35                  40                  45

Glu Thr Thr Asn Thr Ser Gln Thr Ile Ile Asn Asn Tyr Tyr Asn Glu
     50                  55                  60

Thr Asn Ile Thr Asn Ile Gln Met Glu Glu Arg Thr Ser Arg Asn Phe
 65                  70                  75                  80

Asn Asn Leu Thr Lys Gly Leu Cys Thr Ile Asn Ser Trp His Ile Tyr
                 85                  90                  95

Gly Lys Asp Asn Ala Val Arg Ile Gly Glu Ser Ser Asp Val Leu Val
            100                 105                 110

Thr Arg Glu Pro Tyr Val Ser Cys Asp Pro Asp Glu Cys Arg Phe Tyr
        115                 120                 125

Ala Leu Ser Gln Gly Thr Thr Ile Arg Gly Lys His Ser Asn Gly Thr
    130                 135                 140

Ile His Asp Arg Ser Gln Tyr Arg Ala Leu Ile Ser Trp Pro Leu Ser
145                 150                 155                 160

Ser Pro Pro Thr Val Tyr Asn Ser Arg Val Glu Cys Ile Gly Trp Ser
                165                 170                 175

Ser Thr Ser Cys His Asp Gly Lys Ser Arg Met Ser Ile Cys Ile Ser
            180                 185                 190

Gly Pro Asn Asn Asn Ala Ser Ala Val Val Trp Tyr Asn Arg Arg Pro
        195                 200                 205

Val Ala Glu Ile Asn Thr Trp Ala Arg Asn Ile Leu Arg Thr Gln Glu
    210                 215                 220

Ser Glu Cys Val Cys His Asn Gly Val Cys Pro Val Val Phe Thr Asp
225                 230                 235                 240

Gly Ser Ala Thr Gly Pro Ala Asp Thr Arg Ile Tyr Tyr Phe Lys Glu
                245                 250                 255

Gly Lys Ile Leu Lys Trp Glu Ser Leu Thr Gly Thr Ala Lys His Ile
            260                 265                 270

Glu Glu Cys Ser Cys Tyr Gly Glu Arg Thr Gly Ile Thr Cys Thr Cys
        275                 280                 285

Arg Asp Asn Trp Gln Gly Ser Asn Arg Pro Val Ile Gln Ile Asp Pro
    290                 295                 300

Val Ala Met Thr His Thr Ser Gln Tyr Ile Cys Ser Pro Val Leu Thr
305                 310                 315                 320
```

Asp Asn Pro Arg Pro Asn Asp Pro Asn Ile Gly Lys Cys Asn Asp Pro
            325                 330                 335

Tyr Pro Gly Asn Asn Asn Asn Gly Val Lys Gly Phe Ser Tyr Leu Asp
        340                 345                 350

Gly Ala Asn Thr Trp Leu Gly Arg Thr Ile Ser Thr Ala Ser Arg Ser
    355                 360                 365

Gly Tyr Glu Met Leu Lys Val Pro Asn Ala Leu Thr Asp Asp Arg Ser
370                 375                 380

Lys Pro Ile Gln Gly Gln Thr Ile Val Leu Asn Ala Asp Trp Ser Gly
385                 390                 395                 400

Tyr Ser Gly Ser Phe Met Asp Tyr Trp Ala Glu Gly Asp Cys Tyr Arg
                405                 410                 415

Ala Cys Phe Tyr Val Glu Leu Ile Arg Gly Arg Pro Lys Glu Asp Lys
            420                 425                 430

Val Trp Trp Thr Ser Asn Ser Ile Val Ser Met Cys Ser Ser Thr Glu
                435                 440                 445

Phe Leu Gly Gln Trp Asn Trp Pro Asp Gly Ala Lys Ile Glu Tyr Phe
    450                 455                 460

Leu
465

<210> SEQ ID NO 21
<211> LENGTH: 1683
<212> TYPE: DNA
<213> ORGANISM: Influenza A

<400> SEQUENCE: 21
atgaacactc aaatcctggt attcgctctg attgcgatca ttccaacaaa tgcagacaaa      60
atctgcctcg acatcatgc tgtgtcaaac ggaaccaaag taaacacatt aactgaaaga     120
ggagtggaag tcgtcaatgc aactgaaaca gtggaacgaa caaacatccc caggatctgc     180
tcaaaaggga aaggacagt tgacctcggt caatgtggac tcctggggac aatcactgga     240
ccacctcaat gtgaccaatt cctagaattt tcagccgatt taattattga gaggcgagaa     300
ggaagtgatg tctgttatcc tgggaaattc gtgaatgaag aagctctgag gcaaattctc     360
agagaatcag gcggaattga caaggaagca atgggattca catacagtgg aataagaact     420 aatgagcaa ccagttcatg taggagatca ggatcttcat tctatgcaga aatgaaatgg     480
ctcctgtcaa acacagataa tgctgcattc ccgcagatga ctaagtcata taaaaataca     540
agaaaaaacc cagctctaat agtatggggg atccatcatt ccggatcaac tgcagagcaa     600
accaagctat atgggagtgg aaacaaactg gtgacagttg ggagttctaa ttatcaacaa     660
tcttttgtac cgagtccggg agcgagaaca caagttaatg gtcaatctgg aagaattgac     720
tttcattggc taatgctaaa tcccaatgat acagtcactt tcagtttcaa tgggctttc     780 atagctccag accgtgcaag cttcctgaga ggaaaatcta tgggaatcca gagtggagta     840
caggttgatg ccgattgtga agggactgc tattatagtg gagggacaat aataagtaac     900
ttgccatttc agaacataga tagcagggca gttggaaaat gtccgagata tgttaagcaa     960
aggagtctgc tgctagcaac agggatgaag aatgttcctg agattccaaa gggaagaggc    1020
ctatttggtg ctatagcggg tttcattgaa atggatggg aaggcctaat tgatggttgg    1080
tatggtttca gacaccagaa tgcacaggga gagggaactg ctgcagatta caaaagcact    1140
caatcggcaa ttgatcaaat aacaggaaaa ttaaaccggc ttatagaaaa aaccaaccaa    1200

```
caatttgagt tgatagacaa tgaattcact gaggtagaga agcaaatcgg taatgtgata    1260
aattggacca gagattctat aacagaagtg tggtcataca atgctgaact cttggtagca    1320
atggagaacc agcatacaat tgatctggct gattcagaaa tggacaaact gtacgaacga    1380
gtgaaaagac agctgagaga gaatgctgaa gaagatggca ctggttgctt tgaaatattt    1440
cacaagtgtg atgatgactg tatggccagc attagaaata cacctatga tcacagcaaa    1500 tacagggaag aggcaatgca aaatagaata cagattgacc cagtcaaact aagcagcggc    1560
tacaaagatg tgatactttg gtttagcttc ggggcatcat gtttcatact tctagccatt    1620
gcaatgggcc ttgtcttcat atgtgtaaag aatggaaaca tgcggtgcac tatttgtata    1680
taa                                                                 1683
```

<210> SEQ ID NO 22
<211> LENGTH: 560
<212> TYPE: PRT
<213> ORGANISM: Influenza A

<400> SEQUENCE: 22

```
Met Asn Thr Gln Ile Leu Val Phe Ala Leu Ile Ala Ile Ile Pro Thr
 1               5                  10                  15

Asn Ala Asp Lys Ile Cys Leu Gly His His Ala Val Ser Asn Gly Thr
             20                  25                  30

Lys Val Asn Thr Leu Thr Glu Arg Gly Val Glu Val Val Asn Ala Thr
         35                  40                  45

Glu Thr Val Glu Arg Thr Asn Ile Pro Arg Ile Cys Ser Lys Gly Lys
     50                  55                  60

Arg Thr Val Asp Leu Gly Gln Cys Gly Leu Leu Gly Thr Ile Thr Gly
 65                  70                  75                  80

Pro Pro Gln Cys Asp Gln Phe Leu Glu Phe Ser Ala Asp Leu Ile Ile
                 85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
    130                 135                 140

Ser Ser Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Asn Pro Ala Leu Ile Val Trp Gly Ile His
            180                 185                 190

His Ser Gly Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
    210                 215                 220

Ser Pro Gly Ala Arg Thr Gln Val Asn Gly Gln Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asp Cys Glu Gly
        275                 280                 285
```

Asp Cys Tyr Tyr Ser Gly Gly Thr Ile Ile Ser Asn Leu Pro Phe Gln
            290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
                340                 345                 350

Trp Glu Gly Leu Ile Asp Gly Trp Tyr Gly Phe Arg His Gln Asn Ala
                355                 360                 365

Gln Gly Glu Gly Thr Ala Ala Asp Tyr Lys Ser Thr Gln Ser Ala Ile
            370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Thr Glu Val Glu Lys Gln Ile
                405                 410                 415

Gly Asn Val Ile Asn Trp Thr Arg Asp Ser Ile Thr Glu Val Trp Ser
                420                 425                 430

Tyr Asn Ala Glu Leu Leu Val Ala Met Glu Asn Gln His Thr Ile Asp
                435                 440                 445

Leu Ala Asp Ser Glu Met Asp Lys Leu Tyr Glu Arg Val Lys Arg Gln
450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
                500                 505                 510

Asp Pro Val Lys Leu Ser Ser Gly Tyr Lys Asp Val Ile Leu Trp Phe
                515                 520                 525

Ser Phe Gly Ala Ser Cys Phe Ile Leu Leu Ala Ile Ala Met Gly Leu
530                 535                 540

Val Phe Ile Cys Val Lys Asn Gly Asn Met Arg Cys Thr Ile Cys Ile
545                 550                 555                 560

<210> SEQ ID NO 23
<211> LENGTH: 1398
<212> TYPE: DNA
<213> ORGANISM: Influenza A

<400> SEQUENCE: 23
atgaatccaa atcagaagat tctatgcact tcagccactg ctatcataat aggcgcaatc      60
gcagtactca ttggaatagc aaacctagga ttgaacatag gactgcatct aaaaccgagc     120
tgcaattgct cacactcaca acctgaaaca accaacacaa gccaaacaat aataaacaac     180
tattataatg aaacaaacat caccaacatc caaatggaag agagaacaag caggaatttc     240
aataacttaa ctaaagggct ctgtactata aattcatggc acatatatgg aaagacaat      300 gcggtaagaa ttgagagag ctcggatgtt ttagtcacaa gagaacccta tgtttcatgc     360
gacccagatg aatgcaggtt ctatgctctc agccaaggaa caacaatcag gaaaacac       420 tcaaacggaa caatacacga taggtccag tatcgcgccc tgataagctg ccactatca      480 tcaccgccca cagtgtacaa cagcaggggtg gaatgcattg gtggtcaag tactagttgc     540 catgatggca atccaggat gtcaatatgt atatcaggac caaacaacaa tgcatctgca     600

```
gtagtatggt acaacagaag gcctgttgca gaaattaaca catgggcccg aaacatacta    660
agaacacagg aatctgaatg tgtatgccac aacggcgtat gcccagtagt gttcaccgat    720
gggtctgcca ctggacctgc agacacaaga atatactatt ttaaagaggg gaaatatattg   780 aaatgggagt ctctgactgg aactgctaag catattgaag aatgctcatg ttacgggaa     840 cgaacaggaa ttacctgcac atgcaaggac aattggcagg gctcaaatag accagtgatt    900
cagatagatc cagtagcaat gacacacact agtcagtata tatgcagtcc tgttcttaca    960
gacaatcccc gaccgaatga cccaaatata ggtaagtgta atgacccta tccaggtaat     1020 aataacaatg gagtcaaggg attctcatac ctggatgggg ctaacacttg gctagggagg    1080
acaataagca cagcctcgag gtctggatac gagatgttaa aagtgccaaa tgcattgaca    1140
gatgatagat caaagcccat tcaaggtcag acaattgtat taaacgctga ctggagtggt    1200
tacagtggat ctttcatgga ctattgggct gaggggggact gctatcgagc gtgtttttat    1260
gtggaattga tacgtggaag acccaaggag gataaagtgt ggtggaccag caatagtata   1320
gtatcgatgt gttccagtac agaattcctg ggacaatgga actggcctga tggggctaaa   1380
atagagtact tcctctaa                                                  1398

<210> SEQ ID NO 24
<211> LENGTH: 465
<212> TYPE: PRT
<213> ORGANISM: Influenza A

<400> SEQUENCE: 24

Met Asn Pro Asn Gln Lys Ile Leu Cys Thr Ser Ala Thr Ala Ile Ile
 1               5                  10                  15

Ile Gly Ala Ile Ala Val Leu Ile Gly Ile Ala Asn Leu Gly Leu Asn
            20                  25                  30

Ile Gly Leu His Leu Lys Pro Ser Cys Asn Cys Ser His Ser Gln Pro
        35                  40                  45

Glu Thr Thr Asn Thr Ser Gln Thr Ile Ile Asn Asn Tyr Tyr Asn Glu
    50                  55                  60

Thr Asn Ile Thr Asn Ile Gln Met Glu Glu Arg Thr Ser Arg Asn Phe
65                  70                  75                  80

Asn Asn Leu Thr Lys Gly Leu Cys Thr Ile Asn Ser Trp His Ile Tyr
                85                  90                  95

Gly Lys Asp Asn Ala Val Arg Ile Gly Glu Ser Ser Asp Val Leu Val
            100                 105                 110

Thr Arg Glu Pro Tyr Val Ser Cys Asp Pro Asp Glu Cys Arg Phe Tyr
        115                 120                 125

Ala Leu Ser Gln Gly Thr Thr Ile Arg Gly Lys His Ser Asn Gly Thr
    130                 135                 140

Ile His Asp Arg Ser Gln Tyr Arg Ala Leu Ile Ser Trp Pro Leu Ser
145                 150                 155                 160

Ser Pro Pro Thr Val Tyr Asn Ser Arg Val Glu Cys Ile Gly Trp Ser
                165                 170                 175

Ser Thr Ser Cys His Asp Gly Lys Ser Arg Met Ser Ile Cys Ile Ser
            180                 185                 190

Gly Pro Asn Asn Asn Ala Ser Ala Val Val Trp Tyr Asn Arg Arg Pro
        195                 200                 205

Val Ala Glu Ile Asn Thr Trp Ala Arg Asn Ile Leu Arg Thr Gln Glu
    210                 215                 220
```

| | | | | | | | | | | | | | | |
|---|---|---|---|---|---|---|---|---|---|---|---|---|---|---|
| Ser | Glu | Cys | Val | Cys | His | Asn | Gly | Val | Cys | Pro | Val | Val | Phe | Thr | Asp |
| 225 | | | | 230 | | | | | 235 | | | | | 240 |

Gly Ser Ala Thr Gly Pro Ala Asp Thr Arg Ile Tyr Tyr Phe Lys Glu
                245                 250                 255

Gly Lys Ile Leu Lys Trp Glu Ser Leu Thr Gly Thr Ala Lys His Ile
            260                 265                 270

Glu Glu Cys Ser Cys Tyr Gly Glu Arg Thr Gly Ile Thr Cys Thr Cys
        275                 280                 285

Lys Asp Asn Trp Gln Gly Ser Asn Arg Pro Val Ile Gln Ile Asp Pro
    290                 295                 300

Val Ala Met Thr His Thr Ser Gln Tyr Ile Cys Ser Pro Val Leu Thr
305                 310                 315                 320

Asp Asn Pro Arg Pro Asn Asp Pro Asn Ile Gly Lys Cys Asn Asp Pro
                325                 330                 335

Tyr Pro Gly Asn Asn Asn Asn Gly Val Lys Gly Phe Ser Tyr Leu Asp
                340                 345                 350

Gly Ala Asn Thr Trp Leu Gly Arg Thr Ile Ser Thr Ala Ser Arg Ser
            355                 360                 365

Gly Tyr Glu Met Leu Lys Val Pro Asn Ala Leu Thr Asp Asp Arg Ser
        370                 375                 380

Lys Pro Ile Gln Gly Gln Thr Ile Val Leu Asn Ala Asp Trp Ser Gly
385                 390                 395                 400

Tyr Ser Gly Ser Phe Met Asp Tyr Trp Ala Glu Gly Asp Cys Tyr Arg
                405                 410                 415

Ala Cys Phe Tyr Val Glu Leu Ile Arg Gly Arg Pro Lys Glu Asp Lys
            420                 425                 430

Val Trp Trp Thr Ser Asn Ser Ile Val Ser Met Cys Ser Ser Thr Glu
        435                 440                 445

Phe Leu Gly Gln Trp Asn Trp Pro Asp Gly Ala Lys Ile Glu Tyr Phe
    450                 455                 460

Leu
465

<210> SEQ ID NO 25
<211> LENGTH: 2341
<212> TYPE: DNA
<213> ORGANISM: Artificial Sequence
<220> FEATURE:
<223> OTHER INFORMATION: A synthetic oligonucleotide

<400> SEQUENCE: 25

```
agcgaaagca ggtcaattat attcaatatg gaaagaataa agaactacg aaatctaatg      60
tcgcagtctc gcacccgcga gatactcaca aaaccaccg tggaccatat ggccataatc     120
aagaagtaca catcaggaag acaggagaag aacccagcac tgaggatgaa atggatgatg   180
gcaatgaaat atccaattac agcagacaag aggatcaccg aaatgattcc tgagagaaat   240
gagcagggac agactctgtg gagtaaaatg aatgatgccg gatcagaccg agtgatggtg   300
tcacctctgg ctgtgacatg gtggaatagg aatggaccaa tcacaaatac agtgcattat   360
ccaaaaatct acaaaactta ttttgaaaga gtcgaaaggc tgaagcatgg aacctttggc   420
cctgtccatt ttagaaacca ggtcaaaatc cggcggagag tggacatcaa tcctggtcat   480
gcagatctca gtgccaagga ggcacaggat gtgatcatgg aagtggtgtt ccctaacgaa   540
gtgggagcca ggattctgac atccgaatcc cagctgacca ttaccaaaga gaagaaagaa   600
gaactccagg attgcaaaat ttctcctctg atggtggcat acatgctgga gagagaactg   660
```

```
gtccgcaaaa caagattcct cccagtggct ggtggaacaa gcagtgtgta cattgaagtg    720
ctgcatctga ctcagggaac atgctgggaa cagatgtata ctccaggagg ggaagtgagg    780
aatgatgatg tggatcagag cctgattatt gctgctagga acattgtgag aagagctgca    840
gtgtcagcag atccactggc atctctgctg agatgtgcc acagcacaca gattggtgga     900
attaggatgg tggacatcct gaggcagaac ccaacagaag agcaggccgt ggatatttgc    960
aaggctgcaa tgggactgag aattagctca tccttcagtt ttggtggatt cacatttaag   1020
agaacaagcg atcatcagt caagagagag gaagaggtgc tgaccggcaa tctgcagaca    1080
ctgaagatca gagtgcatga gggatatgaa gagttcacaa tggtggggag aagagcaaca   1140
gccatcctca gaaaagcaac caggagactg attcagctga tcgtgagtgg gagagacgaa   1200
cagtccattg ccgaagcaat tattgtggcc atggtgtttt cacaggagga ttgtatgatt   1260
aaagcagtca gaggtgatct gaatttcgtc aatagggcca atcagcgact gaatcctatg   1320
catcagctgc tgagacattt tcagaaggat gccaaagtgc tgtttcagaa ttggggagtg   1380
gaacctatcg acaatgtgat gggaatgatt gggatcctgc ccgacatgac tccaagcatc   1440
gagatgtcaa tgagaggagt gagaatcagc aaaatgggtg tggatgagta ctccagcacc   1500
gagagggtcg tggtgagcat tgacagattt ctgagaatcc gggaccagcg aggaaatgtg   1560
ctcctgtctc ccgaggaggt cagtgaaaca cagggaacag agaaactgac aattacttac   1620
tcatcctcaa tgatgtggga gattaatggt cctgaatcag tgctggtcaa tacctatcag   1680
tggatcatca gaaactggga aactgtgaaa attcagtggt cccagaaccc tacaatgctg   1740
tacaataaaa tggaatttga accatttcag tctctggtgc ctaaggccat tagaggccag   1800
tacagtgggt ttgtgagaac tctgttccag cagatgaggg atgtgctggg gacatttgat   1860
accgcacaga ttattaaact gctgcccttc gcagccgctc caccaaagca gagtagaatg   1920
cagttctcct catttactgt gaatgtgagg ggatcaggaa tgagaatcct ggtgaggggc   1980
aattctcctg tgttcaacta taacaaggcc accaagagac tcacagtgct cggaaaggat   2040
gctggcactc tgactgaaga cccagatgaa ggcacagctg gagtggagtc cgctgtgctg   2100 agggattcc tcattctggg caaagaagac aagagatatg ggccagcact gagcatcaat   2160
gaactgagca acctggccaa aggagagaag gctaatgtgc taattgggca aggagacgtg   2220
gtgttggtaa tgaaacggaa acgggactct agcatactta ctgacagcca gacagcgacc   2280
aaaagaattc ggatggccat caattagtgt cgaatagttt aaaaacgacc ttgtttctac   2340
t                                                                  2341
```

<210> SEQ ID NO 26
<211> LENGTH: 2341
<212> TYPE: DNA
<213> ORGANISM: Artificial Sequence
<220> FEATURE:
<223> OTHER INFORMATION: A synthetic oligonucleotide

<400> SEQUENCE: 26

```
agcgaaagca ggcaaaccat ttgaatggat gtcaatccga ccttactttt cttaaaagtg     60
ccagcacaaa atgctataag cacaactttc ccttatactg agaccctcc ttacagccat    120 gggacaggaa caggatacac catggatact gtcaacagga cacatcagta ctcagaaaag    180
ggaagatgga caacaaacac cgaaactgga gcaccgcaac tcaacccgat tgatgggcca    240
ctgccagaag acaatgaacc aagtggttat gcccaaacag attgtgtatt ggaggcgatg    300
```

```
gctttccttg aggaatccca tcctggtatt tttgaaaact cgtgtattga aacgatggag    360
gttgttcagc aaacacgagt ggacaagctg acacagggcc gacagaccta tgactggact    420
ctgaatagaa accagcctgc tgcaacagca ctggccaaca caatcgaagt gttcagatca    480
aatggcctca ccgccaatga gtctggaagg ctcatcgact tcctgaagga tgtgatggag    540
tcaatgaaca agaagaaat gggatcaca actcattttc agagaaagag acgggtgaga    600
gacaatatga ctaagaaaat gattacacag agaacaatgg gtaaaaagaa gcagagactg    660
aacaaaagga gttatctgat tagagcactg accctgaaca caatgaccaa agatgctgag    720
agagggaagc tgaaacggag agcaattgca accccaggga tgcagattag ggggtttgtg    780
tactttgtgg agacactggc aaggagtatt tgtgagaaac tggaacagtc agggctgcca    840
gtgggaggca atgagaagaa agcaaagctg gcaaatgtgg tgaggaagat gatgaccaat    900
tctcaggaca ccgaactgtc tttccatcc actggagata caccaaatg gaacgaaat    960 cagaatcctc ggatgtttct ggccatgatc acatatatga ccagaaatca gcccgaatgg   1020
ttcagaaatg tgctgagtat tgctccaatt atgttctcaa acaaaatggc cagactggga   1080
aaagggtata tgtttgagag caagagtatg aaactgagaa ctcagattcc tgcagaaatg   1140
ctggcaagca tcgatctgaa atatttcaat gattcaacaa gaagaagat tgaaaaaatc   1200 cgaccctcc tgattgaggg gactgcatca ctgagccctg aatgatgat gggcatgttc   1260 aatatgctga gcactgtgct gggcgtctcc atcctgaatc tgggacagaa gagatacacc   1320
aagactactt actggtggga tggtctgcag tcctctgacg attttgctct gattgtgaat   1380
gcacccaatc atgaagggat tcaggccgga gtcgacaggt tttatcgaac tgtaagctg    1440 ctgggaatca atatgagcaa gaaaaagtct tacatcaaca gaacaggtac atttgaattc   1500
acaagttttt tctatcgcta tgggtttgtg gccaatttca gcatggagct gcccagtttt   1560
ggggtgtctg ggatcaacga gtcagccgac atgagtattg gagtgactgt catcaaaaac   1620
aatatgatca caatgatct gggtccagca acagctcaga tggccctgca gctgttcatc   1680
aaagattaca ggtacaccta ccgatgccat atcggtgaca cacagattca gcccgaaga   1740 tcatttgaaa tcaagaaact gtgggagcag acccgctcca agctggact gctggtctcc   1800 gacggaggcc caaatctgta caacattaga atctccaca ttcctgaagt ctgcctgaaa   1860
tgggaactga tggatgagga ttaccagggg cgcctgtgca cccactgaa cccatttgtc   1920 agccataaag aaattgaatc aatgaacaat gcagtgatga tgccagcaca tggtccagcc   1980
aaaaacatgg agtatgatgc tgtggcaaca acacactcct ggatcccaa aagaaatcga   2040 tccatcctga atacaagtca gagaggagtg ctggaggatg aacagatgta ccagaggtgc   2100
tgcaatctgt ttgaaaaatt cttccccagc agttcataca aagaccagt cgggatctcc   2160 agtatggtgg aggctatggt gtccagagcc cgaattgatg cacggattga tttcgaatct   2220
ggaaggatca agaagaaga gttcactgag atcatgaaga tctgttccac cattgaagag   2280
ctcagacggc aaaatagtg aatttagctt gtccttcatg aaaaaatgcc ttgtttctac   2340
t                                                                  2341
```

<210> SEQ ID NO 27
<211> LENGTH: 2233
<212> TYPE: DNA
<213> ORGANISM: Artificial Sequence
<220> FEATURE:
<223> OTHER INFORMATION: A synthetic oligonucleotide

<400> SEQUENCE: 27

```
agcgaaagca ggtactgatc caaaatggaa gattttgtgc gacaatgctt caatccgatg    60
attgtcgagc ttgcggaaaa aacaatgaaa gagtatgggg aggacctgaa aatcgaaaca   120
aacaaatttg cagcaatatg cactcacttg gaagtatgct tcatgtattc agattttcac   180
ttcatcaatg agcaaggcga gtcaataatc gtagaacttg gtgatccaaa tgcacttttg   240
aagcacagat ttgaaataat cgagggaaga gatcgcacaa tggcctggac agtagtaaac   300
agtatttgca acactacagg ggctgagaaa ccaaagtttc taccagattt gtatgattac   360
aaggagaata gattcatcga aattggagta acaaggagag aagttcacat atactatctg   420
gaaaaggcca ataaaattaa atctgagaaa acacacatcc acattttctc gttcactggg   480
gaagaaatgg ccacaaaggc agactacact ctcgatgaag aaagcagggc taggatcaaa   540
accagactat tcaccataag acaagaaatg gccagcagag gcctctggga ttcctttcgt   600
cagtccgaga gaggagaaga gacaattgaa gaaaggtttg aaatcacagg aacaatgcgc   660
aagcttgccg accaaagtct cccgccgaac ttctccagcc ttgaaaattt tagagcctat   720
gtggatggat tcgaaccgaa cggctacatt gagggcaagc tgtctcaaat gtccaaagaa   780
gtaaatgcta gaattgaacc ttttctgaaa acaacaccac gaccactgag actgcccaat   840
gggcctccct gttctcagcg gtccaaattc ctgctgatgg atgccctgaa actgagcatt   900
gaggacccaa gtcatgaagg agagggaatt cccctgtatg atgcaatcaa atgcatgaga   960
acattctttg gatggaagga acccaatgtg gtgaaaccac acgaaaaggg aatcaatcca  1020
aattatctgc tgtcatggaa gcaggtgctg cagaactgca ggacattga gaatgaggag  1080 aaaattccaa agactaaaaa tatgaagaaa acaagtcagc tgaagtgggc actgggtgag  1140
aacatggcac cagaaaaggt ggactttgac gactgtaaag atgtgggtga tctgaagcag  1200
tatgatagtg atgaaccaga actgaggtcc ctggcaagtt ggattcagaa tgagtttaac  1260
aaggcatgcg aactgacaga ttcaagctgg attgagctcg atgagattgg agaagatgtg  1320
gctccaattg aacacattgc aagcatgaga aggaattatt tcacatcaga ggtgtctcac  1380
tgcagagcca cagaatacat catgaaggga gtgtacatca atactgccct gctgaatgca  1440
tcttgtgcag caatggatga tttccagctg attccaatga tcagcaagtg tagaactaag  1500
gagggaaggc gaaagaccaa cctgtatggt tcatcatca aaggaagatc ccacctgagg  1560
aatgacaccg acgtggtgaa cttttgtgagc atggagtttt ctctcactga cccaagactg  1620
gaaccacata atgggagaa gtactgtgtg ctggagattg agatatgct gatcagaagt  1680 gccattggcc aggtgtcaag gcccatgttc ctgtatgtga aacaaatgg aacctcaaaa  1740 attaaaatga aatggggaat ggagatgagg cgctgcctcc tccagtcact gcagcagatt  1800
gagagtatga ttgaagctga gtcctctgtc aaagagaaag acatgaccaa agagttcttt  1860
gagaacaaat cagaaacatg gcccattgga gagtccccca aggagtggga ggaaagttcc  1920
attgggaagg tctgcaggac tctgctggca agtccgtgt tcaacagcct gtatgcatct  1980
ccacagctgg aaggattttc agctgaatca agaaaactgc tgctgatcgt gcaggctctg  2040
agggacaacc tggaacctgg gaccttgat ctgggggggc tgtatgaagc aattgaggag  2100
tgcctgatta atgatccctg ggtgctgctg aatgcttctt ggttcaactc cttccttaca  2160
catgcattga gttagttgtg gcagtgctac tatttgctat ccatactgtc caaaaaagta  2220
ccttgtttct act                                                      2233

<210> SEQ ID NO 28
```

<211> LENGTH: 1565
<212> TYPE: DNA
<213> ORGANISM: Artificial Sequence
<220> FEATURE:
<223> OTHER INFORMATION: A synthetic oligonucleotide

<400> SEQUENCE: 28

```
agcaaaagca gggtagataa tcactcactg agtgacatca aaatcatggc gtctcaaggc    60
accaaacgat cttacgaaca gatggagact gatggagaac gccagaatgc cactgaaatc   120
agagcatccg tcggaaaaat gattggtgga attggacgat tctacatcca gatgtgcacc   180
gaactcaaac tcagtgatta tgagggacgg ctgatccaga acagcctgac aatcgagaga   240
atggtgctct ctgcttttga cgaaaggaga aataaatacc tggaagaaca tcccagtgcc   300
gggaaagatc ctaagaaaac tggaggacct atctacagga gagtgaacgg aaagtggatg   360
agagaactca tcctgtatga caaagaagaa atcaggcgaa tctggcgcca ggctaataat   420
ggtgacgatg caaccgctgg tctgactcac atgatgatct ggcattccaa tctgaatgat   480
gcaacttatc agaggacaag agctctggtg cgcaccggaa tggatcccag gatgtgctct   540
ctgatgcagg gttcaactct ccctaggagg tctggagccg caggtgctgc agtcaaagga   600
gtgggaacaa tggtgatgga actggtcaga atgatcaaaa gagggatcaa tgatcggaac   660
ttctggaggg gtgagaatgg acgaaaaaca agaattgctt atgaaagaat gtgcaacatt   720
ctcaaaggga aatttcagac tgctgcacag aaagcaatga tggatcaggt gagagagagc   780
cggaacccag ggaatgctga gttcgaagat ctcactttc tggcacggtc tgcactcatc   840
ctgagagggt ccgtggctca caagtcctgc ctgcctgcct gtgtgtatgg acctgccgtg   900
gccagtgggt acgactttga aagggaggga tactctctgg tcggaattga ccctttcaga   960
ctgctgcaga acagccaggt gtacagcctg atcagaccaa atgagaatcc agcacacaag  1020
agtcagctgg tgtggatggc atgccattct gccgcatttg aagatctgag agtgctgagc  1080
ttcatcaaag ggaccaaggt gctcccaaga gggaagctgt ccactagagg agtgcagatt  1140
gcttccaatg aaaatatgga gactatggaa tcaagtacac tggaactgag aagcaggtac  1200
tgggccatca ggaccagaag tggaggaaac accaatcagc agagggcatc tgccggccag  1260
atcagcattc agcctaccct ctcagtgcag agaaatctcc cttttgacag aacaaccatt  1320
atggcagcat tcaatgggaa tacagagggg agaacatctg acatgaggac cgaaatcatc  1380
aggatgatgg aaagtgcaag accagaagat gtgtctttcc aggggcgggg agtcttcgag  1440
ctctcggacg aaaaggcagc gagcccgatc gtgccttcct ttgacatgag taatgaagga  1500
tcttatttct tcggagacaa tgcagaggag tacgacaatt aaagaaaaat acccttgttt  1560
ctact                                                              1565
```